(12) United States Patent
Frackenpohl et al.

(10) Patent No.: US 10,065,926 B2
(45) Date of Patent: Sep. 4, 2018

(54) USE OF SUBSTITUTED DIHYDROOXINDOLYLSULFONAMIDES, OR THE SALTS THEREOF, FOR INCREASING THE STRESS TOLERANCE OF PLANTS

(71) Applicant: BAYER CROPSCIENCE AKTIENGESELLSCHAFT, Monheim Am Rhein (DE)

(72) Inventors: Jens Frackenpohl, Frankfurt (DE); Guido Bojack, Wiesbaden-Naurod (DE); Hendrik Helmke, Liederbach (DE); Stefan Lehr, Liederbach (DE); Thomas Mueller, Frankfurt (DE); Lothar Willms, Hofheim (DE); Jan Dittgen, Frankfurt (DE); Dirk Schmutzler, Hattersheim (DE); Udo Bickers, Kelkheim (DE); Harry Strek, Wiesbaden (DE); Rachel Baltz, Collonges Au Mont d Or (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/025,104

(22) PCT Filed: Oct. 2, 2014

(86) PCT No.: PCT/EP2014/071195
§ 371 (c)(1),
(2) Date: Mar. 25, 2016

(87) PCT Pub. No.: WO2015/049351
PCT Pub. Date: Apr. 9, 2015

(65) Prior Publication Data
US 2016/0237035 A1  Aug. 18, 2016

(30) Foreign Application Priority Data

Oct. 4, 2013 (EP) .................................. 13187361

(51) Int. Cl.
| | |
|---|---|
| *C07D 209/34* | (2006.01) |
| *C07D 209/30* | (2006.01) |
| *C07D 209/96* | (2006.01) |
| *C07D 487/10* | (2006.01) |
| *A01N 43/38* | (2006.01) |
| *A01N 43/90* | (2006.01) |
| *C07D 471/10* | (2006.01) |
| *C07D 491/107* | (2006.01) |
| *A01N 47/16* | (2006.01) |

(52) U.S. Cl.
CPC ........... *C07D 209/96* (2013.01); *A01N 43/38* (2013.01); *A01N 43/90* (2013.01); *A01N 47/16* (2013.01); *C07D 209/30* (2013.01); *C07D 209/34* (2013.01); *C07D 471/10* (2013.01); *C07D 491/107* (2013.01)

(58) Field of Classification Search
CPC .. C07D 209/34; C07D 209/30; C07D 209/96; C07D 471/10; C07D 487/10; A01N 43/38; A01N 43/90
USPC .................. 548/486, 411, 409; 514/411, 409
See application file for complete search history.

(56) References Cited

U.S. PATENT DOCUMENTS

| | | | |
|---|---|---|---|
| 5,201,931 | A | 4/1993 | Abrams et al. |
| 2011/0230350 | A1 | 9/2011 | Frackenpohl et al. |
| 2014/0038822 | A1 | 2/2014 | Frackenpohl et al. |

FOREIGN PATENT DOCUMENTS

| | | |
|---|---|---|
| DE | 847006 C | 8/1952 |
| DE | 2159362 A1 | 6/1973 |
| DE | 2544859 A1 | 4/1976 |
| EP | 0033984 A1 | 8/1981 |
| EP | 0176327 A1 | 4/1986 |
| EP | 2065370 A1 | 6/2009 |
| WO | 9636595 A1 | 11/1996 |
| WO | 9723441 A1 | 7/1997 |
| WO | 00/28055 A2 | 5/2000 |
| WO | 03007931 A1 | 1/2003 |

(Continued)

OTHER PUBLICATIONS

Kurihara, D., S. Matsunaga, A. Kawabe, S. Fujimoto, M. Noda, S. Uchiyama and K. Fukui, "Aurora kinase is required for chromosome segregation in tobacco BY-2 cells" The Plant Journ. (2006), 48: pp. 572-580. (Year: 2006).*

(Continued)

*Primary Examiner* — Matthew P Coughlin
*Assistant Examiner* — Sagar Patel
(74) *Attorney, Agent, or Firm* — McBee Moore Woodward & Vanik IP, LLC

(57) ABSTRACT

The invention relates to the use of substituted dihydrooxindolylsulfonamides or salts thereof of the formula (I)

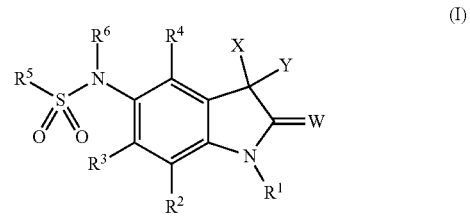

(I)

where the radicals in the general formula (I) correspond to the definitions given in the description, for enhancing stress tolerance in plants to abiotic stress, and/or for increasing plant yield.

20 Claims, No Drawings

(56) References Cited

FOREIGN PATENT DOCUMENTS

| WO | 2004000798 A1 | 12/2003 |
|---|---|---|
| WO | 2005035486 A1 | 4/2005 |
| WO | 2006056433 A2 | 6/2006 |
| WO | 2006124875 A2 | 11/2006 |
| WO | 2007060220 A2 | 5/2007 |
| WO | 2007122219 A1 | 11/2007 |
| WO | 20090011360 A1 | 1/2009 |
| WO | 2009079767 A1 | 7/2009 |
| WO | 2009105774 A2 | 8/2009 |
| WO | 2010077839 A1 | 7/2010 |
| WO | 2011113861 A2 | 9/2011 |
| WO | 2012089721 A1 | 7/2012 |
| WO | 2012089722 A2 | 7/2012 |

OTHER PUBLICATIONS

Churchill et al. "Effects of abscisic acid and abscisic acid analogs on the induction of freezing tolerance of winter rye (Secale cereale L.) seedlings", Plant Growth Regulation (1998) 25:35-45.

Morrison et al. "Variable Increases in Cold Hardiness Induced in Winter Rape by Plant Growth Regulators", J Plant Regul (1992) 11: 113-117.

Cholewa et al. "Cold-shock-stimulated 7-aminobutyric acid synthesis is mediated by an increase in cytosolic Ca2+, not by an increase in cytosolic H+", Can. J. Botany (1997) 75: 375-382.

Park et al. "Abscisic Acid Inhibits Type 2C Protein Phosphatases via the PYR/PYL Family of START Proteins", Science (2009), 324, 1068-1071.

"Database CA, Tan, XP002721167".

"Database CA, Baxter, XP002721168".

\* cited by examiner

USE OF SUBSTITUTED DIHYDROOXINDOLYLSULFONAMIDES, OR THE SALTS THEREOF, FOR INCREASING THE STRESS TOLERANCE OF PLANTS

CROSS REFERENCE TO RELATED APPLICATIONS

This application is a § 371 National Stage Application of PCT/EP2014/071195, filed Oct. 2, 2014, which claims priority to European 13187361.4 filed Oct. 4, 2013.

BACKGROUND

Field of the Invention
Description of Related Art

The invention relates to the use of substituted dihydrooxindolylsulfonamides or salts thereof for enhancing the stress tolerance in plants to abiotic stress, and for enhancing plant growth and/or for increasing plant yield.

It is known that certain arylsulfonamides, for example 2-cyanobenzenesulfonamides, have insecticidal properties (cf., for example, EP0033984 and WO2005035486, WO2006056433, WO2007060220). 2-Cyanobenzenesulfonamides with particular heterocyclic substituents are described in EP2065370. Furthermore, it is known that certain aryl- and heteroaryl-substituted sulfonamides can be used as active compounds for abiotic plant stress (cf. WO2011113861). The action of certain aryl-, heteroaryl- and benzylsulfonamidocarboxylic acids, -carboxylic esters, -carboxamides and -carbonitriles against abiotic plant stress is described in WO 2012089721 and WO 2012089722.

The preparation of sulfamidoalkanecarboxylic acids and sulfamidoalkanecarbonitriles is described in DE847006. The use of selected arylsulfonamides having alkylcarboxyl substituents as growth regulators especially for limiting the longitudinal growth of rice and wheat plants with the aim of minimizing weather-related lodging is described in DE2544859, whereas the fungicidal action of certain N-cyanoalkylsulfonamides is described in EP176327. Furthermore, it is known that substituted N-sulfonylaminoacetonitriles can be used for controlling parasites in warm-blooded animals (cf. WO2004000798).

It is also known that substituted arylsulfonamides (cf., for example, WO2009105774, WO2006124875, WO96/36595) and substituted hetarylsulfonamides (cf. WO2009113600, WO2007122219) can be used as pharmaceutically active compounds. WO2003007931 likewise describes the pharmaceutical use of substituted naphthylsulfonamides, while Eur. J. Med. 2010, 45, 1760 describes naphthylsulfonyl-substituted glutaminamides and their antitumor action. Furthermore, it is known that pyrrolidinyl-substituted arylsulfonamides can be used as cathepsin C inhibitors in the treatment of respiratory disorders (WO2009026197) or as antiinfective agents in the treatment of hepatitis C (WO2007092588). The pharmaceutical use of N-arylsulfonyl derivatives of various other amino acids, for example as urokinase inhibitors (cf. WO200005214), as active compounds for the treatment of diabetes (cf. WO2003091211), as analgesics (cf. WO2008131947) and as γ-secretase modulators (cf. WO2010108067) has also been described.

The preparation of certain N-methyl-substituted dihydrooxindolylsulfonamides is described, for example, in DE2159362 and J. Chem. Soc. C (1971), 952-955, whereas ACS Combinatorial Science (2012), 14, 218 describes the preparation of spiro-pyrrolidinonyl-substituted dihydrooxindolylsulfonamides. It is also known that certain substituted oxindolyl derivatives such as, for example, pyrrolobenzimidazolones, can be used as pharmaceutically active compounds, for example as antiproliferative substances (cf. EP1598353), as CB2 agonists (cf. WO2010077839) or as active compounds with antiarrhythmic and cardiotonic action (cf. EPO431943). EP1598353 teaches synthesis routes for preparing substituted aminodihydrooxindoles. Furthermore, it is known that oxotetrahydroquinolinylsulfonamides can be used as Rho kinase inhibitors (cf. Eur. J. Med. Chem. 2008, 43, 1730).

It is known that plants can react with specific or unspecific defense mechanisms to natural stress conditions, for example cold, heat, drought stress (stress caused by aridity and/or lack of water), injury, pathogenic attack (viruses, bacteria, fungi, insects) etc., but also to herbicides [Pflanzenbiochemie [Plant Biochemistry], p. 393-462, Spektrum Akademischer Verlag, Heidelberg, Berlin, Oxford, Hans W. Heldt, 1996; Biochemistry and Molecular Biology of Plants, p. 1102-1203, American Society of Plant Physiologists, Rockville, Md., eds. Buchanan, Gruissem, Jones, 2000].

Numerous proteins in plants, and the genes that code for them, which are involved in defense reactions to abiotic stress (for example cold, heat, drought, salt, flooding) are known. Some of these form part of signal transduction chains (e.g. transcription factors, kinases, phosphatases) or cause a physiological response of the plant cell (e.g. ion transport, detoxification of reactive oxygen species). The signaling chain genes of the abiotic stress reaction include inter alia transcription factors of the DREB and CBF classes (Jaglo-Ottosen et al., 1998, Science 280: 104-106). Phosphatases of the ATPK and MP2C type are involved in the reaction to salt stress. In addition, in the event of salt stress, the biosynthesis of osmolytes such as proline or sucrose is frequently activated. This involves, for example, sucrose synthase and proline transporters (Hasegawa et al., 2000, Annu Rev Plant Physiol Plant Mol Biol 51: 463-499). The stress defense of the plants to cold and drought uses some of the same molecular mechanisms. There is a known accumulation of what are called late embryogenesis abundant proteins (LEA proteins), which include the dehydrins as an important class (Ingram and Bartels, 1996, Annu Rev Plant Physiol Plant Mol Biol 47: 277-403, Close, 1997, Physiol Plant 100: 291-296). These are chaperones which stabilize vesicles, proteins and membrane structures in stressed plants (Bray, 1993, Plant Physiol 103: 1035-1040). In addition, there is frequently induction of aldehyde dehydrogenases, which detoxify the reactive oxygen species (ROS) which form in the event of oxidative stress (Kirch et al., 2005, Plant Mol Biol 57: 315-332). Heat shock factors (HSF) and heat shock proteins (HSP) are activated in the event of heat stress and play a similar role here as chaperones to that of dehydrins in the event of cold and drought stress (Yu et al., 2005, Mol Cells 19: 328-333).

A number of signaling substances which are endogenous to plants and are involved in stress tolerance or pathogenic defense are already known. Mention should be made here, for example, of salicylic acid, benzoic acid, jasmonic acid or ethylene [Biochemistry and Molecular Biology of Plants, p. 850-929, American Society of Plant Physiologists, Rockville, Md., eds. Buchanan, Gruissem, Jones, 2000]. Some of these substances or the stable synthetic derivatives and derived structures thereof are also effective on external application to plants or in seed dressing, and activate defense reactions which cause elevated stress tolerance or pathogen tolerance of the plant [Sembdner, and Parthier, 1993, Ann. Rev. Plant Physiol. Plant Mol. Biol. 44: 569-589].

It is also known that chemical substances can increase the tolerance of plants to abiotic stress. Such substances are applied either by seed dressing, by leaf spraying or by soil treatment. For instance, an increase in the abiotic stress tolerance of crop plants by treatment with elicitors of systemic acquired resistance (SAR) or abscisic acid derivatives is described (Schading and Wei, WO200028055; Abrams and Gusta, U.S. Pat. No. 5,201,931, Abrams et al., WO97/23441, Churchill et al., 1998, Plant Growth Regul 25: 35-45). In addition, effects of growth regulators on the stress tolerance of crop plants have been described (Morrison and Andrews, 1992, J Plant Growth Regul 11: 113-117, RD-259027). In this context, it is likewise known that a growth-regulating naphthylsulfonamide (4-bromo-N-(pyridin-2-ylmethyl)naphthalene-1-sulfonamide) influences the germination of plant seeds in the same way as abscisic acid (Park et al. Science 2009, 324, 1068-1071). Furthermore, in biochemical receptor tests a naphthylsulfamidocarboxylic acid (N-[(4-bromo-1-naphthyl)sulfonyl]-5-methoxynorvaline) shows a mode of action comparable to 4-bromo-N-(pyridin-2-ylmethyl)naphthalene-1-sulfonamide (Melcher et al. Nature Structural & Molecular Biology 2010, 17, 1102-1108). It is also known that a further naphthylsulfonamide, N-(6-aminohexyl)-5-chloronaphthalene-1-sulfonamide, influences the calcium level in plants which have been exposed to cold shock (Cholewa et al. Can. J. Botany 1997, 75, 375-382).

Similar effects are also observed on application of fungicides, especially from the group of the strobilurins or of the succinate dehydrogenase inhibitors, and are frequently also accompanied by an increase in yield (Draber et al., DE3534948, Bartlett et al., 2002, Pest Manag Sci 60: 309). It is likewise known that the herbicide glyphosate in low dosage stimulates the growth of some plant species (Cedergreen, Env. Pollution 2008, 156, 1099).

In the event of osmotic stress, a protective effect has been observed as a result of application of osmolytes, for example glycine betaine or the biochemical precursors thereof, e.g. choline derivatives (Chen et al., 2000, Plant Cell Environ 23: 609-618, Bergmann et al., DE4103253). The effect of antioxidants, for example naphthols and xanthines, for increasing abiotic stress tolerance in plants has also already been described (Bergmann et al., DD277832, Bergmann et al., DD277835). However, the molecular causes of the antistress action of these substances are largely unknown.

It is additionally known that the tolerance of plants to abiotic stress can be increased by a modification of the activity of endogenous poly-ADP-ribose polymerases (PARP) or poly-(ADP-ribose) glycohydrolases (PARG) (de Block et al., The Plant Journal, 2004, 41, 95; Levine et al., FEBS Lett. 1998, 440, 1; WO0004173; WO04090140).

It is thus known that plants possess several endogenous reaction mechanisms which can bring about an effective defense against a wide variety of different harmful organisms and/or natural abiotic stress. Since the ecologic and economic demands on modern plant treatment compositions are increasing constantly, for example with respect to their toxicity, selectivity, application rate, formation of residues and favorable manufacture, there is a constant need to develop novel plant treatment compositions which have advantages over those known, at least in some areas.

SUMMARY

It was therefore an object of the present invention to provide compounds which further increase tolerance to abiotic stress in plants, bring about invigoration of plant growth and/or contribute to an increase in plant yield. In this context, tolerance to abiotic stress is understood to mean, for example, tolerance to cold, heat, drought stress (stress caused by drought and/or lack of water), salts and flooding, but explicitly not the increased resistance to lodging of the plants or parts thereof, for example during or after heavy rain and thunderstorms.

Surprisingly, it has now been found that substituted dihydrooxindolylsulfonamides can be used for enhancing the stress tolerance in plants to abiotic stress, and for enhancing plant growth and/or for increasing plant yield.

The present invention accordingly provides for the use of substituted dihydrooxindolylsulfonamides of the general formula (I), or salts thereof,

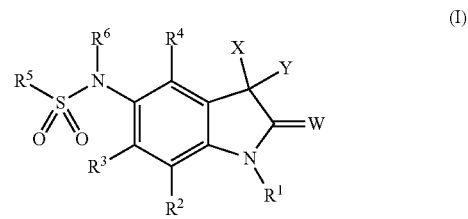

(I)

for increasing tolerance to abiotic stress in plants, where
$R^1$ represents hydrogen, $(C_1-C_{10})$-alkyl, $(C_3-C_8)$-cycloalkyl, $(C_1-C_{10})$-haloalkyl, $(C_3-C_8)$-halocycloalkyl, $(C_2-C_8)$-alkenyl, $(C_2-C_8)$-haloalkenyl, $(C_1-C_8)$-alkoxy-$(C_1-C_8)$-haloalkyl, $(C_2-C_8)$-alkynyl, aryl, aryl-$(C_1-C_8)$-alkyl, heteroaryl, heteroaryl-$(C_1-C_8)$-alkyl, $(C_3-C_8)$-cycloalkyl-$(C_1-C_8)$-alkyl, $(C_2-C_8)$-haloalkynyl, heterocyclyl, heterocyclyl-$(C_1-C_8)$-alkyl, $(C_1-C_8)$-alkoxy-$(C_1-C_8)$-alkyl, $(C_1-C_8)$-alkylcarbonyl-$(C_1-C_8)$-alkyl, hydroxycarbonyl-$(C_1-C_8)$-alkyl, $(C_1-C_8)$-alkoxycarbonyl-$(C_1-C_8)$-alkyl, $(C_2-C_8)$-alkenyloxycarbonyl-$(C_1-C_8)$-alkyl, $(C_2-C_8)$-alkynyloxycarbonyl-$(C_1-C_8)$-alkyl, aryl-$(C_1-C_8)$-alkoxycarbonyl-$(C_1-C_8)$-alkyl, $(C_3-C_8)$-cycloalkoxycarbonyl-$(C_1-C_8)$-alkyl, $(C_3-C_8)$-cycloalkyl-$(C_1-C_8)$-alkoxycarbonyl-$(C_1-C_8)$-alkyl, aminocarbonyl-$(C_1-C_8)$-alkyl, $(C_1-C_8)$-alkylaminocarbonyl-$(C_1-C_8)$-alkyl, $(C_3-C_8)$-cycloalkylaminocarbonyl-$(C_1-C_8)$-alkyl, aryl-$(C_1-C_8)$-alkylaminocarbonyl-$(C_1-C_8)$-alkyl, heteroaryl-$(C_1-C_8)$-alkylaminocarbonyl-$(C_1-C_8)$-alkyl, $(C_1-C_8)$-alkylthio-$(C_1-C_8)$-alkyl, $(C_3-C_8)$-cycloalkylthio-$(C_1-C_8)$-alkyl, arylthio-$(C_1-C_8)$-alkyl, heterocyclylthio-$(C_1-C_8)$-alkyl, heteroarylthio-$(C_1-C_8)$-alkyl, aryl-$(C_1-C_8)$-alkylthio-$(C_1-C_8)$-alkyl, $(C_1-C_8)$-alkylsulfinyl-$(C_1-C_8)$-alkyl, $(C_1-C_8)$-alkylsulfonyl-$(C_1-C_8)$-alkyl, arylsulfinyl-$(C_1-C_8)$-alkyl, arylsulfonyl-$(C_1-C_8)$-alkyl, $(C_3-C_8)$-cycloalkylsulfinyl-$(C_1-C_8)$-alkyl, $(C_3-C_8)$-cycloalkylsulfonyl-$(C_1-C_8)$-alkyl, $(C_1-C_8)$-alkoxy-$(C_1-C_8)$-alkoxy-$(C_1-C_8)$-alkyl, $(C_1-C_8)$-alkylcarbonyl, $(C_1-C_8)$-haloalkylcarbonyl, $(C_3-C_8)$-cycloalkylcarbonyl, $(C_1-C_8)$-alkoxycarbonyl, aryl-$(C_1-C_8)$-alkoxycarbonyl, arylcarbonyl, heteroarylcarbonyl, heterocyclylcarbonyl, aryl-$(C_1-C_8)$-alkylcarbonyl, $(C_1-C_8)$-alkylaminocarbonyl, $(C_3-C_8)$-cycloalkylaminocarbonyl, arylaminocarbonyl, aryl-$(C_1-C_8)$-alkylaminocarbonylheteroarylaminocarbonyl, heterocyclylaminocarbonyl, heteroaryl-$(C_1-C_8)$-alkylaminocarbonyl, heterocyclyl-$(C_1-C_8)$-alkylaminocarbonyl, $(C_1-C_8)$-alkylsulfonyl, $(C_3-C_8)$-cycloalkylsulfonyl, arylsulfonyl, aryl-$(C_1-C_8)$-alkylsulfonyl, heteroarylsulfonyl, heterocyclylsulfonyl, cyano-$(C_1-C_8)$-alkyl, $(C_4-C_8)$-cycloalkenyl-$(C_1-C_8)$-alkyl, nitro-$(C_1-C_8)$-alkyl, halo-$(C_1-C_8)$-alkoxy-$(C_1-C_8)$-alkyl, bis-[$(C_1-C_8)$-alkyl]

aminocarbonyl, $(C_3-C_8)$-cycloalkyl-$[(C_1-C_8)$-alkyl]aminocarbonyl, aryl-$[(C_1-C_8)$-alkyl]aminocarbonyl, aryl-$(C_1-C_8)$-alkyl-$[(C_1-C_8)$-alkyl]aminocarbonyl, $(C_2-C_8)$-alkenylaminocarbonyl, $(C_2-C_8)$-alkynylaminocarbonyl, $(C_1-C_8)$-alkylaminosulfonyl, bis-$[(C_1-C_8)$-alkyl]aminosulfonyl, heterocyclylsulfinyl-$(C_1-C_8)$-alkyl, heteroarylsulfinyl-$(C_1-C_8)$-alkyl, aryl-$(C_1-C_8)$-alkylsulfinyl-$(C_1-C_8)$-alkyl, heterocyclylsulfonyl-$(C_1-C_8)$-alkyl, heteroarylsulfonyl-$(C_1-C_8)$-alkyl, aryl-$(C_1-C_8)$-alkylsulfonyl-$(C_1-C_8)$-alkyl, bis-$[(C_1-C_8)$-alkyl]aminocarbonyl-$(C_1-C_8)$-alkyl, $(C_3-C_8)$-cycloalkyl-$[(C_1-C_8)$-alkyl]aminocarbonyl-$(C_1-C_8)$-alkyl, aryl-$[(C_1-C_8)$-alkyl]aminocarbonyl-$(C_1-C_8)$-alkyl, aryl-$(C_1-C_8)$-alkyl-$[(C_1-C_8)$-alkyl]aminocarbonyl-$(C_1-C_8)$-alkyl, $(C_2-C_8)$-alkenylaminocarbonyl-$(C_1-C_8)$-alkyl, $(C_2-C_8)$-alkynylaminocarbonyl-$(C_1-C_8)$-alkyl, $(C_1-C_8)$-alkylamino, bis-$[(C_1-C_8)$-alkyl]amino, $(C_3-C_8)$-cycloalkyl$[(C_1-C_8)$-alkyl]amino, $R^2$, $R^3$, $R^4$ independently of one another represent hydrogen, halogen, $(C_1-C_8)$-alkoxy, $(C_1-C_8)$-alkyl, $(C_1-C_8)$-haloalkyl, $(C_1-C_8)$-haloalkoxy, $(C_1-C_8)$-alkylthio, $(C_1-C_8)$-haloalkylthio, aryl, aryl-$(C_1-C_8)$-alkyl, heteroaryl, heteroaryl-$(C_1-C_8)$-alkyl, heterocyclyl, heterocyclyl-$(C_1-C_8)$-alkyl, $(C_3-C_8)$-cycloalkyl, nitro, amino, hydroxy, $(C_1-C_8)$-alkylamino, bis-$[(C_1-C_8)$-alkyl]amino, hydrothio, $(C_1-C_8)$-alkylcarbonylamino, $(C_3-C_8)$-cycloalkylcarbonylamino, arylcarbonylamino, heteroarylcarbonylamino, heterocyclylcarbonylamino, formyl, hydroxyiminomethyl, $(C_1-C_8)$-alkoxyiminomethyl, $(C_3-C_8)$-cycloalkoxyiminomethyl, aryloxyiminomethyl, $(C_3-C_8)$-cycloalkyl-$(C_1-C_8)$-alkoxyiminomethyl, thiocyanato, isothiocyanato, aryloxy, heteroaryloxy, $(C_3-C_8)$-cycloalkoxy, $(C_3-C_8)$-cycloalkyl-$(C_1-C_8)$-alkoxy, aryl-$(C_1-C_8)$-alkoxy, $(C_2-C_8)$-alkynyl, $(C_2-C_8)$-alkenyl, aryl-$(C_1-C_8)$-alkynyl, tris-$[(C_1-C_8)$-alkyl]silyl-$(C_2-C_8)$-alkynyl, bis-$[(C_1-C_8)$-alkyl](aryl) silyl-$(C_2-C_8)$-alkynyl, bis-aryl$[(C_1-C_8)$-alkyl]silyl-$(C_2-C_8)$-alkynyl, $(C_3-C_8)$-cycloalkyl-$(C_2-C_8)$-alkynyl, aryl-$(C_2-C_8)$-alkenyl, heteroaryl-$(C_2-C_8)$-alkenyl, $(C_3-C_8)$-cycloalkyl-$(C_2-C_8)$-alkenyl, $(C_3-C_8)$-cycloalkyl-$(C_2-C_8)$-alkyl, $(C_2-C_8)$-haloalkynyl, $(C_2-C_8)$-haloalkenyl, $(C_4-C_8)$-cycloalkenyl, $(C_1-C_8)$-alkoxy-$(C_1-C_8)$-alkoxy-$(C_1-C_8)$-alkyl, $(C_1-C_8)$-alkylsulfonyl, arylsulfonyl, heteroarylsulfonyl, $(C_1-C_8)$-alkylsulfonylamino, arylsulfonylamino, aryl-$(C_1-C_8)$-alkylsulfonylamino, heteroarylsulfonylamino, heteroaryl-$(C_1-C_8)$-alkylsulfonylamino, bis-$[(C_1-C_8)$-alkyl]aminosulfonyl, $(C_4-C_8)$-cycloalkenyl-$(C_1-C_8)$-alkyl, $(C_1-C_8)$-alkylsulfinyl, arylsulfinyl, heteroarylsulfinyl, $R^5$ represents amino, $(C_1-C_8)$-alkyl, $(C_3-C_8)$-cycloalkyl, $(C_3-C_8)$-cycloalkyl-$(C_1-C_8)$-alkyl, $(C_1-C_8)$-haloalkyl, $(C_3-C_8)$-halocycloalkyl, $(C_4-C_8)$-cycloalkenyl, aryl, heteroaryl, heterocyclyl, aryl-$(C_1-C_8)$-alkyl, heteroaryl-$(C_1-C_8)$-alkyl, heterocyclyl-$(C_1-C_8)$-alkyl, $(C_1-C_8)$-alkoxycarbonyl-$(C_1-C_8)$-alkyl, aryl-$(C_1-C_8)$-alkoxycarbonyl-$(C_1-C_8)$-alkyl, $(C_3-C_8)$-cycloalkoxycarbonyl-$(C_1-C_8)$-alkyl, $(C_3-C_8)$-cycloalkyl-$(C_1-C_8)$-alkoxycarbonyl-$(C_1-C_8)$-alkyl, heteroaryl-$(C_1-C_8)$-alkoxycarbonyl-$(C_1-C_8)$-alkyl, aminocarbonyl-$(C_1-C_8)$-alkyl, $(C_1-C_8)$-alkylaminocarbonyl-$(C_1-C_8)$-alkyl, $(C_3-C_8)$-cycloalkylaminocarbonyl-$(C_1-C_8)$-alkyl, aryl-$(C_1-C_8)$-alkylaminocarbonyl-$(C_1-C_8)$-alkyl, $(C_1-C_8)$-alkylamino, arylamino, $(C_3-C_8)$-cycloalkylamino, aryl-$(C_1-C_8)$-alkylamino, heteroaryl-$(C_1-C_8)$-alkylamino, heteroarylamino, heterocyclylamino, aryloxy-$(C_1-C_8)$-alkyl, $(C_1-C_8)$-alkoxy-$(C_1-C_8)$-alkyl, heteroaryloxy-$(C_1-C_8)$-alkyl, $(C_2-C_8)$-alkenyl, $(C_2-C_8)$-alkynyl, $(C_2-C_8)$-alkenylamino, $(C_2-C_8)$-alkynylamino, bis-$[(C_1-C_8)$-alkyl]amino, aryloxy, bis-$[(C_1-C_8)$-alkyl]amino, aryl-$(C_2-C_8)$-alkenyl, heteroaryl-$(C_2-C_8)$-alkenyl, heterocyclyl-$(C_2-C_8)$-alkenyl, aryloxycarbonyl-$(C_1-C_8)$-alkyl, heteroaryloxycarbonyl-$(C_1-C_8)$-alkyl, bis$[(C_1-C_8)$-alkyl]aminocarbonyl-$(C_1-C_8)$-alkyl, $(C_1-C_8)$-alkylthio-$(C_1-C_8)$-alkyl, cyano-$(C_1-C_8)$-alkyl, $(C_1-C_8)$-alkoxy-$(C_1-C_8)$-alkoxy-$(C_1-C_8)$-alkyl, $R^6$ represents hydrogen, $(C_1-C_8)$-alkyl, $(C_3-C_8)$-cycloalkyl, cyano-$(C_1-C_8)$-alkyl, $(C_3-C_8)$-cycloalkyl-$(C_1-C_8)$-alkyl, $(C_1-C_8)$-alkylsulfonyl, arylsulfonyl, heteroarylsulfonyl, $(C_3-C_8)$-cycloalkylsulfonyl, heterocyclylsulfonyl, aryl-$(C_1-C_8)$-alkylsulfonyl, $(C_1-C_8)$-alkylcarbonyl, arylcarbonyl, heteroarylcarbonyl, $(C_3-C_8)$-cycloalkylcarbonyl, heterocyclylcarbonyl, $(C_1-C_8)$-alkoxycarbonyl, aryl-$(C_1-C_8)$-alkoxycarbonyl, $(C_1-C_8)$-haloalkylcarbonyl, $(C_2-C_8)$-alkenyl, $(C_2-C_8)$-alkynyl, $(C_1-C_8)$-haloalkyl, halo-$(C_2-C_8)$-alkynyl, halo-$(C_2-C_8)$-alkenyl, $(C_1-C_8)$-alkoxy-$(C_1-C_8)$-alkyl, W represents oxygen, sulfur, X, Y independently of one another represent hydrogen, $(C_1-C_8)$-alkyl, halogen, $(C_2-C_8)$-alkenyl, $(C_2-C_8)$-alkynyl, $(C_1-C_8)$-haloalkyl, hydroxy-$(C_1-C_8)$-alkyl, cyano-$(C_1-C_8)$-alkyl, aryl, heteroaryl, $(C_3-C_8)$-cycloalkyl, $(C_4-C_8)$-cycloalkenyl, heterocyclyl, cyano, nitro, hydroxy, $(C_1-C_8)$-alkoxy, $(C_1-C_8)$-alkylthio, $(C_1-C_8)$-alkoxy-$(C_1-C_8)$-alkyl, $(C_1-C_8)$-alkylthio-$(C_1-C_8)$-alkyl, aryloxy, aryl-$(C_1-C_8)$-alkoxy, $(C_1-C_8)$-haloalkoxy, $(C_1-C_8)$-haloalkylthio, $(C_1-C_8)$-alkylamino, bis-$[(C_1-C_8)$-alkyl]amino, $(C_1-C_8)$-alkoxy-$(C_1-C_8)$-alkoxy, amino-$(C_1-C_8)$-alkyl, $(C_1-C_8)$-alkylamino-$(C_1-C_8)$-alkyl, $(C_3-C_8)$-cycloalkylamino-$(C_1-C_8)$-alkyl, aryl-$(C_1-C_8)$-alkylamino-$(C_1-C_8)$-alkyl, heteroaryl-$(C_1-C_8)$-alkylamino-$(C_1-C_8)$-alkyl, heterocyclyl-$(C_1-C_8)$-alkylamino-$(C_1-C_8)$-alkyl, heterocyclylamino-$(C_1-C_8)$-alkyl, heteroarylamino-$(C_1-C_8)$-alkyl, $(C_1-C_8)$-alkoxycarbonylamino-$(C_1-C_8)$-alkyl, arylamino-$(C_1-C_8)$-alkyl, aryl-$(C_1-C_8)$-alkoxycarbonylamino-$(C_1-C_8)$-alkyl, $(C_3-C_8)$-cycloalkoxycarbonylamino-$(C_1-C_8)$-alkyl, $(C_3-C_8)$-cycloalkyl-$(C_1-C_8)$-alkoxycarbonylamino-$(C_1-C_8)$-alkyl, heteroaryl-$(C_1-C_8)$-alkoxycarbonylamino-$(C_1-C_8)$-alkyl, $(C_1-C_8)$-alkylcarbonylamino-$(C_1-C_8)$-alkyl, $(C_3-C_8)$-cycloalkylcarbonylamino-$(C_1-C_8)$-alkyl, arylcarbonylamino-$(C_1-C_8)$-alkyl, heteroarylcarbonylamino-$(C_1-C_8)$-alkyl, heterocyclylcarbonylamino-$(C_1-C_8)$-alkyl, $(C_2-C_8)$-alkenyloxycarbonylamino-$(C_1-C_8)$-alkyl, aryl-$(C_2-C_8)$-alkenylamino-$(C_1-C_8)$-alkyl, arylsulfonyl-$(C_1-C_8)$-alkyl, heteroarylsulfonyl-$(C_1-C_8)$-alkyl, $(C_1-C_8)$-alkylsulfonyl-$(C_1-C_8)$-alkyl, $(C_3-C_8)$-cycloalkylsulfonyl-$(C_1-C_8)$-alkyl, arylsulfinyl-heteroarylsulfinyl-$(C_1-C_8)$-alkyl, $(C_1-C_8)$-alkylsulfinyl-$(C_1-C_8)$-alkyl, $(C_3-C_8)$-cycloalkylsulfinyl-$(C_1-C_8)$-alkyl, bis$[(C_1-C_8)$-alkyl]amino-$(C_1-C_8)$-alkyl or X and Y with the carbon atom to which they are attached form a fully saturated or partially saturated 3- to 7-membered monocyclic or bicyclic ring which is optionally interrupted by heteroatoms and optionally substituted further.

DETAILED DESCRIPTION OF A PREFERRED EMBODIMENT

The compounds of the general formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts will comprise the conjugated base of the acid as the anion. Suitable substituents present in deprotonated form, such as, for example, sulfonic acids, certain sulfonamides or carboxylic acids, may form inner salts with groups which for their part can be protonated, such as amino groups. Salts may also be formed by action of a base on compounds of the general formula (I). Examples of suitable bases are organic amines such as trialkylamines, morpholine, piperidine and pyridine, and the hydroxides, carbonates and hydrogencarbonates of ammonium, alkali metals or alkaline earth metals, especially sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula $[NR^aR^bR^cR^d]^+$, in which $R^a$ to $R^d$ are in each case independently an organic radical, especially alkyl, aryl, aralkyl or alkylaryl. Also suitable are alkylsulfonium and alkylsulfoxonium salts, such as $(C_1-C_4)$-trialkylsulfonium and $(C_1-C_4)$-trialkylsulfoxonium salts.

The compounds of the formula (I) used in accordance with the invention and salts thereof are referred to hereinafter as "compounds of the general formula (I)".

Preference is given to the use according to the invention of compounds of the general formula (I) in which $R^1$ represents hydrogen, $(C_1-C_{10})$-alkyl, $(C_3-C_7)$-cycloalkyl, $(C_1-C_{10})$-haloalkyl, $(C_3-C_7)$-halocycloalkyl, $(C_2-C_7)$-alkenyl, $(C_2-C_7)$-haloalkenyl, $(C_1-C_7)$-alkoxy-$(C_1-C_7)$-haloalkyl, $(C_2-C_7)$-alkynyl, aryl, aryl-$(C_1-C_7)$-alkyl, heteroaryl, heteroaryl-$(C_1-C_7)$-alkyl, $(C_3-C_7)$-cycloalkyl-$(C_1-C_7)$-alkyl, $(C_2-C_7)$-haloalkynyl, heterocyclyl, heterocyclyl-$(C_1-C_7)$-alkyl, $(C_1-C_7)$-alkoxy-$(C_1-C_7)$-alkyl, $(C_1-C_7)$-alkylcarbonyl-$(C_1-C_7)$-alkyl, hydroxycarbonyl-$(C_1-C_7)$-alkyl, $(C_1-C_7)$-alkoxycarbonyl-$(C_1-C_7)$-alkyl, $(C_2-C_7)$-alkenyloxycarbonyl-$(C_1-C_7)$-alkyl, $(C_2-C_7)$-alkynyloxycarbonyl-$(C_1-C_7)$-alkyl, aryl-$(C_1-C_7)$-alkoxycarbonyl-$(C_1-C_7)$-alkyl, $(C_3-C_7)$-cycloalkoxycarbonyl-$(C_1-C_7)$-alkyl, $(C_3-C_7)$-cycloalkyl-$(C_1-C_7)$-alkoxycarbonyl-$(C_1-C_7)$-alkyl, aminocarbonyl-$(C_1-C_7)$-alkyl, $(C_1-C_7)$-alkylaminocarbonyl-$(C_1-C_7)$-alkyl, $(C_3-C_7)$-cycloalkylaminocarbonyl-$(C_1-C_7)$-alkyl, aryl-$(C_1-C_7)$-alkylaminocarbonyl-$(C_1-C_7)$-alkyl, heteroaryl-$(C_1-C_7)$-alkylaminocarbonyl-$(C_1-C_7)$-alkyl, $(C_1-C_7)$-alkylthio-$(C_1-C_7)$-alkyl, $(C_3-C_7)$-cycloalkylthio-$(C_1-C_7)$-alkyl, arylthio-$(C_1-C_7)$-alkyl, heterocyclylthio-$(C_1-C_7)$-alkyl, heteroarylthio-$(C_1-C_7)$-alkyl, aryl-$(C_1-C_7)$-alkylthio-$(C_1-C_7)$-alkyl, $(C_1-C_7)$-alkylsulfinyl-$(C_1-C_7)$-alkyl, $(C_1-C_7)$-alkylsulfonyl-$(C_1-C_7)$-alkyl, arylsulfinyl-$(C_1-C_7)$-alkyl, arylsulfonyl-$(C_1-C_7)$-alkyl, $(C_3-C_7)$-cycloalkylsulfinyl-$(C_1-C_7)$-alkyl, $(C_3-C_7)$-cycloalkylsulfonyl-$(C_1-C_7)$-alkyl, $(C_1-C_7)$-alkoxy-$(C_1-C_7)$-alkoxy-$(C_1-C_7)$-alkyl, $(C_1-C_7)$-alkylcarbonyl, $(C_1-C_7)$-haloalkylcarbonyl, $(C_3-C_7)$-cycloalkylcarbonyl, $(C_1-C_7)$-alkoxycarbonyl, aryl-$(C_1-C_7)$-alkoxycarbonyl, arylcarbonyl, heteroarylcarbonyl, heterocyclylcarbonyl, aryl-$(C_1-C_7)$-alkylcarbonyl, $(C_1-C_7)$-alkylaminocarbonyl, $(C_3-C_7)$-cycloalkylaminocarbonyl, arylaminocarbonyl, aryl-$(C_1-C_7)$-alkylaminocarbonyl, heteroarylaminocarbonyl, heterocyclylaminocarbonyl, heteroaryl-$(C_1-C_7)$-alkylaminocarbonyl, heterocyclyl-$(C_1-C_7)$-alkylaminocarbonyl, $(C_1-C_7)$-alkylsulfonyl, $(C_3-C_7)$-cycloalkylsulfonyl, arylsulfonyl, aryl-$(C_1-C_7)$-alkylsulfonyl, heteroarylsulfonyl, heterocyclylsulfonyl, cyano-$(C_1-C_7)$-alkyl, $(C_4-C_7)$-cycloalkenyl-$(C_1-C_7)$-alkyl, nitro-$(C_1-C_7)$-alkyl, halo-$(C_1-C_7)$-alkoxy-$(C_1-C_7)$-alkyl, bis-$[(C_1-C_7)$-alkyl]aminocarbonyl, $(C_3-C_7)$-cycloalkyl-$[(C_1-C_7)$-alkyl]aminocarbonyl, aryl-$[(C_1-C_7)$-alkyl]aminocarbonyl, aryl-$(C_1-C_7)$-alkyl-$[(C_1-C_7)$-alkyl]aminocarbonyl, $(C_2-C_7)$-alkenylaminocarbonyl, $(C_2-C_7)$-alkynylaminocarbonyl, $(C_1-C_7)$-alkylaminosulfonyl, bis-$[(C_1-C_7)$-alkyl]aminosulfonyl, heterocyclylsulfinyl-$(C_1-C_7)$-alkyl, heteroarylsulfinyl-$(C_1-C_7)$-alkyl, aryl-$(C_1-C_7)$-alkylsulfinyl-$(C_1-C_7)$-alkyl, heterocyclylsulfonyl-$(C_1-C_7)$-alkyl, heteroarylsulfonyl-$(C_1-C_7)$-alkyl, aryl-$(C_1-C_7)$-alkylsulfonyl-$(C_1-C_7)$-alkyl, bis-$[(C_1-C_7)$-alkyl]aminocarbonyl-$(C_1-C_7)$-alkyl, $(C_3-C_7)$-cycloalkyl-$[(C_1-C_7)$-alkyl]aminocarbonyl-$(C_1-C_7)$-alkyl, aryl-$[(C_1-C_7)$-alkyl]aminocarbonyl-$(C_1-C_7)$-alkyl, aryl-$(C_1-C_7)$-alkyl-$[(C_1-C_7)$-alkyl]aminocarbonyl-$(C_1-C_7)$-alkyl, $(C_2-C_7)$-alkenylaminocarbonyl-$(C_1-C_7)$-alkyl, $(C_2-C_7)$-alkynylaminocarbonyl-$(C_1-C_7)$-alkyl, bis-$[(C_1-C_7)$-alkyl]amino, $(C_3-C_7)$-cycloalkyl$[(C_1-C_7)$-alkyl]amino, $R^2$, $R^3$, $R^4$ independently of one another represent hydrogen, halogen, $(C_1-C_7)$-alkoxy, $(C_1-C_7)$-alkyl, $(C_1-C_7)$-haloalkyl, $(C_1-C_7)$-haloalkoxy, $(C_1-C_7)$-alkylthio, $(C_1-C_7)$-haloalkylthio, aryl, aryl-$(C_1-C_7)$-alkyl, heteroaryl, heteroaryl-$(C_1-C_7)$-alkyl, heterocyclyl, heterocyclyl-$(C_1-C_7)$-alkyl, $(C_3-C_7)$-cycloalkyl, nitro, amino, hydroxy, $(C_1-C_7)$-alkylamino, bis-$[(C_1-C_7)$-alkyl]amino, hydrothio, $(C_1-C_7)$-alkylcarbonylamino, $(C_3-C_7)$-cycloalkylcarbonylamino, arylcarbonylamino, heteroarylcarbonylamino, heterocyclylcarbonylamino, formyl, hydroxyiminomethyl, $(C_1-C_7)$-alkoxyiminomethyl, $(C_3-C_7)$-cycloalkoxyiminomethyl, aryloxyiminomethyl, $(C_3-C_7)$-cycloalkyl-$(C_1-C_7)$-alkoxyiminomethyl, thiocyanato, isothiocyanato, aryloxy, heteroaryloxy, $(C_3-C_7)$-cycloalkoxy, $(C_3-C_7)$-cycloalkyl-$(C_1-C_7)$-alkoxy, aryl-$(C_1-C_7)$-alkoxy, $(C_2-C_7)$-alkynyl, $(C_2-C_7)$-alkenyl, aryl-$(C_1-C_7)$-alkynyl, tris-$[(C_1-C_7)$-alkyl]silyl-$(C_2-C_7)$-alkynyl, bis-$[(C_1-C_7)$-alkyl](aryl)silyl-$(C_2-C_7)$-alkynyl, bis-aryl$[(C_1-C_7)$-alkyl]silyl-$(C_2-C_7)$-alkynyl, $(C_3-C_7)$-cycloalkyl-$(C_2-C_7)$-alkynyl, aryl-$(C_2-C_7)$-alkenyl, heteroaryl-$(C_2-C_7)$-alkenyl, $(C_3-C_7)$-cycloalkyl-$(C_2-C_7)$-alkenyl, $(C_3-C_7)$-cycloalkyl-$(C_2-C_7)$-alkyl, $(C_2-C_7)$-haloalkynyl, $(C_2-C_7)$-haloalkenyl, $(C_4-C_7)$-cycloalkenyl, $(C_1-C_7)$-alkoxy-$(C_1-C_7)$-alkoxy-$(C_1-C_7)$-alkyl, $(C_1-C_7)$-alkylsulfonyl, arylsulfonyl, heteroarylsulfonyl, $(C_1-C_7)$-alkylsulfonylamino, arylsulfonylamino, aryl-$(C_1-C_7)$-alkylsulfonylamino, heteroarylsulfonylamino, heteroaryl-$(C_1-C_7)$-alkylsulfonylamino, bis-$[(C_1-C_7)$-alkyl]aminosulfonyl, $(C_4-C_7)$-cycloalkenyl-$(C_1-C_7)$-alkyl, $(C_1-C_7)$-alkylsulfinyl, arylsulfinyl, heteroarylsulfinyl, $R^5$ represents amino, $(C_1-C_7)$-alkyl, $(C_3-C_7)$-cycloalkyl, $(C_3-C_7)$-cycloalkyl-$(C_1-C_7)$-alkyl, $(C_1-C_7)$-haloalkyl, $(C_3-C_7)$-halocycloalkyl, $(C_4-C_7)$-cycloalkenyl, aryl, heteroaryl, heterocyclyl, aryl-$(C_1-C_7)$-alkyl, heteroaryl-$(C_1-C_7)$-alkyl, heterocyclyl-$(C_1-C_7)$-alkyl, $(C_1-C_7)$-alkoxycarbonyl-$(C_1-C_7)$-alkyl, aryl-$(C_1-C_7)$-alkoxycarbonyl-$(C_1-C_7)$-alkyl, $(C_3-C_7)$-cycloalkoxycarbonyl-$(C_1-C_7)$-alkyl, $(C_3-C_7)$-cycloalkyl-$(C_1-C_7)$-alkoxycarbonyl-$(C_1-C_7)$-alkyl, heteroaryl-$(C_1-C_7)$-alkoxycarbonyl-$(C_1-C_7)$-alkyl, aminocarbonyl-$(C_1-C_7)$-alkyl, $(C_1-C_7)$-alkylaminocarbonyl-$(C_1-C_7)$-alkyl, $(C_3-C_7)$-cycloalkylaminocarbonyl-$(C_1-C_7)$-alkyl, aryl-$(C_1-C_7)$-alkylaminocarbonyl-$(C_1-C_7)$-alkyl, $(C_1-C_7)$-alkylamino, arylamino, $(C_3-C_7)$-cycloalkylamino, aryl-$(C_1-C_7)$-alkylamino, heteroaryl-$(C_1-C_7)$-alkylamino, heteroarylamino, heterocyclylamino, aryloxy-$(C_1-C_7)$-alkyl, $(C_1-C_7)$-alkoxy-$(C_1-C_7)$-alkyl, heteroaryloxy-$(C_1-C_7)$-alkyl, $(C_2-C_7)$-alkenyl, $(C_2-C_7)$-alkynyl, $(C_2-C_7)$-alkenylamino, ($C_2$-$C_7$)-alkynylamino, bis-[($C_1$-$C_7$)-alkyl]amino, aryloxy, bis-[($C_1$-$C_7$)-alkyl]amino, ($C_1$-$C_7$)-alkyl-[($C_1$-$C_7$)-alkyl]amino, aryl-($C_2$-$C_7$)-alkenyl, heteroaryl-($C_2$-$C_7$)-alkenyl, heterocyclyl-($C_2$-$C_7$)-alkenyl, aryloxycarbonyl-($C_1$-$C_7$)-alkyl, heteroaryloxycarbonyl-($C_1$-$C_7$)-alkyl, bis [($C_1$-$C_7$)-alkyl]aminocarbonyl-($C_1$-$C_7$)-alkyl, ($C_1$-$C_7$)-alkylthio-($C_1$-$C_7$)-alkyl, cyano-($C_1$-$C_7$)-alkyl, ($C_1$-$C_7$)-alkoxy-($C_1$-$C_7$)-alkoxy-($C_1$-$C_7$)-alkyl, $R^6$ represents hydrogen, ($C_1$-$C_7$)-alkyl, ($C_3$-$C_7$)-cycloalkyl, cyano-($C_1$-$C_7$)-alkyl, ($C_3$-$C_7$)-cycloalkyl-($C_1$-$C_7$)-alkyl, ($C_1$-$C_7$)-alkylsulfonyl, arylsulfonyl, heteroarylsulfonyl, ($C_3$-$C_7$)-cycloalkylsulfonyl, heterocyclylsulfonyl, aryl-($C_1$-$C_7$)-alkylsulfonyl, ($C_1$-$C_7$)-alkylcarbonyl, arylcarbonyl, heteroarylcarbonyl, ($C_3$-$C_7$)-cycloalkylcarbonyl, heterocyclylcarbonyl, ($C_1$-$C_7$)-alkoxycarbonyl, aryl-($C_1$-$C_7$)-alkoxycarbonyl, ($C_1$-$C_7$)-haloalkylcarbonyl, ($C_2$-$C_7$)-alkenyl, ($C_2$-$C_7$)-alkynyl, ($C_1$-$C_7$)-haloalkyl, halo-($C_2$-$C_7$)-alkynyl, halo-($C_2$-$C_7$)-alkenyl, ($C_1$-$C_7$)-alkoxy-($C_1$-$C_7$)-alkyl, W represents oxygen, sulfur, X, Y independently of one another represent hydrogen, ($C_1$-$C_7$)-alkyl, halogen, ($C_2$-$C_7$)-alkenyl, ($C_2$-$C_7$)-alkynyl, ($C_1$-$C_7$)-haloalkyl, hydroxy-($C_1$-$C_7$)-alkyl, cyano-($C_1$-$C_7$)-alkyl, aryl, heteroaryl, ($C_3$-$C_7$)-cycloalkyl, ($C_4$-$C_7$)-cycloalkenyl, heterocyclyl, cyano, nitro, hydroxy, ($C_1$-$C_7$)-alkoxy, ($C_1$-$C_7$)-alkylthio, ($C_1$-$C_7$)-alkoxy-($C_1$-$C_7$)-alkyl, ($C_1$-$C_7$)-alkylthio-($C_1$-$C_7$)-alkyl, aryloxy, aryl-($C_1$-$C_7$)-alkoxy, ($C_1$-$C_7$)-haloalkoxy, ($C_1$-$C_7$)-haloalkylthio, ($C_1$-$C_7$)-alkylamino, bis-[($C_1$-$C_7$)-alkyl]amino, ($C_1$-$C_7$)-alkoxy-($C_1$-$C_7$)-alkoxy, amino-($C_1$-$C_7$)-alkyl, ($C_1$-$C_7$)-alkylamino-($C_1$-$C_7$)-alkyl, ($C_3$-$C_7$)-cycloalkylamino-($C_1$-$C_7$)-alkyl, aryl-($C_1$-$C_7$)-alkylamino-($C_1$-$C_7$)-alkyl, heteroaryl-($C_1$-$C_7$)-alkylamino-($C_1$-$C_7$)-alkyl, heterocyclyl-($C_1$-$C_7$)-alkylamino-($C_1$-$C_7$)-alkyl, heterocyclylamino-($C_1$-$C_7$)-alkyl, heteroarylamino-($C_1$-$C_7$)-alkyl, ($C_1$-$C_7$)-alkoxycarbonylamino-($C_1$-$C_7$)-alkyl, arylamino-($C_1$-$C_7$)-alkyl, aryl-($C_1$-$C_7$)-alkoxycarbonylamino-($C_1$-$C_7$)-alkyl, ($C_3$-$C_7$)-cycloalkoxycarbonylamino-($C_1$-$C_7$)-alkyl, ($C_3$-$C_7$)-cycloalkyl-($C_1$-$C_7$)-alkoxycarbonylamino-($C_1$-$C_7$)-alkyl, heteroaryl-($C_1$-$C_7$)-alkoxycarbonylamino-($C_1$-$C_7$)-alkyl, ($C_1$-$C_7$)-alkylcarbonylamino-($C_1$-$C_7$)-alkyl, ($C_3$-$C_7$)-cycloalkylcarbonylamino-($C_1$-$C_7$)-alkyl, arylcarbonylamino-($C_1$-$C_7$)-alkyl, heteroarylcarbonylamino-($C_1$-$C_7$)-alkyl, heterocyclylcarbonylamino-($C_1$-$C_7$)-alkyl, ($C_2$-$C_7$)-alkenyloxycarbonylamino-($C_1$-$C_7$)-alkyl, aryl-($C_2$-$C_7$)-alkenylamino-($C_1$-$C_7$)-alkyl, arylsulfonyl-($C_1$-$C_7$)-alkyl, heteroarylsulfonyl-($C_1$-$C_7$)-alkyl, ($C_1$-$C_7$)-alkylsulfonyl-($C_1$-$C_7$)-alkyl, ($C_3$-$C_7$)-cycloalkylsulfonyl-($C_1$-$C_7$)-alkyl, arylsulfinyl-($C_1$-$C_7$)-alkyl, heteroarylsulfinyl-($C_1$-$C_7$)-alkyl, ($C_1$-$C_7$)-alkylsulfinyl-($C_1$-$C_7$)-alkyl, ($C_3$-$C_7$)-cycloalkylsulfinyl-($C_1$-$C_7$)-alkyl, bis[($C_1$-$C_7$)-alkyl]amino-($C_1$-$C_7$)-alkyl or X and Y with the carbon atom to which they are attached form a fully saturated or partially saturated 3- to 7-membered monocyclic or bicyclic ring which is optionally interrupted by heteroatoms and optionally substituted further.

Particular preference is given to the use according to the invention of compounds of the general formula (I) in which $R^1$ represents hydrogen, ($C_1$-$C_8$)-alkyl, ($C_3$-$C_6$)-cycloalkyl, ($C_1$-$C_8$)-haloalkyl, ($C_3$-$C_6$)-halocycloalkyl, ($C_2$-$C_6$)-alkenyl, ($C_2$-$C_6$)-haloalkenyl, ($C_1$-$C_6$)-alkoxy-($C_1$-$C_6$)-haloalkyl, ($C_2$-$C_6$)-alkynyl, aryl, aryl-($C_1$-$C_6$)-alkyl, heteroaryl, heteroaryl-($C_1$-$C_6$)-alkyl, ($C_3$-$C_6$)-cycloalkyl-($C_1$-$C_6$)-alkyl, ($C_2$-$C_6$)-haloalkynyl, heterocyclyl, heterocyclyl-($C_1$-$C_6$)-alkyl, ($C_1$-$C_6$)-alkoxy-($C_1$-$C_6$)-alkyl, ($C_1$-$C_6$)-alkylcarbonyl-($C_1$-$C_6$)-alkyl, hydroxycarbonyl-($C_1$-$C_6$)-alkyl, ($C_1$-$C_6$)-alkoxycarbonyl-($C_1$-$C_6$)-alkyl, ($C_2$-$C_6$)-alkenyloxycarbonyl-($C_1$-$C_6$)-alkyl, ($C_2$-$C_6$)-alkynyloxycarbonyl-($C_1$-$C_6$)-alkyl, aryl-($C_1$-$C_6$)-alkoxycarbonyl-($C_1$-$C_6$)-alkyl, ($C_3$-$C_6$)-cycloalkoxycarbonyl-($C_1$-$C_6$)-alkyl, ($C_3$-$C_6$)-cycloalkyl-($C_1$-$C_6$)-alkoxycarbonyl-($C_1$-$C_6$)-alkyl, aminocarbonyl-($C_1$-$C_6$)-alkyl, ($C_1$-$C_6$)-alkylaminocarbonyl-($C_1$-$C_6$)-alkyl, ($C_3$-$C_6$)-cycloalkylaminocarbonyl-($C_1$-$C_6$)-alkyl, aryl-($C_1$-$C_6$)-alkylaminocarbonyl-($C_1$-$C_6$)-alkyl, heteroaryl-($C_1$-$C_6$)-alkylaminocarbonyl-($C_1$-$C_6$)-alkyl, ($C_1$-$C_6$)-alkylthio-($C_1$-$C_6$)-alkyl, ($C_3$-$C_6$)-cycloalkylthio-($C_1$-$C_6$)-alkyl, arylthio-($C_1$-$C_6$)-alkyl, heterocyclylthio-($C_1$-$C_6$)-alkyl, heteroarylthio-($C_1$-$C_6$)-alkyl, aryl-($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, arylsulfinyl-($C_1$-$C_6$)-alkyl, arylsulfonyl-($C_1$-$C_6$)-alkyl, ($C_3$-$C_6$)-cycloalkylsulfinyl-($C_1$-$C_6$)-alkyl, ($C_3$-$C_6$)-cycloalkylsulfonyl-($C_1$-$C_6$)-alkyl, ($C_1$-$C_6$)-alkoxy-($C_1$-$C_6$)-alkoxy-($C_1$-$C_6$)-alkyl, ($C_1$-$C_6$)-alkylcarbonyl, ($C_1$-$C_6$)-haloalkylcarbonyl, ($C_3$-$C_6$)-cycloalkylcarbonyl, ($C_1$-$C_6$)-alkoxycarbonyl, aryl-($C_1$-$C_6$)-alkoxycarbonyl, arylcarbonyl, heteroarylcarbonyl, heterocyclylcarbonyl, aryl-($C_1$-$C_6$)-alkylcarbonyl, ($C_1$-$C_6$)-alkylaminocarbonyl, ($C_3$-$C_6$)-cycloalkylaminocarbonyl, arylaminocarbonyl, aryl-($C_1$-$C_6$)-alkylaminocarbonyl, heteroarylaminocarbonyl, heterocyclylaminocarbonyl, heteroaryl-($C_1$-$C_6$)-alkylaminocarbonyl, heterocyclyl-($C_1$-$C_6$)-alkylaminocarbonyl, ($C_1$-$C_6$)-alkylsulfonyl, ($C_3$-$C_6$)-cycloalkylsulfonyl, arylsulfonyl, aryl-($C_1$-$C_6$)-alkylsulfonyl, heteroarylsulfonyl, heterocyclylsulfonyl, cyano-($C_1$-$C_6$)-alkyl, ($C_4$-$C_6$)-cycloalkenyl-($C_1$-$C_6$)-alkyl, nitro-($C_1$-$C_6$)-alkyl, halo-($C_1$-$C_6$)-alkoxy-($C_1$-$C_6$)-alkyl, bis-[($C_1$-$C_6$)-alkyl]aminocarbonyl, ($C_3$-$C_6$)-cycloalkyl-[($C_1$-$C_6$)-alkyl]aminocarbonyl, aryl-[($C_1$-$C_6$)-alkyl]aminocarbonyl, aryl-($C_1$-$C_6$)-alkyl-[($C_1$-$C_6$)-alkyl]aminocarbonyl, ($C_2$-$C_6$)-alkenylaminocarbonyl, ($C_2$-$C_6$)-alkynylaminocarbonyl, ($C_1$-$C_6$)-alkylaminosulfonyl, bis-[($C_1$-$C_6$)-alkyl]aminosulfonyl, heterocyclylsulfinyl-($C_1$-$C_6$)-alkyl, heteroarylsulfinyl-($C_1$-$C_6$)-alkyl, aryl-($C_1$-$C_6$)-alkylsulfinyl-($C_1$-$C_6$)-alkyl, heterocyclylsulfonyl-($C_1$-$C_6$)-alkyl, heteroarylsulfonyl-($C_1$-$C_6$)-alkyl, aryl-($C_1$-$C_6$)-alkylsulfonyl-($C_1$-$C_6$)-alkyl, bis-[($C_1$-$C_6$)-alkyl]aminocarbonyl-($C_1$-$C_6$)-alkyl, ($C_3$-$C_6$)-cycloalkyl-[($C_1$-$C_6$)-alkyl]aminocarbonyl-($C_1$-$C_6$)-alkyl, aryl-[($C_1$-$C_6$)-alkyl]aminocarbonyl-($C_1$-$C_6$)-alkyl, aryl-($C_1$-$C_6$)-alkyl-[($C_1$-$C_6$)-alkyl]aminocarbonyl-($C_1$-$C_6$)-alkyl, ($C_2$-$C_6$)-alkenylaminocarbonyl-($C_1$-$C_6$)-alkyl, ($C_2$-$C_6$)-alkynylaminocarbonyl-($C_1$-$C_6$)-alkyl, bis-[($C_1$-$C_6$)-alkyl]amino, ($C_3$-$C_6$)-cycloalkyl[($C_1$-$C_6$)-alkyl]amino, $R^2$, $R^3$, $R^4$ independently of one another represent hydrogen, halogen, ($C_1$-$C_6$)-alkoxy, ($C_1$-$C_6$)-alkyl, ($C_1$-$C_6$)-haloalkyl, ($C_1$-$C_6$)-haloalkoxy, ($C_1$-$C_6$)-alkylthio, ($C_1$-$C_6$)-haloalkylthio, aryl, aryl-($C_1$-$C_6$)-alkyl, heteroaryl, heteroaryl-($C_1$-$C_6$)-alkyl, heterocyclyl, heterocyclyl-($C_1$-$C_6$)-alkyl, ($C_3$-$C_6$)-cycloalkyl, nitro, amino, hydroxy, ($C_1$-$C_6$)-alkylamino, bis-[($C_1$-$C_6$)-alkyl]amino, hydrothio, ($C_1$-$C_6$)-alkylcarbonylamino, ($C_3$-$C_6$)-cycloalkylcarbonylamino, arylcarbonylamino, heteroarylcarbonylamino, heterocyclylcarbonylamino, formyl, hydroxyiminomethyl, ($C_1$-$C_6$)-alkoxyiminomethyl, ($C_3$-$C_6$)-cycloalkoxyiminomethyl, aryloxyiminomethyl, ($C_3$-$C_6$)-cycloalkyl-($C_1$-$C_6$)-alkoxyiminomethyl, thiocyanato, isothiocyanato, aryloxy, heteroaryloxy, ($C_3$-$C_6$)-cycloalkoxy, ($C_3$-$C_6$)-cycloalkyl-($C_1$-$C_6$)-alkoxy, aryl-($C_1$-$C_6$)-alkoxy, ($C_2$-$C_6$)-alkynyl, ($C_2$-$C_6$)-alkenyl, aryl-($C_1$-$C_6$)-alkynyl, tris-[($C_1$-$C_6$)-alkyl]silyl-($C_2$-$C_6$)-alkynyl, bis-[($C_1$-$C_6$)-alkyl](aryl)silyl-($C_2$-$C_6$)-alkynyl, bis-aryl[($C_1$-$C_6$)-alkyl]silyl-($C_2$-

$C_6$)-alkynyl, ($C_3$-$C_6$)-cycloalkyl-($C_2$-$C_6$)-alkynyl, aryl-($C_2$-$C_6$)-alkenyl, heteroaryl-($C_2$-$C_6$)-alkenyl, ($C_3$-$C_6$)-cycloalkyl-($C_2$-$C_6$)-alkenyl, ($C_3$-$C_6$)-cycloalkyl-($C_2$-$C_6$)-alkyl, ($C_2$-$C_6$)-haloalkynyl, ($C_2$-$C_6$)-haloalkenyl, ($C_4$-$C_6$)-cycloalkenyl, ($C_1$-$C_6$)-alkoxy-($C_1$-$C_6$)-alkoxy-($C_1$-$C_6$)-alkyl, ($C_1$-$C_6$)-alkylsulfonyl, arylsulfonyl, heteroarylsulfonyl, ($C_1$-$C_6$)-alkylsulfonylamino, arylsulfonylamino, aryl-($C_1$-$C_6$)-alkylsulfonylamino, heteroarylsulfonylamino, heteroaryl-($C_1$-$C_6$)-alkylsulfonylamino, bis-[($C_1$-$C_6$)-alkyl]aminosulfonyl, $R^5$ represents amino, ($C_1$-$C_6$)-alkyl, ($C_3$-$C_6$)-cycloalkyl, ($C_3$-$C_6$)-cycloalkyl-($C_1$-$C_6$)-alkyl, ($C_1$-$C_6$)-haloalkyl, ($C_3$-$C_6$)-halocycloalkyl, ($C_4$-$C_6$)-cycloalkenyl, aryl, heteroaryl, heterocyclyl, aryl-($C_1$-$C_6$)-alkyl, heteroaryl-($C_1$-$C_6$)-alkyl, heterocyclyl-($C_1$-$C_6$)-alkyl, ($C_1$-$C_6$)-alkoxycarbonyl-($C_1$-$C_6$)-alkyl, aryl-($C_1$-$C_6$)-alkoxycarbonyl-($C_1$-$C_6$)-alkyl, ($C_3$-$C_6$)-cycloalkoxycarbonyl-($C_1$-$C_6$)-alkyl, ($C_3$-$C_6$)-cycloalkyl-($C_1$-$C_6$)-alkoxycarbonyl-($C_1$-$C_6$)-alkyl, heteroaryl-($C_1$-$C_6$)-alkoxycarbonyl-($C_1$-$C_6$)-alkyl, aminocarbonyl-($C_1$-$C_6$)-alkyl, ($C_1$-$C_6$)-alkylaminocarbonyl-($C_1$-$C_6$)-alkyl, ($C_3$-$C_6$)-cycloalkylaminocarbonyl-($C_1$-$C_6$)-alkyl, aryl-($C_1$-$C_6$)-alkylaminocarbonyl-($C_1$-$C_6$)-alkyl, ($C_1$-$C_6$)-alkylamino, arylamino, ($C_3$-$C_6$)-cycloalkylamino, aryl-($C_1$-$C_6$)-alkylamino, heteroaryl-($C_1$-$C_6$)-alkylamino, heteroarylamino, heterocyclylamino, aryloxy-($C_1$-$C_6$)-alkyl, ($C_1$-$C_6$)-alkoxy-($C_1$-$C_6$)-alkyl, heteroaryloxy-($C_1$-$C_6$)-alkyl, ($C_2$-$C_6$)-alkenyl, ($C_2$-$C_6$)-alkynyl, ($C_2$-$C_6$)-alkenylamino, ($C_2$-$C_6$)-alkynylamino, bis-[($C_1$-$C_6$)-alkyl]amino, aryloxy, bis-[($C_1$-$C_7$)-alkyl]amino, aryl-($C_2$-$C_7$)-alkenyl, heteroaryl-($C_2$-$C_7$)-alkenyl, heterocyclyl-($C_2$-$C_7$)-alkenyl, $R^6$ represents hydrogen, ($C_1$-$C_6$)-alkyl, ($C_3$-$C_6$)-cycloalkyl, cyano-($C_1$-$C_6$)-alkyl, ($C_3$-$C_6$)-cycloalkyl-($C_1$-$C_6$)-alkyl, ($C_1$-$C_6$)-alkylsulfonyl, arylsulfonyl, heteroarylsulfonyl, ($C_3$-$C_6$)-cycloalkylsulfonyl, heterocyclylsulfonyl, aryl-($C_1$-$C_6$)-alkylsulfonyl, ($C_1$-$C_6$)-alkylcarbonyl, arylcarbonyl, heteroarylcarbonyl, ($C_3$-$C_6$)-cycloalkylcarbonyl, heterocyclylcarbonyl, ($C_1$-$C_6$)-alkoxycarbonyl, aryl-($C_1$-$C_6$)-alkoxycarbonyl, ($C_1$-$C_6$)-haloalkylcarbonyl, ($C_2$-$C_6$)-alkenyl, ($C_2$-$C_6$)-alkynyl, ($C_1$-$C_6$)-haloalkyl, halo-($C_2$-$C_6$)-alkynyl, halo-($C_2$-$C_6$)-alkenyl, ($C_1$-$C_6$)-alkoxy-($C_1$-$C_6$)-alkyl, W represents oxygen, sulfur, X, Y independently of one another represent hydrogen, ($C_1$-$C_6$)-alkyl, fluorine, chlorine, ($C_2$-$C_6$)-alkenyl, ($C_1$-$C_6$)-haloalkyl, ($C_3$-$C_6$)-cycloalkyl, ($C_4$-$C_6$)-cycloalkenyl, heterocyclyl, ($C_1$-$C_6$)-alkoxy, ($C_1$-$C_6$)-alkylthio, ($C_1$-$C_6$)-alkoxy-($C_1$-$C_6$)-alkyl, ($C_1$-$C_6$)-alkylthio-($C_1$-$C_6$)-alkyl, ($C_1$-$C_6$)-haloalkoxy, ($C_1$-$C_6$)-haloalkylthio, ($C_1$-$C_6$)-alkoxy-($C_1$-$C_6$)-alkoxy, amino-($C_1$-$C_6$)-alkyl, ($C_1$-$C_6$)-alkylamino-($C_1$-$C_6$)-alkyl, ($C_3$-$C_6$)-cycloalkylamino-($C_1$-$C_6$)-alkyl, aryl-($C_1$-$C_6$)-alkylamino-($C_1$-$C_6$)-alkyl, heteroaryl-($C_1$-$C_6$)-alkylamino-($C_1$-$C_6$)-alkyl, heterocyclyl-($C_1$-$C_6$)-alkylamino-($C_1$-$C_6$)-alkyl, heterocyclylamino-($C_1$-$C_6$)-alkyl, heteroarylamino-($C_1$-$C_6$)-alkyl, ($C_1$-$C_6$)-alkoxycarbonylamino-($C_1$-$C_6$)-alkyl, arylamino-($C_1$-$C_6$)-alkyl, aryl-($C_1$-$C_6$)-alkoxycarbonylamino-($C_1$-$C_6$)-alkyl, ($C_3$-$C_6$)-cycloalkoxycarbonylamino-($C_1$-$C_6$)-alkyl, ($C_3$-$C_6$)-Cycloalkyl-($C_1$-$C_6$)-alkoxycarbonylamino-($C_1$-$C_6$)-alkyl, heteroaryl-($C_1$-$C_6$)-alkoxycarbonylamino-($C_1$-$C_6$)-alkyl, ($C_1$-$C_6$)-alkylcarbonylamino-($C_1$-$C_6$)-alkyl, ($C_3$-$C_6$)-cycloalkylcarbonylamino-($C_1$-$C_6$)-alkyl, arylcarbonylamino-($C_1$-$C_6$)-alkyl, heteroarylcarbonylamino-($C_1$-$C_6$)-alkyl, heterocyclylcarbonylamino-($C_1$-$C_6$)-alkyl, ($C_2$-$C_6$)-alkenyloxycarbonylamino-($C_1$-$C_6$)-alkyl, aryl-($C_2$-$C_6$)-alkenylamino-($C_1$-$C_6$)-alkyl, arylsulfonyl-($C_1$-$C_6$)-alkyl, heteroarylsulfonyl-($C_1$-$C_6$)-alkyl, ($C_1$-$C_6$)-alkylsulfonyl-($C_1$-$C_6$)-alkyl, ($C_3$-$C_6$)-cycloalkylsulfonyl-($C_1$-$C_6$)-alkyl, arylsulfinyl-($C_1$-$C_6$)-alkyl, ($C_1$-$C_6$)-alkylsulfinyl-($C_1$-$C_6$)-alkyl, ($C_3$-$C_6$)-cycloalkylsulfinyl-($C_1$-$C_6$)-alkyl, bis[($C_1$-$C_6$)-alkyl]amino-($C_1$-$C_6$)-alkyl or X and Y with the carbon atom to which they are attached form a fully saturated or partially saturated 3- to 7-membered monocyclic or bicyclic ring which is optionally interrupted by O (oxygen), S (sulfur), N—H, ($C_1$-$C_6$)-alkyl-N, ($C_1$-$C_6$)-alkoxy-N, ($C_1$-$C_6$)-alkoxycarbonyl-N, aryl-($C_1$-$C_6$)-alkoxycarbonyl-N and optionally substituted further, where not more than two identical or different heteroatoms from the group consisting of O, S, N are adjacent to one another.

Very particular preference is given to the use according to the invention of compounds of the general formula (I) which are described by formulae (Ia) to (Iz) and (Iab)

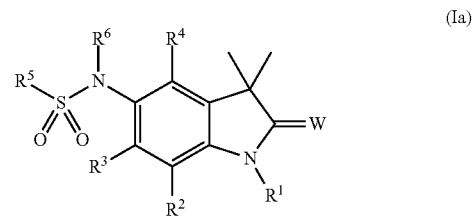

(Ia)

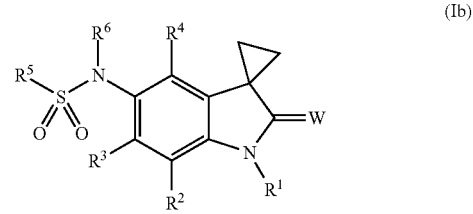

(Ib)

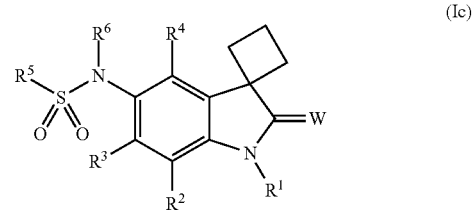

(Ic)

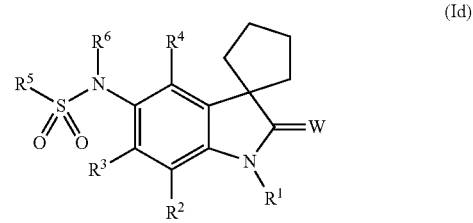

(Id)

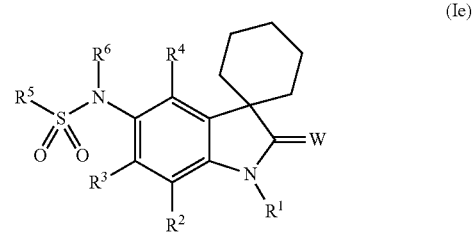

(Ie)

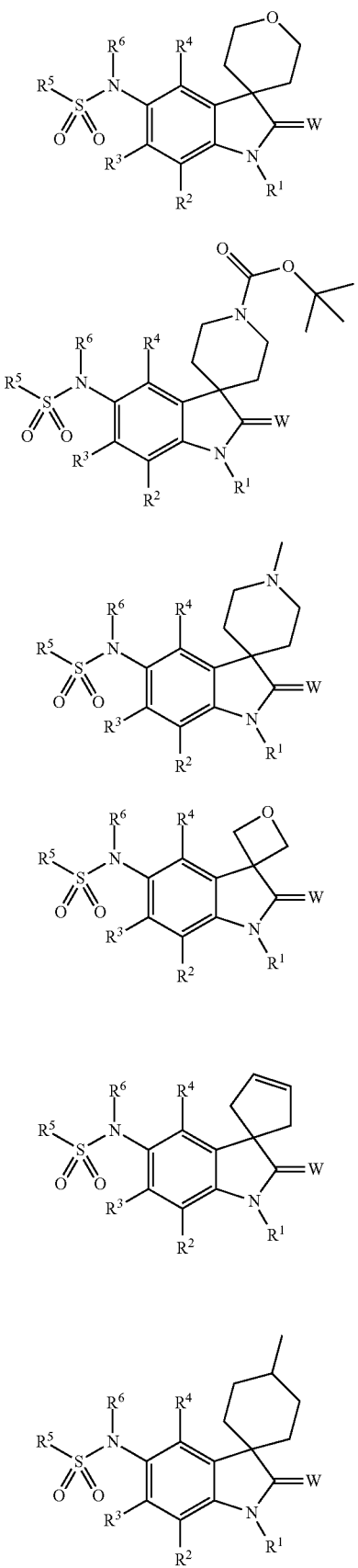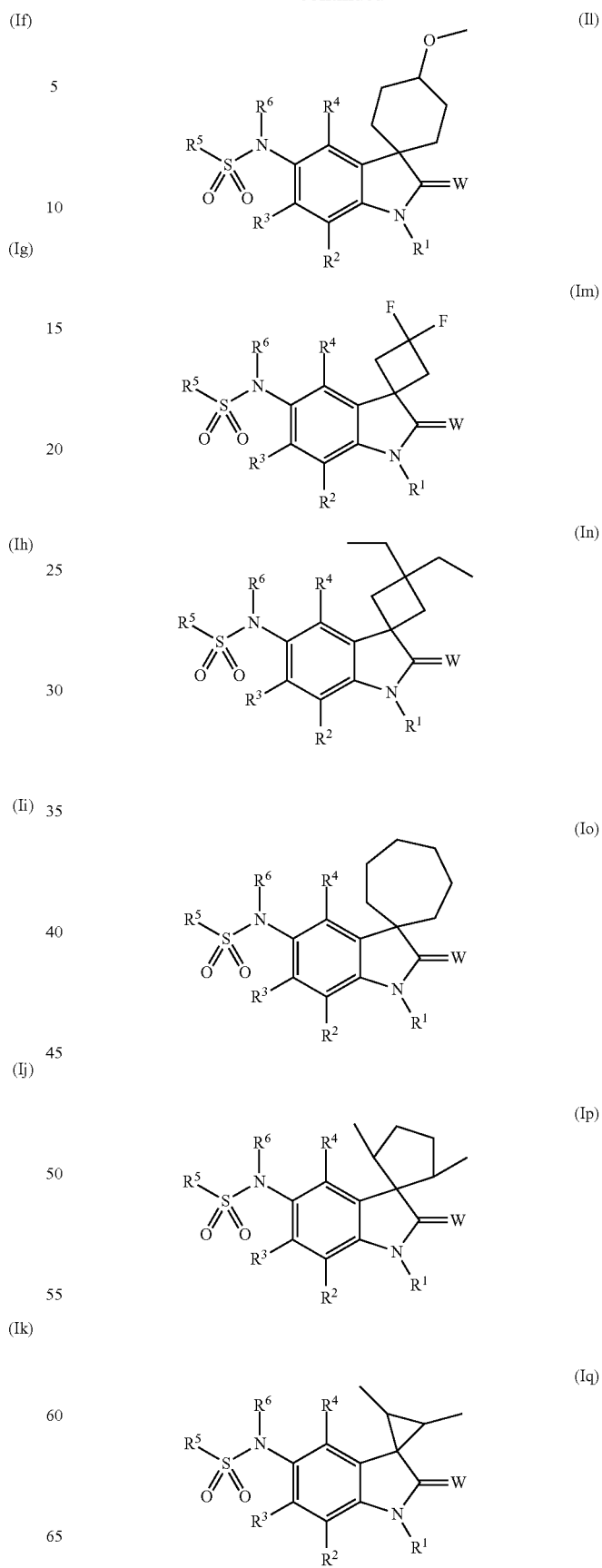

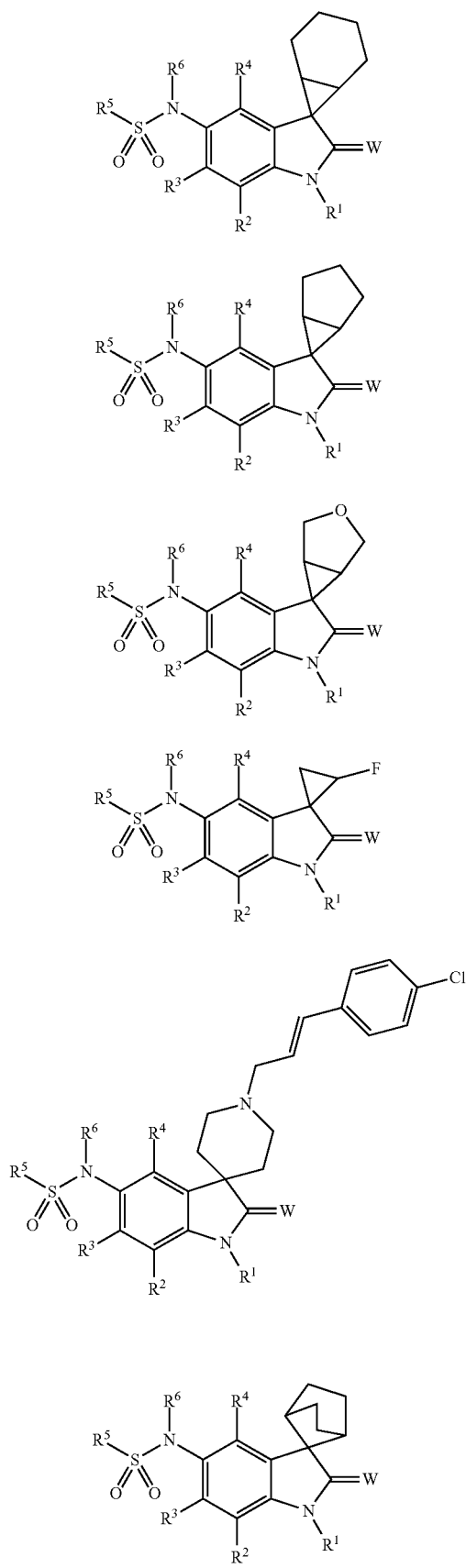

in which
R¹ represents hydrogen, (C₁-C₆)-alkyl, (C₃-C₆)-cycloalkyl, (C₁-C₆)-haloalkyl, (C₃-C₆)-halocycloalkyl, (C₂-C₆)-alkenyl, (C₂-C₆)-haloalkenyl, (C₁-C₅)-alkoxy-(C₁-C₅)-haloalkyl, (C₂-C₅)-alkynyl, aryl, aryl-(C₁-C₅)-alkyl, heteroaryl, heteroaryl-(C₁-C₅)-alkyl, (C₃-C₆)-cycloalkyl-(C₁-C₅)-alkyl, (C₂-C₅)-haloalkynyl, heterocyclyl, heterocyclyl-(C₁-C₅)-alkyl, (C₁-C₅)-alkoxy-(C₁-C₅)-alkyl, (C₁-C₅)-alkylcarbonyl-(C₁-C₅)-alkyl, hydroxycarbonyl-(C₁-C₅)-alkyl, (C₁-C₅)-alkoxycarbonyl-(C₁-C₅)-alkyl, (C₂-C₅)-alkenyloxycarbonyl-(C₁-C₅)-alkyl, (C₂-C₅)-alkynyloxycarbonyl-(C₁-C₅)-alkyl, aryl-(C₁-C₅)-alkoxycarbonyl-(C₁-C₅)-alkyl, (C₃-C₆)-cycloalkoxycarbonyl-(C₁-C₅)-alkyl, (C₃-C₆)-cycloalkyl-(C₁-C₅)-alkoxycarbonyl-(C₁-C₅)-alkyl, aminocarbonyl-(C₁-C₅)-alkyl, (C₁-C₅)-alkylaminocarbonyl-(C₁-C₅)-alkyl, (C₃-C₆)-cycloalkylaminocarbonyl-(C₁-C₅)-alkyl, aryl-(C₁-C₅)-alkylaminocarbonyl-(C₁-C₅)-alkyl, heteroaryl-(C₁-C₅)-alkylaminocarbonyl-(C₁-C₅)-alkyl, (C₁-C₅)-alkoxy-(C₁-C₅)-alkoxy-(C₁-C₅)-alkyl, (C₁-C₅)-alkylcarbonyl, (C₁-C₅)-haloalkylcarbonyl, (C₃-C₆)-cycloalkylcarbonyl, (C₁-C₅)-alkoxycarbonyl, aryl-(C₁-C₅)-alkoxycarbonyl, arylcarbonyl, heteroarylcarbonyl, heterocyclylcarbonyl, aryl-(C₁-C₆)-alkylcarbonyl, (C₁-C₆)-alkylaminocarbonyl, (C₃-C₅)-cycloalkylaminocarbonyl, arylaminocarbonyl, aryl-(C₁-C₆)-alkylaminocarbonyl, heteroarylaminocarbonyl, heterocyclylaminocarbonyl, heteroaryl-($C_1$-$C_6$)-alkylaminocarbonyl, heterocyclyl-($C_1$-$C_6$)-alkylaminocarbonyl, ($C_1$-$C_6$)-alkylsulfonyl, ($C_3$-$C_6$)-cycloalkylsulfonyl, arylsulfonyl, aryl-($C_1$-$C_6$)-alkylsulfonyl, heteroarylsulfonyl, heterocyclylsulfonyl, cyano-($C_1$-$C_5$)-alkyl, bis-[($C_1$-$C_5$)-alkyl]amino, ($C_3$-$C_6$)-cycloalkyl[($C_1$-$C_5$)-alkyl]amino, $R^2$, $R^3$, $R^4$ independently of one another represent hydrogen, halogen, ($C_1$-$C_5$)-alkoxy, ($C_1$-$C_5$)-alkyl, ($C_1$-$C_5$)-haloalkyl, ($C_1$-$C_5$)-haloalkoxy, ($C_1$-$C_5$)-alkylthio, ($C_1$-$C_5$)-haloalkylthio, aryl, aryl-($C_1$-$C_5$)-alkyl, heteroaryl, heteroaryl-($C_1$-$C_5$)-alkyl, heterocyclyl, heterocyclyl-($C_1$-$C_5$)-alkyl, ($C_3$-$C_6$)-Cycloalkyl, nitro, amino, hydroxy, ($C_1$-$C_5$)-alkylamino, bis-[($C_1$-$C_5$)-alkyl]amino, hydrothio, ($C_1$-$C_5$)-alkylcarbonylamino, ($C_3$-$C_6$)-cycloalkylcarbonylamino, arylcarbonylamino, heteroarylcarbonylamino, heterocyclylcarbonylamino, formyl, hydroxyiminomethyl, ($C_1$-$C_5$)-alkoxyiminomethyl, ($C_3$-$C_6$)-cycloalkoxyiminomethyl, aryloxyiminomethyl, ($C_3$-$C_6$)-cycloalkyl-($C_1$-$C_5$)-alkoxyiminomethyl, thiocyanato, isothiocyanato, aryloxy, heteroaryloxy, ($C_3$-$C_6$)-cycloalkoxy, ($C_3$-$C_6$)-cycloalkyl-($C_1$-$C_5$)-alkoxy, aryl-($C_1$-$C_5$)-alkoxy, ($C_2$-$C_5$)-alkynyl, ($C_2$-$C_5$)-alkenyl, aryl-($C_1$-$C_5$)-alkynyl, tris-[($C_1$-$C_5$)-alkyl]silyl-($C_2$-$C_5$)-alkynyl, bis-[($C_1$-$C_5$)-alkyl](aryl)silyl-($C_2$-$C_5$)-alkynyl, bis-aryl[($C_1$-$C_5$)-alkyl]silyl-($C_2$-$C_5$)-alkynyl, ($C_3$-$C_6$)-cycloalkyl-($C_2$-$C_5$)-alkynyl, aryl-($C_2$-$C_5$)-alkenyl, heteroaryl-($C_2$-$C_5$)-alkenyl, ($C_3$-$C_6$)-cycloalkyl-($C_2$-$C_5$)-alkenyl, ($C_2$-$C_5$)-haloalkynyl, ($C_2$-$C_5$)-haloalkenyl, ($C_4$-$C_5$)-cycloalkenyl, ($C_1$-$C_5$)-alkoxy-($C_1$-$C_5$)-alkoxy-($C_1$-$C_5$)-alkyl, ($C_1$-$C_5$)-alkylsulfonyl, arylsulfonyl, heteroarylsulfonyl, ($C_1$-$C_5$)-alkylsulfonylamino, arylsulfonylamino, aryl-($C_1$-$C_5$)-alkylsulfonylamino, heteroarylsulfonylamino, heteroaryl-($C_1$-$C_5$)-alkylsulfonylamino, bis-[($C_1$-$C_5$)-alkyl]aminosulfonyl, $R^5$ represents amino, ($C_1$-$C_5$)-alkyl, ($C_3$-$C_6$)-cycloalkyl, ($C_3$-$C_6$)-cycloalkyl-($C_1$-$C_5$)-alkyl, ($C_1$-$C_5$)-haloalkyl, ($C_3$-$C_6$)-halocycloalkyl, ($C_4$-$C_6$)-cycloalkenyl, aryl, heteroaryl, heterocyclyl, aryl-($C_1$-$C_5$)-alkyl, heteroaryl-($C_1$-$C_5$)-alkyl, heterocyclyl-($C_1$-$C_5$)-alkyl, ($C_1$-$C_5$)-alkoxycarbonyl-($C_1$-$C_5$)-alkyl, aryl-($C_1$-$C_5$)-alkoxycarbonyl-($C_1$-$C_5$)-alkyl, ($C_3$-$C_6$)-cycloalkoxycarbonyl-($C_1$-$C_5$)-alkyl, ($C_3$-$C_6$)-cycloalkyl-($C_1$-$C_5$)-alkoxycarbonyl-($C_1$-$C_5$)-alkyl, heteroaryl-($C_1$-$C_5$)-alkoxycarbonyl-($C_1$-$C_5$)-alkyl, aminocarbonyl-($C_1$-$C_5$)-alkyl, ($C_1$-$C_5$)-alkylaminocarbonyl-($C_1$-$C_5$)-alkyl, ($C_3$-$C_6$)-cycloalkylaminocarbonyl-($C_1$-$C_5$)-alkyl, aryl-($C_1$-$C_5$)-alkylaminocarbonyl-($C_1$-$C_5$)-alkyl, ($C_1$-$C_5$)-alkylamino, arylamino, ($C_3$-$C_6$)-cycloalkylamino, aryl-($C_1$-$C_5$)-alkylamino, heteroaryl-($C_1$-$C_5$)-alkylamino, heteroarylamino, heterocyclylamino, aryloxy-($C_1$-$C_5$)-alkyl, ($C_1$-$C_5$)-alkoxy-($C_1$-$C_5$)-alkyl, heteroaryloxy-($C_1$-$C_5$)-alkyl, ($C_2$-$C_5$)-alkenyl, ($C_2$-$C_5$)-alkynyl, ($C_2$-$C_5$)-alkenylamino, ($C_2$-$C_5$)-alkynylamino, bis-[($C_1$-$C_5$)-alkyl]amino, aryloxy, ($C_3$-$C_6$)-cycloalkyl-($C_2$-$C_5$)-alkyl, bis-[($C_1$-$C_5$)-alkyl]amino, aryl-($C_2$-$C_5$)-alkenyl, heteroaryl-($C_2$-$C_5$)-alkenyl, heterocyclyl-($C_2$-$C_5$)-alkenyl, $R^6$ represents hydrogen, ($C_1$-$C_5$)-alkyl, ($C_3$-$C_6$)-cycloalkyl, cyano-($C_1$-$C_5$)-alkyl, ($C_3$-$C_6$)-cycloalkyl-($C_1$-$C_5$)-alkyl, ($C_1$-$C_5$)-alkylsulfonyl, arylsulfonyl, heteroarylsulfonyl, ($C_3$-$C_6$)-cycloalkylsulfonyl, heterocyclylsulfonyl, aryl-($C_1$-$C_5$)-alkylsulfonyl, ($C_1$-$C_5$)-alkylcarbonyl, arylcarbonyl, heteroarylcarbonyl, ($C_3$-$C_6$)-cycloalkylcarbonyl, heterocyclylcarbonyl, ($C_1$-$C_5$)-alkoxycarbonyl, aryl-($C_1$-$C_5$)-alkoxycarbonyl, ($C_1$-$C_5$)-haloalkylcarbonyl, ($C_2$-$C_5$)- alkenyl, ($C_2$-$C_5$)-alkynyl, ($C_1$-$C_5$)-haloalkyl, halo-($C_2$-$C_5$)-alkynyl, halo-($C_2$-$C_5$)-alkenyl, ($C_1$-$C_5$)-alkoxy-($C_1$-$C_5$)-alkyl, W represents oxygen or sulfur, preferably oxygen.

Special preference is given to the use according to the invention of compounds of the general formula (I) which are described by formulae (Ia) to (Iz) and (Iab)

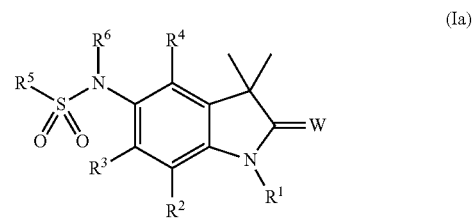

(Ia)

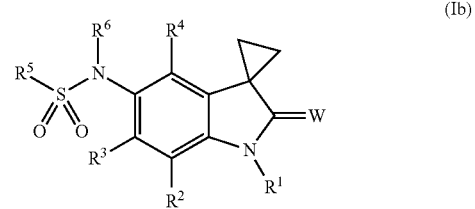

(Ib)

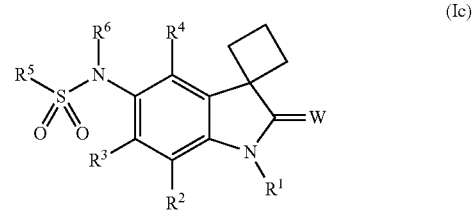

(Ic)

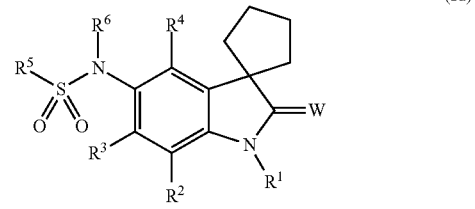

(Id)

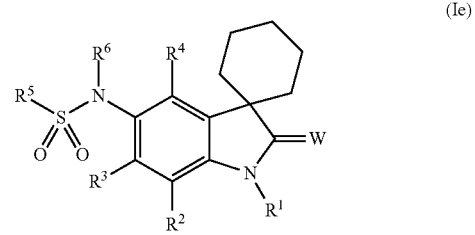

(Ie)

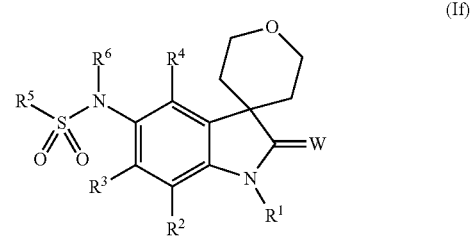

(If)

-continued
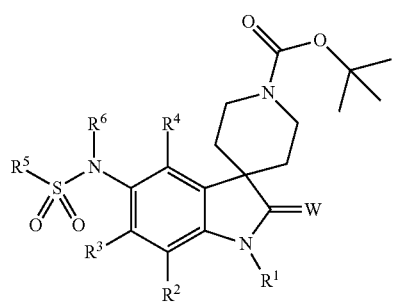
(Ig)
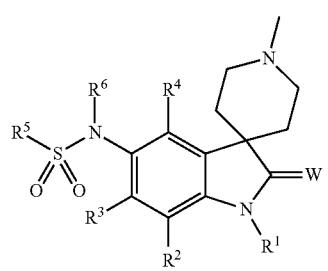
(Ih)
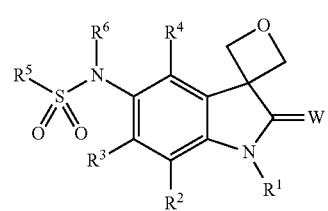
(Ii)
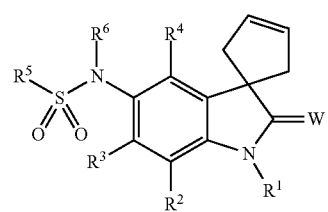
(Ij)
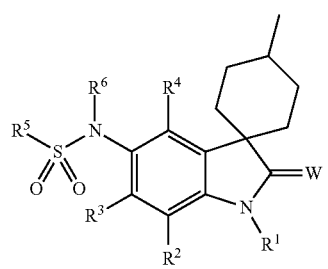
(Ik)
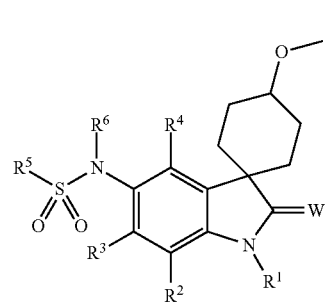
(Il)
-continued
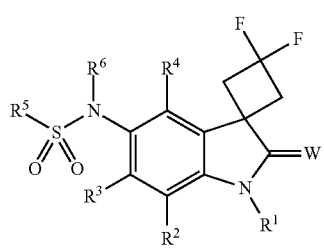
(Im)
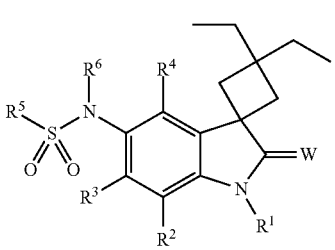
(In)
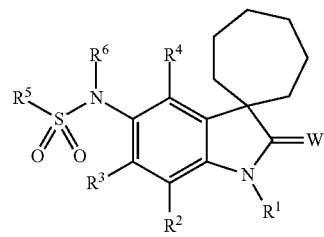
(Io)
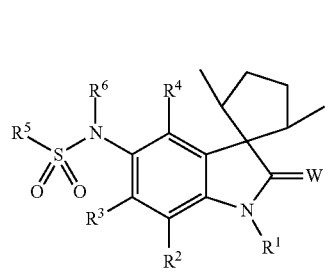
(Ip)
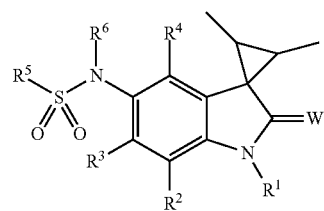
(Iq)
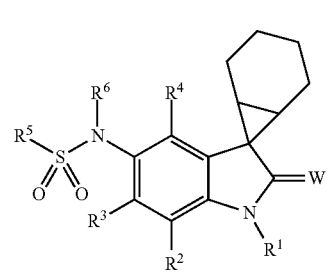
(Ir)

-continued (Is) 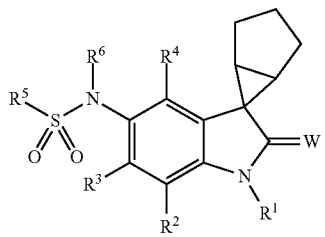

(It) 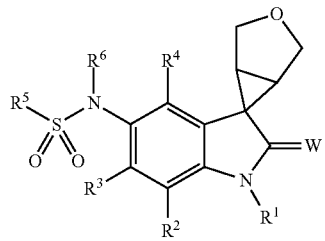

(Iu) 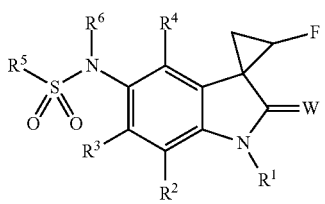

(Iv) 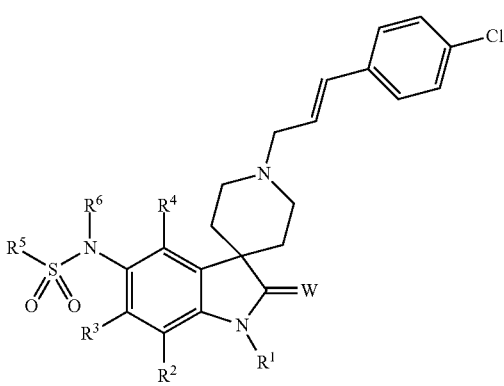

(Iw) 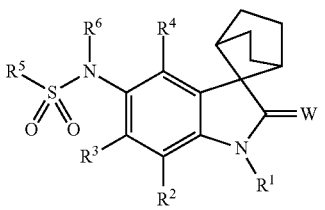

(Ix) 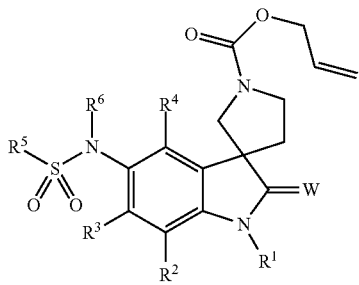

-continued (Iy) 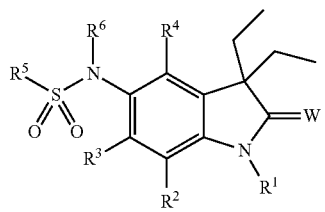

(Iz) 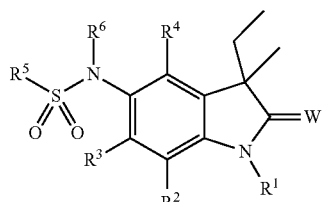

(Iab) 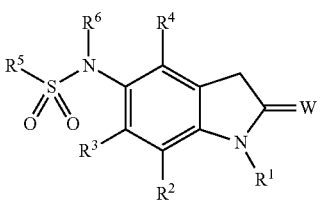

in which $R^1$ represents hydrogen, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-allylcyclopropyl, 1-vinylcyclobutyl, 1-vinylcyclopropyl, 1-ethylcyclopropyl, 2-ethylcyclopropyl, 1-ethylcyclobutyl, 2-ethylcyclobutyl, 3-ethylcyclobutyl, 4-methylcyclohexyl, 4-methoxycyclohexyl, 4-ethoxycyclohexyl, 4-n-propyloxycyclohexyl, 4-hydroxycyclohexyl, 4-methoxycyclobutyl, 1-cyclopropylcyclobutyl, 1-prop-2-enylcyclobutyl, 2-ethyl-3-methylcyclobutyl, 1-propylcyclopropyl, 1-methyl-2-propylcyclopropyl, 2-propylcyclopropyl, 1-propylcyclobutyl, 2-propylcyclobutyl, 3-propylcyclobutyl, 1-isopropylcyclobutyl, 1-isopropylcyclopropyl, 2-isopropylcyclopropyl, 3-isopropylcyclobutyl, 2-dimethylaminocyclobutyl, 3-dimethylaminocyclobutyl, 1-butylcyclobutyl, 2-butylcyclobutyl, 1-butylcyclopropyl, 3-butylcyclobutyl, 2-butylcyclopropyl, 1-isobutylcyclobutyl, 3-tert-butylcyclobutyl, 3,3-diethylcyclobutyl, 2,2-diethylcyclopropyl, 2-methylidencyclopropyl, 1-methoxymethylcyclopropyl, 1-isobutylcyclopropyl, 2,2-difluoroethyl, 2,2,2-trifluoroethyl, 3,3,3-trifluorpropyl, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, cyanomethyl, cyanoethyl, cyano-n-propyl, cyano-n-butyl, $(C_2-C_6)$-haloalkenyl, $(C_1-C_5)$-alkoxy-$(C_1-C_5)$-haloalkyl, optionally substituted phenyl, aryl-$(C_1-C_5)$-alkyl, heteroaryl, heteroaryl-$(C_1-C_5)$-alkyl, $(C_3-C_6)$-cycloalkyl-$(C_1-C_5)$-alkyl, $(C_2-C_5)$-haloalkynyl, heterocyclyl, heterocyclyl-$(C_1-C_5)$-alkyl, $(C_1-C_5)$-alkoxy-$(C_1-C_5)$-alkyl, $(C_1-C_5)$-alkylcarbonyl-$(C_1-C_5)$-alkyl, hydroxycarbonyl-$(C_1-C_5)$-alkyl, $(C_1-C_5)$-alkoxycarbonyl-$(C_1-C_5)$-alkyl, $(C_2-C_5)$-alkenyloxycarbonyl-$(C_1-C_5)$-alkyl, $(C_2-C_5)$-alkynyloxycarbonyl-$(C_1-C_5)$-alkyl, aryl-$(C_1-C_5)$-alkoxycarbonyl-$(C_1-C_5)$-alkyl, $(C_3-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, heteroaryl-$(C_1-C_5)$-alkylaminocarbonyl-$(C_1-C_5)$-alkyl, $(C_1-C_5)$-alkoxy-$(C_1-C_5)$-alkoxy-$(C_1-C_5)$-alkyl, $(C_1-C_5)$-alkylcarbonyl, $(C_1-C_5)$-haloalkylcarbonyl, $(C_3-C_6)$-cycloalkylcarbonyl, $(C_1-C_5)$-alkoxycarbonyl, aryl-$(C_1-C_5)$-alkoxycarbonyl, arylcarbonyl, heteroarylcarbonyl, heterocyclylcarbonyl, aryl-$(C_1-C_6)$-alkylcarbonyl, $(C_1-C_6)$-alkylaminocarbonyl, $(C_3-C_6)$-cycloalkylaminocarbonyl, arylaminocarbonyl, aryl-$(C_1-C_6)$-alkylaminocarbonyl, heteroarylaminocarbonyl, heterocyclylaminocarbonyl, heteroaryl-$(C_1-C_6)$-alkylaminocarbonyl, heterocyclyl-$(C_1-C_6)$-alkylaminocarbonyl, $(C_1-C_6)$-alkylsulfonyl, $(C_3-C_6)$-cycloalkylsulfonyl, arylsulfonyl, aryl-$(C_1-C_6)$-alkylsulfonyl, heteroarylsulfonyl, heterocyclylsulfonyl, dimethylamino, diethylamino, methyl(ethyl)amino, methyl(n-propyl)amino, methyl(isopropyl)amino, $R^2$, $R^3$, $R^4$ independently of one another represent hydrogen, fluorine, chlorine, bromine, iodine, methoxy, ethoxy, n-propyloxy, isopropyloxy, methyl, ethyl, isopropyl, trifluoromethyl, difluoromethyl, pentafluoroethyl, trifluoromethoxy, difluoromethoxy, 2,2-difluoroethoxy, 3,3,3-trifluoroethoxy, methylthio, ethylthio, trifluoromethylthio, optionally substituted phenyl, benzyl, phenylethyl, p-chlorophenylethyl, heteroaryl, heterocyclyl, cyclopropyl, cyclobutyl, nitro, hydroxy, dimethylamino, diethylamino, formyl, hydroxyiminomethyl, methoxyiminomethyl, ethoxyiminomethyl, cyclopropylmethoxymethyl, phenyloxy, p-chlorophenyloxy, p-trifluoromethylphenyloxy, m-chlorophenyloxy, m-trifluoromethylphenyloxy, 2,4-dichlorophenyloxy, heteroaryloxy, benzyloxy, ethynyl, prop-1-ynyl, $(C_2-C_5)$-alkenyl, phenylethynyl, p-chlorophenylethynyl, p-trifluoromethylphenylethynyl, p-methoxyphenylethynyl, p-fluorophenylethynyl, m-chlorophenylethynyl, m-trifluoromethylphenylethynyl, m-methoxyphenylethynyl, m-fluorophenylethynyl, trimethylsilylethynyl, triethylsilylethynyl, triisopropylsilylethynyl, 2-pyridylethynyl, 3-pyridylethynyl, 4-chloro-3-pyridylethynyl, $R^5$ represents amino, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, cyclopropyl, cyclobutyl, cyclopentyl, cyclohexyl, cyclopropylmethyl, cyclobutylmethyl, cyclopentylmethyl, cyclohexylmethyl, trifluoromethyl, difluoromethyl, 2,2-difluoroethyl, 2,2,2-trifluoroethyl, 3,3,3-trifluoropropyl, pentafluoroethyl, heptafluoro-n-propyl, heptafluoroisopropyl, nonafluoro-n-butyl, $(C_3-C_6)$-halocycloalkyl, $(C_4-C_6)$-cycloalkenyl, optionally substituted phenyl, heteroaryl, heterocyclyl, aryl-$(C_1-C_5)$-alkyl, heteroaryl-$(C_1-C_5)$-alkyl, heterocyclyl-$(C_1-C_5)$-alkyl, $(C_1-C_5)$-alkoxycarbonyl-$(C_1-C_5)$-alkyl, aryl-$(C_1-C_5)$-alkoxycarbonyl-$(C_1-C_5)$-alkyl, $(C_3-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, heteroaryl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, $(C_1-C_5)$-alkylamino, arylamino, $(C_3-C_6)$-cycloalkylamino, aryl-$(C_1-C_5)$-alkylamino, heteroaryl-$(C_1-C_5)$-alkylamino, heteroarylamino, heterocyclylamino, aryloxy-$(C_1-C_5)$-alkyl, $(C_1-C_5)$-alkoxy-$(C_1-C_5)$-alkyl, heteroaryloxy-$(C_1-C_5)$-alkyl, $(C_2-C_5)$-alkenyl, $(C_2-C_5)$-alkynyl, $(C_2-C_5)$-alkenylamino, $(C_2-C_5)$-alkynylamino, bis-[$(C_1-C_5)$-alkyl]amino, aryloxy, bis-[$(C_1-C_5)$-alkyl]amino, aryl-$(C_2-C_5)$-alkenyl, heteroaryl-$(C_2-C_5)$-alkenyl, heterocyclyl-$(C_2-C_5)$-alkenyl, R⁶ represents hydrogen, methyl, ethyl, isopropyl, n-propyl, n-butyl, isobutyl, tert-butyl, n-pentyl, isopentyl, neopentyl, n-hexyl, cyclopropyl, cyclobutyl, cyclopentyl, cyclohexyl, cyclopropylmethyl, cyclobutylmethyl, cyclopentylmethyl, cyclohexylmethyl, cyanomethyl, cyanoethyl, cyano-n-propyl, $(C_1$-$C_5)$-alkylsulfonyl, arylsulfonyl, heteroarylsulfonyl, $(C_3$-$C_6)$-cycloalkylsulfonyl, heterocyclylsulfonyl, aryl-$(C_1$-$C_5)$-alkylsulfonyl, $(C_1$-$C_5)$-alkylcarbonyl, arylcarbonyl, heteroarylcarbonyl, $(C_3$-$C_6)$-cycloalkylcarbonyl, heterocyclylcarbonyl, $(C_1$-$C_5)$-alkoxycarbonyl, aryl-$(C_1$-$C_5)$-alkoxycarbonyl, $(C_1$-$C_5)$-haloalkylcarbonyl, $(C_2$-$C_5)$-alkenyl, $(C_2$-$C_5)$-alkynyl, 2,2-difluoroethyl, 2,2,2-trifluoroethyl, 3,3,3-trifluoropropyl, halo-$(C_2$-$C_5)$-alkynyl, halo-$(C_2$-$C_5)$-alkenyl, $(C_1$-$C_5)$-alkoxy-$(C_1$-$C_5)$-alkyl and W represents oxygen or sulfur, preferably oxygen.

The abovementioned general or preferred radical definitions apply both to the end products of the general formula (I) and, correspondingly, to the starting materials or the intermediates required in each case for the preparation. These radical definitions can be combined with one another as desired, i.e. including combinations between the given preferred ranges.

The substituted dihydrooxindolylsulfonamides of the general formula (I) mentioned above are substantially likewise as yet unknown in the prior art. Thus, the invention furthermore provides substituted dihydrooxindolylsulfonamides of the general formula (I) or salts thereof described by the formulae (Ib) to (If), (Ii) to (Iu) and (Iw)

(Ib)

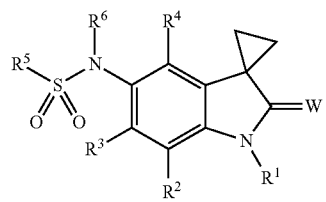

(Ic)

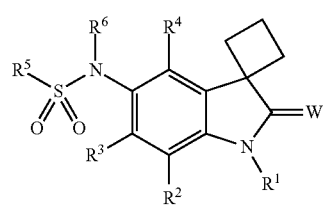

(Id)

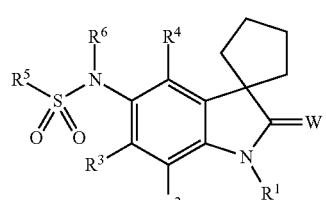

(Ie)

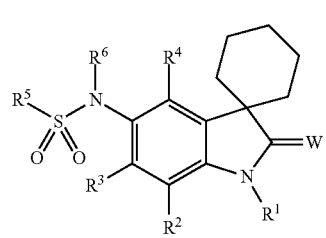

(If)

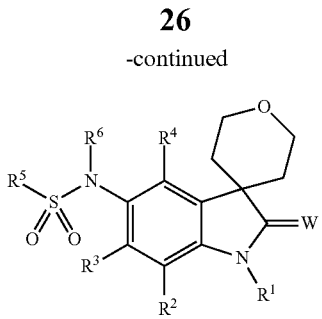

(Ii)

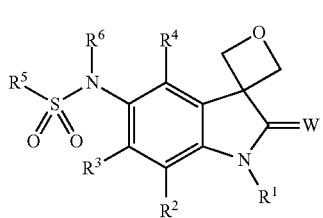

(Ij)

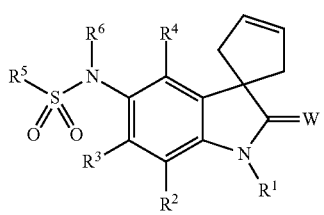

(Ik)

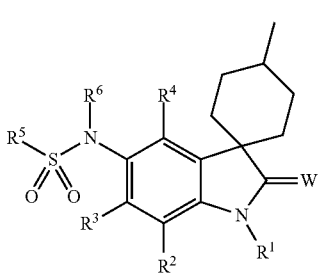

(Il)

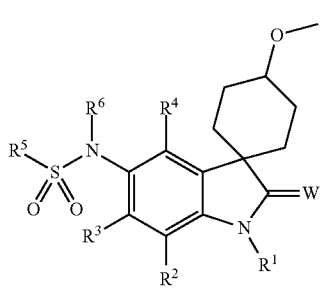

(Im)

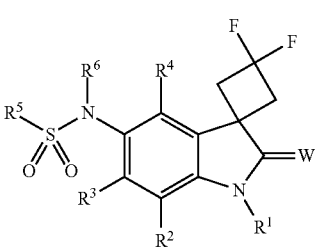

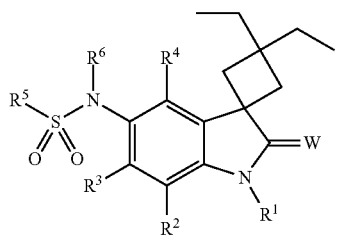 (In)

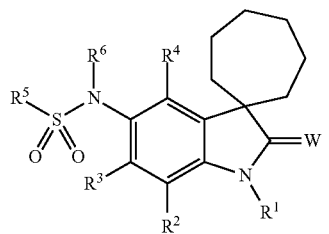 (Io)

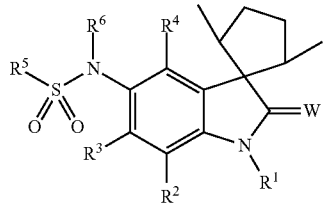 (Ip)

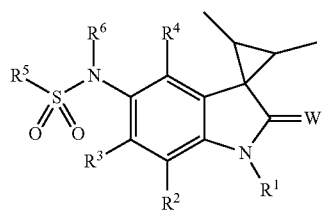 (Iq)

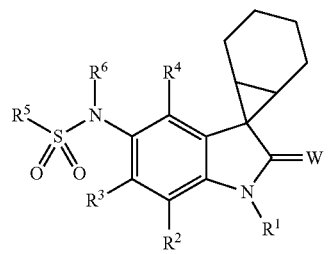 (Ir)

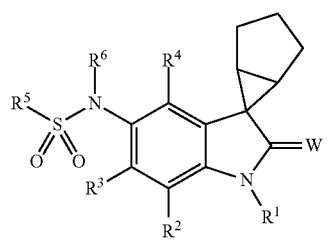 (Is)

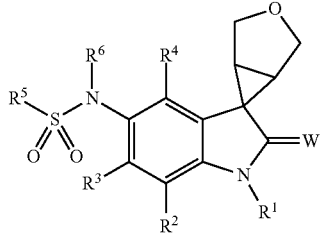 (It)

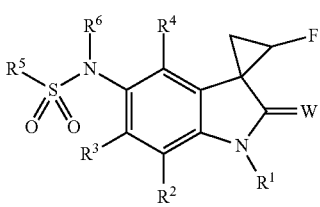 (Iu)

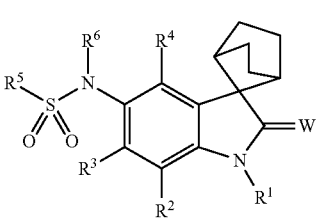 (Iw)

in which $R^1$ represents hydrogen, $(C_1-C_6)$-alkyl, $(C_3-C_6)$-cycloalkyl, $(C_1-C_6)$-haloalkyl, $(C_3-C_6)$-halocycloalkyl, $(C_2-C_6)$-alkenyl, $(C_2-C_6)$-haloalkenyl, $(C_1-C_5)$-alkoxy-$(C_1-C_5)$-haloalkyl, $(C_2-C_6)$-alkynyl, aryl-$(C_1-C_5)$-alkyl, heteroaryl-$(C_1-C_5)$-alkyl, $(C_3-C_6)$-cycloalkyl-$(C_1-C_5)$-alkyl, $(C_2-C_5)$-haloalkynyl, heterocyclyl, heterocyclyl-$(C_1-C_5)$-alkyl, $(C_1-C_5)$-alkoxy-$(C_1-C_5)$-alkyl, $(C_1-C_5)$-alkylcarbonyl-$(C_1-C_5)$-alkyl, hydroxycarbonyl-$(C_1-C_5)$-alkyl, $(C_1-C_5)$-alkoxycarbonyl-$(C_1-C_5)$-alkyl, $(C_2-C_5)$-alkenyloxycarbonyl-$(C_1-C_5)$-alkyl, $(C_2-C_5)$-alkynyloxycarbonyl-$(C_1-C_5)$-alkyl, aryl-$(C_1-C_5)$-alkoxycarbonyl-$(C_1-C_5)$-alkyl, $(C_3-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, heteroaryl-$(C_1-C_5)$-alkylaminocarbonyl-$(C_1-C_5)$-alkyl, $(C_1-C_5)$-alkylthio-$(C_1-C_5)$-alkyl, $(C_3-C_6)$-cycloalkylthio-$(C_1-C_5)$-alkyl, arylthio-$(C_1-C_5)$-alkyl, heterocyclylthio-$(C_1-C_5)$-alkyl, heteroarylthio-$(C_1-C_5)$-alkyl, aryl-$(C_1-C_5)$-alkylthio-$(C_1-C_5)$-alkyl, $(C_1-C_5)$-alkylsulfinyl-$(C_1-C_5)$-alkyl, $(C_1-C_5)$-alkylsulfonyl-$(C_1-C_5)$-alkyl, arylsulfinyl-$(C_1-C_5)$-alkyl, arylsulfonyl-$(C_1-C_5)$-alkyl, $(C_3-C_6)$-cycloalkylsulfinyl-$(C_1-C_5)$-alkyl, $(C_3-C_6)$-cycloalkylsulfonyl-$(C_1-C_5)$-alkyl, $(C_1-C_5)$-alkoxy-$(C_1-C_5)$-alkoxy-$(C_1-C_5)$-alkyl, $(C_1-C_5)$-alkylcarbonyl, $(C_3-C_6)$-cycloalkylcarbonyl, $(C_1-C_5)$-alkoxycarbonyl, aryl-$(C_1-C_5)$-alkoxycarbonyl, arylcarbonyl, heteroarylcarbonyl, heterocyclylcarbonyl, aryl-$(C_1-C_5)$-alkylcarbonyl, $(C_1-C_5)$-alkylaminocarbonyl, $(C_3-C_6)$-cycloalkylaminocarbonyl, arylaminocarbonyl, aryl-$(C_1-C_5)$-alkylaminocarbonyl, $(C_1-C_5)$-alkylsulfonyl, $(C_3-C_6)$-cycloalkylsulfonyl, arylsulfonyl, heteroarylsulfonyl, heterocyclylsulfonyl, cyano-$(C_1-C_5)$-alkyl, bis-[$(C_1-C_5)$-alkyl]amino, $(C_3-C_6)$-cycloalkyl[$(C_1-C_5)$-alkyl]amino, $R^2$, $R^3$, $R^4$ independently of one another represent hydrogen, fluorine, chlorine, bromine, iodine, ($C_1$-$C_5$)-alkoxy, ($C_1$-$C_5$)-alkyl, ($C_1$-$C_5$)-haloalkyl, ($C_1$-$C_5$)-haloalkoxy, ($C_1$-$C_5$)-alkylthio, ($C_1$-$C_5$)-haloalkylthio, aryl, heteroaryl, heterocyclyl, ($C_3$-$C_6$)-cycloalkyl, $R^5$ represents amino, ($C_1$-$C_5$)-alkyl, ($C_3$-$C_6$)-cycloalkyl, ($C_3$-$C_6$)-cycloalkyl-($C_1$-$C_5$)-alkyl, ($C_1$-$C_5$)-haloalkyl, ($C_3$-$C_6$)-halocycloalkyl, ($C_4$-$C_6$)-cycloalkenyl, optionally substituted phenyl, heteroaryl, heterocyclyl, aryl-($C_1$-$C_5$)-alkyl, heteroaryl-($C_1$-$C_5$)-alkyl, heterocyclyl-($C_1$-$C_5$)-alkyl, ($C_1$-$C_5$)-alkoxycarbonyl-($C_1$-$C_5$)-alkyl, aryl-($C_1$-$C_5$)-alkoxycarbonyl-($C_1$-$C_5$)-alkyl, ($C_3$-$C_6$)-cycloalkoxycarbonyl-($C_1$-$C_6$)-alkyl, ($C_3$-$C_6$)-cycloalkyl-($C_1$-$C_5$)-alkoxycarbonyl-($C_1$-$C_5$)-alkyl, heteroaryl-($C_1$-$C_5$)-alkoxycarbonyl-($C_1$-$C_5$)-alkyl, aminocarbonyl-($C_1$-$C_5$)-alkyl, ($C_1$-$C_5$)-alkylaminocarbonyl-($C_1$-$C_5$)-alkyl, ($C_3$-$C_6$)-cycloalkylaminocarbonyl-($C_1$-$C_5$)-alkyl, aryl-($C_1$-$C_5$)-alkylaminocarbonyl-($C_1$-$C_5$)-alkyl, ($C_1$-$C_5$)-alkylamino, bis-[($C_1$-$C_5$)-alkyl]amino, arylamino, ($C_3$-$C_6$)-cycloalkylamino, aryl-($C_1$-$C_5$)-alkylamino, heteroaryl-($C_1$-$C_5$)-alkylamino, heteroarylamino, heterocyclylamino, ($C_2$-$C_5$)-alkenylamino, ($C_2$-$C_5$)-alkynylamino, aryloxy-($C_1$-$C_5$)-alkyl, heteroaryloxy-($C_1$-$C_5$)-alkyl, ($C_1$-$C_5$)-alkoxy-($C_1$-$C_5$)-alkyl, ($C_2$-$C_6$)-alkenyl, ($C_2$-$C_6$)-alkynyl, cyano-($C_1$-$C_5$)-alkyl, aryloxy, aryl-($C_2$-$C_5$)-alkenyl, heteroaryl-($C_2$-$C_5$)-alkenyl, heterocyclyl-($C_2$-$C_5$)-alkenyl, $R^6$ represents hydrogen, ($C_1$-$C_5$)-alkyl, ($C_3$-$C_6$)-cycloalkyl, cyano-($C_1$-$C_5$)-alkyl, ($C_3$-$C_6$)-cycloalkyl-($C_1$-$C_5$)-alkyl, ($C_1$-$C_5$)-alkylsulfonyl, arylsulfonyl, aryl-($C_1$-$C_5$)-alkylsulfonyl, heteroarylsulfonyl, ($C_3$-$C_6$)-cycloalkylsulfonyl, heterocyclylsulfonyl, ($C_1$-$C_5$)-alkylcarbonyl, arylcarbonyl, heteroarylcarbonyl, ($C_3$-$C_6$)-cycloalkylcarbonyl, heterocyclylcarbonyl, ($C_1$-$C_5$)-alkoxycarbonyl, aryl-($C_1$-$C_5$)-alkoxycarbonyl, ($C_1$-$C_5$)-haloalkylcarbonyl, ($C_2$-$C_5$)-alkenyl, ($C_2$-$C_5$)-alkynyl, ($C_1$-$C_5$)-haloalkyl, halo-($C_2$-$C_5$)-alkynyl, halo-($C_2$-$C_5$)-alkenyl, ($C_1$-$C_5$)-alkoxy-($C_1$-$C_5$)-alkyl, W represents oxygen or sulfur, preferably oxygen.

Particular preference is given to compounds of the general formula (I) which are described by the formulae (Ib) to (Ie), (Ij) to (Is), (Iu) and (Iw)

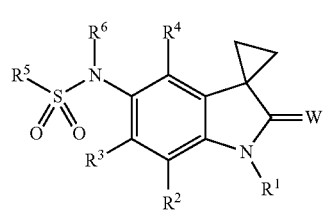

(Ib)

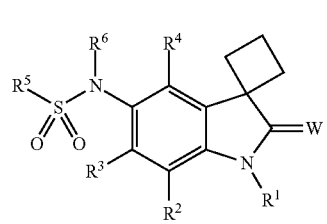

(Ic)

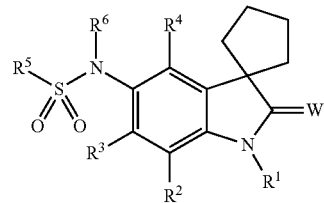

(Id)

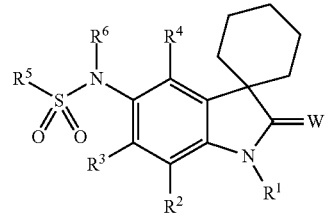

(Ie)

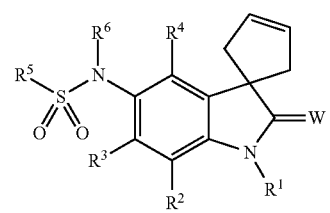

(Ij)

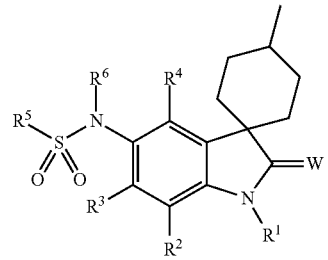

(Ik)

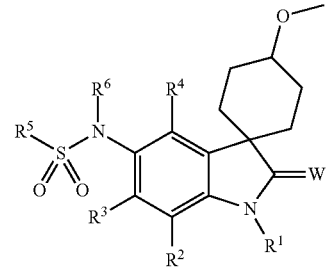

(Il)

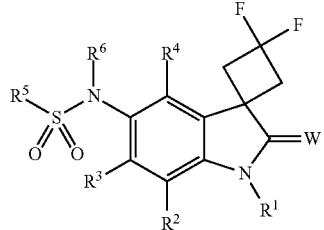

(Im)

-continued (In)
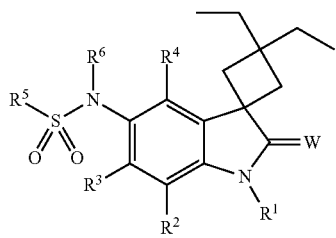

(Io)
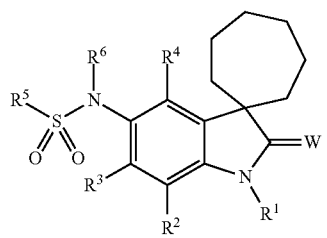

(Ip)
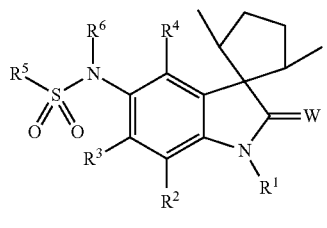

(Iq)
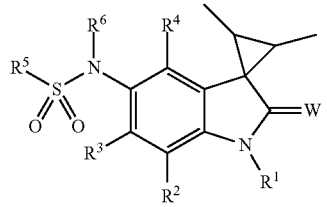

(Ir)
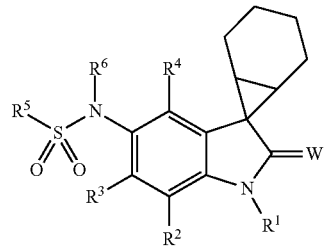

(Is)
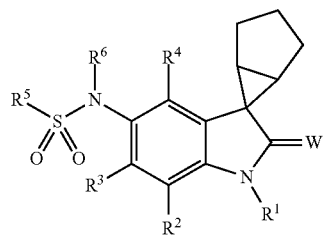

(Iu)
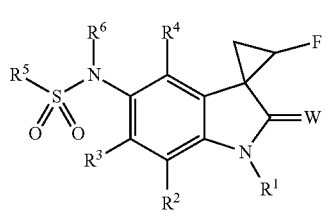

-continued (Iw)
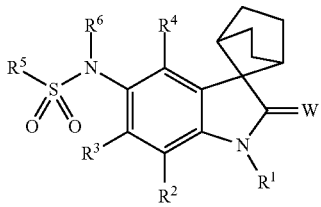

in which $R^1$ represents hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-allylcyclopropyl, 1-vinylcyclobutyl, 1-vinylcyclopropyl, 1-ethylcyclopropyl, 2-ethylcyclopropyl, 1-ethylcyclobutyl, 2-ethylcyclobutyl, 3-ethylcyclobutyl, 4-methylcyclohexyl, 4-methoxycyclohexyl, 4-ethoxycyclohexyl, 4-n-propyloxycyclohexyl, 4-hydroxycyclohexyl, 4-methoxycyclobutyl, 1-cyclopropylcyclobutyl, 1-prop-2-enylcyclobutyl, 2-ethyl-3-methylcyclobutyl, 1-propylcyclopropyl, 1-methyl-2-propylcyclopropyl, 2-propylcyclopropyl, 1-propylcyclobutyl, 2-propylcyclobutyl, 3-propylcyclobutyl, 1-isopropylcyclobutyl, 1-isopropylcyclopropyl, 2-isopropylcyclopropyl, 3-isopropylcyclobutyl, 2-dimethylaminocyclobutyl, 3-dimethylaminocyclobutyl, 1-butylcyclobutyl, 2-butylcyclobutyl, 1-butylcyclopropyl, 3-butylcyclobutyl, 2-butylcyclopropyl, 1-isobutylcyclobutyl, 3-tert-butylcyclobutyl, 3,3-diethylcyclobutyl, 2,2-diethylcyclopropyl, 2-methylidenecyclopropyl, 1-methoxymethylcyclopropyl, 1-isobutylcyclopropyl, 2,2-difluoroethyl, 2,2,2-trifluoroethyl, 3,3,3-trifluoropropyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1- pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, $(C_3-C_6)$-halocycloalkyl, $(C_2-C_5)$-haloalkenyl, $(C_1-C_5)$-alkoxy-$(C_1-C_5)$-haloalkyl, benzyl, p-chlorobenzyl, p-methoxybenzyl, p-trifluoromethylbenzyl, p-methylbenzyl, p-fluorobenzyl, p-bromobenzyl, p-iodobenzyl, p-methylthiobenzyl, p-trifluoromethoxybenzyl, p-nitrobenzyl, p-trifluoromethylthiobenzyl, m-chlorobenzyl, m-methoxybenzyl, m-trifluoromethylbenzyl, m-methylbenzyl, m-fluorobenzyl, m-bromobenzyl, m-iodobenzyl, m-methylthiobenzyl, m-trifluoromethoxybenzyl, m-nitrobenzyl, m-trifluoromethylthiobenzyl, o-chlorobenzyl, o-methoxybenzyl, o-trifluoromethylbenzyl, o-methylbenzyl, o-fluorobenzyl, o-bromobenzyl, o-iodobenzyl, o-methylthiobenzyl, o-trifluoromethoxybenzyl, o-nitrobenzyl, o-trifluoromethylthiobenzyl, p-m ethoxycarbonylbenzyl, p-ethoxycarbonylbenzyl, m-methoxycarbonylbenzyl, m-ethoxycarbonylbenzyl, 2,4-dichlorobenzyl, 3,5-dichlorobenzyl, 2,4-difluorobenzyl, 3,5-difluorobenzyl, 3,4-dichlorobenzyl, 3,4-difluorobenzyl, 2,5-dichlorobenzyl, phenylethyl, p-chlorophenylethyl, p-methoxyphenylethyl, p-trifluoromethylphenylethyl, p-fluorophenylethyl, p-trifluoromethoxyphenylethyl, p-trifluoromethylthiophenylethyl, p-methylphenylethyl, p-nitrophenylethyl, p-methoxycarbonylphenylethyl, p-ethoxycarbonylphenylethyl, m-chlorophenylethyl, m-methoxyphenylethyl, m-trifluoromethylphenylethyl, m-fluorophenylethyl, m-trifluoromethoxyphenylethyl, m-trifluoromethylthiophenylethyl, m-methylphenylethyl, m-nitrophenylethyl, m-methoxycarbonylphenylethyl, m-ethoxycarbonylphenylethyl, o-chlorophenylethyl, o-methoxyphenylethyl, o-trifluoromethylphenylethyl, o-fluorophenylethyl, o-trifluoromethoxyphenylethyl, o-trifluoromethylthiophenylethyl, o-methylphenylethyl, o-nitrophenylethyl, o-methoxycarbonylphenylethyl, o-ethoxycarbonylphenylethyl, heteroaryl-$(C_1-C_5)$-alkyl, $(C_1-C_5)$-haloalkenyl, heterocyclyl, heterocyclyl-$(C_1-C_5)$-alkyl, $(C_1-C_5)$-alkoxy-$(C_1-C_5)$-alkyl, $(C_1-C_5)$-alkylcarbonyl-$(C_1-C_5)$-alkyl, hydroxycarbonyl-$(C_1-C_5)$-alkyl, $(C_1-C_5)$-alkoxycarbonyl-$(C_1-C_5)$-alkyl, $(C_2-C_5)$-alkenyloxycarbonyl-$(C_1-C_5)$-alkyl, $(C_2-C_5)$-alkynyloxycarbonyl-$(C_1-C_5)$-alkyl, aryl-$(C_1-C_5)$-alkoxycarbonyl-$(C_1-C_5)$-alkyl, $(C_3-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, heteroaryl-$(C_1-C_5)$-alkylaminocarbonyl-$(C_1-C_5)$-alkyl, $(C_3-C_5)$-cycloalkylthio-$(C_1-C_5)$-alkyl, arylthio-$(C_1-C_5)$-alkyl, heterocyclylthio-$(C_1-C_5)$-alkyl, heteroarylthio-$(C_1-C_5)$-alkyl, $(C_1-C_5)$-alkylsulfinyl-$(C_1-C_5)$-alkyl, $(C_1-C_5)$-alkylsulfonyl-$(C_1-C_5)$-alkyl, arylsulfinyl-$(C_1-C_5)$-alkyl, arylsulfonyl-$(C_1-C_5)$-alkyl, $(C_3-C_6)$-cycloalkylsulfinyl-$(C_1-C_5)$-alkyl, $(C_3-C_6)$-cycloalkylsulfonyl-$(C_1-C_5)$-alkyl, $(C_1-C_5)$-alkoxy-$(C_1-C_5)$-alkoxy-$(C_1-C_5)$-alkyl, $(C_1-C_5)$-alkylcarbonyl, $(C_3-C_6)$-cycloalkylcarbonyl, $(C_1-C_5)$-alkoxycarbonyl, aryl-$(C_1-C_5)$-alkoxycarbonyl, arylcarbonyl, heteroarylcarbonyl, heterocyclylcarbonyl, aryl-$(C_1-C_5)$-alkylcarbonyl, $(C_1-C_5)$-alkylaminocarbonyl, $(C_3-C_6)$-cycloalkylaminocarbonyl, arylaminocarbonyl, aryl-$(C_1-C_5)$-alkylaminocarbonyl, $(C_1-C_5)$-alkylsulfonyl, $(C_3-C_6)$-cycloalkylsulfonyl, arylsulfonyl, heteroarylsulfonyl, heterocyclylsulfonyl, bis-[$(C_1-C_5)$-alkyl]amino, $(C_3-C_6)$-cycloalkyl[$(C_1-C_5)$-alkyl]amino, $R^2$, $R^3$, $R^4$ independently of one another represent hydrogen, fluorine, chlorine, bromine, iodine, methoxy, ethoxy, n-propyloxy, isopropyloxy, methyl, ethyl, isopropyl, trifluoromethyl, difluoromethyl, pentafluoroethyl, trifluoromethoxy, difluoromethoxy, 2,2-difluoroethoxy, 3,3,3-trifluoroethoxy, methylthio, ethylthio, trifluoromethylthio, optionally substituted phenyl, heteroaryl, heterocyclyl, cyclopropyl, cyclobutyl, cyclopentyl, cyclohexyl, $R^5$ represents amino, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, cyclopropylmethyl, cyclobutylmethyl, cyclopentylmethyl, cyclohexylmethyl, trifluoromethyl, difluoromethyl, 2,2-difluoroethyl, 2,2,2-trifluoroethyl, 3,3,3-trifluoropropyl, pentafluoroethyl, heptafluoro-n-propyl, heptafluoroisopropyl, nonafluoro-n-butyl, $(C_3-C_6)$-halocycloalkyl, $(C_4-C_6)$-cycloalkenyl, optionally substituted phenyl, heteroaryl, heterocyclyl, aryl-$(C_1-C_5)$-alkyl, heteroaryl-$(C_1-C_5)$-alkyl, heterocyclyl-$(C_1-C_5)$-alkyl, $(C_1-C_5)$-alkoxycarbonyl-$(C_1-C_5)$-alkyl, aryl-$(C_1-C_5)$-alkoxycarbonyl-$(C_1-C_5)$-alkyl, $(C_1-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, heteroaryl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, $(C_1-C_5)$-alkylamino, arylamino, $(C_3-C_6)$-cycloalkylamino, aryl-$(C_1-C_5)$-alkylamino, heteroaryl-$(C_1-C_5)$-alkylamino, heteroarylamino, heterocyclylamino, $(C_2-C_5)$-alkenylamino, $(C_2-C_5)$-alkynylamino, aryloxy-$(C_1-C_5)$-alkyl, heteroaryloxy-$(C_1-C_5)$-alkyl, $(C_1-C_5)$-alkoxy-$(C_1-C_5)$-alkyl, phenylethenyl, p-chlorophenylethenyl, p-methylphenylethenyl, p-methoxyphenylethenyl, p-trifluoromethylphenylethenyl, p-fluorophenylethenyl, p-cyanophenylethenyl, p-trifluoromethoxyphenylethenyl, p-nitrophenylethenyl, p-bromophenylethenyl, p-iodophenylethenyl, m-chlorophenylethenyl, m-methylphenylethenyl, m-methoxyphenylethenyl, m-trifluoromethylphenylethenyl, m-fluorophenylethenyl, m-cyanophenylethenyl, m-trifluoromethoxyphenylethenyl, m-nitrophenylethenyl, m-bromophenylethenyl, m-iodophenylethenyl, p-methoxycarbonylphenylethenyl, m-methoxycarbonylphenylethenyl, o-methoxycarbonylphenylethenyl, p-ethoxycarbonylphenylethenyl, m-ethoxycarbonylphenylethenyl, o-ethoxycarbonylphenylethenyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, cyanoethyl, cyanomethyl, cyano-n-propyl, cyano-n-butyl, aryloxy, bis-[$(C_1-C_5)$-alkyl]amino, aryl-$(C_2-C_5)$-alkenyl, heteroaryl-$(C_2-C_5)$-alkenyl, heterocyclyl-$(C_2-C_5)$-alkenyl, $R^6$ represents hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, cyclopentylmethyl, cyclohexylmethyl, 2,2-difluoroethyl, 2,2,2-trifluoroethyl, 3,3,3-trifluoropropyl, cyanomethyl, cyanoethyl, cyano-n-propyl, cyclopropylcarbonyl, cyclobutylcarbonyl, cyclopentylcarbonyl, cyclohexylcarbonyl, methoxycarbonyl, $(C_1-C_5)$-alkylsulfonyl, arylsulfonyl, aryl-$(C_1-C_5)$-alkylsulfonyl, heteroarylsulfonyl, $(C_3-C_6)$-cycloalkylsulfonyl, heterocyclylsulfonyl, $(C_1-C_5)$-alkylcarbonyl, arylcarbonyl, heteroarylcarbonyl, heterocyclylcarbonyl, $(C_1-C_5)$-alkoxycarbonyl, aryl-$(C_1-C_5)$-alkoxycarbonyl, $(C_1-C_5)$-haloalkylcarbonyl, $(C_2-C_5)$-alkenyl, $(C_2-C_5)$-alkynyl, halo-$(C_2-C_5)$-alkynyl, halo-$(C_2-C_5)$-alkenyl, $(C_1-C_5)$-alkoxy-$(C_1-C_5)$-alkyl, W represents oxygen or sulfur, preferably oxygen.

Very particular preference is given to compounds of the general formula (I) which are described by the formulae (Ib) to (Ie), (Ij) to (Is), (Iu) and (Iw)

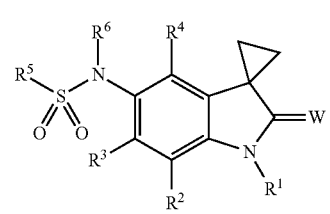

(Ib)

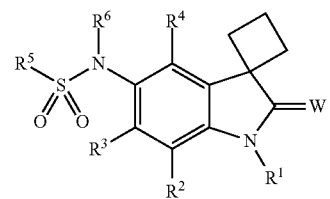

(Ic)

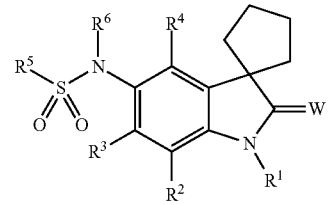

(Id)

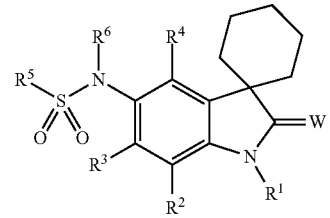

(Ie)

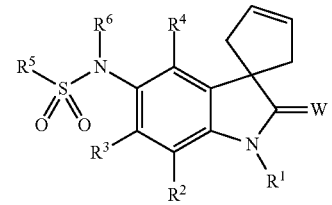

(Ij)

-continued

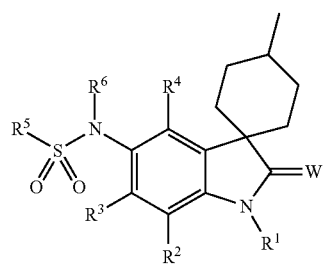
(Ik)

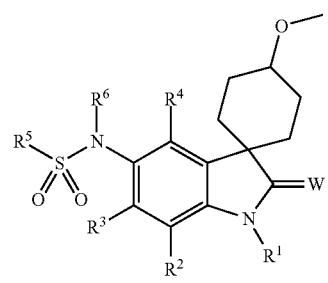
(Il)

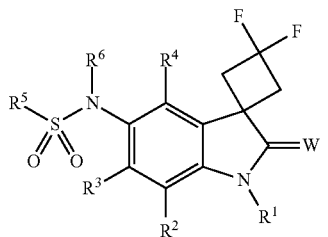
(Im)

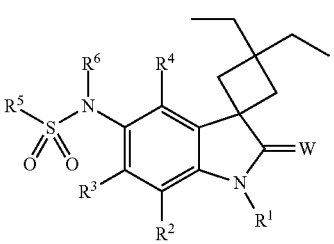
(In)

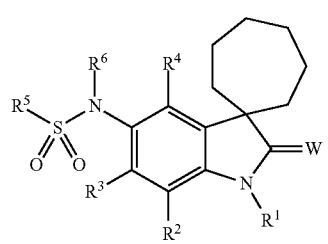
(Io)

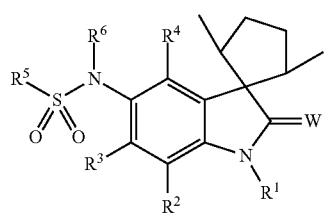
(Ip)

-continued

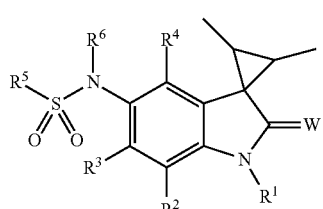
(Iq)

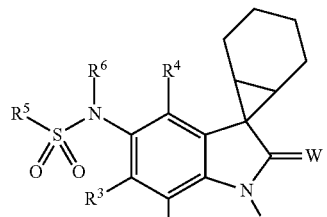
(Ir)

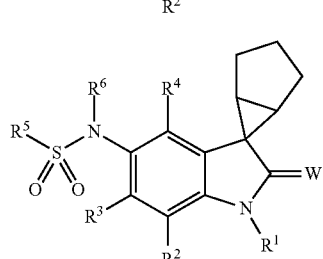
(Is)

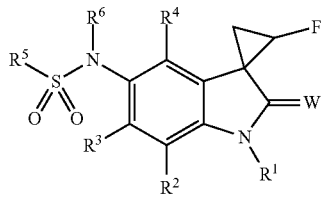
(Iu)

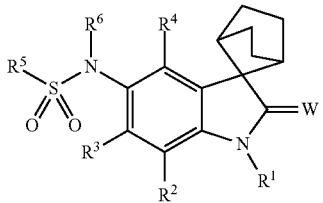
(Iw)

in which $R^1$ represents methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-allylcyclopropyl, 1-vinylcyclobutyl, 1-vinylcyclopropyl, 1-ethylcyclopropyl, 2-ethylcyclopropyl, 1-ethylcyclobutyl, 2-ethylcyclobutyl, 3-ethylcyclobutyl, 4-methylcyclohexyl, 4-methoxycyclohexyl, 4-ethoxycyclohexyl, 4-n-propyloxycyclohexyl, 4-hydroxycyclohexyl, 4-methoxycyclobutyl, 1-cyclopropylcyclobutyl, 1-prop-2-enylcyclobutyl, 2-ethyl-3-methylcyclobutyl, 1-propylcyclopropyl, 1-methyl-2-propylcyclopropyl, 2-propylcyclopropyl, 1-propylcyclobutyl, 2-propylcyclobutyl, 3-propylcyclobutyl, 1-isopropylcyclobutyl, 1-isopropylcyclopropyl, 2-isopropylcyclopropyl, 3-isopropylcyclobutyl, 2-dimethylaminocyclobutyl, 3-dimethylaminocyclobutyl, 1-butylcyclobutyl, 2-butylcyclobutyl, 1-butylcyclopropyl, 3-butylcyclobutyl, 2-butylcyclopropyl, 1-isobutylcyclobutyl, 3-tert-butylcyclobutyl, 3,3-diethylcyclobutyl, 2,2-diethylcyclopropyl, 2-methylidenecyclopropyl, 1-methoxymethylcyclopropyl, 1-isobutylcyclopropyl, 2,2-difluoroethyl, 2,2,2-trifluoroethyl, 3,3,3-trifluoropropyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, ($C_3$-$C_6$)-halocycloalkyl, ($C_2$-$C_5$)-haloalkenyl, ($C_1$-$C_5$)-alkoxy-($C_1$-$C_5$)-haloalkyl, benzyl, p-chlorobenzyl, p-methoxybenzyl, p-trifluoromethylbenzyl, p-methylbenzyl, p-fluorobenzyl, p-bromobenzyl, p-iodobenzyl, p-methylthiobenzyl, p-trifluoromethoxybenzyl, p-nitrobenzyl, p-trifluoromethylthiobenzyl, m-chlorobenzyl, m-methoxybenzyl, m-trifluoromethylbenzyl, m-methylbenzyl, m-fluorobenzyl, m-bromobenzyl, m-iodobenzyl, m-methylthiobenzyl, m-trifluoromethoxybenzyl, m-nitrobenzyl, m-trifluoromethylthiobenzyl, o-chlorobenzyl, o-methoxybenzyl, o-trifluoromethylbenzyl, o-methylbenzyl, o-fluorobenzyl, o-bromobenzyl, o-iodobenzyl, o-methylthiobenzyl, o-trifluoromethoxybenzyl, o-nitrobenzyl, o-trifluoromethylthiobenzyl, p-methoxycarbonylbenzyl, p-ethoxycarbonylbenzyl, m-methoxycarbonylbenzyl, m-ethoxycarbonylbenzyl, 2,4-dichlorobenzyl, 3,5-dichlorobenzyl, 2,4-difluorobenzyl, 3,5-difluorobenzyl, 3,4-dichlorobenzyl, 3,4-difluorobenzyl, 2,5-dichlorobenzyl, phenylethyl, p-chlorophenylethyl, p-methoxyphenylethyl, p-trifluoromethylphenylethyl, p-fluorophenylethyl, p-trifluoromethoxyphenylethyl, p-trifluoromethylthiophenylethyl, p-methylphenylethyl, p-nitrophenylethyl, p-methoxycarbonylphenylethyl, p-ethoxycarbonylphenylethyl, m-chlorophenylethyl, m-methoxyphenylethyl, m-trifluoromethylphenylethyl, m-fluorophenylethyl, m-trifluoromethoxyphenylethyl, m-trifluoromethylthiophenylethyl, m-methylphenylethyl, m-nitrophenylethyl, m-methoxycarbonylphenylethyl, m-ethoxycarbonylphenylethyl, o-chlorophenylethyl, o-methoxyphenylethyl, o-trifluoromethylphenylethyl, o-fluorophenylethyl, o-trifluoromethoxyphenylethyl, o-trifluoromethylthiophenylethyl, o-methylphenylethyl, o-nitrophenylethyl, o-methoxycarbonylphenylethyl, o-ethoxycarbonylphenylethyl, heteroaryl-($C_1$-$C_5$)-alkyl, ($C_1$-$C_5$)-haloalkenyl, heterocyclyl, heterocyclyl-($C_1$-$C_5$)-alkyl, ($C_1$-$C_5$)-alkoxy-($C_1$-$C_5$)-alkyl, ($C_1$-$C_5$)-alkylcarbonyl-($C_1$-$C_5$)-alkyl, hydroxycarbonyl-($C_1$-$C_5$)-alkyl, ($C_1$-$C_5$)-alkoxycarbonyl-($C_1$-$C_5$)-alkyl, ($C_2$-$C_5$)-alkenyloxycarbonyl-($C_1$-$C_5$)-alkyl, ($C_2$-$C_5$)-alkynyloxycarbonyl-($C_1$-$C_5$)-alkyl, aryl-($C_1$-$C_5$)-alkoxycarbonyl-($C_1$-$C_5$)-alkyl, ($C_3$-$C_6$)-cycloalkoxycarbonyl-($C_1$-$C_5$)-alkyl, ($C_3$-$C_6$)-cycloalkyl-($C_1$-$C_5$)-alkoxycarbonyl-($C_1$-$C_5$)-alkyl, aminocarbonyl-($C_1$-$C_5$)-alkyl, ($C_1$-$C_5$)-alkylaminocarbonyl-($C_1$-$C_5$)-alkyl, ($C_3$-$C_6$)-cycloalkylaminocarbonyl-($C_1$-$C_5$)-alkyl, aryl-($C_1$-$C_5$)-alkylaminocarbonyl-($C_1$-$C_5$)-alkyl, heteroaryl-($C_1$-$C_5$)-alkylaminocarbonyl-($C_1$-$C_5$)-alkyl, ($C_1$-$C_5$)-alkylthio-($C_1$-$C_5$)-alkyl, ($C_3$-$C_5$)-cycloalkylthio-($C_1$-$C_5$)-alkyl, arylthio-($C_1$-$C_5$)-alkyl, heterocyclylthio-($C_1$-$C_5$)-alkyl, heteroarylthio-($C_1$-$C_5$)-alkyl, aryl-($C_1$-$C_5$)-alkylthio-($C_1$-$C_5$)-alkyl, ($C_1$-$C_5$)-alkylsulfinyl-($C_1$-$C_5$)-alkyl, ($C_1$-$C_5$)-alkylsulfonyl-($C_1$-$C_5$)-alkyl, arylsulfinyl-($C_1$-$C_5$)-alkyl, arylsulfonyl-($C_1$-$C_5$)-alkyl, ($C_3$-$C_6$)-cycloalkylsulfinyl-($C_1$-$C_5$)-alkyl, ($C_3$-$C_6$)-cycloalkylsulfonyl-($C_1$-$C_5$)-alkyl, ($C_1$-$C_5$)-alkoxy-($C_1$-$C_5$)-alkoxy-($C_1$-$C_5$)-alkyl, ($C_1$-$C_5$)-alkylcarbonyl, ($C_3$-$C_6$)-cycloalkylcarbonyl, ($C_1$-$C_5$)-alkoxycarbonyl, aryl-($C_1$-$C_5$)-alkoxycarbonyl, arylcarbonyl, heteroarylcarbonyl, heterocyclylcarbonyl, aryl-($C_1$-$C_5$)-alkylcarbonyl, ($C_1$-$C_5$)-alkylaminocarbonyl, ($C_3$-$C_6$)-cycloalkylaminocarbonyl, arylaminocarbonyl, aryl-($C_1$-$C_5$)-alkylaminocarbonyl, ($C_1$-$C_5$)-alkylsulfonyl, ($C_3$-$C_6$)-cycloalkylsulfonyl, arylsulfonyl, heteroarylsulfonyl, heterocyclylsulfonyl, bis-[($C_1$-$C_5$)-alkyl]amino, ($C_3$-$C_6$)-cycloalkyl[($C_1$-$C_5$)-alkyl]amino, $R^2$, $R^3$, $R^4$ independently of one another represent hydrogen, fluorine, chlorine, bromine, iodine, methoxy, ethoxy, n-propyloxy, isopropyloxy, methyl, ethyl, isopropyl, trifluoromethyl, difluoromethyl, pentafluoroethyl, trifluoromethoxy, difluoromethoxy, 2,2-difluoroethoxy, 3,3,3-trifluoroethoxy, methylthio, ethylthio, trifluoromethylthio, optionally substituted phenyl, heteroaryl, heterocyclyl, cyclopropyl, cyclobutyl, cyclopentyl, cyclohexyl, $R^5$ represents optionally substituted phenyl, heteroaryl, heterocyclyl, aryl-$(C_1$-$C_5)$-alkyl, heteroaryl-$(C_1$-$C_5)$-alkyl, heterocyclyl-$(C_1$-$C_5)$-alkyl, $(C_1$-$C_5)$-alkoxycarbonyl-$(C_1$-$C_5)$-alkyl, aryl-$(C_1$-$C_5)$-alkoxycarbonyl-$(C_1$-$C_5)$-alkyl, $(C_1$-$C_6)$-cycloalkoxycarbonyl-$(C_1$-$C_5)$-alkyl, $(C_3$-$C_6)$-cycloalkyl-$(C_1$-$C_5)$-alkoxycarbonyl-$(C_1$-$C_5)$-alkyl, heteroaryl-$(C_1$-$C_5)$-alkoxycarbonyl-$(C_1$-$C_5)$-alkyl, aminocarbonyl-$(C_1$-$C_5)$-alkyl, $(C_1$-$C_5)$-alkylaminocarbonyl-$(C_1$-$C_5)$-alkyl, $(C_3$-$C_6)$-cycloalkylaminocarbonyl-$(C_1$-$C_5)$-alkyl, aryl-$(C_1$-$C_5)$-alkylaminocarbonyl-$(C_1$-$C_5)$-alkyl, aryloxy-$(C_1$-$C_5)$-alkyl, heteroaryloxy-$(C_1$-$C_5)$-alkyl, phenylethenyl, p-chlorophenylethenyl, p-methylphenylethenyl, p-methoxyphenylethenyl, p-trifluoromethylphenylethenyl, p-fluorophenylethenyl, p-cyanophenylethenyl, p-trifluoromethoxyphenylethenyl, p-nitrophenylethenyl, p-bromophenylethenyl, p-iodophenylethenyl, m-chlorophenylethenyl, m-methylphenylethenyl, m-methoxyphenylethenyl, m-trifluoromethylphenylethenyl, m-fluorophenylethenyl, m-cyanophenylethenyl, m-trifluoromethoxyphenylethenyl, m-nitrophenylethenyl, m-bromophenylethenyl, m-iodophenylethenyl, p-methoxycarbonylphenylethenyl, m-methoxycarbonylphenylethenyl, o-methoxycarbonylphenylethenyl, p-ethoxycarbonylphenylethenyl, m-ethoxycarbonylphenylethenyl, o-ethoxycarbonylphenylethenyl, heteroaryl-$(C_2$-$C_5)$-alkenyl, heterocyclyl-$(C_2$-$C_5)$-alkenyl, $R^6$ represents hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, cyclopentylmethyl, cyclohexylmethyl, 2,2-difluoroethyl, 2,2,2-trifluoroethyl, 3,3,3-trifluoropropyl, cyanomethyl, cyanoethyl, cyano-n-propyl, cyclopropylcarbonyl, cyclobutylcarbonyl, cyclopentylcarbonyl, cyclohexylcarbonyl, methoxycarbonyl, $(C_1$-$C_5)$-alkylsulfonyl, arylsulfonyl, aryl-$(C_1$-$C_5)$-alkylsulfonyl, heteroarylsulfonyl, $(C_3$-$C_6)$-cycloalkylsulfonyl, heterocyclylsulfonyl, $(C_1$-$C_5)$-alkylcarbonyl, arylcarbonyl, heteroarylcarbonyl, heterocyclylcarbonyl, $(C_1$-$C_5)$-alkoxycarbonyl, aryl-$(C_1$-$C_5)$-alkoxycarbonyl, $(C_1$-$C_5)$-haloalkylcarbonyl, $(C_2$-$C_5)$-alkenyl, $(C_2$-$C_5)$-alkynyl, halo-$(C_2$-$C_5)$-alkynyl, halo-$(C_2$-$C_5)$-alkenyl, $(C_1$-$C_5)$-alkoxy-$(C_1$-$C_5)$-alkyl, W represents oxygen or sulfur, preferably oxygen.

Special preference is given to compounds of the general formula (I) which are described by the formulae (Ib) to (Ie), (Ij) to (Il) and (Io) to (Iq)

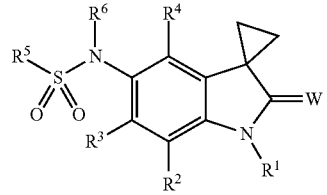
(Ib)

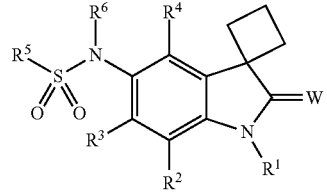
(Ic)

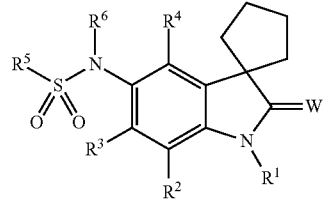
(Id)

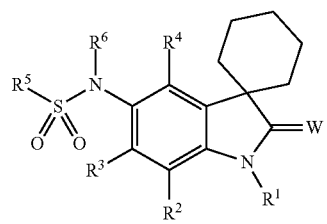
(Ie)

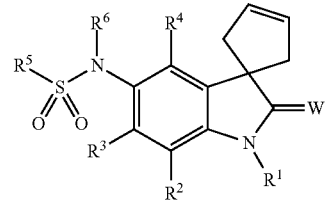
(Ij)

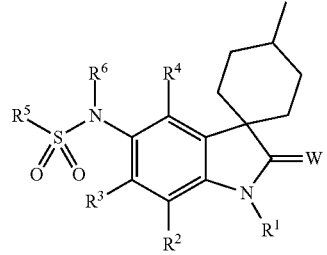
(Ik)

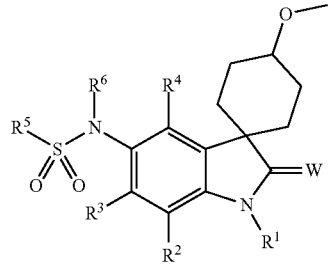
(Il)

-continued

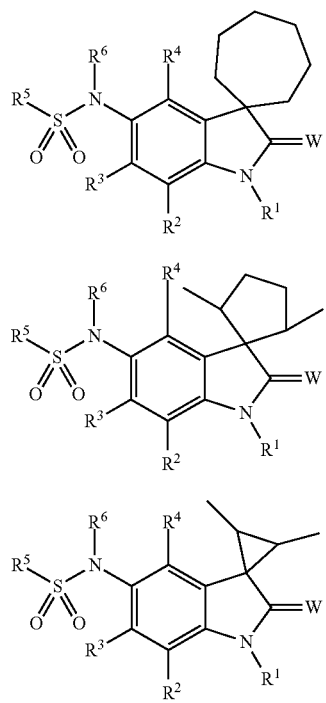

in which

R¹ represents methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-allylcyclopropyl, 1-vinylcyclobutyl, 1-vinylcyclopropyl, 1-ethylcyclopropyl, 2-ethylcyclopropyl, 1-ethylcyclobutyl, 2-ethylcyclobutyl, 3-ethylcyclobutyl, 4-methylcyclohexyl, 4-methoxycyclohexyl, 4-ethoxycyclohexyl, 4-n-propyloxycyclohexyl, 4-hydroxycyclohexyl, 4-methoxycyclobutyl, 1-cyclopropylcyclobutyl, 1-prop-2-enylcyclobutyl, 2-ethyl-3-methylcyclobutyl, 1-propylcyclopropyl, 1-methyl-2-propylcyclopropyl, 2-propylcyclopropyl, 1-propylcyclobutyl, 2-propylcyclobutyl, 3-propylcyclobutyl, 1-isopropylcyclobutyl, 1-isopropylcyclopropyl, 2-isopropylcyclopropyl, 3-isopropylcyclobutyl, 2-dimethylaminocyclobutyl, 3-dimethylaminocyclobutyl, 1-butylcyclobutyl, 2-butylcyclobutyl, 1-butylcyclopropyl, 3-butylcyclobutyl, 2-butylcyclopropyl, 1-isobutylcyclobutyl, 3-tert-butylcyclobutyl, 3,3-diethylcyclobutyl, 2,2-diethylcyclopropyl, 2-methylidenecyclopropyl, 1-methoxymethylcyclopropyl, 1-isobutylcyclopropyl, 2,2-difluoroethyl, 2,2,2-trifluoroethyl, 3,3,3-trifluoropropyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenydi 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, ($C_3$-$C_6$)-halocycloalkyl, ($C_2$-$C_5$)-haloalkenyl, ($C_1$-$C_5$)-alkoxy-($C_1$-$C_5$)-haloalkyl, benzyl, p-chlorobenzyl, p-methoxybenzyl, p-trifluoromethylbenzyl, p-methylbenzyl, p-fluorobenzyl, p-bromobenzyl, p-iodobenzyl, p-methylthiobenzyl, p-trifluoromethoxybenzyl, p-nitrobenzyl, p-trifluoromethylthiobenzyl, m-chlorobenzyl, m-methoxybenzyl, m-trifluoromethylbenzyl, m-methylbenzyl, m-fluorobenzyl, m-bromobenzyl, m-iodobenzyl, m-methylthiobenzyl, m-trifluoromethoxybenzyl, m-nitrobenzyl, m-trifluoromethylthiobenzyl, o-chlorobenzyl, o-methoxybenzyl, o-trifluoromethylbenzyl, o-methylbenzyl, o-fluorobenzyl, o-bromobenzyl, o-iodobenzyl, o-methylthiobenzyl, o-trifluoromethoxybenzyl, o-nitrobenzyl, o-trifluoromethylthiobenzyl, p-methoxycarbonylbenzyl, p-ethoxycarbonylbenzyl, m-methoxycarbonylbenzyl, m-ethoxycarbonylbenzyl, 2,4-dichlorobenzyl, 3,5-dichlorobenzyl, 2,4-difluorobenzyl, 3,5-difluorobenzyl, 3,4-dichlorobenzyl, 3,4-difluorobenzyl, 2,5-dichlorobenzyl, phenylethyl, p-chlorophenylethyl, p-methoxyphenylethyl, p-trifluoromethylphenylethyl, p-fluorophenylethyl, p-trifluoromethoxyphenylethyl, p-trifluoromethylthiophenylethyl, p-methylphenylethyl, p-nitrophenylethyl, p-methoxycarbonylphenylethyl, p-ethoxycarbonylphenylethyl, m-chlorophenylethyl, m-methoxyphenylethyl, m-trifluoromethylphenylethyl, m-fluorophenylethyl, m-trifluoromethoxyphenylethyl, m-trifluoromethylthiophenylethyl, m-methylphenylethyl, m-nitrophenylethyl, m-methoxycarbonylphenylethyl, m-ethoxycarbonylphenylethyl, o-chlorophenylethyl, o-methoxyphenylethyl, o-trifluoromethylphenylethyl, o-fluorophenylethyl, o-trifluoromethoxyphenylethyl, o-trifluoromethylthiophenylethyl, o-methylphenylethyl, o-nitrophenylethyl, o-methoxycarbonylphenylethyl, o-ethoxycarbonylphenylethyl, heteroaryl-($C_1$-$C_5$)-alkyl, ($C_1$-$C_5$)-haloalkenyl, heterocyclyl, heterocyclyl-($C_1$-$C_5$)-alkyl, ($C_1$-$C_5$)-alkoxy-($C_1$-$C_5$)-alkyl, ($C_1$-$C_5$)-alkylcarbonyl-($C_1$-$C_5$)-alkyl, hydroxycarbonyl-($C_1$-$C_5$)-alkyl, ($C_1$-$C_5$)-alkoxycarbonyl-($C_1$-$C_5$)-alkyl, ($C_2$-$C_5$)-alkenyloxycarbonyl-($C_1$-$C_5$)-alkyl, ($C_2$-$C_5$)-alkynyloxycarbonyl-($C_1$-$C_5$)-alkyl, aryl-($C_1$-$C_5$)-alkoxycarbonyl-($C_1$-$C_5$)-alkyl, ($C_3$-$C_6$)-cycloalkoxycarbonyl-($C_1$-$C_5$)-alkyl, ($C_3$-$C_6$)-cycloalkyl-($C_1$-$C_5$)-alkoxycarbonyl-($C_1$-$C_5$)-alkyl, aminocarbonyl-($C_1$-$C_5$)-alkyl, ($C_1$-$C_5$)-alkylaminocarbonyl-($C_1$-$C_5$)-alkyl, ($C_3$-$C_6$)-cycloalkylaminocarbonyl-($C_1$-$C_5$)-alkyl, aryl-($C_1$-$C_5$)-alkylaminocarbonyl-($C_1$-$C_5$)-alkyl, heteroaryl-($C_1$-$C_5$)-alkylaminocarbonyl-($C_1$-$C_5$)-alkyl, ($C_1$-$C_5$)-alkylthio-($C_1$-$C_5$)-alkyl, ($C_3$-$C_5$)-cycloalkylthio-($C_1$-$C_5$)-alkyl, arylthio-($C_1$-$C_5$)-alkyl, heterocyclylthio-($C_1$-$C_5$)-alkyl, heteroarylthio-($C_1$-$C_5$)-alkyl, aryl-($C_1$-$C_5$)-alkylthio-($C_1$-$C_5$)-alkyl, ($C_1$-$C_5$)-alkylsulfinyl-($C_1$-$C_5$)-alkyl, ($C_1$-$C_5$)-alkylsulfonyl-($C_1$-$C_5$)-alkyl, arylsulfinyl-($C_1$-$C_5$)-alkyl, arylsulfonyl-($C_1$-$C_5$)-alkyl, ($C_3$-$C_6$)-cycloalkylsulfinyl-($C_1$-$C_5$)-alkyl, ($C_3$-$C_6$)-cycloalkylsulfonyl-($C_1$-$C_5$)-alkyl, ($C_1$-$C_5$)-alkoxy-($C_1$-$C_5$)-alkoxy-($C_1$-$C_5$)-alkyl, ($C_1$-$C_5$)-alkylcarbonyl, ($C_3$-$C_6$)-cycloalkylcarbonyl, ($C_1$-$C_5$)-alkoxycarbonyl, aryl-($C_1$-$C_5$)-alkoxycarbonyl, arylcarbonyl, heteroarylcarbonyl, heterocyclylcarbonyl, aryl-($C_1$-$C_5$)-alkylcarbonyl, ($C_1$-$C_5$)-alkylaminocarbonyl, ($C_3$-$C_6$)-cycloalkylaminocarbonyl, arylaminocarbonyl, aryl-($C_1$-$C_5$)-alkylaminocarbonyl, ($C_1$-$C_5$)-alkylsulfonyl, ($C_3$-$C_6$)-cycloalkylsulfonyl, arylsulfonyl, heteroarylsulfonyl, heterocyclylsulfonyl, bis-[($C_1$-$C_5$)-alkyl]amino, ($C_3$-$C_6$)-cycloalkyl[($C_1$-$C_5$)-alkyl]amino, $R^2$, $R^3$, $R^4$ independently of one another represent hydrogen, fluorine, chlorine, bromine, iodine, methoxy, ethoxy, n-propyloxy, isopropyloxy, methyl, ethyl, isopropyl, trifluoromethyl, difluoromethyl, pentafluoroethyl, trifluoromethoxy, difluoromethoxy, 2,2-difluoroethoxy, 3,3,3-trifluoroethoxy, methylthio, ethylthio, trifluoromethylthio, optionally substituted phenyl, heteroaryl, heterocyclyl, cyclopropyl, cyclobutyl, cyclopentyl, cyclohexyl, $R^5$ represents aryl-($C_1$-$C_5$)-alkyl, heteroaryl-($C_1$-$C_5$)-alkyl, heterocyclyl-($C_1$-$C_5$)-alkyl, aryloxy-($C_1$-$C_5$)-alkyl, heteroaryloxy-($C_1$-$C_5$)-alkyl, phenylethenyl, p-chlorophenylethenyl, p-methylphenylethenyl, p-methoxyphenylethenyl, p-trifluoromethylphenylethenyl, p-fluorophenylethenyl, p-cyanophenylethenyl, p-trifluoromethoxyphenylethenyl, p-nitrophenylethenyl, p-bromophenylethenyl, p-iodophenylethenyl, m-chlorophenylethenyl, m-methylphenylethenyl, m-methoxyphenylethenyl, m-trifluoromethylphenylethenyl, m-fluorophenylethenyl, m-cyanophenylethenyl, m-trifluoromethoxyphenylethenyl, m-nitrophenylethenyl, m-bromophenylethenyl, m-iodophenylethenyl, p-methoxycarbonylphenylethenyl, m-methoxycarbonylphenylethenyl, o-methoxycarbonylphenylethenyl, p-ethoxycarbonylphenylethenyl, m-ethoxycarbonylphenylethenyl, o-ethoxycarbonylphenylethenyl, heteroaryl-($C_2$-$C_5$)-alkenyl, heterocyclyl-($C_2$-$C_5$)-alkenyl, $R^6$ represents hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, cyclopentylmethyl, cyclohexylmethyl, 2,2-difluoroethyl, 2,2,2-trifluoroethyl, 3,3,3-trifluoropropyl, cyanomethyl, cyanoethyl, cyano-n-propyl, cyclopropylcarbonyl, cyclobutylcarbonyl, cyclopentylcarbonyl, cyclohexylcarbonyl, methoxycarbonyl, ($C_1$-$C_5$)-alkylsulfonyl, arylsulfonyl, aryl-($C_1$-$C_5$)-alkylsulfonyl, heteroarylsulfonyl, ($C_3$-$C_6$)-cycloalkylsulfonyl, heterocyclylsulfonyl, ($C_1$-$C_5$)-alkylcarbonyl, arylcarbonyl, heteroarylcarbonyl, heterocyclylcarbonyl, ($C_1$-$C_5$)-alkoxycarbonyl, aryl-($C_1$-$C_5$)-alkoxycarbonyl, ($C_1$-$C_5$)-haloalkylcarbonyl, ($C_2$-$C_5$)-alkenyl, ($C_2$-$C_5$)-alkynyl, halo-($C_2$-$C_5$)-alkynyl, halo-($C_2$-$C_5$)-alkenyl, ($C_1$-$C_5$)-alkoxy-($C_1$-$C_5$)-alkyl, W represents oxygen or sulfur, preferably oxygen.

With regard to the compounds according to the invention, the terms used above and further below will be elucidated. These are familiar to the person skilled in the art and especially have the definitions elucidated hereinafter:

According to the invention, "arylsulfonyl" represents optionally substituted phenylsulfonyl or optionally substituted polycyclic arylsulfonyl, here especially optionally substituted naphthylsulfonyl, for example substituted by fluorine, chlorine, bromine, iodine, cyano, nitro, alkyl, haloalkyl, haloalkoxy, amino, alkylamino, alkylcarbonylamino, dialkylamino or alkoxy groups.

According to the invention, "cycloalkylsulfonyl"—alone or as part of a chemical group—represents optionally substituted cycloalkylsulfonyl, preferably having 3 to 6 carbon atoms, for example cyclopropylsulfonyl, cyclobutylsulfonyl, cyclopentylsulfonyl or cyclohexylsulfonyl.

According to the invention, "alkylsulfonyl"—alone or as part of a chemical group—represents straight-chain or branched alkylsulfonyl, preferably having 1 to 8 or 1 to 6 carbon atoms, for example (but not limited to) ($C_1$-$C_6$)-alkylsulfonyl such as methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2- trimethylpropylsulfonyl, 1-ethyl-1-methylpropylsulfonyl and 1-ethyl-2-methylpropylsulfonyl.

According to the invention, "heteroarylsulfonyl" represents optionally substituted pyridylsulfonyl, pyrimidinylsulfonyl, pyrazinylsulfonyl or optionally substituted polycyclic heteroarylsulfonyl, here in particular optionally substituted quinolinylsulfonyl, for example substituted by fluorine, chlorine, bromine, iodine, cyano, nitro, alkyl, haloalkyl, haloalkoxy, amino, alkylamino, alkylcarbonylamino, dialkylamino or alkoxy groups.

According to the invention, "alkylthio"—alone or as part of a chemical group—represents straight-chain or branched S-alkyl, preferably having 1 to 8 or 1 to 6 carbon atoms, such as $(C_1-C_{10})$-, $(C_1-C_6)$- or $(C_1-C_4)$-alkylthio, for example (but not limited to) $(C_1-C_6)$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio.

According to the invention, alkenylthio means an alkenyl radical bonded via a sulfur atom, alkynylthio is an alkynyl radical bonded via a sulfur atom, cycloalkylthio is a cycloalkyl radical bonded via a sulfur atom, and cycloalkenylthio is a cycloalkenyl radical bonded via a sulfur atom.

According to the invention, alkylsulfinyl (alkyl-S(=O)—), unless defined differently elsewhere, represents alkyl radicals which are attached to the skeleton via —S(=O)—, such as $(C_1-C_{10})$-, $(C_1-C_6)$- or $(C_1-C_4)$-alkylsulfinyl, for example (but not limited to) $(C_1-C_6)$-alkylsulfinyl such as methylsulfinyl, ethylsulfinyl, propylsulfinyl, 1-methylethylsulfinyl, butylsulfinyl, 1-methylpropylsulfinyl, 2-methylpropylulfinyl, 1,1-dimethylethylsulfinyl, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

According to the invention, alkenylsulfinyl and alkynylsulfinyl are defined analogously as alkenyl and alkynyl radicals, respectively, which are attached to the skeleton via —S(=O)—, such as $(C_2-C_{10})$-, $(C_2-C_6)$- or $(C_2-C_4)$-alkenylsulfinyl or $(C_3-C_{10})$-, $(C_3-C_6)$- or $(C_3-C_4)$-alkynylsulfinyl.

According to the invention, alkenylsulfonyl and alkynylsulfonyl are defined analogously as alkenyl and alkynyl radicals, respectively, which are attached to the skeleton via —S(=O)$_2$—, such as $(C_2-C_{10})$-, $(C_2-C_6)$- or $(C_2-C_4)$-alkenylsulfonyl or $(C_3-C_{10})$-, $(C_3-C_6)$- or $(C_3-C_4)$-alkynylsulfonyl.

"Alkoxy" represents an alkyl radical which is attached via an oxygen atom, for example (but not limited to) $(C_1-C_6)$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Alkenyloxy means an alkenyl radical which is attached via an oxygen atom, alkynyloxy means an alkynyl radical which is attached via an oxygen atom, such as $(C_2-C_{10})$-, $(C_2-C_6)$- or $(C_2-C_4)$-alkenoxy and $(C_3-C_{10})$-, $(C_3-C_6)$- or $(C_3-C_4)$-alkynoxy, respectively.

"Cycloalkyloxy" means a cycloalkyl radical which is attached via an oxygen atom and cycloalkenyloxy means a cycloalkenyl radical which is attached via an oxygen atom.

According to the invention, "alkylcarbonyl" (alkyl-C(=O)—), unless defined differently elsewhere, represents alkyl radicals which are attached to the skeleton via —C(=O)—, such as $(C_1-C_{10})$-, $(C_1-C_6)$- or $(C_1-C_4)$-alkylcarbonyl. Here, the number of the carbon atoms refers to the alkyl radical in the alkylcarbonyl group.

According to the invention, "alkenylcarbonyl" and "alkynylcarbonyl", unless defined differently elsewhere, analogously represent alkenyl and alkynyl radicals, respectively, which are attached to the skeleton via —C(=O)—, such as $(C_2-C_{10})$-, $(C_2-C_6)$- or $(C_2-C_4)$-alkenylcarbonyl and $(C_2-C_{10})$-, $(C_2-C_6)$- and $(C_2-C_4)$-alkynylcarbonyl, respectively. Here, the number of the carbon atoms refers to the alkenyl or alkynyl radical in the alkenyl or alkynyl group.

Alkoxycarbonyl (alkyl-O—C(=O)—), unless defined differently elsewhere: alkyl radicals which are attached to the skeleton via —O—C(=O)—, such as $(C_1-C_{10})$-, $(C_1-C_6)$- or $(C_1-C_4)$-alkoxycarbonyl. Here, the number of the carbon atoms refers to the alkyl radical in the alkoxycarbonyl group.

According to the invention, "alkenyloxycarbonyl" and "alkynyloxycarbonyl", unless defined differently elsewhere, analogously represent alkenyl and alkynyl radicals, respectively, which are attached to the skeleton via —O—C(=O)—, such as $(C_2-C_{10})$-, $(C_2-C_6)$- or $(C_2-C_4)$-alkenyloxycarbonyl and $(C_3-C_{10})$-, $(C_3-C_6)$- and $(C_3-C_4)$-alkynyloxycarbonyl, respectively. Here, the number of the carbon atoms refers to the alkenyl or alkynyl radical in the alkenyloxycarbonyl or alkynyloxycarbonyl group.

According to the invention, the term "alkylcarbonyloxy" (alkyl-C(=O)—O—), unless defined differently elsewhere, represents alkyl radicals which are attached to the skeleton via the oxygen of a carbonyloxy group (—C(=O)—O—), such as $(C_1-C_{10})$-, $(C_1-C_6)$- or $(C_1-C_4)$-alkylcarbonyloxy. Here, the number of the carbon atoms refers to the alkyl radical in the alkylcarbonyloxy group.

According to the invention, "alkenylcarbonyloxy" and "alkynylcarbonyloxy" are defined analogously as alkenyl and alkynyl radicals, respectively, which are attached to the skeleton via the oxygen of (—C(=O)—O—), such as $(C_2-C_{10})$-, $(C_2-C_6)$- or $(C_2-C_4)$-alkenylcarbonyloxy or $(C_2-C_{10})$-, $(C_2-C_6)$- or $(C_2-C_4)$-alkynylcarbonyloxy. Here, the number of the carbon atoms refers to the alkenyl or alkynyl radical in the alkenyl- or alkynylcarbonyloxy group respectively.

The term "aryl" means an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems, such as tetrahydronaphthyl, indenyl, indanyl, fluorenyl, biphenylyl, where the bonding site is on the aromatic system. In systematic terms, "aryl" is generally also encompassed by the term "optionally substituted phenyl". Here, preferred aryl substituents are, for example, hydrogen, halogen, alkyl, cycloalkyl, cycloalkylalkyl, cycloalkenyl, halocycloalkyl, alkenyl, alkynyl, aryl, arylalkyl, arylalkenyl, heteroaryl, heteroarylalkyl, heterocyclyl, heterocyclylalkyl, alkoxyalkyl, alkylthio, haloalkylthio, haloalkyl, alkoxy, haloalkoxy, cycloalkoxy, cycloalkylalkoxy, aryloxy, heterorary1oxy, alkoxyalkoxy, alkynylalkoxy, alkenyloxy, bis-alkylaminoalkoxy, tris-[alkyl]silyl, bis-[alkyl]arylsilyl, bis-[alkyl]alkylsilyl, tris-[alkyl]silylalkynyl, arylalkynyl, heteroarylalkynyl, alkylalkynyl, cycloalkylalkynyl, haloalkylalkynyl, heterocyclyl-N-alkoxy, nitro, cyano, amino, alkylamino, bis-alkylamino, alkylcarbonylamino, cycloalkylcarbonylamino, arylcarbonylamino, alkoxycarbonylamino, alkoxycarbonylalkylamino, arylalkoxycarbonylalkylamino, hydroxycarbonyl, alkoxycarbonyl, aminocarbonyl, alkylaminocarbonyl, cycloalkylaminocarbonyl, bis-alkylaminocarbonyl, heteroarylalkoxy, arylalkoxy.

A heterocyclic radical (heterocyclyl) contains at least one heterocyclic ring (=carbocyclic ring in which at least one carbon atom has been replaced by a heteroatom, preferably by a heteroatom from the group of N, O, S, P) which is saturated, unsaturated, partly saturated or heteroaromatic and may be unsubstituted or substituted, in which case the bonding site is localized on a ring atom. If the heterocyclyl radical or the heterocyclic ring is optionally substituted, it may be fused to other carbocyclic or heterocyclic rings. In the case of optionally substituted heterocyclyl, polycyclic systems are also included, for example 8-azabicyclo[3.2.1]octanyl, 8-azabicyclo[2.2.2]octanyl or 1-azabicyclo[2.2.1]heptyl. In the case of optionally substituted heterocyclyl, spirocyclic systems are also included, for example 1-oxa-5-azaspiro[2.3]hexyl. Unless defined otherwise, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group of N, O and S, although no two oxygen atoms should be directly adjacent to one another, for example having one heteroatom from the group of N, O and S 1- or 2- or 3-pyrrolidinyl, 3,4-dihydro-2H-pyrrol-2- or 3-yl, 2,3-dihydro-1H-pyrrol-1- or 2- or 3- or 4- or 5-yl, 2,5-dihydro-1H-pyrrol-1- or 2- or 3-yl, 1- or 2- or 3- or 4-piperidinyl; 2,3,4,5-tetrahydropyridin-2- or 3- or 4- or 5-yl or 6-yl; 1,2,3,6-tetrahydropyridin-1- or 2- or 3- or 4- or 5- or 6-yl, 1,2,3,4-tetrahydropyridin-1- or 2- or 3- or 4- or 5- or 6-yl; 1,4-dihydropyridin-1- or 2- or 3- or 4-yl; 2,3-dihydropyridin-2- or 3- or 4- or 5- or 6-yl, 2,5-dihydropyridin-2- or 3- or 4- or 5- or 6-yl, 1- or 2- or 3- or 4-azepanyl, 2,3,4,5-tetrahydro-1H-azepin-1- or 2- or 3- or 4- or 5- or 6- or 7-yl, 2,3,4,7-tetrahydro-1H-azepin-1- or 2- or 3- or 4- or 5- or 6- or 7-yl; 2,3,6,7-tetrahydro-1H-azepin-1- or 2- or 3- or 4-yl; 3,4,5,6-tetrahydro-2H-azepin-2- or 3- or 4- or 5- or 6- or 7-yl; 4,5-dihydro-1H-azepin-1- or 2- or 3- or 4-yl, 2,5-dihydro-1H-azepin-1- or -2- or 3- or 4- or 5- or 6- or 7-yl, 2,7-dihydro-1H-azepin-1- or -2- or 3- or 4-yl, 2,3-dihydro-1H-azepin-1- or -2- or 3- or 4- or 5- or 6- or 7-yl, 3,4-dihydro-2H-azepin-2- or 3- or 4- or 5- or 6- or 7-yl; 3,6-dihydro-2H-azepin-2- or 3- or 4- or 5- or 6- or 7-yl; 5,6-dihydro-2H-azepin-2- or 3- or 4- or 5- or 6- or 7-yl; 4,5-dihydro-3H-azepin-2- or 3- or 4- or 5- or 6- or 7-yl; 1H-azepin-1- or -2- or 3- or 4- or 5- or 6- or 7-yl; 2H-azepin-2- or 3- or 4- or 5- or 6- or 7-yl; 3H-azepin-2- or 3- or 4- or 5- or 6- or 7-yl; 4H-azepin-2- or 3- or 4- or 5- or 6- or 7-yl, 2- or 3-oxolanyl (=2- or 3-tetrahydrofuranyl); 2,3-dihydrofuran-2- or 3- or 4- or 5-yl; 2,5-dihydrofuran-2- or 3-yl, 2- or 3- or 4-oxanyl (=2- or 3- or 4-tetrahydropyranyl), 3,4-dihydro-2H-pyran-2- or 3- or 4- or 5- or 6-yl; 3,6-dihydro-2H-pyran-2- or 3- or 4- or 5- or 6-yl; 2H-pyran-2- or 3- or 4- or 5- or 6-yl; 4H-pyran-2- or 3- or 4-yl, 2- or 3- or 4-oxepanyl; 2,3,4,5-tetrahydrooxepin-2- or 3- or 4- or 5- or 6- or 7-yl; 2,3,4,7-tetrahydrooxepin-2- or 3- or 4- or 5- or 6- or 7-yl; 2,3,6,7-tetrahydrooxepin-2- or 3- or 4-yl; 2,3-dihydrooxepin-2- or 3- or 4- or 5- or 6- or 7-yl; 4,5-dihydrooxepin-2- or 3- or 4-yl; 2,5-dihydrooxepin-2- or 3- or 4- or 5- or 6- or 7-yl; oxepin-2- or 3- or 4- or 5- or 6- or 7-yl; 2- or 3-tetrahydrothiophenyl; 2,3-dihydrothiophen-2- or 3- or 4- or 5-yl; 2,5-dihydrothiophen-2- or 3-yl; tetrahydro-2H-thiopyran-2- or 3- or 4-yl; 3,4-dihydro-2H-thiopyran-2- or 3- or 4- or 5- or 6-yl; 3,6-dihydro-2H-thiopyran-2- or 3- or 4- or 5- or 6-yl; 2H-thiopyran-2- or 3- or 4- or 5- or 6-yl; 4H-rhiopyran-2- or 3- or 4-yl. Preferred 3-membered and 4-membered heterocycles are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl. Further examples of "heterocyclyl" are a partly or fully hydrogenated heterocyclic radical having two heteroatoms from the group of N, O and S, for example 1- or 2- or 3- or 4-pyrazolidinyl; 4,5-dihydro-3H-pyrazol-3- or 4- or 5-yl; 4,5-dihydro-1H-pyrazol-1- or 3- or 4- or 5-yl; 2,3-dihydro-1H-pyrazol-1- or 2- or 3- or 4- or 5-yl; 1- or 2- or 3- or 4-imidazolidinyl, 2,3-dihydro-1H-imidazol-1- or 2- or 3- or 4-yl; 2,5-dihydro-1H-imidazol-1- or 2- or 4- or 5-yl; 4,5-dihydro-1H-imidazol-1- or 2- or 4- or 5-yl; hexahydropyridazin-1- or 2- or 3- or 4-yl, 1,2,3,4-tetrahydropyridazin-1- or 2- or 3- or 4- or 5- or 6-yl, 1,2,3,6-tetrahydropyridazin-1- or 2- or 3- or 4- or 5- or 6-yl, 1,4,5,6-tetrahydropyridazin-1- or 3- or 4- or 5- or 6-yl; 3,4,5,6-tetrahydropyridazin-3- or 4- or 5-yl; 4,5-dihydropyridazin-3- or 4-yl; 3,4-dihydropyridazin-3- or 4- or 5- or 6-yl; 3,6-dihydropyridazin-3- or 4-yl; 1,6-dihydropyriazin-1- or 3- or 4- or 5- or 6-yl, hexahydropyrimidin-1- or 2- or 3- or 4-yl, 1,4,5,6-tetrahydropyrimidin-1- or 2- or 4- or 5- or 6-yl; 1,2,5,6-tetrahydropyrimidin-1- or 2- or 4- or 5- or 6-yl; 1,2,3,4-tetrahydropyrimidin-1- or 2- or 3- or 4- or 5- or 6-yl; 1,6-dihydropyrimidin-1- or 2- or 4- or 5- or 6-yl, 1,2-dihydropyrimidin-1- or 2- or 4- or 5- or 6-yl; 2,5-dihydropyrimidin-2- or 4- or 5-yl; 4,5-dihydropyrimidin-4- or 5- or 6-yl; 1,4-dihydropyrimidin-1- or 2- or 4- or 5- or 6-yl, 1- or 2- or 3-piperazinyl, 1,2,3,6-tetrahydropyrazin-1- or 2- or 3- or 5- or 6-yl; 1,2,3,4-tetrahydropyrazin-1- or 2- or 3- or 4- or 5- or 6-yl, 1,2-dihydropyrazin-1- or 2- or 3- or 5- or 6-yl, 1,4-dihydropyrazin-1- or 2- or 3-yl; 2,3-dihydropyrazin-2- or 3- or 5- or 6-yl; 2,5-dihydropyrazin-2- or 3-yl; 1,3-dioxolan-2- or 4- or 5-yl; 1,3-dioxol-2- or 4-yl; 1,3-dioxan-2- or 4- or 5-yl; 4H-1,3-dioxin-2- or 4- or 5- or 6-yl; 1,4-dioxan-2- or 3- or 5- or 6-yl; 2,3-dihydro-1,4-dioxin-2- or 3- or 5- or 6-yl; 1,4-dioxin-2- or 3-yl; 1,2-dithiolan-3- or 4-yl; 3H-1,2-dithiol-3- or 4- or 5-yl; 1,3-dithiolan-2- or 4-yl; 1,3-dithiol-2- or 4-yl; 1,2-dithian-3- or 4-yl; 3,4-dihydro-1,2-dithiin-3- or 4- or 5- or 6-yl; 3,6-dihydro-1,2-dithiin-3- or 4-yl; 1,2-dithiin-3- or 4-yl; 1,3-dithian-2- or 4- or 5-yl; 4H-1,3-dithiin-2- or 4- or 5- or 6-yl; isoxazolidin-2- or 3- or 4- or 5-yl; 2,3-dihydroisoxazol-2- or 3- or 4- or 5-yl; 2,5-dihydroisoxazol-2- or 3- or 4- or 5-yl; 4,5-dihydroisoxazol-3- or 4- or 5-yl; 1,3-oxazolidin-2- or 3- or 4- or 5-yl; 2,3-dihydro-1,3-oxazol-2- or 3- or 4- or 5-yl; 2,5-dihydro- 1,3-oxazol-2- or 4- or 5-yl; 4,5-dihydro-1,3-oxazol-2- or 4- or 5-yl; 1,2-oxazinan-2- or 3- or 4- or 5- or 6-yl; 3,4-dihydro-2H-1,2-oxazin-2- or 3- or 4- or 5- or 6-yl; 3,6-dihydro-2H-1,2-oxazin-2- or 3- or 4- or 5- or 6-yl; 5,6-dihydro-2H-1,2-oxazin-2- or 3- or 4- or 5- or 6-yl; 5,6-dihydro-4H-1,2-oxazin-3- or 4- or 5- or 6-yl; 2H-1,2-oxazin-2- or 3- or 4- or 5- or 6-yl; 6H-1,2-oxazin-3- or 4- or 5- or 6-yl; 4H-1,2-oxazin-3- or 4- or 5- or 6-yl; 1,3-oxazinan-2- or 3- or 4- or 5- or 6-yl; 3,4-dihydro-2H-1,3-oxazin-2- or 3- or 4- or 5- or 6-yl; 3,6-dihydro-2H-1,3-oxazin-2- or 3- or 4- or 5- or 6-yl; 5,6-dihydro-2H-1,3-oxazin-2- or 4- or 5- or 6-yl; 5,6-dihydro-4H-1,3-oxazin-2- or 4- or 5- or 6-yl; 2H-1,3-oxazin-2- or 4- or 5- or 6-yl; 6H-1,3-oxazin-2- or 4- or 5- or 6-yl; 4H-1,3-oxazin-2- or 4- or 5- or 6-yl; morpholin-2- or 3- or 4-yl; 3,4-dihydro-2H-1,4-oxazin-2- or 3- or 4- or 5- or 6-yl; 3,6-dihydro-2H-1,4-oxazin-2- or 3- or 5- or 6-yl; 2H-1,4-oxazin-2- or 3- or 5- or 6-yl; 4H-1,4-oxazin-2- or 3-yl; 1,2-oxazepan-2- or 3- or 4- or 5- or 6- or 7-yl; 2,3,4,5-tetrahydro-1,2-oxazepin-2- or 3- or 4- or 5- or 6- or 7-yl; 2,3,4,7-tetrahydro-1,2-oxazepin-2- or 3- or 4- or 5- or 6- or 7-yl; 2,3,6,7-tetrahydro-1,2-oxazepin-2- or 3- or 4- or 5- or 6- or 7-yl; 2,5,6,7-tetrahydro-1,2-oxazepin-2- or 3- or 4- or 5- or 6- or 7-yl; 4,5,6,7-tetrahydro-1,2-oxazepin-3- or 4- or 5- or 6- or 7-yl; 2,3-dihydro-1,2-oxazepin-2- or 3- or 4- or 5- or 6- or 7-yl; 2,5-dihydro-1,2-oxazepin-2- or 3- or 4- or 5- or 6- or 7-yl; 2,7-dihydro-1,2-oxazepin-2- or 3- or 4- or 5- or 6- or 7-yl; 4,5-dihydro-1,2-oxazepin-3- or 4- or 5- or 6- or 7-yl; 4,7-dihydro-1,2-oxazepin-3- or 4- or 5- or 6- or 7-yl; 6,7-dihydro-1,2-oxazepin-3- or 4- or 5- or 6- or 7-yl; 1,2-oxazepin-3- or 4- or 5- or 6- or 7-yl; 1,3-oxazepan-2- or 3- or 4- or 5- or 6- or 7-yl; 2,3,4,5-tetrahydro-1,3-oxazepin-2- or 3- or 4- or 5- or 6- or 7-yl; 2,3,4,7-tetrahydro-1,3-oxazepin-2- or 3- or 4- or 5- or 6- or 7-yl; 2,3,6,7-tetrahydro-1,3-oxazepin-2- or 3- or 4- or 5- or 6- or 7-yl; 2,5,6,7-tetrahydro-1,3-oxazepin-2- or 4- or 5- or 6- or 7-yl; 4,5,6,7-tetrahydro-1,3-oxazepin-2- or 4- or 5- or 6- or 7-yl; 2,3-dihydro-1,3-oxazepin-2- or 3- or 4- or 5- or 6- or 7-yl; 2,5-dihydro-1,3-oxazepin-2- or 4- or 5- or 6- or 7-yl; 2,7-dihydro-1,3-oxazepin-2- or 4- or 5- or 6- or 7-yl; 4,5-dihydro-1,3-oxazepin-2- or 4- or 5- or 6- or 7-yl; 4,7-dihydro-1,3-oxazepin-2- or 4- or 5- or 6- or 7-yl; 6,7-dihydro-1,3-oxazepin-2- or 4- or 5- or 6- or 7-yl; 1,3-oxazepin-2- or 4- or 5- or 6- or 7-yl; 1,4-oxazepan-2- or 3- or 5- or 6- or 7-yl; 2,3,4,5-tetrahydro-1,4-oxazepin-2- or 3- or 4- or 5- or 6- or 7-yl; 2,3,4,7-tetrahydro-1,4-oxazepin-2- or 3- or 4- or 5- or 6- or 7-yl; 2,3,6,7-tetrahydro-1,4-oxazepin-2- or 3- or 5- or 6- or 7-yl; 2,5,6,7-tetrahydro-1,4-oxazepin-2- or 3- or 5- or 6- or 7-yl; 4,5,6,7-tetrahydro-1,4-oxazepin-2- or 3- or 4- or 5- or 6- or 7-yl; 2,3-dihydro-1,4-oxazepin-2- or 3- or 5- or 6- or 7-yl; 2,5-dihydro-1,4-oxazepin-2- or 3- or 5- or 6- or 7-yl; 2,7-dihydro-1,4-oxazepin-2- or 3- or 5- or 6- or 7-yl; 4,5-dihydro-1,4-oxazepin-2- or 3- or 4- or 5- or 6- or 7-yl; 4,7-dihydro-1,4-oxazepin-2- or 3- or 4- or 5- or 6- or 7-yl; 6,7-dihydro-1,4-oxazepin-2- or 3- or 5- or 6- or 7-yl; 1,4-oxazepin-2- or 3- or 5- or 6- or 7-yl; isothiazolidin-2- or 3- or 4- or 5-yl; 2,3-dihydroisothiazol-2- or 3- or 4- or 5-yl; 2,5-dihydroisothiazol-2- or 3- or 4- or 5-yl; 4,5-dihydroisothiazol-3- or 4- or 5-yl; 1,3-thiazolidin-2- or 3- or 4- or 5-yl; 2,3-dihydro-1,3-thiazol-2- or 3- or 4- or 5-yl; 2,5-dihydro-1,3-thiazol-2- or 4- or 5-yl; 4,5-dihydro-1,3-thiazol-2- or 4- or 5-yl; 1,3-thiazinan-2- or 3- or 4- or 5- or 6-yl; 3,4-dihydro-2H-1,3-thiazin-2- or 3- or 4- or 5- or 6-yl; 3,6-dihydro-2H-1,3-thiazin-2- or 3- or 4- or 5- or 6-yl; 5,6-dihydro-2H-1,3-thiazin-2- or 4- or 5- or 6-yl; 5,6-dihydro-4H-1,3-thiazin-2- or 4- or 5- or 6-yl; 2H-1,3-thiazin-2- or 4- or 5- or 6-yl; 6H-1,3-thiazin-2- or 4- or 5- or 6-yl; 4H-1,3-thiazin-2- or 4- or 5- or 6-yl. Further examples of "heterocyclyl" are a partly or fully hydrogenated heterocyclic radical having 3 heteroatoms from the group of N, O and S, for example 1,4,2-dioxazolidin-2- or 3- or 5-yl; 1,4,2-dioxazol-3- or 5-yl; 1,4,2-dioxazinan-2- or -3- or 5- or 6-yl; 5,6-dihydro-1,4,2-dioxazin-3- or 5- or 6-yl; 1,4,2-dioxazin-3- or 5- or 6-yl; 1,4,2-dioxazepan-2- or 3- or 5- or 6- or 7-yl; 6,7-dihydro-5H-1,4,2-dioxazepin-3- or 5- or 6- or 7-yl; 2,3-dihydro-7H-1,4,2-dioxazepin-2- or 3- or 5- or 6- or 7-yl; 2,3-dihydro-5H-1,4,2-dioxazepin-2- or 3- or 5- or 6- or 7-yl; 5H-1,4,2-dioxazepin-3- or 5- or 6- or 7-yl; 7H-1,4,2-dioxazepin-3- or 5- or 6- or 7-yl. Structural examples of heterocycles which are optionally substituted further are also listed below:

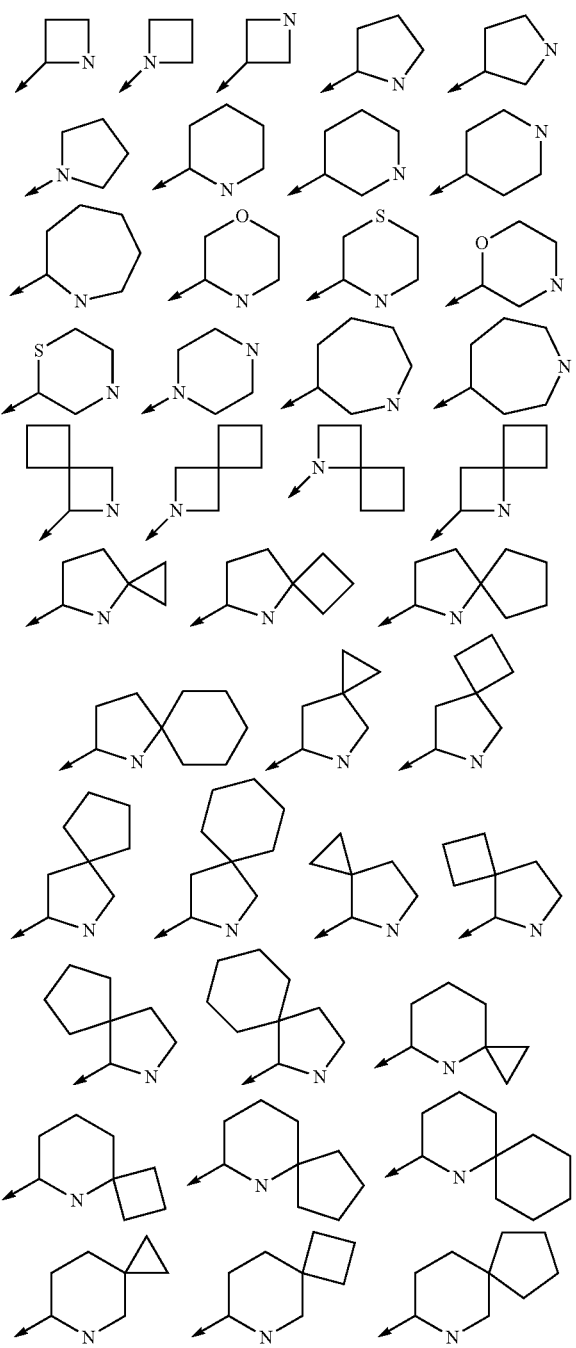

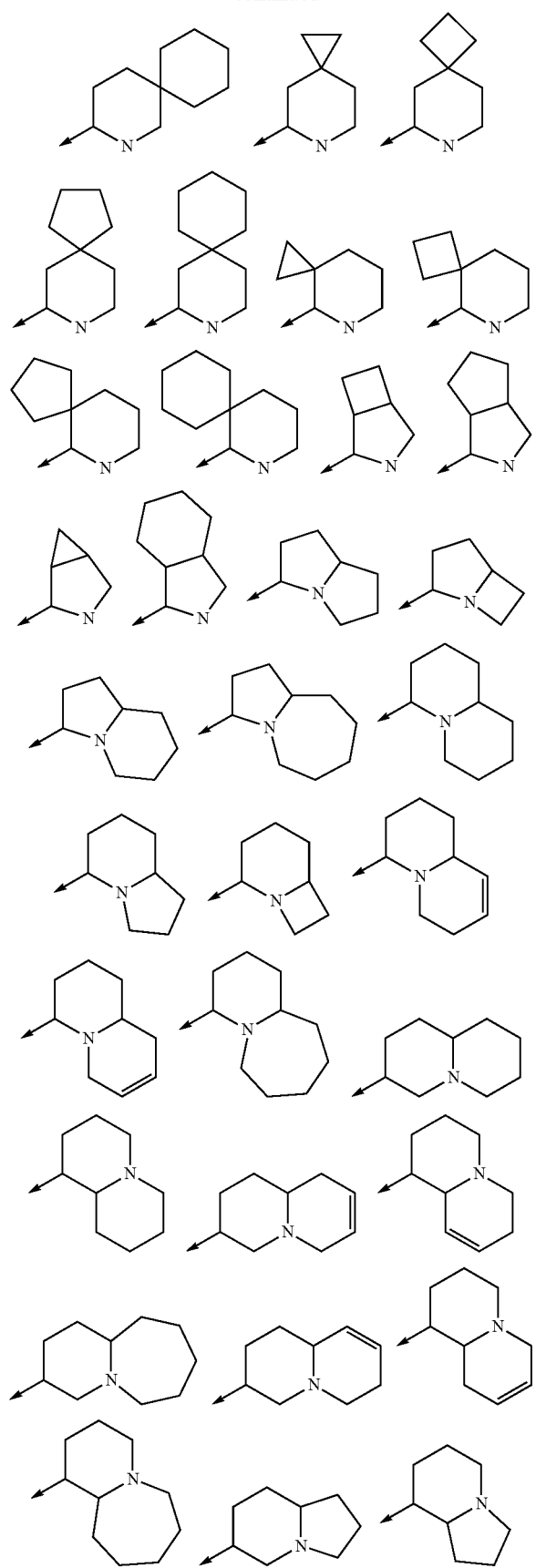
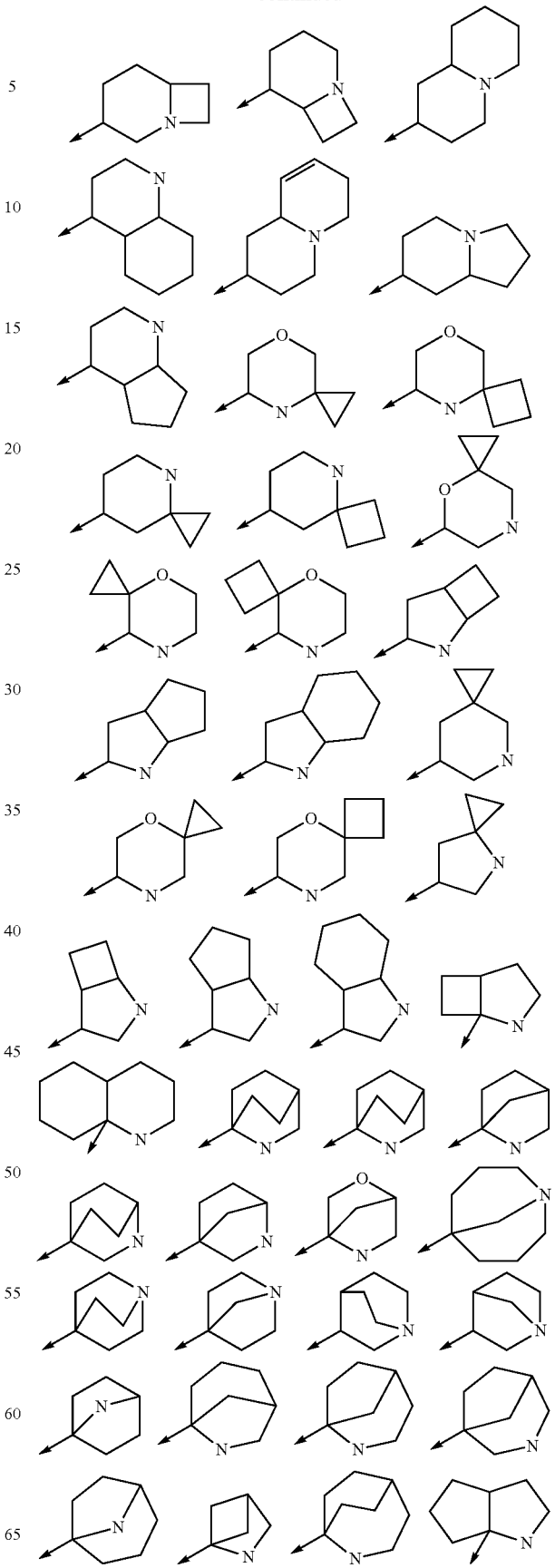

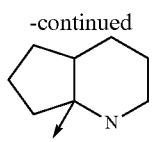

The heterocycles listed above are preferably substituted, for example, by hydrogen, halogen, alkyl, haloalkyl, hydroxyl, alkoxy, cycloalkoxy, aryloxy, alkoxyalkyl, alkoxyalkoxy, cycloalkyl, halocycloalkyl, aryl, arylalkyl, heteroaryl, heterocyclyl, alkenyl, alkylcarbonyl, cycloalkylcarbonyl, arylcarbonyl, heteroarylcarbonyl, alkoxycarbonyl, hydroxycarbonyl, cycloalkoxycarbonyl, cycloalkylalkoxycarbonyl, alkoxycarbonylalkyl, arylalkoxycarbonyl, arylalkoxycarbonylalkyl, alkynyl, alkynylalkyl, alkylalkynyl, trisalkylsilylalkynyl, nitro, amino, cyano, haloalkoxy, haloalkylthio, alkylthio, hydrothio, hydroxyalkyl, oxo, heteroarylalkoxy, arylalkoxy, heterocyclylalkoxy, heterocyclylalkylthio, heterocyclyloxy, heterocyclylthio, heteroaryloxy, bisalkylamino, alkylamino, cycloalkylamino, hydroxycarbonylalkylamino, alkoxycarbonylalkylamino, arylalkoxycarbonylalkylamino, alkoxycarbonylalkyl(alkyl)amino, aminocarbonyl, alkylaminocarbonyl, bisalkylaminocarbonyl, cycloalkylaminocarbonyl, hydroxycarbonylalkylaminocarbonyl, alkoxycarbonylalkylaminocarbonyl, arylalkoxycarbonylalkylaminocarbonyl.

When a base structure is substituted "by one or more radicals" from a list of radicals (=group) or a generically defined group of radicals, this in each case includes simultaneous substitution by a plurality of identical and/or structurally different radicals.

In the case of a partly or fully saturated nitrogen heterocycle, this may be joined to the remainder of the molecule either via carbon or via the nitrogen.

Suitable substituents for a substituted heterocyclic radical are the substituents specified further down, and additionally also oxo and thioxo. The oxo group as a substituent on a ring carbon atom is then, for example, a carbonyl group in the heterocyclic ring. As a result, lactones and lactams are preferably also included. The oxo group may also be present on the ring heteroatoms, which can exist in various oxidation states, for example on N and S, in which case they form, for example, the divalent groups N(O), S(O) (also SO for short) and S(O)2 (also SO2 for short) in the heterocyclic ring. In the case of —N(O)— and —S(O)— groups, both enantiomers in each case are included.

According to the invention, the expression "heteroaryl" represents heteroaromatic compounds, i.e. fully unsaturated aromatic heterocyclic compounds, preferably 5- to 7-membered rings having 1 to 4, preferably 1 or 2, identical or different heteroatoms, preferably O, S or N. Heteroaryls according to the invention are, for example, 1H-pyrrol-1-yl, 1H-pyrrol-2-yl; 1H-pyrrol-3-yl; furan-2-yl; furan-3-yl; thien-2-yl; thien-3-yl; 1H-imidazol-1-yl, 1H-imidazol-2-yl; 1H-imidazol-4-yl; 1H-imidazol-5-yl; 1H-pyrazol-1-yl, 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3, 2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl. The heteroaryl groups according to the invention may also be substituted by one or more identical or different radicals. If two adjacent carbon atoms are part of a further aromatic ring, the systems are fused heteroaromatic systems, such as benzofused or polyannulated heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazolines cinnoline; 1,5-naphthyridine, 1,6-naphthyridine, 1,7-naphthyridine, 1,8-naphthyridine, 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzofused rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol-4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" means, for example, fluorine, chlorine, bromine or iodine. If the term is used for a radical, "halogen" means, for example, a fluorine, chlorine, bromine or iodine atom.

According to the invention, "alkyl" means a straight-chain or branched open-chain, saturated hydrocarbon radical which is optionally mono- or polysubstituted. Preferred substituents are halogen atoms, alkoxy, haloalkoxy, cyano, alkylthio, haloalkylthio, amino or nitro groups, particular preference being given to methoxy, methyl, fluoroalkyl, cyano, nitro, fluorine, chlorine, bromine or iodine. The prefix "bis" also includes the combination of different alkyl radicals, e.g. ethyl(methyl) or methyl(ethyl).

"Haloalkyl", "-alkenyl" and "-alkynyl" are, respectively, alkyl, alkenyl and alkynyl partly or fully substituted by identical or different halogen atoms, for example monohaloalkyl such as $CH_2CH_2Cl$, $CH_2CH_2Br$, $CHClCH_3$, $CH_2Cl$, $CH_2F$; perhaloalkyl such as $CCl_3$, $CClF_2$, $CFCl_2$, $CF_2CClF_2$, $CF_2CClFCF_3$, polyhaloalkyl such as $CH_2CHFCl$, $CF_2CClFH$, $CF_2CBrFH$, $CH_2CF_3$, the term perhaloalkyl also encompasses the term perfluoroalkyl.

Partly fluorinated alkyl means a straight-chain or branched, saturated hydrocarbon which is mono- or polysubstituted by fluorine, where the fluorine atoms in question may be present as substituents on one or more different carbon atoms of the straight-chain or branched hydrocarbon chain, for example $CHFCH_3$, $CH_2CH_2F$, $CH_2CH_2CF_3$, $CHF_2$, $CH_2F$, $CHFCF_2CF_3$.

Partly fluorinated haloalkyl means a straight-chain or branched, saturated hydrocarbon which is substituted by different halogen atoms with at least one fluorine atom, where any other halogen atoms optionally present are selected from the group consisting of fluorine, chlorine or bromine, iodine. The corresponding halogen atoms may be present as substituents on one or more different carbon atoms of the straight-chain or branched hydrocarbon chain. Partly fluorinated haloalkyl also includes full substitution of the straight or branched chain by halogen including at least one fluorine atom.

Haloalkoxy is, for example, $OCF_3$, $OCHF_2$, $OCH_2F$, $OCF_2CF_3$, $OCH_2CF_3$ and $OCH_2CH_2Cl$, the situation is equivalent for haloalkenyl and other halogen-substituted radicals.

The expression "$(C_1-C_4)$-alkyl" mentioned here by way of example is a brief notation for straight-chain or branched alkyl having one to 4 carbon atoms according to the range stated for carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbyl radicals such as alkyl, alkenyl and alkynyl radicals, including in composite radicals. Alkyl radicals, including in composite radicals such as alkoxy, haloalkyl, etc., are, for example, methyl, ethyl, n-propyl or i-propyl, n-, t- or 2-butyl, pentyls, hexyls such as n-hexyl, i-hexyl and 1,3-dimethylbutyl, heptyls such as n-heptyl, 1-methylhexyl and 1,4-dimethylpentyl, alkenyl and alkynyl radicals are defined as the possible unsaturated radicals corresponding to the alkyl radicals, where at least one double bond or triple bond is present. Preference is given to radicals having one double bond or triple bond.

The term "alkenyl" also includes, in particular, straight-chain or branched open-chain hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl means, for example, vinyl which may optionally be substituted by further alkyl radicals, for example (but not limited thereto) $(C_2-C_6)$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "alkynyl" also includes, in particular, straight-chain or branched open-chain hydrocarbon radicals having more than one triple bond, or else having one or more triple bonds and one or more double bonds, for example 1,3-butatrienyl or 3-penten-1-yn-1-yl. $(C_2-C_6)$-Alkynyl is, for example, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

The term "cycloalkyl" means a carbocyclic saturated ring system having preferably 3-8 ring carbon atoms, for example cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene. In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), bicyclo[2.2.2]octan-2-yl, adamantan-1-yl and adamantan-2-yl. The term "$(C_3-C_7)$-cycloalkyl" is a brief notation for cycloalkyl having three to 7 carbon atoms, corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl.

"Cycloalkenyl" means a carbocyclic, nonaromatic, partly unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

The term "alkylidene", also, for example, in the form $(C_1-C_{10})$-alkylidene, means the radical of a straight-chain or branched open-chain hydrocarbon radical which is attached via a double bond. Possible bonding sites for alkylidene are naturally only positions on the base structure where two hydrogen atoms can be replaced by the double bond; radicals are, for example, =CH$_2$, =CH—CH$_3$, =C(CH$_3$)—CH$_3$, =C(CH$_3$)—C$_2$H$_5$ or =C(C$_2$H$_5$)—C$_2$H$_5$. Cycloalkylidene is a carbocyclic radical bonded via a double bond.

Depending on the nature of the substituents and the manner in which they are attached, the compounds of the general formula (I) may be present as stereoisomers. The formula (I) embraces all possible stereoisomers defined by the specific three-dimensional form thereof, such as enantiomers, diastereomers, Z and E isomers. If, for example, one or more alkenyl groups are present, diastereomers (Z and E isomers) may occur. If, for example, one or more asymmetric carbon atoms are present, enantiomers and diastereomers may occur. Stereoisomers can be obtained from the mixtures obtained in the preparation by customary separation methods. The chromatographic separation can be effected either on the analytical scale to find the enantiomeric excess or the diastereomeric excess, or else on the preparative scale to produce test specimens for biological testing. It is likewise possible to selectively prepare stereoisomers by using stereoselective reactions with use of optically active starting materials and/or auxiliaries. The invention thus also relates to all stereoisomers which are embraced by the general formula (I) but are not shown in their specific stereomeric form, and to mixtures thereof.

Synthesis of Dihydrooxindolylsulfonamides:

The dihydrooxindolylsulfonamides of the general formula (I) according to the invention, optionally with further substitution, can be prepared by known processes. The synthesis routes used and examined proceed from commercially available or easily preparable dihydrooxindolylamines and the corresponding sulfonyl chlorides. Hereinbelow, the synthesis of dihydrooxindolylamines is illustrated in an exemplary, but not limiting, manner by the preparation of spiro-cyclopropyl- and spiro-cyclobutyldihydrooxindolylamines. The other dihydrooxindolylamines required for the preparation of the sulfonamides of the general formula (I) according to the invention can be prepared by analogous synthesis routes. An aniline correspondingly monosubstituted at nitrogen by R$^1$ and optionally further substituted at the other positions is reacted with chloroacetyl chloride or bromoacetyl bromide using a suitable base in a polar aprotic solvent. The corresponding reaction product is cyclized under Friedel-Crafts conditions using a suitable Lewis acid to give the desired dihydrooxindole (A), which is optionally substituted further (Scheme 1). Alternatively, the dihydrooxindoles (A) can be prepared from an isatin, which is optionally substituted further (cf. WO2006106426) by initially introducing, at the nitrogen, the appropriate substituent R$^1$ (in the case of R$^1$=n-propyl using n-propyl iodide and a suitable carbonate base, for example potassium carbonate or cesium carbonate, in a suitable polar aprotic solvent, for example N,N-dimethylformamide, cf. Tetrahedron: Asymmetry 2009, 20(14), 1697), and subsequently converting the second carbonyl group into a CH$_2$ group by reaction with hydrazine hydrate at elevated temperature according to a Wolff-Kishner reaction. In Scheme 1, the reaction sequences for the preparation of spiro-cyclopropyldihydrooxindolylamines are shown in an exemplary, but not limiting, manner for R$^1$=n-propyl and R$^2$, R$^3$, R$^4$=hydrogen.

Scheme 1.

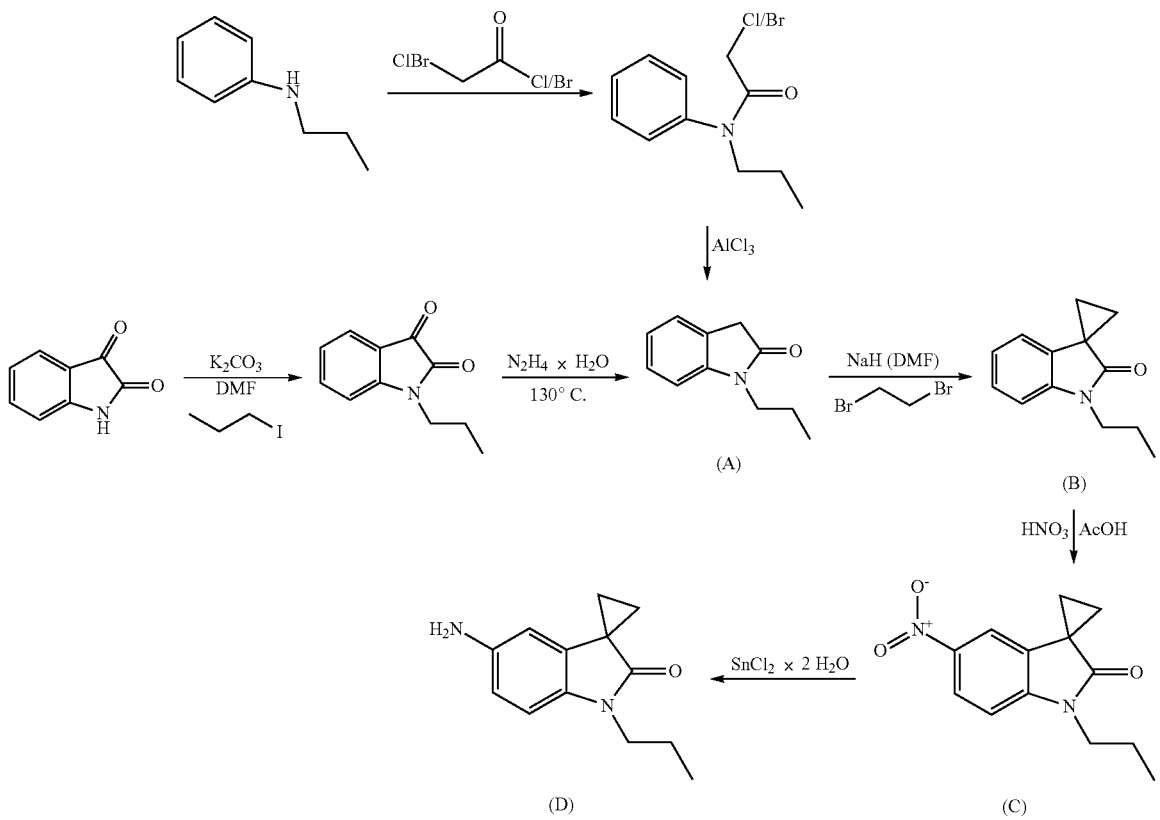

Appropriately substituted dihydrooxindoles (A) are then converted using a suitable base (for example sodium hydride) in a suitable polar aprotic solvent (for example N,N-dimethylformamide or tetrahydrofuran) in an exemplary, but not limiting, manner with 1,2-dibromoethane into the corresponding spiro-cyclopropyldihydrooxindole (B). In the next step, the product (B) can be nitrated using nitric acid in acetic acid (cf. US20070037791, J. Am. Chem. Soc. 1953, 75, 2572). The corresponding nitro derivative (C) can then be converted using a suitable reducing agent (for example tin(II) chloride dihydrate) into the desired exemplary spiro-cyclopropyldihydrooxindolylamine (D) (cf. EP1598353 and Farmaco Ed. Sci. 1977, 32, 703) (Scheme 1).

A further alternative preparation route for substituted dihydrooxindolylamines is offered by the reaction of a p-acetylaminoaniline, which is optionally substituted further, with an optionally substituted bromoacetyl bromide and subsequent Lewis acid-mediated cyclization (for example with aluminum trichloride) and subsequent removal of the acetyl protective group with a suitable acid (for example hydrochloric acid, cf. EP1598353). In Scheme 2, this reaction sequence for producing substituted dihydrooxindolylamines is shown in an exemplary, but not limiting, manner with $R^2$, $R^3$, $R^4$=hydrogen, where X, Y and $R^1$ have the meanings defined above.

Scheme 2.

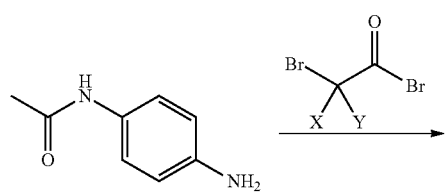

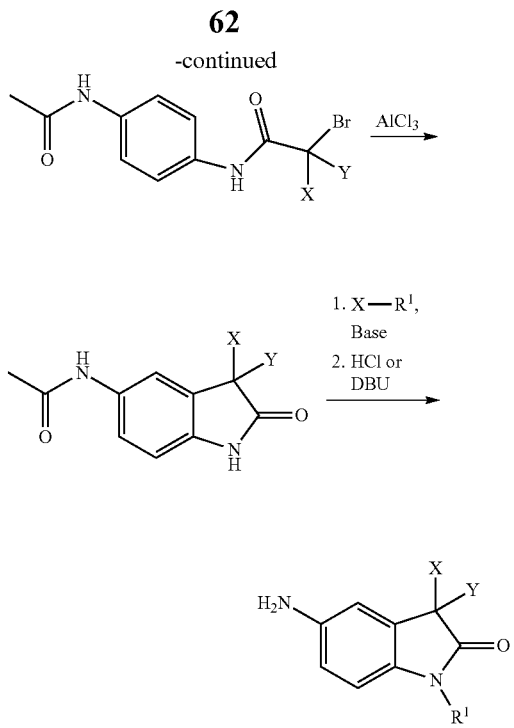

spiro-Cyclobutyldihydrooxindolylamines (E), optionally with further substitution, can be prepared analogously by the synthesis routes described in Schemes 1 and 2, where in this case optionally further substituted 1,3-dibromopropanes are used. In Scheme 3, this reaction sequences for the preparation of optionally substituted spiro-cyclobutyldihydrooxindolylamines is shown in an exemplary, but not limiting, manner for $R^1$=methyl and $R^2$, $R^3$, $R^4$=hydrogen.

Scheme 3.

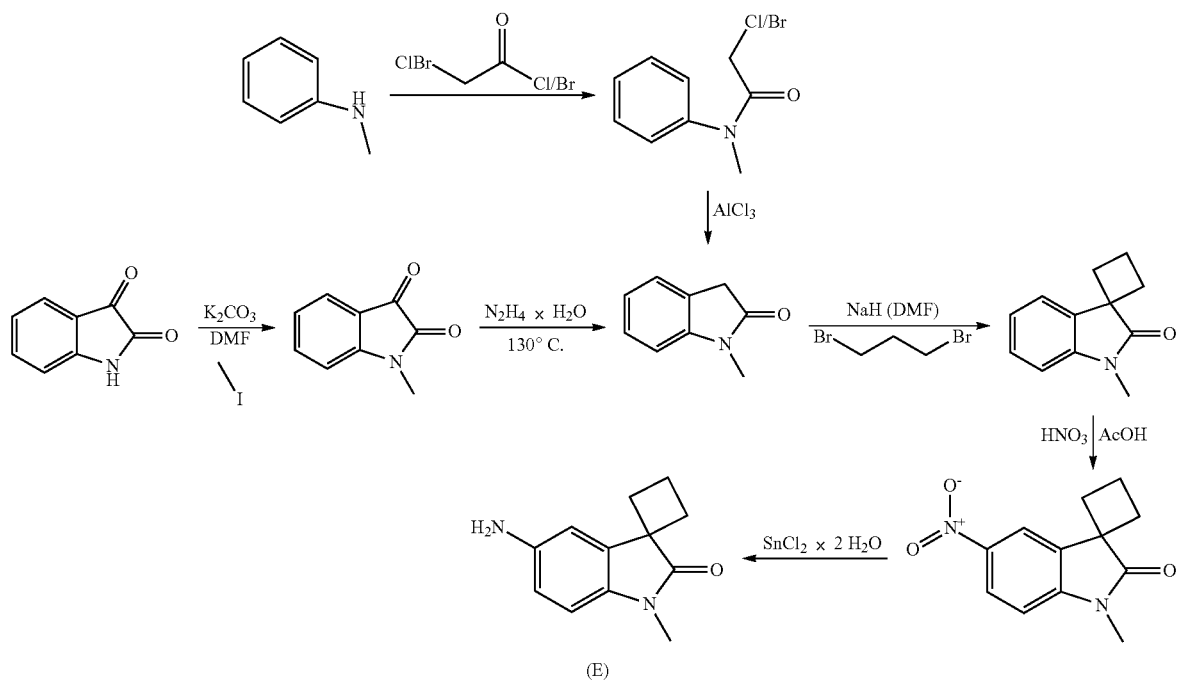

Aryl- and heteroarylsulfonyl chloride precursors can be prepared, for example, by direct chlorosulfonation of the corresponding substituted aromatics and heteroaromatics (cf. Eur J. Med. Chem. 2010, 45, 1760) or by diazotization of an amino-substituted aromatic or heteroaromatic and subsequent chlorosulfonation (cf. WO2005035486). Coupling of the corresponding substituted sulfonyl chloride precursors with the appropriate dihydrooxindolylamines, which are optionally substituted further, with the aid of a suitable base (for example triethylamine, pyridine or sodium hydroxide) in a suitable solvent (for example tetrahydrofuran, acetonitrile, DMSO or dichloromethane) affords the dihydrooxindolylsulfonamides according to the invention, optionally with further substitution (for example sub-classes (Ic), (Id)). $R^1$, $R^2$, $R^3$, $R^4$, $R^5$ and $R^6$ in Scheme 4 below are each as defined above. In an exemplary, but not limiting, manner, X and Y are represented by $CH_2$, a spiro-cyclopropyl group and a spiro-cyclobutyl group.

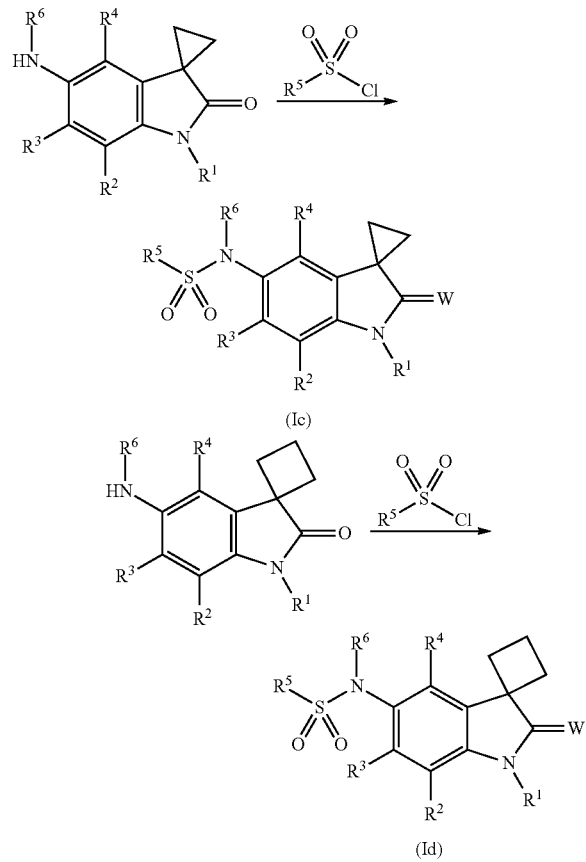

Selected detailed synthesis examples for the inventive compounds of the general formula (I) are given below. The example numbers mentioned correspond to the numbering scheme in Tables A1 to J3 below. The $^1$H NMR, $^{13}$C-NMR and $^{19}$F-NMR spectroscopy data reported for the chemical examples described in the sections which follow (400 MHz for $^1$H-NMR and 150 MHz for $^{13}$C-NMR and 375 MHz for $^{19}$F-NMR, solvent $CDCl_3$, $CD_3OD$ or $d_6$-DMSO, internal standard: tetramethylsilane δ=0.00 ppm), were obtained on a Bruker instrument, and the signals listed have the meanings given below: br=broad; s=singlet, d=doublet, t=triplet, dd=doublet of doublets, ddd=doublet of a doublet of doublets, m=multiplet, q=quartet, quint=quintet, sext=sextet, sept=septet, dq=doublet of quartets, dt=doublet of triplets. In the case of diastereomer mixtures, either the significant signals for each of the two diastereomers are reported or the characteristic signal of the main diastereomer is reported. The abbreviations used for chemical groups are defined as follows: $Me=CH_3$, $Et=CH_2CH_3$, $t-Hex=C(CH_3)_2CH(CH_3)_2$, $t-Bu=C(CH_3)_3$, n-Bu=unbranched butyl, n-Pr=unbranched propyl, c-Hex=cyclohexyl.

No. A1-173: 1-(3-Bromophenyl)-N-(1'-methyl-2'-oxo-1',2'-dihydrospiro[cyclopropane-1,3'-indol]-5-yl)methanesulfonamide

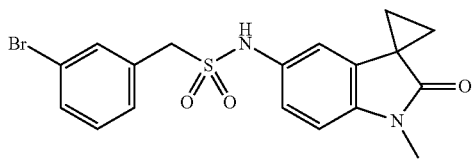 [SMILES: CN1C(=O)C2(CC2)c2cc(NS(=O)(=O)Cc3cccc(Br)c3)ccc21]

Together, 1-methyl-1,3-dihydro-2H-indol-2-one (2.00 g, 14 mmol) and 1,2-dibromoethane (3.83 g, 20 mmol) were dissolved in abs. N,N-dimethylformamide (15 ml), sodium hydride (1.68 g, 42 mmol, 60% strength dispersion) was then added carefully a little at a time at a temperature of 10-15° C. and the mixture was stirred for another one and a half hours. Methanol and aqueous ammonium chloride solution were then added to the reaction mixture, and the aqueous phase was extracted intensively with ethyl acetate. The combined organic phases were dried over magnesium sulfate, filtered and concentrated under reduced pressure. Purification of the resulting crude product by column chromatography (gradient ethyl acetate/heptane) gave 1'-methylspiro[cyclopropane-1,3'-indol]-2'(1'H)-one (2500 mg, 92% of theory). $^1$H-NMR (400 MHz, $CDCl_3$ δ, ppm) 7.25 (m, 1H), 7.03 (m, 1H), 6.91 (d, 1H), 6.83 (d, 1H), 3.30 (s, 3H), 1.73 (m, 2H), 1.52 (m, 2H). 1'-Methylspiro[cyclopropane-1,3'-indol]-2'(1'H)-one (2.50 g, 13 mmol) was added to glacial acetic acid (23 ml), and fuming nitric acid (4 ml) was then added slowly and carefully. The resulting reaction mixture was stirred at room temperature for 30 minutes and then slowly diluted with ice-water. The aqueous phase was then repeatedly extracted with ethyl acetate, and the combined organic phases were washed with saturated sodium carbonate solution and then dried over magnesium sulfate, filtered and concentrated under reduced pressure. Purification of the resulting crude product by column chromatography (gradient ethyl acetate/heptane) gave 1'-methyl-5'-nitrospiro[cyclopropane-1,3'-indol]-2'(1'H)-one (1800 mg, 57% of theory) as a colorless solid. $^1$H-NMR (400 MHz, $CDCl_3$ δ, ppm) 8.25 (dd, 1H), 7.74 (d, 1H), 6.97 (d, 1H), 3.36 (s, 3H), 1.88 (m, 2H), 1.69 (m, 2H). In the next step, 1'-methyl-5-nitrospiro[cyclopropane-1,3'-indol]-2'(1'H)-one (1.80 g, 8 mmol) and tin(II) chloride dihydrate (7.45 g, 33 mmol) were added together to abs. ethanol and stirred under argon at a temperature of 80° C. for 5 h. After cooling to room temperature, the reaction mixture was poured into ice-water and then adjusted to pH 12 using aqueous NaOH. The aqueous phase was then repeatedly extracted with ethyl acetate. The combined organic phases were dried over magnesium sulfate, filtered and concentrated under reduced pressure. Purification of the resulting crude product by column chromatography (gradient ethyl acetate/heptane) gave 5'-amino-1'-methylspiro[cyclopropane-1,3'-indol]-2'(1'H)-one (1226 mg, 79% of theory) as a colorless solid. ¹H-NMR (400 MHz, CDC138, ppm) 6.71 (d, 1H), 6.60 (dd, 1H), 6.25 (d, 1H), 3.52 (br. s, 2H, NH), 3.24 (t, 2H), 1.71 (m, 2H), 1.43 (m, 2H). In a round-bottom flask under argon, 5'-amino-1'-methylspiro[cyclopropane-1,3'-indol]-2'(1'H)-one (130 mg, 1.0 equiv.) and (3-bromophenyl)methanesulfonyl chloride (261 mg, 1.4 equiv.) were dissolved together in abs. acetonitrile, pyridine (0.11 ml, 2.0 equiv.) and dimethyl sulfoxide (0.03 ml, 0.60 mmol) were then added and the mixture was stirred at room temperature for 6 h. The reaction mixture was then concentrated under reduced pressure, water and dichloromethane were added to the residue that remained and the aqueous phase was extracted repeatedly with dichloromethane. The combined organic phases were dried over magnesium sulfate, filtered and concentrated under reduced pressure. Purification of the resulting crude product by column chromatography (gradient ethyl acetate/heptane) gave 1-(3-bromophenyl)-N-(1'-methyl-2'-oxo-1',2'-dihydrospiro[cyclopropane-1,3'-indol]-5-yl)methanesulfonamide (235 mg, 81% of theory) as a colorless solid. ¹H-NMR (400 MHz, CDCl₃ δ, ppm) 7.52 (m, 1H), 7.39 (m, 1H), 7.29 (m, 1H), 7.24 (m, 1H), 7.04 (m, 1H), 6.87 (d, 1H), 6.65 (d, 1H), 6.26 (s, 1H, NH), 4.13 (s, 2H), 3.30 (s, 3H), 1.78 (m, 2H), 1.54 (m, 2H). ¹³C-NMR (150 MHz, CDCl₃ δ, ppm) 176.8, 141.7, 133.7, 132.6, 132.1, 130.8, 130.4, 129.5, 122.6, 120.8, 113.3, 108.3, 56.8, 27.4, 26.7, 19.7.

No. A1-181: 1-(4-Cyanophenyl)-N-(1'-methyl-2'-oxo-1',2'-dihydrospiro[cyclopropane-1,3'-indol]-5-yl)methanesulfonamide

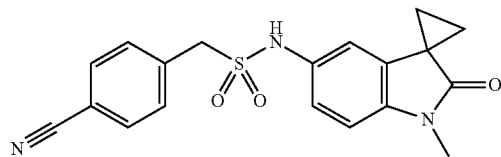 [SMILES: CN1C(=O)C2(CC2)c2cc(NS(=O)(=O)Cc3ccc(C#N)cc3)ccc21]

In a round-bottom flask under argon, 5-amino-1-methylspiro[cyclopropane-1,3-indol]-2(1H)-one (150 mg, 0.79 mmol) and (4-cyanophenyl)methanesulfonyl chloride (258 mg, 1.19 mmol) were dissolved together in abs. acetonitrile, pyridine (0.13 ml, 1.59 mmol) and dimethyl sulfoxide (0.03 ml, 0.48 mmol) were then added and the mixture was stirred at room temperature for 6 h. The reaction mixture was then concentrated under reduced pressure, water and dichloromethane were added to the residue that remained and the aqueous phase was extracted repeatedly with dichloromethane. The combined organic phases were dried over magnesium sulfate, filtered and concentrated under reduced pressure. Purification of the resulting crude product by column chromatography (gradient ethyl acetate/heptane) gave 1-(4-cyanophenyl)-N-(1'-methyl-2'-oxo-1',2'-dihydrospiro[cyclopropane-1,3'-indol]-5'-yl)methanesulfonamide (245 mg, 84% of theory) as a colorless solid. ¹H-NMR (400 MHz, d₆-DMSO δ, ppm) 9.64 (s, 1H, NH), 7.84 (d, 2H), 7.48 (d, 2H), 7.05 (m, 2H), 6.78 (d, 1H), 4.54 (s, 2H), 3.20 (s, 3H), 1.57 (m, 2H), 1.53 (m, 2H).

No. A2-176: N-(1'-Ethyl-2'-oxo-1',2'-dihydrospiro[cyclopropane-1,3'-indol]-5'-yl)-1-(3-nitrophenyl)methanesulfonamide

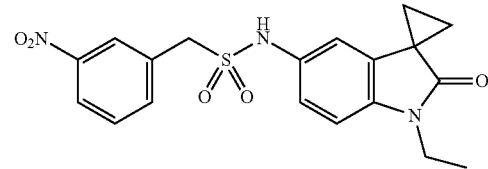 [SMILES: CCN1C(=O)C2(CC2)c2cc(NS(=O)(=O)Cc3cccc([N+](=O)[O-])c3)ccc21]

In a round-bottom flask under argon, isatin (5.00 g, 34 mmol) was dissolved in N,N-dimethylformamide (50 ml), and 1-iodoethane (68 mmol) and potassium carbonate (9.39 g, 68 mmol) were added. The resulting reaction mixture was stirred at room temperature for 6 h, and water and ethyl acetate were then added. The aqueous phase was then extracted repeatedly with ethyl acetate, and the combined organic phases were dried over magnesium sulfate, filtered and concentrated under reduced pressure. Purification of the resulting crude product by column chromatography (gradient ethyl acetate/heptane) gave 1-ethyl-1H-indole-2,3-dione which was then heated together with hydrazine hydrate (30.96 g, 612 mmol) at 130° C. for 4 h and, after cooling to room temperature, added to ice-water. The aqueous phase was subsequently extracted repeatedly with ethyl acetate, and the combined organic phases were dried over magnesium sulfate, filtered and concentrated under reduced pressure. Purification of the resulting crude product by column chromatography (gradient ethyl acetate/heptane) gave 1-ethyl-1,3-dihydro-2H-indol-2-one which, in the next step, was, at a temperature of 15° C., dissolved together with 1,2-dibromoethane (6.27 g, 33 mmol) in a mixture of abs. tetrahydrofuran (25 ml) and abs. N,N-dimethylformamide (1 ml), followed by careful addition, a little at a time, of sodium hydride (2.76 g, 69 mmol, 60% strength dispersion) and stirring under reflux conditions for 1 h. After cooling to room temperature, methanol and water were added to the reaction mixture. The aqueous phase was extracted intensively with ethyl acetate and the combined organic phases were additionally washed in each case once with saturated sodium carbonate solution and water. The combined organic phases were dried over magnesium sulfate, filtered and concentrated under reduced pressure. Purification of the resulting crude product by column chromatography (gradient ethyl acetate/heptane) gave 1'-ethylspiro[cyclopropane-1,3'-indol]-2'(1'H)-one. I-Ethylspiro[cyclopropane-1,3'-indol]-2'(1'H)-one (5.00 g, 21 mmol) was added to glacial acetic acid (35 ml), and fuming nitric acid (7 ml) was then added slowly and carefully. The resulting reaction mixture was stirred at room temperature for 2 h and then slowly diluted with ice-water. The aqueous phase was then repeatedly extracted with ethyl acetate, and the combined organic phases were washed with saturated sodium carbonate solution and then dried over magnesium sulfate, filtered and concentrated under reduced pressure. Purification of the resulting crude product by column chromatography (gradient ethyl acetate/heptane) gave 1'-ethyl 5'-nitro-spiro[cyclopropane-1,3'-indol]-2'(1'H)-one (3900 mg, 79% of theory) as a colorless solid. In the next step, 1'-ethyl 5'-nitro-spiro[cyclopropane-1,3'-indol]-2'(1'H)-one (3.90 g, 17 mmol) was added together with tin(II) chloride dihydrate (15.16 g, 67 mmol) to abs. ethanol and the mixture was stirred under argon at a temperature of 80° C. for 5 h. After cooling to room temperature, the reaction mixture was poured into ice-water and then adjusted to pH 12 using aqueous NaOH. The aqueous phase was then repeatedly extracted with ethyl acetate. The combined organic phases were dried over magnesium sulfate, filtered and concentrated under reduced pressure. Purification of the resulting crude product by column chromatography (gradient ethyl acetate/heptane) gave 5'-amino-1'-ethylspiro[cyclopropane-1,3'-indol]-2'(1'H)-one (2700 mg, 79% of theory) as a colorless solid. $^1$H-NMR (400 MHz, CDCl$_3$ δ, ppm) 6.73 (d, 1H), 6.59 (dd, 1H), 6.26 (d, 1H), 3.80 (q, 2H), 1.71 (m, 2H), 1.42 (m, 2H), 1.28 (t, 3H). In a round-bottom flask under argon, 5'-amino-1'-ethylspiro[cyclopropane-1,3'-indol]-2'(1'H)-one (110 mg, 1.0 equiv.) and (3-nitrophenyl)methanesulfonyl chloride (161 mg, 1.4 equiv.) were dissolved together in abs. acetonitrile, pyridine (0.08 ml, 2.1 equiv.) and dimethyl sulfoxide (0.02 ml, 0.60 mmol) were then added and the mixture was stirred at room temperature for 6 h. The reaction mixture was then concentrated under reduced pressure, water and dichloromethane were added to the residue that remained and the aqueous phase was extracted repeatedly with dichloromethane. The combined organic phases were dried over magnesium sulfate, filtered and concentrated under reduced pressure. Purification of the resulting crude product by column chromatography (gradient ethyl acetate/heptane) gave N-r-ethyl-2'-oxo-1',2'-dihydrospiro[cyclopropane-1,3'-indol]-5'-yl)-1-(3-nitrophenyl)methanesulfonamide (123 mg, 55% of theory) as a colorless solid.
$^1$H-NMR (400 MHz, CDCl$_3$ δ, ppm) 8.23 (m, 1H), 8.12 (m, 1H), 7.75 (d, 1H), 7.58 (m, 1H), 7.08 (dd, 1H), 6.91 (d, 1H), 6.77 (d, 1H), 6.32 (s, 1H, NH), 4.38 (s, 2H), 3.86 (q, 2H), 1.80 (m, 2H), 1.57 (m, 2H), 1.32 (t, 3H).

No. A3-167: 1-(3,4-Dichlorophenyl)-N-(2'-oxo-1'-propyl-1',2'-dihydrospiro[cyclopropane-1,3'-indol]-5'-yl)methanesulfonamide

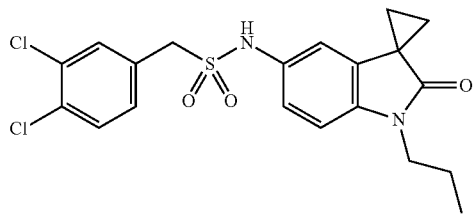 [SMILES: CCCN1C(=O)C2(CC2)c2cc(NS(=O)(=O)Cc3ccc(Cl)c(Cl)c3)ccc21]

In a round-bottom flask under argon, isatin (5.00 g, 34 mmol) was dissolved in N,N-dimethylformamide (50 ml), and 1-iodopropane (11.56 g, 68 mmol) and potassium carbonate (9.39 g, 68 mmol) were added. The resulting reaction mixture was stirred at room temperature for 6 h, and water and ethyl acetate were then added. The aqueous phase was then extracted repeatedly with ethyl acetate, and the combined organic phases were dried over magnesium sulfate, filtered and concentrated under reduced pressure. Purification of the resulting crude product by column chromatography (gradient ethyl acetate/heptane) gave 1-propyl-1H-indole-2,3-dione (6.10 g, 93% of theory). $^1$H-NMR (400 MHz, CDCl$_3$ δ, ppm) 7.59 (m, 2H), 7.11 (m, 1H), 6.89 (d, 1H), 3.71 (t, 2H), 1.76 (sext, 2H), 1.00 (t, 3H). Subsequently, 1-propyl-1H-indole-2,3-dione (6.10 g, 32 mmol) was heated together with hydrazine hydrate (30.96 g, 612 mmol) at 130° C. for 4 h, and after cooling to room temperature the mixture was added to ice-water. The aqueous phase was subsequently extracted repeatedly with ethyl acetate, and the combined organic phases were dried over magnesium sulfate, filtered and concentrated under reduced pressure. Purification of the resulting crude product by column chromatography (gradient ethyl acetate/heptane) gave 1-propyl-1,3-dihydro-2H-indol-2-one (4.50 g, 81% of theory). $^1$H-NMR (400 MHz, CDCl$_3$ δ, ppm) 7.28 (m, 2H), 7.02 (m, 1H), 6.84 (d, 1H), 3.68 (t, 2H), 3.52 (s, 2H), 1.71 (sext, 2H), 0.97 (t, 3H). In the next step, 1-propyl-1,3-dihydro-2H-indol-2-one (3.90 g, 22 mmol) was, at a temperature of 15° C., dissolved together with 1,2-dibromoethane (6.27 g, 33 mmol) in a mixture of abs. tetrahydrofuran (25 ml) and abs. N,N-dimethylformamide (1 ml), followed by careful addition, a little at a time, of sodium hydride (2.76 g, 69 mmol, 60% strength dispersion) and stirring under reflux conditions for 1 h. After cooling to room temperature, methanol and water were added to the reaction mixture. The aqueous phase was extracted intensively with ethyl acetate and the combined organic phases were additionally washed in each case once with saturated sodium carbonate solution and water. The combined organic phases were dried over magnesium sulfate, filtered and concentrated under reduced pressure. Purification of the resulting crude product by column chromatography (gradient ethyl acetate/heptane) gave 1'-propylspiro[cyclopropane-1,3'-indol]-2'(1'H)-one (4000 mg, 89% of theory). $^1$H-NMR (400 MHz, CDCl$_3$ δ, ppm) 7.22 (m, 1H), 7.00 (m, 1H), 6.92 (d, 1H), 6.83 (d, 1H), 3.75 (t, 2H), 1.74 (m, 2H), 1.50 (m, 2H), 1.26 (m, 2H), 0.98 (t, 3H). 1'-Propylspiro[cyclopropane-1,3'-indol]-2'(1'H)-one (5.20 g, 21 mmol) was added to glacial acetic acid (35 ml), and fuming nitric acid (7 ml) was then added slowly and carefully. The resulting reaction mixture was stirred at room temperature for 2 h and then slowly diluted with ice-water. The aqueous phase was then repeatedly extracted with ethyl acetate, and the combined organic phases were washed with saturated sodium carbonate solution and then dried over magnesium sulfate, filtered and concentrated under reduced pressure. Purification of the resulting crude product by column chromatography (gradient ethyl acetate/heptane) gave 5'-nitro-1'-propylspiro[cyclopropane-1,3'-indol]-2'(1'H)-one (3600 mg, 71% of theory) as a colorless solid. $^1$H-NMR (400 MHz, CDCl$_3$ δ, ppm) 8.26 (dd, 1H), 7.73 (d, 1H), 6.98 (d, 1H), 3.30 (t, 2H), 1.87 (m, 2H), 1.75 (sext, 1H), 1.68 (m, 2H), 1.00 (t, 3H). In the next step, 5'-nitro-1'-propylspiro[cyclopropane-1,3'-indol]-2'(1'H)-one (3.60 g, 15 mmol) and tin(II) chloride dihydrate (13.19 g, 58 mmol) were added together to abs. ethanol and stirred under argon at a temperature of 80° C. for 5 h. After cooling to room temperature, the reaction mixture was poured into ice-water and then adjusted to pH 12 using aqueous NaOH. The aqueous phase was then repeatedly extracted with ethyl acetate. The combined organic phases were dried over magnesium sulfate, filtered and concentrated under reduced pressure. Purification of the resulting crude product by column chromatography (gradient ethyl acetate/heptane) gave 5'-amino-1'-propylspiro[cyclopropane-1,3'-indol]-2'(1'H)-one (3100 mg, 98% of theory) as a colorless solid. $^1$H-NMR (400 MHz, CDCl$_3$ δ, ppm) 6.71 (d, 1H), 6.58 (dd, 1H), 6.25 (d, 1H), 3.71 (t, 2H), 1.73 (m, 2H), 1.42 (m, 2H), 1.25 (m, 2H), 0.98 (t, 3H). Under argon, 5'-amino-1'-propylspiro[cyclopropane-1,3'-indol]-2'(1'H)-one (100 mg, 1.0 equiv.) and (3,4-dichlorophenyl)methanesulfonyl chloride (168 mg, 1.4 equiv.) were dissolved in abs. acetonitrile in a round-bottom flask, pyridine (0.08 ml, 2.1 equiv.) and dimethyl sulfoxide (0.04 ml, 0.60 mmol) were then added and the mixture was stirred at room temperature for 6 h. The reaction mixture was then concentrated under reduced pressure, water and dichloromethane were added to the residue that remained and the aqueous phase was extracted repeatedly with dichloromethane. The combined organic phases were dried over magnesium sulfate, filtered and concentrated under reduced pressure. Purification of the resulting crude product by column chromatography (gradient ethyl acetate/heptane) gave 1-(3,4-dichlorophenyl)-N-(2'-oxo-1'-propyl-1',2'-dihydrospiro[cyclopropane-1,3'-indol]-5'-yl)methanesulfonamide (147 mg, 68% of theory) as a colorless solid. $^1$H-NMR (400 MHz, CDCl$_3$ δ, ppm) 7.42 (d, 1H), 7.36 (d, 1H), 7.19 (m, 1H), 7.01 (m, 1H), 6.85 (d, 1H), 6.67 (d, 1H), 6.33 (s, 1H, NH), 4.24 (s, 2H), 3.74 (t, 2H), 1.78 (m, 2H), 1.73 (sext, 2H), 1.52 (m, 2H), 0.99 (t, 3H).

No. B1-152: N-(1'-Methyl-2'-oxo-1',2'-dihydrospiro[cyclobutane-1,3'-indol]-5-yl)-1-(4-methylphenyl)methanesulfonamide

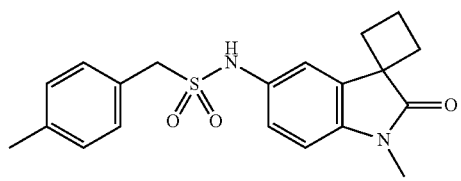 [SMILES: Cc1ccc(CS(=O)(=O)Nc2ccc3c(c2)C2(CCC2)C(=O)N3C)cc1]

In a round-bottom flask which had been dried by heating, and under argon, 1-methyl-1,3-dihydro-2H-indol-2-one (1.00 g, 7 mmol) and 1,3-dibromopropane (2.06 g, 10 mmol) were dissolved in abs. N,N-dimethylformamide, and the mixture was stirred at room temperature for 5 min. The reaction solution was then cooled to 0° C., and sodium hydride (0.82 g, 20 mmol, 60% strength dispersion) was then added a little at a time. The resulting reaction mixture was stirred for about 2 h, methanol (4 ml) was then added and after a further 5 min sat. ammonium chloride solution (15 ml) and water (200 ml) were added. The aqueous phase was extracted intensively with ethyl acetate. The combined organic phases were dried over magnesium sulfate, filtered and concentrated under reduced pressure. Purification of the resulting crude product by column chromatography (gradient ethyl acetate/heptane) gave 1'-methylspiro[cyclobutane-1,3'-indol]-2'(1'H)-one (360 mg, 29% of theory). $^1$H-NMR (400 MHz, CDCl$_3$ δ, ppm) 7.52 (d, 1H), 7.27 (m, 1H), 7.09 (m, 1H), 6.77 (d, 1H), 3.20 (s, 3H), 2.67 (m, 2H), 2.33 (m, 4H). 1'-Methylspiro[cyclobutane-1,3'-indol]-2'(1'H)-one (360 mg, 1.92 mmol) was added to conc. acetic acid (5 ml), and fuming nitric acid (0.21 ml, 5.06 mmol) was then added carefully. The resulting reaction mixture was stirred at room temperature for 2 h and then diluted with ice-water. The aqueous phase was then repeatedly extracted with ethyl acetate. The combined organic phases were dried over magnesium sulfate, filtered and concentrated under reduced pressure. Purification of the resulting crude product by column chromatography (gradient ethyl acetate/heptane) gave 1'-methyl-5'-nitrospiro[cyclobutane-1,3'-indol]-2'(1'H)-one (380 mg, 85% of theory) as a colorless solid. $^1$H-NMR (400 MHz, CDCl$_3$ δ, ppm) 8.38 (d, 1H), 8.26 (dd, 1H), 6.86 (d, 1H), 3.25 (s, 3H), 2.70 (m, 2H), 2.42 (m, 4H). In the next step, 1'-methyl-5'-nitrospiro[cyclobutane-1,3'-indol]-2'(1'H)-one (450 mg, 1.55 mmol) and tin(II) chloride dihydrate (1.40 g, 6.20 mmol) were added together to abs. ethanol and stirred under argon at a temperature of 80° C. for 5 h. After cooling to room temperature, the reaction mixture was poured into ice-water and then adjusted to pH 12 using aqueous NaOH. The aqueous phase was then repeatedly extracted with ethyl acetate. The combined organic phases were dried over magnesium sulfate, filtered and concentrated under reduced pressure. Purification of the resulting crude product by column chromatography (gradient ethyl acetate/heptane) gave 5'-amino-1'-methylspiro[cyclobutane-1,3'-indol]-2'(1'H)-one (230 mg, 66% of theory) as a colorless solid. $^1$H-NMR (400 MHz, CDCl$_3$ δ, ppm) 6.98 (d, 1H), 6.62 (m, 2H), 3.14 (s, 3H), 2.64 (m, 2H), 2.38-2.20 (m, 4H). Under argon, 5'-amino-1'-methylspiro[cyclobutane-1,3'-indol]-2'(1'H)-one (150 mg, 0.79 mmol) and (4-methylphenyl)methanesulfonyl chloride (156 mg, 0.76 mmol) were dissolved in abs. acetonitrile (5 ml) in a round-bottom flask which had been dried by heating, pyridine (0.11 ml, 1.38 mmol) and dimethyl sulfoxide (0.03 ml, 0.42 mmol) were then added and the mixture was stirred at room temperature for 6 h. The reaction mixture was then concentrated under reduced pressure, water, dil. hydrochloric acid and dichloromethane were added to the residue that remained and the aqueous phase was extracted repeatedly with dichloromethane. The combined organic phases were dried over magnesium sulfate, filtered and concentrated under reduced pressure. Purification of the resulting crude product by column chromatography (gradient ethyl acetate/heptane) gave N-(1'-methyl-2'-oxo-1',2'-dihydrospiro[cyclobutane-1,3'-indol]-5'-yl)-1-(4-methylphenyl)methanesulfonamide (118 mg, 46% of theory) as a colorless solid. $^1$H-NMR (400 MHz, CDCl$_3$ δ, ppm) 7.29 (m, 3H), 7.16 (d, 1H), 6.96 (br. s, 1H, NH), 6.61 (d, 1H), 4.30 (s, 2H), 3.13 (s, 3H), 2.62 (m, 2H), 2.33 (s, 3H), 2.32-2.17 (m, 4H).

No. E1-152: N-(1'-Methyl-2'-oxo-1',2'-dihydrospiro[cyclopent-3-ene-1,3'-indol]-5'-yl)-1-(4-methylphenyl)methanesulfonamide

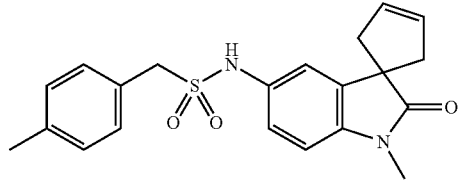 [SMILES: Cc1ccc(CS(=O)(=O)Nc2ccc3c(c2)C2(CC=CC2)C(=O)N3C)cc1]

In a round-bottom flask under argon, 3,3-diallyl-5-nitro-1,3-dihydro-2H-indol-2-one (340 mg, 1.0 equiv) was dissolved in N,N-dimethylformamide (5 ml), and methyl iodide (0.16 ml, 2.0 equiv.) and potassium carbonate (364 mg, 2.0 equiv.) were added. The resulting reaction mixture was stirred at room temperature for 6 h, and water and ethyl acetate were then added. The aqueous phase was then extracted repeatedly with ethyl acetate, and the combined organic phases were dried over magnesium sulfate, filtered and concentrated under reduced pressure. Purification of the resulting crude product by column chromatography (gradient ethyl acetate/heptane) gave 3,3-diallyl-1-methyl-5-nitro-1,3-dihydro-2H-indol-2-one which was reacted further directly after purification. $^1$H-NMR (400 MHz, CDCl$_3$ δ, ppm) 8.28 (m, 1H), 8.09 (d, 1H), 6.90 (d, 1H), 5.38 (m, 2H), 5.04 (m, 2H), 4.96 (m, 2H), 3.25 (s, 3H), 2.62 (m, 4H), 1.00. 3,3-Diallyl-1-methyl-5-nitro-1,3-dihydro-2H-indol-2-one (550 mg, 2.00 mmol) was added to abs. toluene (10 ml), and (1,3-bis-(2,4,6-trimethylphenyl)-2-imidazolidinylidene)dichloro(o-isopropoxyphenylmethylene)ruthenium (2.5 mg, 2 mol %) was then added under argon. The resulting reaction mixture was stirred at a temperature of 90-100° C. for one day and, after cooling to room temperature, diluted with water and ammonium chloride solution. The aqueous phase was then repeatedly extracted with ethyl acetate. The combined organic phases were dried over magnesium sulfate, filtered and concentrated under reduced pressure. Purification of the resulting crude product by column chromatography (gradient ethyl acetate/heptane) gave 1'-methyl-5'-nitrospiro[cyclopent-3-ene-1,3'-indol]-2'(1'H)-one.
$^1$H-NMR (400 MHz, CDCl$_3$ δ, ppm) 8.27 (dd, 1H), 8.14 (d, 1H), 6.91 (d, 1H), 5.88 (m, 2H), 3.30 (s, 3H), 3.07 (m, 2H), 2.64 (m, 2H). In the next step, 1'-methyl-5'-nitrospiro[cyclopent-3-ene-1,3'-indol]-2'(1'H)-one (500 mg, 2.03 mmol) and tin(II) chloride dihydrate (1.66 g, 4.0 equiv.) were added together to abs. ethanol (15 ml) and stirred under argon at a temperature of 80° C. for 3 h. After cooling to room temperature, the reaction mixture was poured into ice-water and then adjusted to pH 12 using aqueous NaOH. The aqueous phase was then repeatedly extracted with ethyl acetate. The combined organic phases were dried over magnesium sulfate, filtered and concentrated under reduced pressure. Purification of the resulting crude product by column chromatography (gradient ethyl acetate/heptane) gave 5'-amino-1-methylspiro[cyclopent-3-ene-1,3'-indol]-2'(1'H)-one. $^1$H-NMR (400 MHz, CDCl$_3$ δ, ppm) 6.71 (d, 1H), 6.62 (m, 2H), 5.82 (m, 2H), 3.18 (s, 3H), 3.01 (m, 2H), 2.58 (m, 2H). In a round-bottom flask which had been dried by heating and under argon, 5'-amino-1'-methylspiro[cyclopent-3-ene-1,3'-indol]-2'(1'H)-one (200 mg, 0.94 mmol) and (4-methylphenyl)methanesulfonyl chloride (248 mg, 1.3 equiv) were dissolved together in abs. acetonitrile (5 ml), pyridine (0.23 ml, 3.1 equiv.) was then added and the mixture was stirred at 70° C. for 1 h. The reaction mixture was then concentrated under reduced pressure, water, dil. hydrochloric acid and dichloromethane were added to the residue that remained and the aqueous phase was extracted repeatedly with dichloromethane. The combined organic phases were dried over magnesium sulfate, filtered and concentrated under reduced pressure. Purification of the resulting crude product by column chromatography (gradient ethyl acetate/heptane) gave N-(1'-methyl-2'-oxo-1',2'-dihydrospiro[cyclopent-3-en-1,3'-indol]-5'-yl)-1-(4-methylphenyl)methanesulfonamide (169 mg, 47% of theory) as a colorless solid. $^1$H-NMR (400 MHz, CDCl$_3$ δ, ppm) 7.20 (d, 2H), 7.18 (d, 2H), 7.11 (dd, 1H), 6.99 (d, 1H), 6.79 (d, 1H), 5.99 (br. s, 1H, NH), 5.85 (m, 2H), 4.25 (s, 2H), 3.23 (s, 3H), 3.04 (m, 2H), 2.59 (m, 2H).

No. H1-181: 1-(4-Cyanophenyl)-N-(1-methyl-2-oxo-1,2,2',3',5',6'-hexahydrospiro[indol-3,4'-pyran]-5-yl)methanesulfonamide

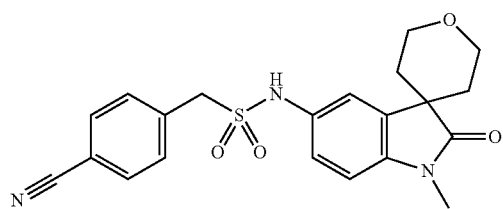 [SMILES: CN1C(=O)C2(CCOCC2)c2cc(NS(=O)(=O)Cc3ccc(C#N)cc3)ccc21]

In a round-bottom flask which had been dried by heating, and under argon, 1-methyl-1,3-dihydro-2H-indol-2-one (2.50 g, 17 mmol) was dissolved in abs. N,N-dimethylformamide, and the mixture was stirred at room temperature for 5 min. The reaction solution was then cooled to 0° C., and sodium hydride (2.11 g, 53 mmol, 60% strength dispersion) was then added a little at a time. The resulting reaction mixture was stirred at room temperature for about 1 h, 2-[2-(4-methylphenyl)sulfonyloxyethoxy]ethyl-4-methylphenylsulfonate (5.63 g, 14 mmol) was then added and the mixture was stirred at a temperature of 50° C. for a further 4 h. After cooling to room temperature, methanol (4 ml) was added and after a further 5 min sat. ammonium chloride solution (15 ml) and water (200 ml) were added. The aqueous phase was extracted intensively with ethyl acetate. The combined organic phases were dried over magnesium sulfate, filtered and concentrated under reduced pressure. Purification of the resulting crude product by column chromatography (gradient ethyl acetate/heptane) gave 1-methyl-2',3',5',6'-tetrahydrospiro[indole-3,4'-pyran]-2(1H)-one (1.60 g, 43% of theory). $^1$H-NMR (400 MHz, CDCl$_3$ δ, ppm) 7.37 (d, 1H), 7.30 (m, 1H), 7.09 (m, 1H), 6.86 (d, 1H), 4.28 (m, 2H), 3.93 (m, 2H), 3.21 (s, 3H), 1.86 (m, 4H). 1-Methyl-2',3',5',6'-tetrahydrospiro[indole-3,4'-pyran]-2(1H)-one (1.60 g, 7.37 mmol) was added to conc. acetic acid (12 ml), and fuming nitric acid (3.0 ml) was then added carefully. The resulting reaction mixture was stirred at room temperature for 2 h and then diluted with ice-water. The aqueous phase was then repeatedly extracted with ethyl acetate. The combined organic phases were dried over magnesium sulfate, filtered and concentrated under reduced pressure. Purification of the resulting crude product by column chromatography (gradient ethyl acetate/heptane) gave 1-methyl-5-nitro-2',3',5',6'-tetrahydrospiro[indole-3,4'-pyran]-2(1H)-one (1.90 mg, 98% of theory) as a colorless solid. $^1$H-NMR (400 MHz, CDCl$_3$ δ, ppm) 8.30 (d, 1H), 8.27 (dd, 1H), 6.94 (d, 1H), 4.29 (m, 2H), 3.96 (m, 2H), 3.28 (s, 3H), 1.95-1.86 (m, 4H). In the next step, 1-methyl-5-nitro-2',3',5',6'-tetrahydrospiro[indole-3,4'-pyran]-2(1H)-one (1.90 g, 7.25 mmol) and tin(II) chloride dihydrate (6.19 g, 27 mmol) were added together to abs. ethanol (30 ml) and stirred under argon at a temperature of 80° C. for 3 h. After cooling to room temperature, the reaction mixture was poured into ice-water and then adjusted to pH 12 using aqueous NaOH. The aqueous phase was then repeatedly extracted with ethyl acetate. The combined organic phases were dried over magnesium sulfate, filtered and concentrated under reduced pressure. Purification of the resulting crude product by column chromatography (gradient ethyl acetate/heptane) gave 5-amino-1-methyl-2',3',5',6'-tetrahydrospiro[indole-3,4'-pyran]-2(1H)-one (1.06 g, 63% of theory). $^1$H-NMR (400 MHz, CDCl$_3$ δ, ppm) 6.79 (d, 1H), 6.64 (m, 2H), 4.28 (m, 2H), 3.91 (m, 2H), 3.16 (s, 3H), 1.87-1.80 (m, 4H). In a round-bottom flask which had been dried by heating and under argon, 5-amino-1-methyl-2',3',5',6'-tetrahydrospiro[indole-3,4'-pyran]-2(1H)-one (150 mg, 0.64 mmol) and (4-cyanophenyl)methanesulfonyl chloride (181 mg, 1.3 equiv) were dissolved together in abs. acetonitrile (5 ml), pyridine (0.16 ml, 3.1 equiv.) was then added and the mixture was stirred at 70° C. for 1 h. The reaction mixture was then concentrated under reduced pressure, water, dil. hydrochloric acid and dichloromethane were added to the residue that remained and the aqueous phase was extracted repeatedly with dichloromethane. The combined organic phases were dried over magnesium sulfate, filtered and concentrated under reduced pressure. Purification of the resulting crude product by column chromatography (gradient ethyl acetate/heptane) gave 1-(4-cyanophenyl)-N-(1-methyl-2-oxo-1,2,2',3',5',6'-hexahydrospiro[indole-3,4'-pyran]-5-yl)methanesulfonamide (181 mg, 68% of theory) as a colorless solid. $^1$H-NMR (400 MHz, CDCl$_3$ δ, ppm) 7.69 (d, 2H), 7.48 (d, 2H), 7.22 (d, 1H), 7.07 (dd, 1H), 6.82 (d, 1H), 6.24 (br. s, 1H, NH), 4.36 (s, 2H), 4.28 (m, 2H), 3.92 (m, 2H), 3.22 (s, 3H), 1.86 (m, 4H).

The compounds listed below are obtained analogously to the preparation examples given above and referred to at the appropriate place and taking into account the general information regarding the preparation of substituted dihydrooxindolylsulfonamides of the general formula (I).

A1. Compounds A1-1 to A1-600 of the general formula (Ib) in which $R^1$ represents methyl, $R^2$, $R^3$ and $R^4$ represent hydrogen and W, $R^5$, $R^6$ correspond to the definitions (Nos 1 to 600; corresponding to Compounds A1-1 to A1-600) in Table 1 below. An arrow in one of the definitions of $R^5$, $R^6$ listed in Table 1 represents a bond of the radical in question to the core structure (Ib).

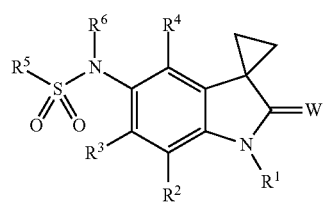

(Ib)

TABLE 1

| No. | $R^5$ | W | $R^6$ |
|---|---|---|---|
| 1 | CH₃ | O | H |
| 2 | ethyl | O | H |
| 3 | n-propyl | O | H |
| 4 | isopropyl | O | H |
| 5 | n-butyl | O | H |
| 6 | c-propyl | O | H |
| 7 | c-butyl | O | H |
| 8 | c-pentyl | O | H |
| 9 | c-hexyl | O | H |
| 10 | CH₃ | S | H |
| 11 | CH₃ | O | (acetyl) |
| 12 | CH₃ | O | (cyclopropanecarbonyl) |
| 13 | CH₃ | O | (cyclobutanecarbonyl) |
| 14 | CH₃ | O | CH₃ |
| 15 | CH₃ | O | (4-chlorobenzoyl) |
| 16 | CH₃ | O | ethyl |
| 17 | ethyl | O | CH₃ |
| 18 | isopropyl | O | CH₃ |
| 19 | c-propyl | O | CH₃ |
| 20 | (NHCH₃) | O | H |
| 21 | (N(CH₃)₂) | O | H |
| 22 | (NHEt) | O | H |
| 23 | (NHPr) | O | H |
| 24 | (NHiPr) | O | H |
| 25 | (OCH₃) | O | H |
| 26 | (CH₂CH₂OCH₃) | O | H |
| 27 | (N(CH₃)₂) | S | H |
| 28 | (N(CH₃)₂) | O | CH₃ |
| 29 | (phenyl) | O | H |
| 30 | (4-hydroxyphenyl) | O | H |
| 31 | (4-phenoxyphenyl) | O | H |
| 32 | (4-(4-chlorophenoxy)phenyl) | O | H |
| 33 | (biphenyl) | O | H |
| 34 | (4-fluorophenyl) | O | H |

TABLE 1-continued
| No. | R⁵ | W | R⁶ |
|---|---|---|---|
| 35 | 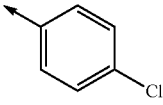 4-Cl-phenyl | O | H |
| 36 | 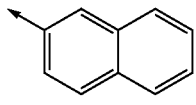 2-naphthyl | O | H |
| 37 | 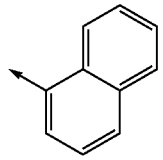 1-naphthyl | O | H |
| 38 | 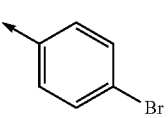 4-Br-phenyl | O | H |
| 39 | 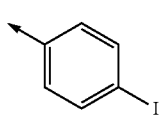 4-I-phenyl | O | H |
| 40 | 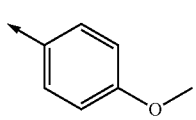 4-OMe-phenyl | O | H |
| 41 | 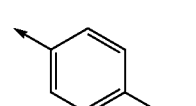 4-CF₃-phenyl | O | H |
| 42 | 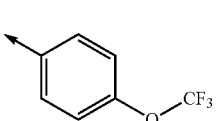 4-OCF₃-phenyl | O | H |
| 43 | 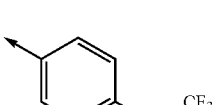 4-SCF₃-phenyl | O | H |
| 44 | 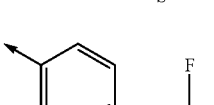 4-OCHF₂-phenyl | O | H |
| 45 | 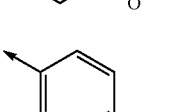 4-CN-phenyl | O | H |
| 46 | 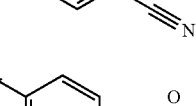 4-NHAc-phenyl | O | H |
| 47 | 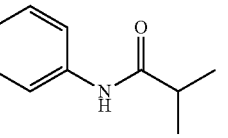 | O | H |
| 48 | 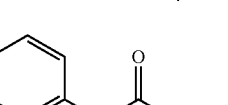 | O | H |
| 49 | NH₂ | O | H |
| 50 |  4-Me-phenyl | O | H |
| 51 |  3,4-diMe-phenyl | O | H |
| 52 |  2,3,4-triMe-phenyl | O | H |
| 53 |  | O | H |
| 54 |  3-Cl-phenyl | O | H |
| 55 |  3-Me-phenyl | O | H |
| 56 |  3-CN-phenyl | O | H |
| 57 |  2,4-diCl-phenyl | O | H |
| 58 |  3,5-diCl-phenyl | O | H |

TABLE 1-continued

| No. | R⁵ | W | R⁶ |
|---|---|---|---|
| 59 | 2,5-dichlorophenyl | O | H |
| 60 | 2,4-dichlorophenyl | O | H |
| 61 | 2-chlorophenyl | O | H |
| 62 | 2-fluorophenyl | O | H |
| 63 | 3,4-difluorophenyl | O | H |
| 64 | 3-fluorophenyl | O | H |
| 65 | 3,5-difluorophenyl | O | H |
| 66 | 3-(difluoromethoxy)phenyl | O | H |
| 67 | 3-(trifluoromethoxy)phenyl | O | H |
| 68 | 2,3-dichlorophenyl | O | H |
| 69 | 2-(trifluoromethyl)phenyl | O | H |
| 70 | 2-methoxyphenyl | O | H |
| 71 | 3-bromophenyl | O | H |
| 72 | 3-iodophenyl | O | H |
| 73 | 3-methoxyphenyl | O | H |
| 74 | 3-hydroxyphenyl | O | H |
| 75 | pyridin-3-yl | O | H |
| 76 | pyridin-4-yl | O | H |
| 77 | 4-bromonaphthalen-1-yl | O | H |
| 78 | 4-fluoronaphthalen-1-yl | O | H |
| 79 | 4-methoxynaphthalen-1-yl | O | H |
| 80 | 4-chloronaphthalen-1-yl | O | H |

TABLE 1-continued

| No. | R⁵ | W | R⁶ |
|---|---|---|---|
| 81 | 4-ethoxynaphthalen-1-yl | O | H |
| 82 | quinolin-8-yl | O | H |
| 83 | quinoxalin-5-yl | O | H |
| 84 | quinolin-5-yl | O | H |
| 85 | isoquinolin-5-yl | O | H |
| 86 | 4-acetamidonaphthalen-1-yl | O | H |
| 87 | 4-aminophenyl | O | H |
| 88 | 4-(methylamino)phenyl | O | H |
| 89 | 4-(ethylamino)phenyl | O | H |
| 90 | 4-(dimethylamino)phenyl | O | H |

TABLE 1-continued

| No. | R⁵ | W | R⁶ |
|---|---|---|---|
| 91 | 4-fluorophenyl | S | H |
| 92 | 4-chlorophenyl | S | H |
| 93 | naphthalen-2-yl | S | H |
| 94 | naphthalen-1-yl | S | H |
| 95 | 4-bromophenyl | S | H |
| 96 | 4-iodophenyl | S | H |
| 97 | 4-methoxyphenyl | S | H |
| 98 | 4-(trifluoromethyl)phenyl | S | H |
| 99 | 4-(trifluoromethoxy)phenyl | S | H |
| 100 | 4-cyanophenyl | S | H |
| 101 | 4-fluorophenyl | O | CH₃ |
| 102 | 4-chlorophenyl | O | CH₃ |
| 103 | naphthalen-2-yl | O | CH₃ |

TABLE 1-continued

| No. | R⁵ | W | R⁶ |
|---|---|---|---|
| 104 | 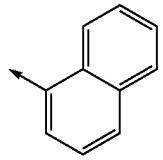 1-naphthyl | O | CH₃ |
| 105 | 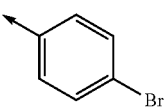 4-Br-C₆H₄ | O | CH₃ |
| 106 | 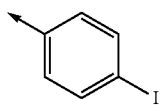 4-I-C₆H₄ | O | CH₃ |
| 107 | 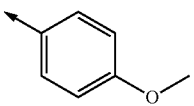 4-OCH₃-C₆H₄ | O | CH₃ |
| 108 | 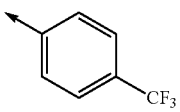 4-CF₃-C₆H₄ | O | CH₃ |
| 109 | 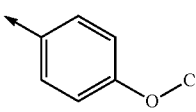 4-OCF₃-C₆H₄ | O | CH₃ |
| 110 | 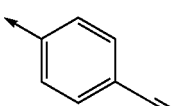 4-CN-C₆H₄ | O | 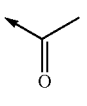 C(O)CH₃ |
| 111 | 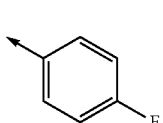 4-F-C₆H₄ | O | 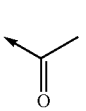 C(O)CH₃ |
| 112 | 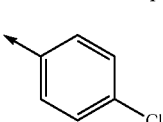 4-Cl-C₆H₄ | O | 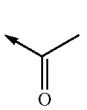 C(O)CH₃ |
| 113 | 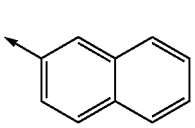 2-naphthyl | O | 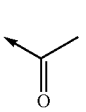 C(O)CH₃ |
| 114 | 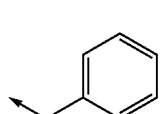 1-naphthyl | O | 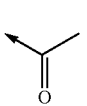 C(O)CH₃ |
| 115 | 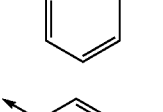 4-Br-C₆H₄ | O |  C(O)CH₃ |
| 116 | 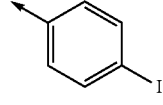 4-I-C₆H₄ | O | 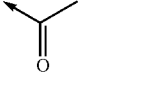 C(O)CH₃ |
| 117 | 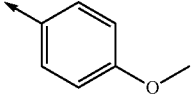 4-OCH₃-C₆H₄ | O | 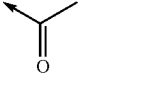 C(O)CH₃ |
| 118 | 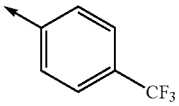 4-CF₃-C₆H₄ | O | 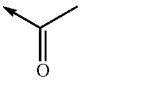 C(O)CH₃ |
| 119 | 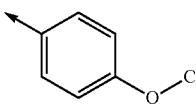 4-OCF₃-C₆H₄ | O | 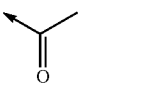 C(O)CH₃ |
| 120 | 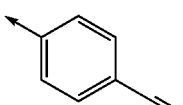 4-CN-C₆H₄ | O | 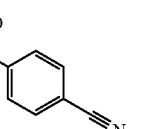 4-CN-C₆H₄-SO₂ |
| 121 | 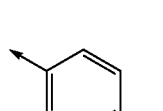 4-F-C₆H₄ | O | 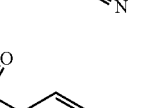 4-F-C₆H₄-SO₂ |
| 122 | 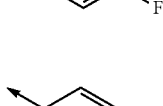 4-Cl-C₆H₄ | O | 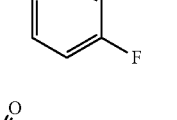 4-Cl-C₆H₄-SO₂ |
| 123 | 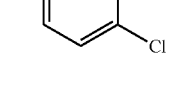 2-naphthyl | O | 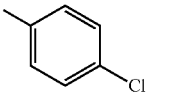 2-naphthyl-SO₂ |
| 124 | 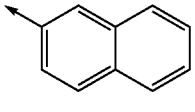 1-naphthyl | O | 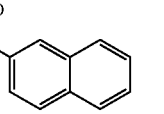 1-naphthyl-SO₂ |
| 125 | 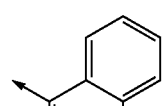 4-Br-C₆H₄ | O | 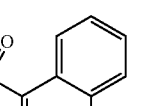 4-Br-C₆H₄-SO₂ |
| 126 | 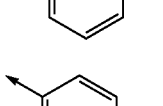 4-I-C₆H₄ | O | 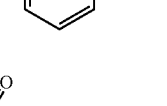 4-I-C₆H₄-SO₂ |

TABLE 1-continued

| No. | R⁵ | W | R⁶ |
|---|---|---|---|
| 127 | 4-methoxyphenyl | O | 4-methoxyphenylsulfonyl |
| 128 | 4-(trifluoromethyl)phenyl | O | 4-(trifluoromethyl)phenylsulfonyl |
| 129 | 4-(trifluoromethoxy)phenyl | O | 4-(trifluoromethoxy)phenylsulfonyl |
| 130 | 3-cyanophenyl | O | 3-cyanophenylsulfonyl |
| 131 | 4-fluorophenyl | O | tert-butoxycarbonyl |
| 132 | 4-chlorophenyl | O | tert-butoxycarbonyl |
| 133 | naphthalen-2-yl | O | tert-butoxycarbonyl |
| 134 | naphthalen-1-yl | O | tert-butoxycarbonyl |
| 135 | 4-bromophenyl | O | tert-butoxycarbonyl |
| 136 | 4-iodophenyl | O | tert-butoxycarbonyl |
| 137 | 4-methoxyphenyl | O | tert-butoxycarbonyl |
| 138 | 4-(trifluoromethyl)phenyl | O | tert-butoxycarbonyl |
| 139 | 4-(trifluoromethoxy)phenyl | O | tert-butoxycarbonyl |
| 140 | 4-cyanophenyl | O | tert-butoxycarbonyl |
| 141 | 4-carboxyphenyl | O | H |
| 142 | 4-(methoxycarbonyl)phenyl | O | H |
| 143 | 4-(ethoxycarbonyl)phenyl | O | H |
| 144 | 4-(tert-butoxycarbonyl)phenyl | O | H |
| 145 | 3-carboxyphenyl | O | H |
| 146 | 3-(methoxycarbonyl)phenyl | O | H |
| 147 | 3-(ethoxycarbonyl)phenyl | O | H |

TABLE 1-continued
| No. | R⁵ | W | R⁶ |
|---|---|---|---|
| 148 | 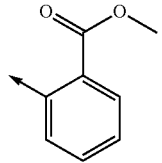 | O | H |
| 149 | 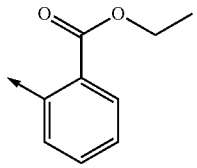 | O | H |
| 150 | 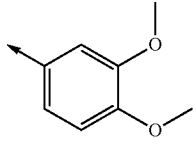 | O | H |
| 151 | 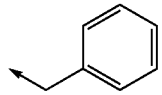 | O | H |
| 152 | 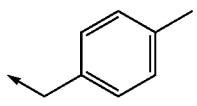 | O | H |
| 153 | 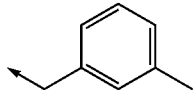 | O | H |
| 154 | 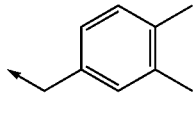 | O | H |
| 155 | 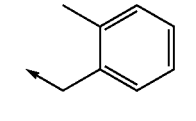 | O | H |
| 156 | 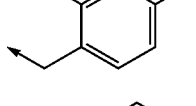 | O | H |
| 157 | 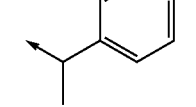 | O | H |
| 158 | 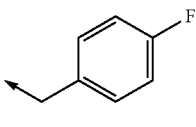 | O | H |
| 159 | 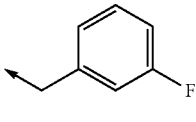 | O | H |
| 160 | 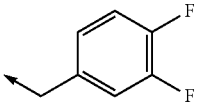 | O | H |
| 161 | 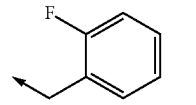 | O | H |
| 162 | 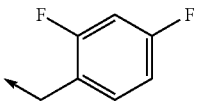 | O | H |
| 163 | 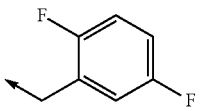 | O | H |
| 164 | 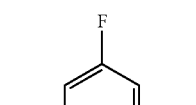 | O | H |
| 165 | 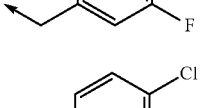 | O | H |
| 166 | 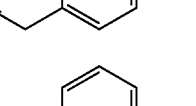 | O | H |
| 167 | 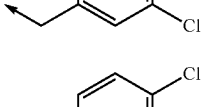 | O | H |
| 168 | 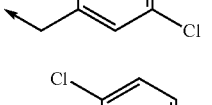 | O | H |
| 169 | 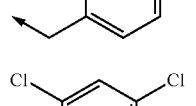 | O | H |
| 170 | 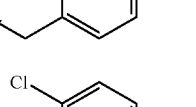 | O | H |
| 171 | 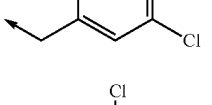 | O | H |

TABLE 1-continued

| No. | R⁵ | W | R⁶ |
|-----|----|----|----|
| 172 | 4-Br-benzyl | O | H |
| 173 | 3-Br-benzyl | O | H |
| 174 | 2-Br-benzyl | O | H |
| 175 | 4-NO₂-benzyl | O | H |
| 176 | 3-NO₂-benzyl | O | H |
| 177 | 2-NO₂-benzyl | O | H |
| 178 | 4-CF₃-benzyl | O | H |
| 179 | 3-CF₃-benzyl | O | H |
| 180 | 2-CF₃-benzyl | O | H |
| 181 | 4-CN-benzyl | O | H |
| 182 | 3-CN-benzyl | O | H |
| 183 | 2-CN-benzyl | O | H |
| 184 | 4-OCF₃-benzyl | O | H |
| 185 | 3-OCF₃-benzyl | O | H |
| 186 | 4-SCF₃-benzyl | O | H |
| 187 | 3-SCF₃-benzyl | O | H |
| 188 | 4-OCHF₂-benzyl | O | H |
| 189 | 3-OCHF₃-benzyl | O | H |
| 190 | 4-(methoxycarbonyl)benzyl | O | H |
| 191 | 3-(methoxycarbonyl)benzyl | O | H |
| 192 | 4-(ethoxycarbonyl)benzyl | O | H |
| 193 | 3-(ethoxycarbonyl)benzyl | O | H |
| 194 | 4-carboxybenzyl | O | H |
| 195 | 3-carboxybenzyl | O | H |

TABLE 1-continued
| No. | R⁵ | W | R⁶ |
|---|---|---|---|
| 196 | 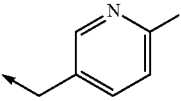 | O | H |
| 197 | 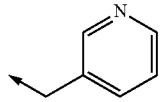 | O | H |
| 198 | 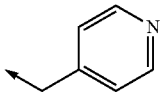 | O | H |
| 199 | 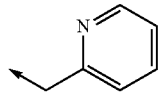 | O | H |
| 200 | 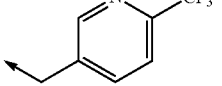 | O | H |
| 201 | 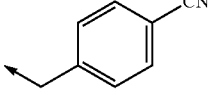 | S | H |
| 202 | 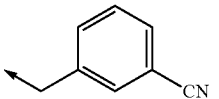 | S | H |
| 203 | 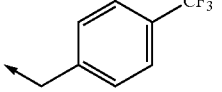 | S | H |
| 204 | 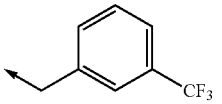 | S | H |
| 205 | 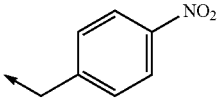 | S | H |
| 206 | 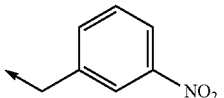 | S | H |
| 207 | 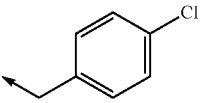 | S | H |
| 208 | 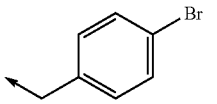 | S | H |
| 209 | 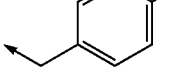 | S | H |
| 210 | 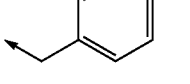 | S | H |
| 211 | 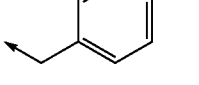 | O | CH₃ |
| 212 | 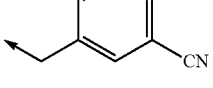 | O | CH₃ |
| 213 | 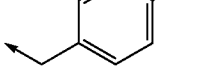 | O | CH₃ |
| 214 | 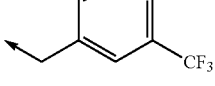 | O | CH₃ |
| 215 | 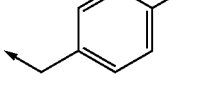 | O | CH₃ |
| 216 | 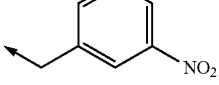 | O | CH₃ |
| 217 | 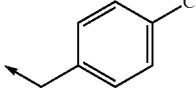 | O | CH₃ |
| 218 | 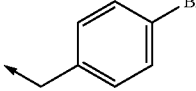 | O | CH₃ |
| 219 | 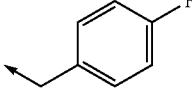 | O | CH₃ |
| 220 | 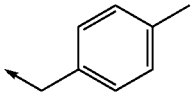 | O | CH₃ |
| 221 | 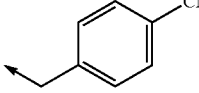 | O | ethyl |

TABLE 1-continued

| No. | R⁵ | W | R⁶ |
|-----|-----|---|-----|
| 222 | 3-CN-benzyl | O | ethyl |
| 223 | 4-CF₃-benzyl | O | ethyl |
| 224 | 3-CF₃-benzyl | O | ethyl |
| 225 | 4-NO₂-benzyl | O | ethyl |
| 226 | 2-OCF₃-benzyl | O | H |
| 227 | 4-Cl-benzyl | O | ethyl |
| 228 | 4-Br-benzyl | O | ethyl |
| 229 | 4-F-benzyl | O | ethyl |
| 230 | 4-methyl-benzyl | O | ethyl |
| 231 | 4-CN-benzyl | O | acetyl |
| 232 | 3-CN-benzyl | O | acetyl |
| 233 | 4-CF₃-benzyl | O | acetyl |
| 234 | 3-CF₃-benzyl | O | acetyl |
| 235 | 4-NO₂-benzyl | O | acetyl |
| 236 | 3-NO₂-benzyl | O | acetyl |
| 237 | 4-Cl-benzyl | O | acetyl |
| 238 | 4-Br-benzyl | O | acetyl |
| 239 | 4-F-benzyl | O | acetyl |
| 240 | 4-methyl-benzyl | O | acetyl |
| 241 | 4-CN-benzyl | O | cyclopropanecarbonyl |
| 242 | 3-CN-benzyl | O | cyclopropanecarbonyl |
| 243 | 4-CF₃-benzyl | O | cyclopropanecarbonyl |
| 244 | 3-CF₃-benzyl | O | cyclopropanecarbonyl |
| 245 | 4-NO₂-benzyl | O | cyclopropanecarbonyl |
| 246 | 3-NO₂-benzyl | O | cyclopropanecarbonyl |

TABLE 1-continued

| No. | R⁵ | W | R⁶ |
|---|---|---|---|
| 247 | 4-Cl-C₆H₄-CH₂- | O | cyclopropyl-C(=O)- |
| 248 | 4-Br-C₆H₄-CH₂- | O | cyclopropyl-C(=O)- |
| 249 | 4-F-C₆H₄-CH₂- | O | cyclopropyl-C(=O)- |
| 250 | 4-CH₃-C₆H₄-CH₂- | O | cyclopropyl-C(=O)- |
| 251 | 4-CN-C₆H₄-CH₂- | O | iPr-C(=O)- |
| 252 | 3-CN-C₆H₄-CH₂- | O | iPr-C(=O)- |
| 253 | 4-CF₃-C₆H₄-CH₂- | O | iPr-C(=O)- |
| 254 | 3-CF₃-C₆H₄-CH₂- | O | iPr-C(=O)- |
| 255 | 4-NO₂-C₆H₄-CH₂- | O | iPr-C(=O)- |
| 256 | 3-NO₂-C₆H₄-CH₂- | O | iPr-C(=O)- |
| 257 | 4-Cl-C₆H₄-CH₂- | O | iPr-C(=O)- |
| 258 | 4-Br-C₆H₄-CH₂- | O | iPr-C(=O)- |
| 259 | 4-F-C₆H₄-CH₂- | O | iPr-C(=O)- |
| 260 | 4-CH₃-C₆H₄-CH₂- | O | iPr-C(=O)- |
| 261 | 4-CN-C₆H₄-CH₂- | O | MeO-C(=O)- |
| 262 | 3-CN-C₆H₄-CH₂- | O | MeO-C(=O)- |
| 263 | 4-CF₃-C₆H₄-CH₂- | O | MeO-C(=O)- |
| 264 | 3-CF₃-C₆H₄-CH₂- | O | MeO-C(=O)- |
| 265 | 4-NO₂-C₆H₄-CH₂- | O | MeO-C(=O)- |
| 266 | 3-NO₂-C₆H₄-CH₂- | O | MeO-C(=O)- |
| 267 | 4-Cl-C₆H₄-CH₂- | O | MeO-C(=O)- |
| 268 | 4-Br-C₆H₄-CH₂- | O | MeO-C(=O)- |
| 269 | 4-F-C₆H₄-CH₂- | O | MeO-C(=O)- |
| 270 | 4-CH₃-C₆H₄-CH₂- | O | MeO-C(=O)- |
| 271 | 4-CN-C₆H₄-CH₂- | O | tBuO-C(=O)- |

TABLE 1-continued
| No. | R⁵ | W | R⁶ |
|---|---|---|---|
| 272 | 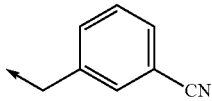 | O | 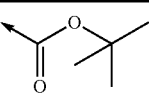 |
| 273 | 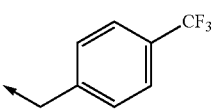 | O | 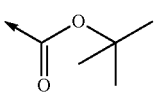 |
| 274 | 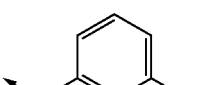 | O | 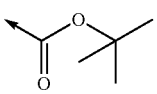 |
| 275 | 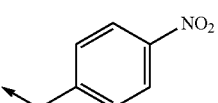 | O | 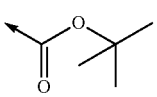 |
| 276 | 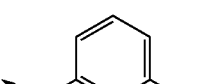 | O | 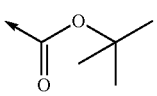 |
| 277 | 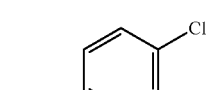 | O | 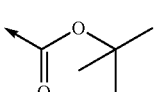 |
| 278 |  | O | 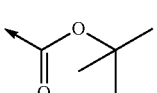 |
| 279 | 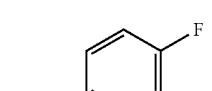 | O | 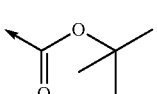 |
| 280 | 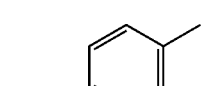 | O | 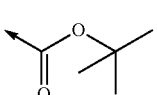 |
| 281 |  | O | 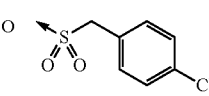 |
| 282 | 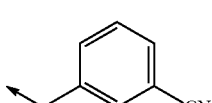 | O | 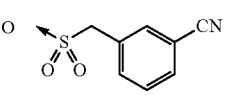 |
| 283 |  | O | 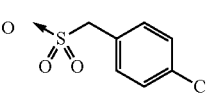 |
| 284 |  | O | 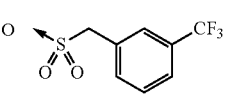 |
| 285 | 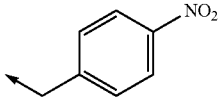 | O | 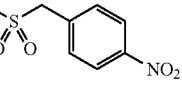 |
| 286 | 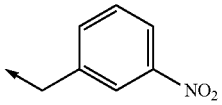 | O | 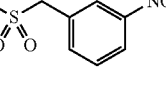 |
| 287 | 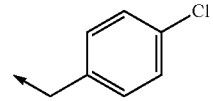 | O | 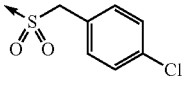 |
| 288 | 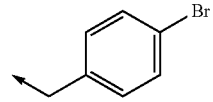 | O | 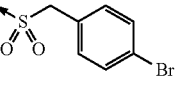 |
| 289 | 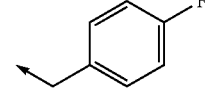 | O | 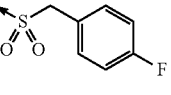 |
| 290 | 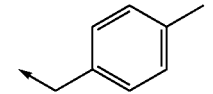 | O | 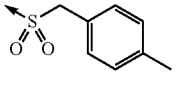 |
| 291 | 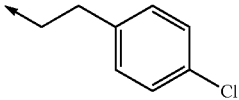 | O | H |
| 292 | 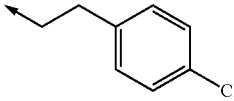 | O | H |
| 293 | 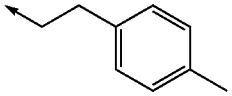 | O | H |
| 294 | 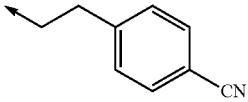 | O | H |
| 295 | 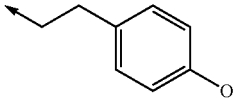 | O | H |
| 296 | 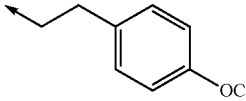 | O | H |
| 297 | 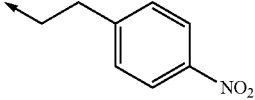 | O | H |

TABLE 1-continued

| No. | R⁵ | W | R⁶ |
|---|---|---|---|
| 298 | 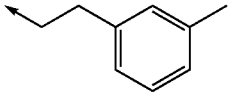 | O | H |
| 299 | 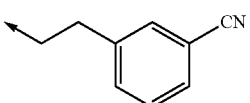 | O | H |
| 300 | 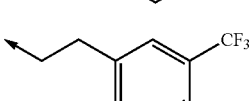 | O | H |
| 301 | 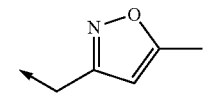 | O | H |
| 302 | pyrimidin-4-ylmethyl | O | H |
| 303 | pyrazin-2-ylmethyl | O | H |
| 304 | pyridazin-3-ylmethyl | O | H |
| 305 | pyridazin-4-ylmethyl | O | H |
| 306 | pyrimidin-2-ylmethyl | O | H |
| 307 | pyrimidin-5-ylmethyl | O | H |
| 308 | (6-methylpyridin-2-yl)methyl | O | H |
| 309 | 1-(pyridin-3-yl)ethyl | O | H |
| 310 | 1-(pyridin-2-yl)ethyl | O | H |
| 311 | (2-methylpyridin-4-yl)methyl | O | H |
| 312 | (4-hydroxyphenyl)methyl | O | H |
| 313 | (3-hydroxyphenyl)methyl | O | H |
| 314 | 1-(pyrazin-2-yl)ethyl | O | H |
| 315 | (5-methylpyrazin-2-yl)methyl | O | H |
| 316 | (2-methylpyrimidin-2-yl)methyl | O | H |
| 317 | (2-cyanopyridin-4-yl)methyl | O | H |
| 318 | (4-ethenylphenyl)methyl | O | H |
| 319 | 2,3-dihydro-1H-indan-1-yl | O | H |
| 320 | (2-formylphenyl)methyl | O | H |
| 321 | (3-formylphenyl)methyl | O | H |
| 322 | (4-formylphenyl)methyl | O | H |
| 323 | (2-ethylphenyl)methyl | O | H |
| 324 | (3-ethylphenyl)methyl | O | H |
| 325 | (4-ethylphenyl)methyl | O | H |
| 326 | 1-phenylpropan-1-yl | O | H |
| 327 | (2-isopropylphenyl)methyl | O | H |
| 328 | (3-isopropylphenyl)methyl | O | H |
| 329 | (4-isopropylphenyl)methyl | O | H |
| 330 | (2-tert-butylphenyl)methyl | O | H |
| 331 | (3-tert-butylphenyl)methyl | O | H |
| 332 | (4-tert-butylphenyl)methyl | O | H |
| 333 | (2-n-propylphenyl)methyl | O | H |
| 334 | (3-n-propylphenyl)methyl | O | H |
| 335 | (4-n-propylphenyl)methyl | O | H |
| 336 | (2-c-propylphenyl)methyl | O | H |
| 337 | (3-c-propylphenyl)methyl | O | H |
| 338 | (4-c-propylphenyl)methyl | O | H |
| 339 | 1-(4-methylphenyl)ethyl | O | H |
| 340 | 1-(3-methylphenyl)ethyl | O | H |
| 341 | 1-(2-methylphenyl)ethyl | O | H |
| 342 | (2,5-dimethylphenyl)methyl | O | H |
| 343 | (3,5-dimethylphenyl)methyl | O | H |
| 344 | (2,3-dimethylphenyl)methyl | O | H |
| 345 | (2,6-dimethylphenyl)methyl | O | H |
| 346 | (2-methoxyphenyl)methyl | O | H |
| 347 | (3-methoxyphenyl)methyl | O | H |
| 348 | (4-methoxyphenyl)methyl | O | H |
| 349 | (2,5-dimethoxyphenyl)methyl | O | H |
| 350 | (3,5-dimethoxyphenyl)methyl | O | H |
| 351 | (2,4-dimethoxyphenyl)methyl | O | H |
| 352 | (6-methoxypyridin-2-yl)methyl | O | H |
| 353 | (5-methoxypyridin-2-yl)methyl | O | H |
| 354 | (6-methoxypyridin-3-yl)methyl | O | H |
| 355 | (5-methoxypyrazin-2-yl)methyl | O | H |
| 356 | (2-methoxypyrimidin-5-yl)methyl | O | H |
| 357 | (3-fluoro-4-methylphenyl)methyl | O | H |
| 358 | (2-fluoro-4-methylphenyl)methyl | O | H |
| 359 | (4-fluoro-2-methylphenyl)methyl | O | H |
| 360 | (4-fluoro-3-methylphenyl)methyl | O | H |
| 361 | 1-(3-fluorophenyl)ethyl | O | H |
| 362 | 1-(4-fluorophenyl)ethyl | O | H |
| 363 | 1-(2-fluorophenyl)ethyl | O | H |
| 364 | 1-(2-chlorophenyl)ethyl | O | H |
| 365 | 1-(3-chlorophenyl)ethyl | O | H |
| 366 | 1-(4-chlorophenyl)ethyl | O | H |
| 367 | 1-(2-bromophenyl)ethyl | O | H |
| 368 | 1-(3-bromophenyl)ethyl | O | H |
| 369 | 1-(4-bromophenyl)ethyl | O | H |
| 370 | 1-(2-cyanophenyl)ethyl | O | H |
| 371 | 1-(3-cyanophenyl)ethyl | O | H |
| 372 | 1-(4-cyanophenyl)ethyl | O | H |
| 373 | 1-(2-trifluoromethylphenyl)ethyl | O | H |
| 374 | 1-(3-trifluoromethylphenyl)ethyl | O | H |
| 375 | 1-(4-trifluoromethylphenyl)ethyl | O | H |
| 376 | 1-(2-methoxyphenyl)ethyl | O | H |
| 377 | 1-(3-methoxyphenyl)ethyl | O | H |
| 378 | 1-(4-methoxyphenyl)ethyl | O | H |
| 379 | (4-chloropyridin-2-yl)methyl | O | H |
| 380 | (3-chloropyridin-4-yl)methyl | O | H |
| 381 | (2-chloropyridin-3-yl)methyl | O | H |
| 382 | (2-chloropyridin-4-yl)methyl | O | H |
| 383 | (2,6-difluorophenyl)methyl | O | H |
| 384 | (2,3-difluorophenyl)methyl | O | H |
| 385 | (5-chloropyrazin-2-yl)methyl | O | H |
| 386 | (2-chloropyrimidin-5-yl)methyl | O | H |
| 387 | 1-benzofuran-5-ylmethyl | O | H |
| 388 | cyclopropyl(phenyl)methyl | O | H |
| 389 | cyclopropyl(4-chlorophenyl)methyl | O | H |
| 390 | cyclopropyl(4-methylphenyl)methyl | O | H |
| 391 | cyclopropyl(4-cyanophenyl)methyl | O | H |
| 392 | cyclopropyl(4-fluorophenyl)methyl | O | H |
| 393 | indan-5-ylmethyl | O | H |
| 394 | (2,4,6-trimethylphenyl)methyl | O | H |
| 395 | (2,6-dichloro-4-methylphenyl)methyl | O | H |
| 396 | 1-(3-fluorophenyl)propyl | O | H |
| 397 | 1-(4-fluorophenyl)propyl | O | H |
| 398 | 1-(2-fluorophenyl)propyl | O | H |
| 399 | 1-(2-chlorophenyl)propyl | O | H |
| 400 | 1-(3-chlorophenyl)propyl | O | H |
| 401 | 1-(4-chlorophenyl)propyl | O | H |
| 402 | 1-(2-bromophenyl)propyl | O | H |
| 403 | 1-(3-bromophenyl)propyl | O | H |
| 404 | 1-(4-bromophenyl)propyl | O | H |
| 405 | 1-(2-cyanophenyl)propyl | O | H |
| 406 | 1-(3-cyanophenyl)propyl | O | H |
| 407 | 1-(4-cyanophenyl)propyl | O | H |
| 408 | 1-(2-trifluoromethylphenyl)propyl | O | H |
| 409 | 1-(3-trifluoromethylphenyl)propyl | O | H |
| 410 | 1-(4-trifluoromethylphenyl)propyl | O | H |
| 411 | 1-(2-methoxyphenyl)propyl | O | H |
| 412 | 1-(3-methoxyphenyl)propyl | O | H |
| 413 | 1-(4-methoxyphenyl)propyl | O | H |
| 414 | 1-(2-methylphenyl)propyl | O | H |
| 415 | 1-(3-methylphenyl)propyl | O | H |
| 416 | 1-(4-methylphenyl)propyl | O | H |
| 417 | 1-(2,4-dimethylphenyl)ethyl | O | H |
| 418 | 1-(4-ethylphenyl)ethyl | O | H |
| 419 | 1-(3,4-dimethylphenyl)ethyl | O | H |
| 420 | 1-(2,5-dimethylphenyl)ethyl | O | H |
| 421 | 1-(phenyl)butyl | O | H |
| 422 | 2-methyl-1-(phenyl)propyl | O | H |
| 423 | (2,4,5-trimethylphenyl)methyl | O | H |
| 424 | (5-cyano-2-fluorophenyl)methyl | O | H |
| 425 | (4-cyano-2-fluorophenyl)methyl | O | H |
| 426 | (2-cyano-4-fluorophenyl)methyl | O | H |
| 427 | (2-cyano-5-fluorophenyl)methyl | O | H |
| 428 | 4-(dimethylamino)phenylmethyl | O | H |
| 429 | 3-(dimethylamino)phenylmethyl | O | H |

TABLE 1-continued

| No. | R⁵ | W | R⁶ |
|---|---|---|---|
| 430 | benzo[1,3]dioxol-5-ylmethyl | O | H |
| 431 | 4-(methoxymethyl)phenylmethyl | O | H |
| 432 | 3-(methoxymethyl)phenylmethyl | O | H |
| 433 | 2-(methoxymethyl)phenylmethyl | O | H |
| 434 | (2-methoxy-5-methylphenyl)methyl | O | H |
| 435 | (3-fluoro-4-methoxyphenyl)methyl | O | H |
| 436 | (2-fluoro-4-methoxyphenyl)methyl | O | H |
| 437 | (2-fluoro-5-methoxyphenyl)methyl | O | H |
| 438 | 1-(2,6-difluorophenyl)ethyl | O | H |
| 439 | 1-(2,5-difluorophenyl)ethyl | O | H |
| 440 | 1-(2,4-difluorophenyl)ethyl | O | H |
| 441 | 1-(2,6-dichlorophenyl)ethyl | O | H |
| 442 | 1-(2,5-dichlorophenyl)ethyl | O | H |
| 443 | 1-(2,4-dichlorophenyl)ethyl | O | H |
| 444 | 1-(2,3-dichlorophenyl)ethyl | O | H |
| 445 | 1-(3,5-dichlorophenyl)ethyl | O | H |
| 446 | 2-naphthylmethyl | O | H |
| 447 | 1-naphthylmethyl | O | H |
| 448 | quinolin-4-ylmethyl | O | H |
| 449 | quinolin-6-ylmethyl | O | H |
| 450 | quinolin-8-ylmethyl | O | H |
| 451 | quinolin-2-ylmethyl | O | H |
| 452 | quinoxalin-2-ylmethyl | O | H |
| 453 | (5-chloro-2-fluorophenyl)methyl | O | H |
| 454 | (4-chloro-2-fluorophenyl)methyl | O | H |
| 455 | (2-chloro-4-fluorophenyl)methyl | O | H |
| 456 | (2-chloro-5-fluorophenyl)methyl | O | H |
| 457 | (3-chloro-2-fluorophenyl)methyl | O | H |
| 458 | (3-chloro-4-fluorophenyl)methyl | O | H |
| 459 | (3-chloro-5-fluorophenyl)methyl | O | H |
| 460 | (4-chloro-3-fluorophenyl)methyl | O | H |
| 461 | (2-chloro-6-fluorophenyl)methyl | O | H |
| 462 | (2,4,5-trifluorophenyl)methyl | O | H |
| 463 | (2,4,6-trifluorophenyl)methyl | O | H |
| 464 | (3,4,5-trifluorophenyl)methyl | O | H |
| 465 | (3-cyano-4-methoxyphenyl)methyl | O | H |
| 466 | (4-cyano-3-methoxyphenyl)methyl | O | H |
| 467 | (4-cyano-2-methoxyphenyl)methyl | O | H |
| 468 | (4-cyclopropoxyphenyl)methyl | O | H |
| 469 | 1-benzothiophen-6-ylmethyl | O | H |
| 470 | 1-benzothiophen-5-ylmethyl | O | H |
| 471 | 1-(2,4,5-trimethylphenyl)ethyl | O | H |
| 472 | 1-(4-ethylphenyl)propyl | O | H |
| 473 | 1-(4-propan-2-ylphenyl)ethyl | O | H |
| 474 | 3-methyl-1-phenylbutan-1-yl | O | H |
| 475 | (3-acetamidophenyl)methyl | O | H |
| 476 | (4-acetamidophenyl)methyl | O | H |
| 477 | [4-(methylcarbamoyl)phenyl]methyl | O | H |
| 478 | [3-(methylcarbamoyl)phenyl]methyl | O | H |
| 479 | [4-(ethylcarbamoyl)phenyl]methyl | O | H |
| 480 | [3-(ethylcarbamoyl)phenyl]methyl | O | H |
| 481 | 1-(2,4,6-trimethylpyridin-3-yl)ethyl | O | H |
| 482 | [4-(propan-2-yloxy)phenyl]nethyl | O | H |
| 483 | [3-(propan-2-yloxy)phenyl]nethyl | O | H |
| 484 | [2-methyl-6-nitrophenyl)methyl | O | H |
| 485 | (4-methyl-3-nitrophenyl)methyl | O | H |
| 486 | (2-methyl-3-nitrophenyl)methyl | O | H |
| 487 | (2-methyl-4-nitrophenyl)methyl | O | H |
| 488 | 1-(2-nitrophenyl)ethyl | O | H |
| 489 | 1-(3-nitrophenyl)ethyl | O | H |
| 490 | 1-(4-nitrophenyl)ethyl | O | H |
| 491 | (3,4-dimethoxyphenyl)methyl | O | H |
| 492 | (4-methoxy-3,5-dimethylpyridin-2-yl)methyl | O | H |
| 493 | (4,5-dimethoxypyridin-2-yl)methyl | O | H |
| 494 | 1-(2-naphthyl)methyl | O | H |
| 495 | 1-(1-naphthyl)methyl | O | H |
| 496 | (3-chloro-4-methoxyphenyl)methyl | O | H |
| 497 | (4-chloro-3-methoxyphenyl)methyl | O | H |
| 498 | (4-chloro-2-methoxyphenyl)methyl | O | H |
| 499 | (5-chloro-2-methoxyphenyl)methyl | O | H |
| 500 | (3-chloro-5-methoxyphenyl)methyl | O | H |
| 501 | (2-methylquinolin-4-yl)methyl | O | H |
| 502 | 1-(5-chloro-2-fluorophenyl)ethyl | O | H |
| 503 | 1-(4-chloro-2-fluorophenyl)ethyl | O | H |
| 504 | 1-(2-chloro-4-fluorophenyl)ethyl | O | H |
| 505 | 1-(2-chloro-5-fluorophenyl)ethyl | O | H |
| 506 | 1-(3-chloro-2-fluorophenyl)ethyl | O | H |
| 507 | 1-(3-chloro-4-fluorophenyl)ethyl | O | H |
| 508 | 1-(3-chloro-5-fluorophenyl)ethyl | O | H |
| 509 | 1-(4-chloro-3-fluorophenyl)ethyl | O | H |
| 510 | 1-(2-chloro-6-fluorophenyl)ethyl | O | H |
| 511 | (2-hydroxyquinolin-3-yl)methyl | O | H |
| 512 | 1-(5,6,7,8-tetrahydronaphthalin-2-yl)ethyl | O | H |
| 513 | [5-(trifluoromethyl)pyridin-2-yl]methyl | O | H |
| 514 | [2-(trifluoromethyl)pyridin-4-yl]methyl | O | H |
| 515 | (3,6-dichloropyridin-2-yl)methyl | O | H |
| 516 | [5-(trifluoromethyl)pyrazin-2-yl]methyl | O | H |
| 517 | [2-(trifluoromethyl)pyrimidin-2-yl]methyl | O | H |
| 518 | 1-phenylhexan-1-yl | O | H |
| 519 | 1-(3-tert-butylphenyl)ethyl | O | H |
| 520 | 1-(4-tert-butylphenyl)ethyl | O | H |
| 521 | 1-(2-nitrophenyl)propyl | O | H |
| 522 | 1-(3-nitrophenyl)propyl | O | H |
| 523 | 1-(4-nitrophenyl)propyl | O | H |
| 524 | (2-methoxy-5-nitrophenyl)methyl | O | H |
| 525 | (4-methoxy-3-nitrophenyl)methyl | O | H |
| 526 | (2-methoxy-4-nitrophenyl)methyl | O | H |
| 527 | (3-methoxy-4-nitrophenyl)methyl | O | H |
| 528 | diphenylmethyl | O | H |
| 529 | (4-phenylphenyl)methyl | O | H |
| 530 | phenyl(pyridin-2-yl)methyl | O | H |
| 531 | phenyl(pyridin-3-yl)methyl | O | H |
| 532 | phenyl(pyridin-4-yl)methyl | O | H |
| 533 | (5-chloro-2-ethoxyphenyl)methyl | O | H |
| 534 | (5-chloro-2-nitrophenyl)methyl | O | H |
| 535 | (4-chloro-2-nitrophenyl)methyl | O | H |
| 536 | (2-chloro-4-nitrophenyl)methyl | O | H |
| 537 | (2-chloro-5-nitrophenyl)methyl | O | H |
| 538 | (3-chloro-2-nitrophenyl)methyl | O | H |
| 539 | (3-chloro-4-nitrophenyl)methyl | O | H |
| 540 | (3-chloro-5-nitrophenyl)methyl | O | H |
| 541 | (4-chloro-3-nitrophenyl)methyl | O | H |
| 542 | (2-chloro-6-nitrophenyl)methyl | O | H |
| 543 | (5-bromopyridin-2-yl)methyl | O | H |
| 544 | (2-bromopyridin-4-yl)methyl | O | H |
| 545 | (6-bromopyridin-2-yl)methyl | O | H |
| 546 | (2,4-difluoro-5-nitrophenyl)methyl | O | H |
| 547 | (3-methyl-2-trifluoromethylphenyl)methyl | O | H |
| 548 | 3,3,3-trifluoro-1-phenylpropyl | O | H |
| 549 | cyclohexyl(phenyl)methyl | O | H |
| 550 | cyclopentyl(phenyl)methyl | O | H |
| 551 | 1-(3,4-dichlorophenyl)ethyl | O | H |
| 552 | [4-(cyclopentyloxy)phenyl]methyl | O | H |
| 553 | [2-fluoro-4-(trifluoromethyl)phenyl]methyl | O | H |
| 554 | [3-fluoro-4-(trifluoromethyl)phenyl]methyl | O | H |
| 555 | [2-fluoro-5-(trifluoromethyl)phenyl]methyl | O | H |
| 556 | [3-fluoro-5-(trifluoromethyl)phenyl]methyl | O | H |
| 557 | 1-(2-nitrophenyl)butyl | O | H |
| 558 | 1-(3-nitrophenyl)butyl | O | H |
| 559 | 1-(4-nitrophenyl)butyl | O | H |
| 560 | 1-(2-cyanophenyl)butyl | O | H |
| 561 | 1-(3-cyanophenyl)butyl | O | H |
| 562 | 1-(4-cyanophenyl)butyl | O | H |
| 563 | 1-(2-fluorophenyl)butyl | O | H |
| 564 | 1-(3-fluorophenyl)butyl | O | H |
| 565 | 1-(4-fluorophenyl)butyl | O | H |
| 566 | 1-(2-chlorophenyl)butyl | O | H |
| 567 | 1-(3-chlorophenyl)butyl | O | H |
| 568 | 1-(4-chlorophenyl)butyl | O | H |
| 569 | (2,4-dinitrophenyl)methyl | O | H |
| 570 | (2-methylphenyl)(phenyl)methyl | O | H |

TABLE 1-continued

| No. | R⁵ | W | R⁶ |
|---|---|---|---|
| 571 | 1,2-diphenylethyl | O | H |
| 572 | 1-(4-phenylphenyl)ethyl | O | H |
| 573 | (4-bromo-3-methylphenyl)methyl | O | H |
| 574 | (4-bromo-3-fluorophenyl)methyl | O | H |
| 575 | (4-bromo-3-chlorophenyl)methyl | O | H |
| 576 | (3-bromo-4-chlorophenyl)methyl | O | H |
| 577 | (3-bromo-5-chlorophenyl)methyl | O | H |
| 578 | 4-bromo-3-methylphenyl | O | H |
| 579 | 4-bromo-3-fluorophenyl | O | H |
| 580 | 4-bromo-3-chlorophenyl | O | H |
| 581 | 3-bromo-4-chlorophenyl | O | H |
| 582 | 3-bromo-5-chlorophenyl | O | H |
| 583 | 4-bromo-2-fluorophenyl | O | H |
| 584 | (5-bromo-2-fluorophenyl)methyl | O | H |
| 585 | (2-bromo-4-fluorophenyl)methyl | O | H |
| 586 | (4-bromo-2-fluorophenyl)methyl | O | H |
| 587 | (3-bromo-5-fluorophenyl)methyl | O | H |
| 588 | 5-bromo-2-fluorophenyl | O | H |
| 589 | 2-bromo-4-fluorophenyl | O | H |
| 590 | 3-bromo-5-fluorophenyl | O | H |
| 591 | 1-(2,4-dichlorophenyl)propyl | O | H |
| 592 | 1-(3,4-dichlorophenyl)propyl | O | H |
| 593 | 1-(2,6-dichloro-3-fluorophenyl)ethyl | O | H |
| 594 | 1-(2,4-dichloro-5-fluorophenyl)ethyl | O | H |
| 595 | (2-chloro-6-trifluoromethylphenyl)methyl | O | H |
| 596 | (2-chloro-4-trifluoromethylphenyl)methyl | O | H |
| 597 | (4-chloro-3-trifluoromethylphenyl)methyl | O | H |
| 598 | (2-chloro-4-trifluoromethylphenyl)methyl | O | H |
| 599 | (3-bromo-4-methoxyphenyl)methyl | O | H |
| 600 | 4-bromo-3-methoxyphenyl | O | H |

A2. Compounds A2-1 to A2-600 of the general formula (Ib) in which $R^1$ represents ethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds A2-1 to A2-600).

A3. Compounds A3-1 to A3-600 of the general formula (Ib) in which $R^1$ represents n-propyl, $R^2$, $R^3$ and $R^4$ represent hydrogen and W, $R^5$, $R^6$ for the individual compound in question correspond to the radical definitions given in Table 1 (Nos 1 to 600; corresponding to Compounds A3-1 to A3-600).

A4. Compounds A4-1 to A4-600 of the general formula (Ib) in which $R^1$ represents isopropyl, $R^2$, $R^3$ and $R^4$ represent hydrogen and W, $R^5$, $R^6$ for the individual compound in question correspond to the radical definitions given in Table 1 (Nos 1 to 600; corresponding to Compounds A4-1 to A4-600).

A5. Compounds A5-1 to A5-600 of the general formula (Ib) in which $R^1$ represents n-butyl, $R^2$, $R^3$ and $R^4$ represent hydrogen and W, $R^5$, $R^6$ for the individual compound in question correspond to the radical definitions given in Table 1 (Nos 1 to 600; corresponding to Compounds A5-1 to A5-600).

A6. Compounds A6-1 to A6-600 of the general formula (Ib) in which $R^1$ represents 3-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds A6-1 to A6-600).

A7. Compounds A7-1 to A7-600 of the general formula (Ib) in which $R^1$ represents 2-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds A7-1 to A7-600).

A8. Compounds A8-1 to A8-600 of the general formula (Ib) in which $R^1$ represents methyl, $R^2$ represents fluorine, $R^3$ and $R^4$ represent hydrogen and W, $R^5$, $R^6$ for the individual compound in question correspond to the radical definitions given in Table 1 (Nos 1 to 600; corresponding to Compounds A8-1 to A8-600).

A9. Compounds A9-1 to A9-600 of the general formula (Ib) in which $R^1$ represents ethyl, $R^2$ represents fluorine, $R^3$ and $R^4$ represent hydrogen and W, $R^5$, $R^6$ for the individual compound in question correspond to the radical definitions given in Table 1 (Nos 1 to 600; corresponding to Compounds A9-1 to A9-600).

A10. Compounds A10-1 to A10-600 of the general formula (Ib) in which $R^1$ represents n-propyl, $R^2$ represents fluorine, $R^3$ and $R^4$ represent hydrogen and W, $R^5$, $R^6$ for the individual compound in question correspond to the radical definitions given in Table 1 (Nos 1 to 600; corresponding to Compounds A10-1 to A10-600).

A11. Compounds A11-1 to A11-600 of the general formula (Ib) in which $R^1$ represents isopropyl, $R^2$ represents fluorine, $R^3$ and $R^4$ represent hydrogen and W, $R^5$, $R^6$ for the individual compound in question correspond to the radical definitions given in Table 1 (Nos 1 to 600; corresponding to Compounds A11-1 to A11-600).

A12. Compounds A12-1 to A12-600 of the general formula (Ib) in which $R^1$ represents methyl, $R^3$ represents fluorine, $R^2$ and $R^4$ represent hydrogen and W, $R^5$, $R^6$ for the individual compound in question correspond to the radical definitions given in Table 1 (Nos 1 to 600; corresponding to Compounds A12-1 to A12-600).

A13. Compounds A13-1 to A13-600 of the general formula (Ib) in which $R^1$ represents ethyl, $R^3$ represents fluorine, $R^2$ and $R^4$ represent hydrogen and W, $R^5$, $R^6$ for the individual compound in question correspond to the radical definitions given in Table 1 (Nos 1 to 600; corresponding to Compounds A13-1 to A13-600).

A14. Compounds A14-1 to A14-600 of the general formula (Ib) in which $R^1$ represents n-propyl, $R^3$ represents fluorine, $R^2$ and $R^4$ represent hydrogen and W, $R^5$, $R^6$ for the individual compound in question correspond to the radical definitions given in Table 1 (Nos 1 to 600; corresponding to Compounds A14-1 to A14-600).

A15. Compounds A15-1 to A15-600 of the general formula (Ib) in which $R^1$ represents isopropyl, $R^3$ represents fluorine, $R^2$ and $R^4$ represent hydrogen and W, $R^5$, $R^6$ for the individual compound in question correspond to the radical definitions given in Table 1 (Nos 1 to 600; corresponding to Compounds A15-1 to A15-600).

A16. Compounds A16-1 to A16-600 of the general formula (Ib) in which $R^1$ represents methyl, $R^2$ represents methyl, $R^3$ and $R^4$ represent hydrogen and W, $R^5$, $R^6$ for the individual compound in question correspond to the radical definitions given in Table 1 (Nos 1 to 600; corresponding to Compounds A16-1 to A16-600).

A17. Compounds A17-1 to A17-600 of the general formula (Ib) in which $R^1$ represents methyl, $R^3$ represents methyl, $R^2$ and $R^4$ represent hydrogen and W, $R^5$, $R^6$ for the individual compound in question correspond to the radical definitions given in Table 1 (Nos 1 to 600; corresponding to Compounds A17-1 to A17-600).

A18. Compounds A18-1 to A18-600 of the general formula (Ib) in which $R^1$ represents benzyl, $R^2$, $R^3$ and $R^4$ represent hydrogen and W, $R^5$, $R^6$ for the individual compound in question correspond to the radical definitions given in Table 1 (Nos 1 to 600; corresponding to Compounds A18-1 to A18-600).

A19. Compounds A19-1 to A19-600 of the general formula (Ib) in which $R^1$ represents cyclopropylmethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds A19-1 to A19-600).

A20. Compounds A20-1 to A20-600 of the general formula (Ib) in which $R^1$ represents methyl, $R^3$ represents chlorine, $R^2$ and $R^4$ represent hydrogen and W, $R^5$, $R^6$ for the individual compound in question correspond to the radical definitions given in Table 1 (Nos 1 to 600; corresponding to Compounds A20-1 to A20-600).

A21. Compounds A21-1 to A21-600 of the general formula (Ib) in which $R^1$ represents n-pentyl, $R^2$, $R^3$ and $R^4$ represent hydrogen and W, $R^5$, $R^6$ for the individual compound in question correspond to the radical definitions given in Table 1 (Nos 1 to 600; corresponding to Compounds A21-1 to A21-600).

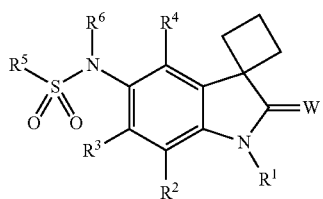

(Ic)

B1. Compounds B1-1 to B1-600 of the general formula (Ic) shown above in which $R^1$ represents methyl, $R^2$, $R^3$ and $R^4$ represent hydrogen and W, $R^5$, $R^6$ for the individual compound in question correspond to the radical definitions given in Table 1 (Nos 1 to 600; corresponding to Compounds B1-1 to B1-600).

B2. Compounds B2-1 to B2-600 of the general formula (Ic) in which $R^1$ represents ethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds B2-1 to B2-600).

B3. Compounds B3-1 to B3-600 of the general formula (Ic) in which $R^1$ represents n-propyl, $R^2$, $R^3$ and $R^4$ represent hydrogen and W, $R^5$, $R^6$ for the individual compound in question correspond to the radical definitions given in Table 1 (Nos 1 to 600; corresponding to Compounds B3-1 to B3-600).

B4. Compounds B4-1 to B4-600 of the general formula (Ic) in which $R^1$ represents isopropyl, $R^2$, $R^3$ and $R^4$ represent hydrogen and W, $R^5$, $R^6$ for the individual compound in question correspond to the radical definitions given in Table 1 (Nos 1 to 600; corresponding to Compounds B4-1 to B4-600).

B5. Compounds B5-1 to B5-600 of the general formula (Ic) in which $R^1$ represents n-butyl, $R^2$, $R^3$ and $R^4$ represent hydrogen and W, $R^5$, $R^6$ for the individual compound in question correspond to the radical definitions given in Table 1 (Nos 1 to 600; corresponding to Compounds B5-1 to B5-600).

B6. Compounds B6-1 to B6-600 of the general formula (Ic) in which $R^1$ represents 3-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds B6-1 to B6-600).

B7. Compounds B7-1 to B7-600 of the general formula (Ic) in which $R^1$ represents 2-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds B7-1 to B7-600).

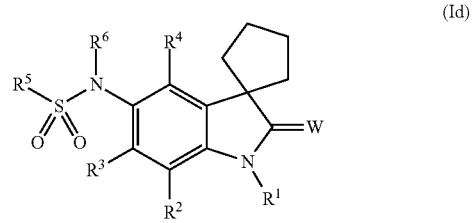

(Id)

C1. Compounds C1-1 to C1-600 of the general formula (Id) shown above in which $R^1$ represents methyl, $R^2$, $R^3$ and $R^4$ represent hydrogen and W, $R^5$, $R^6$ for the individual compound in question correspond to the radical definitions given in Table 1 (Nos 1 to 600; corresponding to Compounds C1-1 to C1-600).

C2. Compounds C2-1 to C2-600 of the general formula (Id) in which $R^1$ represents ethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds C2-1 to C2-600).

C3. Compounds C3-1 to C3-600 of the general formula (Id) in which $R^1$ represents n-propyl, $R^2$, $R^3$ and $R^4$ represent hydrogen and W, $R^5$, $R^6$ for the individual compound in question correspond to the radical definitions given in Table 1 (Nos 1 to 600; corresponding to Compounds C3-1 to C3-600).

C4. Compounds C4-1 to C4-600 of the general formula (Id) in which $R^1$ represents isopropyl, $R^2$, $R^3$ and $R^4$ represent hydrogen and W, $R^5$, $R^6$ for the individual compound in question correspond to the radical definitions given in Table 1 (Nos 1 to 600; corresponding to Compounds C4-1 to C4-600).

C5. Compounds $C_5$-1 to $C_5$-600 of the general formula (Id) in which $R^1$ represents n-butyl, $R^2$, $R^3$ and $R^4$ represent hydrogen and W, $R^5$, $R^6$ for the individual compound in question correspond to the radical definitions given in Table 1 (Nos 1 to 600; corresponding to Compounds C5-1 to C5-600).

C6. Compounds C6-1 to C6-600 of the general formula (Id) in which $R^1$ represents 3-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds C6-1 to C6-600).

C7. Compounds C7-1 to C7-600 of the general formula (Id) in which $R^1$ represents 2-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds C7-1 to C7-600).

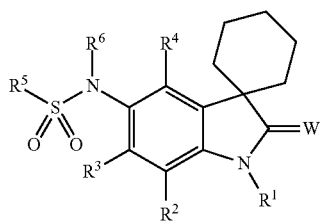
(Ie)

D1. Compounds D1-1 to D1-600 of the general formula (Ie) shown above in which $R^1$ represents methyl, $R^2$, $R^3$ and $R^4$ represent hydrogen and W, $R^5$, $R^6$ for the individual compound in question correspond to the radical definitions given in Table 1 (Nos 1 to 600; corresponding to Compounds D1-1 to D1-600).

D2. Compounds D2-1 to D2-600 of the general formula (Ie) in which $R^1$ represents ethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds D2-1 to D2-600).

D3. Compounds D3-1 to D3-600 of the general formula (Ie) in which $R^1$ represents n-propyl, $R^2$, $R^3$ and $R^4$ represent hydrogen and W, $R^5$, $R^6$ for the individual compound in question correspond to the radical definitions given in Table 1 (Nos 1 to 600; corresponding to Compounds D3-1 to D3-600).

D4. Compounds D4-1 to D4-600 of the general formula (Ie) in which $R^1$ represents isopropyl, $R^2$, $R^3$ and $R^4$ represent hydrogen and W, $R^5$, $R^6$ for the individual compound in question correspond to the radical definitions given in Table 1 (Nos 1 to 600; corresponding to Compounds D4-1 to D4-600).

D5. Compounds D5-1 to D5-600 of the general formula (Ie) in which $R^1$ represents n-butyl, $R^2$, $R^3$ and $R^4$ represent hydrogen and W, $R^5$, $R^6$ for the individual compound in question correspond to the radical definitions given in Table 1 (Nos 1 to 600; corresponding to Compounds D5-1 to D5-600).

D6. Compounds D6-1 to D6-600 of the general formula (Ie) in which $R^1$ represents 3-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds D6-1 to D6-600).

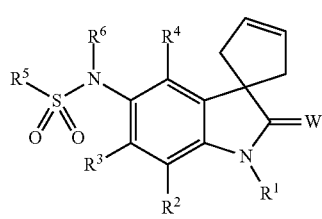
(Ij)

E1. Compounds E1-1 to E1-600 of the general formula (Ij) shown above in which $R^1$ represents methyl, $R^2$, $R^3$ and $R^4$ represent hydrogen and W, $R^5$, $R^6$ for the individual compound in question correspond to the radical definitions given in Table 1 (Nos 1 to 600; corresponding to Compounds E1-1 to E1-600).

E2. Compounds E2-1 to E2-600 of the general formula (Ij) in which $R^1$ represents ethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds E2-1 to E2-600).

E3. Compounds E3-1 to E3-600 of the general formula (Ij) in which $R^1$ represents n-propyl, $R^2$, $R^3$ and $R^4$ represent hydrogen and W, $R^5$, $R^6$ for the individual compound in question correspond to the radical definitions given in Table 1 (Nos 1 to 600; corresponding to Compounds E3-1 to E3-600).

E4. Compounds E4-1 to E4-600 of the general formula (Ij) in which $R^1$ represents isopropyl, $R^2$, $R^3$ and $R^4$ represent hydrogen and W, $R^5$, $R^6$ for the individual compound in question correspond to the radical definitions given in Table 1 (Nos 1 to 600; corresponding to Compounds E4-1 to E4-600).

E5. Compounds E5-1 to E5-600 of the general formula (Ij) in which $R^1$ represents n-butyl, $R^2$, $R^3$ and $R^4$ represent hydrogen and W, $R^5$, $R^6$ for the individual compound in question correspond to the radical definitions given in Table 1 (Nos 1 to 600; corresponding to Compounds E5-1 to E5-600).

E6. Compounds E6-1 to E6-600 of the general formula (Ij) in which $R^1$ represents 3-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds E6-1 to E6-600).

E7. Compounds E7-1 to E7-600 of the general formula (Ij) in which $R^1$ represents Allyl, $R^2$, $R^3$ and $R^4$ represent hydrogen and W, $R^5$, $R^6$ for the individual compound in question correspond to the radical definitions given in Table 1 (Nos 1 to 600; corresponding to Compounds E7-1 to E7-600).

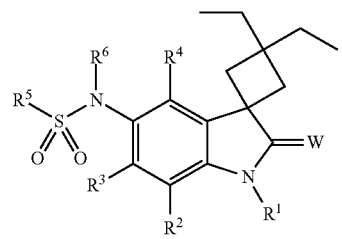
(In)

F1. Compounds F1-1 to F1-600 of the general formula (In) shown above in which $R^1$ represents methyl, $R^2$, $R^3$ and $R^4$ represent hydrogen and W, $R^5$, $R^6$ for the individual compound in question correspond to the radical definitions given in Table 1 (Nos 1 to 600; corresponding to Compounds F1-1 to F1-600).

F2. Compounds F2-1 to F2-600 of the general formula (In) in which $R^1$ represents ethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds F2-1 to F2-600).

F3. Compounds F3-1 to F3-600 of the general formula (In) in which $R^1$ represents n-propyl, $R^2$, $R^3$ and $R^4$ represent hydrogen and W, $R^5$, $R^6$ for the individual compound in question correspond to the radical definitions given in Table 1 (Nos 1 to 600; corresponding to Compounds F3-1 to F3-600).

F4. Compounds F4-1 to F4-600 of the general formula (In) in which R¹ represents isopropyl, R², R³ and R⁴ represent hydrogen and W, R⁵, R⁶ for the individual compound in question correspond to the radical definitions given in Table 1 (Nos 1 to 600; corresponding to Compounds F4-1 to F4-600).

F5. Compounds F5-1 to F5-600 of the general formula (In) in which R¹ represents n-butyl, R², R³ and R⁴ represent hydrogen and W, R⁵, R⁶ for the individual compound in question correspond to the radical definitions given in Table 1 (Nos 1 to 600; corresponding to Compounds F5-1 to F5-600).

(Ia)

G1. Compounds G1-1 bis G1-600 of the general formula (Ia) in which R¹ represents methyl, R², R³ and R⁴ represent hydrogen and W, R⁵, R⁶ for the individual compound in question correspond to the radical definitions given in Table 1 (Nos 1 to 600; corresponding to Compounds G1-1 to G1-600).

G2. Compounds G2-1 to G2-600 of the general formula (Ia) in which R¹ represents ethyl, R², R³ and R⁴ represent hydrogen and W, R⁵, R⁶ for the individual compound in question correspond to the radical definitions given in Table 1 (Nos 1 to 600; corresponding to Compounds G2-1 to G2-600).

G3. Compounds G3-1 to G3-600 of the general formula (Ia) in which R¹ represents n-propyl, R², R³ and R⁴ represent hydrogen and W, R⁵, R⁶ for the individual compound in question correspond to the radical definitions given in Table 1 (Nos 1 to 600; corresponding to Compounds G3-1 to G3-600).

G4. Compounds G4-1 to G4-600 of the general formula (Ia) in which R¹ represents isopropyl, R², R³ and R⁴ represent hydrogen and W, R⁵, R⁶ for the individual compound in question correspond to the radical definitions given in Table 1 (Nos 1 to 600; corresponding to Compounds G4-1 to G4-600).

G5. Compounds G5-1 to G5-600 of the general formula (Ia) in which R¹ represents n-butyl, R², R³ and R⁴ represent hydrogen and W, R⁵, R⁶ for the individual compound in question correspond to the radical definitions given in Table 1 (Nos 1 to 600; corresponding to Compounds G5-1 to G5-600).

G6. Compounds G6-1 to G6-600 of the general formula (Ia) in which R¹ represents 3-methylbutyl, R², R³ and R⁴ represent hydrogen and W, R⁵, R⁶ for the individual compound in question correspond to the radical definitions given in Table 1 (Nos 1 to 600; corresponding to Compounds G6-1 to G6-600).

G7. Compounds G7-1 to G7-600 of the general formula (Ia) in which R¹ represents 2-methylbutyl, R², R³ and R⁴ represent hydrogen and W, R⁵, R⁶ for the individual compound in question correspond to the radical definitions given in Table 1 (Nos 1 to 600; corresponding to Compounds G7-1 to G7-600).

G8. Compounds G8-1 to G8-600 of the general formula (Ia) in which R¹ represents methyl, R² represents fluorine, R³ and R⁴ represent hydrogen and W, R⁵, R⁶ for the individual compound in question correspond to the radical definitions given in Table 1 (Nos 1 to 600; corresponding to Compounds G8-1 to G8-600).

G9. Compounds G9-1 to G9-600 of the general formula (Ia) in which R¹ represents ethyl, R² represents fluorine, R³ and R⁴ represent hydrogen and W, R⁵, R⁶ for the individual compound in question correspond to the radical definitions given in Table 1 (Nos 1 to 600; corresponding to Compounds G9-1 to G9-600).

G10. Compounds G10-1 to G10-600 of the general formula (Ia) in which R¹ represents n-propyl, R² represents fluorine, R³ and R⁴ represent hydrogen and W, R⁵, R⁶ for the individual compound in question correspond to the radical definitions given in Table 1 (Nos 1 to 600; corresponding to Compounds G10-1 to G10-600).

G11. Compounds G11-1 to G11-600 of the general formula (Ia) in which R¹ represents isopropyl, R² represents fluorine, R³ and R⁴ represent hydrogen and W, R⁵, R⁶ for the individual compound in question correspond to the radical definitions given in Table 1 (Nos 1 to 600; corresponding to Compounds G11-1 to G11-600).

G12. Compounds G12-1 to G12-600 of the general formula (Ia) in which R¹ represents methyl, R³ represents fluorine, R² and R⁴ represent hydrogen and W, R⁵, R⁶ for the individual compound in question correspond to the radical definitions given in Table 1 (Nos 1 to 600; corresponding to Compounds G12-1 to G12-600).

G13. Compounds G13-1 to G13-600 of the general formula (Ia) in which R¹ represents ethyl, R³ represents fluorine, R² and R⁴ represent hydrogen and W, R⁵, R⁶ for the individual compound in question correspond to the radical definitions given in Table 1 (Nos 1 to 600; corresponding to Compounds G13-1 to G13-600).

G14. Compounds G14-1 to G14-600 of the general formula (Ia) in which R¹ represents n-propyl, R³ represents fluorine, R² and R⁴ represent hydrogen and W, R⁵, R⁶ for the individual compound in question correspond to the radical definitions given in Table 1 (Nos 1 to 600; corresponding to Compounds G14-1 to G14-600).

G15. Compounds G15-1 to G15-600 of the general formula (Ia) in which R¹ represents isopropyl, R³ represents fluorine, R² and R⁴ represent hydrogen and W, R⁵, R⁶ for the individual compound in question correspond to the radical definitions given in Table 1 (Nos 1 to 600; corresponding to Compounds G15-1 to G15-600).

G16. Compounds G16-1 to G16-600 of the general formula (Ia) in which R¹ represents methyl, R² represents methyl, R³ and R⁴ represent hydrogen and W, R⁵, R⁶ for the individual compound in question correspond to the radical definitions given in Table 1 (Nos 1 to 600; corresponding to Compounds G16-1 to G16-600).

G17. Compounds G17-1 to G17-600 of the general formula (Ia) in which R¹ represents methyl, R³ represents methyl, R² and R⁴ represent hydrogen and W, R⁵, R⁶ for the individual compound in question correspond to the radical definitions given in Table 1 (Nos 1 to 600; corresponding to Compounds G17-1 to G17-600).

G18. Compounds G18-1 to G18-600 of the general formula (Ia) in which R¹ represents benzyl, R², R³ and R⁴ represent hydrogen and W, R⁵, R⁶ for the individual compound in question correspond to the radical definitions given in Table 1 (Nos 1 to 600; corresponding to Compounds G18-1 to G18-600).

G19. Compounds G19-1 to G19-600 of the general formula (Ia) in which $R^1$ represents cyclopropylmethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds G19-1 to G19-600).

G20. Compounds G20-1 to G20-600 of the general formula (Ia) in which $R^1$ represents methyl, $R^3$ represents chlorine, $R^2$ and $R^4$ represent hydrogen and W, $R^5$, $R^6$ for the individual compound in question correspond to the radical definitions given in Table 1 (Nos 1 to 600; corresponding to Compounds G20-1 to G20-600).

G21. Compounds G21-1 to G21-600 of the general formula (Ia) in which $R^1$ represents n-pentyl, $R^2$, $R^3$ and $R^4$ represent hydrogen and W, $R^5$, $R^6$ for the individual compound in question correspond to the radical definitions given in Table 1 (Nos 1 to 600; corresponding to Compounds G21-1 to G21-600).

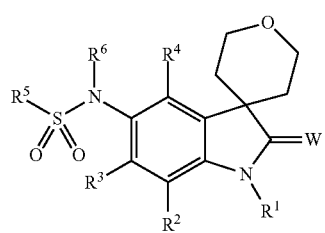

(If)

H1. Compounds H1-1 to H1-600 of the general formula (If) shown above in which $R^1$ represents methyl, $R^2$, $R^3$ and $R^4$ represent hydrogen and W, $R^5$, $R^6$ for the individual compound in question correspond to the radical definitions given in Table 1 (Nos 1 to 600; corresponding to Compounds H1-1 to H1-600).

H2. Compounds H2-1 to H2-600 of the general formula (If) in which $R^1$ represents ethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds H2-1 to H2-600).

H3. Compounds H3-1 to H3-600 of the general formula (If) in which $R^1$ represents n-propyl, $R^2$, $R^3$ and $R^4$ represent hydrogen and W, $R^5$, $R^6$ for the individual compound in question correspond to the radical definitions given in Table 1 (Nos 1 to 600; corresponding to Compounds H3-1 to H3-600).

H4. Compounds H4-1 to H4-600 of the general formula (If) in which $R^1$ represents isopropyl, $R^2$, $R^3$ and $R^4$ represent hydrogen and W, $R^5$, $R^6$ for the individual compound in question correspond to the radical definitions given in Table 1 (Nos 1 to 600; corresponding to Compounds H4-1 to H4-600).

H5. Compounds H5-1 to H5-600 of the general formula (If) in which $R^1$ represents n-butyl, $R^2$, $R^3$ and $R^4$ represent hydrogen and W, $R^5$, $R^6$ for the individual compound in question correspond to the radical definitions given in Table 1 (Nos 1 to 600; corresponding to Compounds H5-1 to H5-600).

H6. Compounds H6-1 to H6-600 of the general formula (If) in which $R^1$ represents 3-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds H6-1 to H6-600).

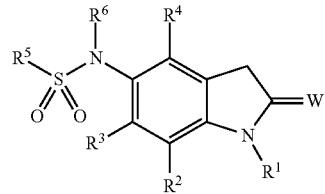

(Iab)

I1. Compounds I1-1 to I1-600 of the general formula (Iab) in which $R^1$ represents methyl, $R^2$, $R^3$ and $R^4$ represent hydrogen and W, $R^5$, $R^6$ for the individual compound in question correspond to the radical definitions given in Table 1 (Nos 1 to 600; corresponding to Compounds I1-1 to I1-600).

I2. Compounds I2-1 to I2-600 of the general formula (Iab) in which $R^1$ represents ethyl, $R^2$, $R^3$ and $R^4$ represent hydrogen and W, $R^5$, $R^6$ for the individual compound in question correspond to the radical definitions given in Table 1 (Nos 1 to 600; corresponding to Compounds I2-1 to I2-600).

I3. Compounds I3-1 to I3-600 of the general formula (Iab) in which $R^1$ represents n-propyl, $R^2$, $R^3$ and $R^4$ represent hydrogen and W, $R^5$, $R^6$ for the individual compound in question correspond to the radical definitions given in Table 1 (Nos 1 to 600; corresponding to Compounds I3-1 to I3-600).

I4. Compounds I4-1 to I4-600 of the general formula (Iab) in which $R^1$ represents isopropyl, $R^2$, $R^3$ and $R^4$ represent hydrogen and W, $R^5$, $R^6$ for the individual compound in question correspond to the radical definitions given in Table 1 (Nos 1 to 600; corresponding to Compounds I4-1 to I4-600).

I5. Compounds I5-1 to I5-600 of the general formula (Iab) in which $R^1$ represents n-butyl, $R^2$, $R^3$ and $R^4$ represent hydrogen and W, $R^5$, $R^6$ for the individual compound in question correspond to the radical definitions given in Table 1 (Nos 1 to 600; corresponding to Compounds I5-1 to I5-600).

I6. Compounds I6-1 to I6-600 of the general formula (Iab) in which $R^1$ represents 3-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds I6-1 to I6-600).

I7. Compounds I7-1 to I7-600 of the general formula (Iab) in which $R^1$ represents 2-methylbutyl, $R^2$, $R^3$ and $R^4$ represent hydrogen and W, $R^5$, $R^6$ for the individual compound in question correspond to the radical definitions given in Table 1 (Nos 1 to 600; corresponding to Compounds I7-1 to I7-600).

I8. Compounds I8-1 to I8-600 of the general formula (Iab) in which $R^1$ represents methyl, $R^2$ represents fluorine, $R^3$ and $R^4$ represent hydrogen and W, $R^5$, $R^6$ for the individual compound in question correspond to the radical definitions given in Table 1 (Nos 1 to 600; corresponding to Compounds I8-1 to I8-600).

I9. Compounds I9-1 to I9-600 of the general formula (Iab) in which $R^1$ represents ethyl, $R^2$ represents fluorine, $R^3$ and $R^4$ represent hydrogen and W, $R^5$, $R^6$ for the individual compound in question correspond to the radical definitions given in Table 1 (Nos 1 to 600; corresponding to Compounds I9-1 to I9-600).

I10. Compounds I10-1 to I10-600 of the general formula (Iab) in which $R^1$ represents n-propyl, $R^2$ represents fluorine, R³ and R⁴ represent hydrogen and W, R⁵, R⁶ for the individual compound in question correspond to the radical definitions given in Table 1 (Nos 1 to 600; corresponding to Compounds I10-1 to I10-600).

I11. Compounds I11-1 to I11-600 of the general formula (Iab) in which R¹ represents isopropyl, R² represents fluorine, R³ and R⁴ represent hydrogen and W, R⁵, R⁶ for the individual compound in question correspond to the radical definitions given in Table 1 (Nos 1 to 600; corresponding to Compounds I11-1 to I11-600).

I12. Compounds I12-1 to I12-600 of the general formula (Iab) in which R¹ represents methyl, R³ represents fluorine, R² and R⁴ represent hydrogen and W, R⁵, R⁶ for the individual compound in question correspond to the radical definitions given in Table 1 (Nos 1 to 600; corresponding to Compounds I12-1 to I12-600).

I13. Compounds I13-1 to I13-600 of the general formula (Iab) in which R¹ represents ethyl, R³ represents fluorine, R² and R⁴ represent hydrogen and W, R⁵, R⁶ for the individual compound in question correspond to the radical definitions given in Table 1 (Nos 1 to 600; corresponding to Compounds I13-1 to I13-600).

I14. Compounds I14-1 to I14-600 of the general formula (Iab) in which R¹ represents n-propyl, R³ represents fluorine, R² and R⁴ represent hydrogen and W, R⁵, R⁶ for the individual compound in question correspond to the radical definitions given in Table 1 (Nos 1 to 600; corresponding to Compounds I14-1 to I14-600).

I15. Compounds I15-1 to I15-600 of the general formula (Iab) in which R¹ represents isopropyl, R³ represents fluorine, R² and R⁴ represent hydrogen and W, R⁵, R⁶ for the individual compound in question correspond to the radical definitions given in Table 1 (Nos 1 to 600; corresponding to Compounds I15-1 to I15-600).

I16. Compounds I16-1 to I16-600 of the general formula (Iab) in which R¹ represents methyl, R² represents methyl, R³ and R⁴ represent hydrogen and W, R⁵, R⁶ for the individual compound in question correspond to the radical definitions given in Table 1 (Nos 1 to 600; corresponding to Compounds I16-1 to I16-600).

I17. Compounds I17-1 to I17-600 of the general formula (Iab) in which R¹ represents methyl, R³ represents methyl, R² and R⁴ represent hydrogen and W, R⁵, R⁶ for the individual compound in question correspond to the radical definitions given in Table 1 (Nos 1 to 600; corresponding to Compounds I17-1 to I17-600).

I18. Compounds I18-1 to I18-600 of the general formula (Iab) in which R¹ represents benzyl, R², R³ and R⁴ represent hydrogen and W, R⁵, R⁶ for the individual compound in question correspond to the radical definitions given in Table 1 (Nos 1 to 600; corresponding to Compounds I18-1 to I18-600).

I19. Compounds I19-1 to I19-600 of the general formula (Iab) in which R¹ represents cyclopropylmethyl, R², R³ and R⁴ represent hydrogen and W, R⁵, R⁶ for the individual compound in question correspond to the radical definitions given in Table 1 (Nos 1 to 600; corresponding to Compounds I19-1 to I19-600).

I20. Compounds I20-1 to I20-600 of the general formula (Iab) in which R¹ represents methyl, R³ represents chlorine, R² and R⁴ represent hydrogen and W, R⁵, R⁶ for the individual compound in question correspond to the radical definitions given in Table 1 (Nos 1 to 600; corresponding to Compounds I20-1 to I20-600).

I21. Compounds I21-1 to I21-600 of the general formula (Iab) in which R¹ represents n-pentyl, R², R³ and R⁴ represent hydrogen and W, R⁵, R⁶ for the individual compound in question correspond to the radical definitions given in Table 1 (Nos 1 to 600; corresponding to Compounds I21-1 to I21-600).

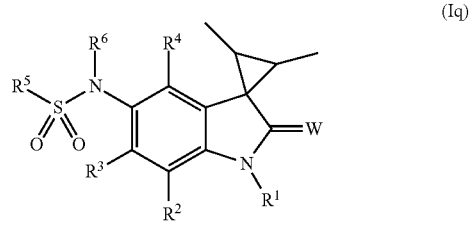

(Iq)

J1. Compounds J1-1 to J1-600 of the general formula (Iq) shown above in which R¹ represents methyl, R², R³ and R⁴ represent hydrogen and W, R⁵, R⁶ for the individual compound in question correspond to the radical definitions given in Table 1 (Nos 1 to 600; corresponding to Compounds J1-1 to J1-600).

J2. Compounds J2-1 to J2-600 of the general formula (Iq) in which R¹ represents ethyl, R², R³ and R⁴ represent hydrogen and W, R⁵, R⁶ for the individual compound in question correspond to the radical definitions given in Table 1 (Nos 1 to 600; corresponding to Compounds J2-1 to J2-600).

J3. Compounds J3-1 to J3-600 of the general formula (Iq) in which R¹ represents n-propyl, R², R³ and R⁴ represent hydrogen and W, R⁵, R⁶ for the individual compound in question correspond to the radical definitions given in Table 1 (Nos 1 to 600; corresponding to Compounds J3-1 to J3-600).

Spectroscopic data of selected table examples:

Example No. A1-1:
$^1$H-NMR (400 MHz, CDCl$_3$) δ 7.11 (dd, 1H), 6.87 (d, 1H), 6.83 (d, 1H), 6.22 (br. s, 1H, NH), 3.29 (s, 3H), 2.96 (s, 3H), 1.78 (m, 2H), 1.55 (m, 2H), Example No. A1-3:
$^1$H-NMR (400 MHz, CDCl$_3$) δ 7.01 (dd, 1H), 6.96 (d, 1H), 6.81 (d, 1H), 6.11 (br. s, 1H, NH), 3.18 (s, 3H), 2.78 (t, 2H), 1.55 (m, 2H), 1.52 (m, 2H), 1.38 (sext, 2H), 0.77 (t, 3H).

Example No. A1-20:
$^1$H-NMR (400 MHz, d$_6$-DMSO) δ 9.36 (br. s, 1H, NH), 7.12 (br. q, 1H, NH), 7.04 (dd, 1H), 6.99 (d, 1H), 6.82 (d, 1H), 3.18 (s, 3H), 2.42 (d, 3H) 1.54 (m, 2H), 1.51 (m, 2H).

Example No. A1-21:
$^1$H-NMR (400 MHz, CDCl$_3$) δ 7.08 (dd, 1H), 6.82 (d, 1H), 6.80 (d, 1H), 6.13 (br. s, 1H, NH), 3.28 (s, 3H), 2.82 (s, 6H), 1.77 (m, 2H), 1.53 (m, 2H).

Example No. A1-23:
$^1$H-NMR (400 MHz, d$_6$-DMSO) δ 9.33 (br. s, 1H, NH), 7.26 (br. t, 1H, NH), 7.01 (dd, 1H), 6.96 (d, 1H), 6.81 (d, 1H), 6.11 (br. s, 1H, NH), 3.18 (s, 3H), 2.78 (t, 2H), 1.55 (m, 2H), 1.52 (m, 2H), 1.38 (sext, 2H), 0.77 (t, 3H).

Example No. A1-26:
$^1$H-NMR (400 MHz, CDCl$_3$) δ 7.11 (dd, 1H), 6.84 (d, 1H), 6.83 (d, 1H), 6.29 (br. s, 1H, NH), 3.85 (m 2H), 3.46 (s, 3H), 3.29 (s, 3H), 3.19 (m, 2H), 1.77 (m, 2H), 1.54 (m, 2H).

Example No. A1-37:
$^1$H-NMR (400 MHz, CHCl$_3$) δ 8.69 (d, 1H), 8.07 (m, 1H), 8.04 (d, 1H), 7.96 (m, 1H), 7.69-7.60 (m, 2H), 7.41 (m, 1H), 6.68 (m, 1H), 6.64 (br. s, 1H, NH), 6.59 (m, 1H), 6.37 (d, 1H), 3.18 (s, 3H), 1.65 (m, 2H), 1.26 (m, 2H).

Example No. A1-53:
¹H-NMR (400 MHz, CHCl₃) δ 7.81 (m, 1H), 7.57 (m, 1H), 7.18 (m, 1H), 6.83 (dd, 1H), 6.73 (dd, 1H), 6.58 (d, 1H), 6.51 (br. s, 1H, NH), 3.23 (s, 3H), 2.70 (s, 3H), 1.74 (m, 2H), 1.43 (m, 2H).

Example No. A1-66:
¹H-NMR (400 MHz, CHCl₃) δ 7.53 (m, 1H), 7.45 (m, 2H), 7.31 (m, 1H), 6.86 (dd, 1H), 6.73 (d, 1H), 6.62 (d, 1H), 6.52 (br. s, 1H, NH), 6.67-6.31 (t, 1H, OCHF₂), 3.25 (s, 3H), 1.74 (m, 2H), 1.45 (m, 2H).

Example No. A1-152:
¹H-NMR (400 MHz, d₆-DMSO) δ 9.55 (br. s, 1H, NH), 7.30 (d, 2H), 7.17 (d, 2H), 6.97 (m, 2H), 6.83 (d, 1H), 4.34 (s, 2H), 3.17 (s, 3H), 2.28 (s, 3H), 1.53 (m, 4H).

Example No. A1-153:
¹H-NMR (400 MHz, d₆-DMSO) δ 9.53 (br. s, 1H, NH), 7.23 (m, 1H), 7.16 (m, 1H), 7.97 (m, 2H), 7.05 (m, 2H), 6.75 (d, 1H), 4.33 (s, 2H), 3.20 (s, 3H), 2.27 (s, 3H), 1.53 (m, 4H).

Example No. A1-158:
¹H-NMR (400 MHz, d₆-DMSO) δ 9.54 (br. s, 1H, NH), 7.32 (m, 2H), 7.19 (m, 2H), 7.05 (m, 2H), 6.75 (d, 1H), 4.40 (s, 2H), 3.20 (s, 3H), 1.55 (m, 4H).

Example No A1-159:
¹H-NMR (400 MHz, CDCl₃) δ 7.50 (m, 1H), 7.39 (m, 1H), 7.30 (m, 1H), 7.20 (m, 1H), 7.09 (m, 2H), 6.83 (d, 1H), 6.40 (br. s, 1H, NH), 4.37 (s, 2H), 3.25 (s, 3H), 1.78 (m, 2H), 1.58 (m, 2H).

Example No A1-161:
¹H-NMR (400 MHz, CDCl₃) δ 7.47 (m, 1H), 7.38 (m, 1H), 7.18 (m, 1H), 7.09 (m, 1H), 7.02 (dd, 1H), 6.84 (d, 1H), 6.67 (d, 1H), 6.13 (br. s, 1H, NH), 4.39 (s, 2H), 3.29 (s, 3H), 1.77 (m, 2H), 1.51 (m, 2H).

Example No. A1-165:
¹H-NMR (400 MHz, d₆-DMSO) δ 9.56 (br. s, 1H, NH), 7.41 (d, 2H), 7.30 (d, 2H), 7.06 (dd, 1H), 7.03 (d, 1H), 6.75 (d, 1H), 4.42 (s, 2H), 3.20 (s, 3H), 1.54 (m, 4H).

Example No A1-166:
¹H-NMR (400 MHz, CDCl₃) δ 7.39-7.29 (m, 3H), 7.23 (m, 1H), 7.03 (dd, 1H), 6.87 (d, 1H), 6.65 (d, 1H), 6.12 (br. s, 1H, NH), 4.26 (s, 2H), 3.30 (s, 3H), 1.78 (m, 2H), 1.53 (m, 2H).

Example No. A1-167:
¹H-NMR (400 MHz, CDCl₃) δ 7.45 (d, 1H), 7.34 (d, 1H), 7.20 (dd, 1H), 7.02 (dd, 1H), 6.86 (d, 1H), 6.67 (d, 1H), 6.13 (br. s, 1H, NH), 4.24 (s, 2H), 3.30 (s, 3H), 1.78 (m, 2H), 1.52 (m, 2H).

Example No. A1-169:
¹H-NMR (400 MHz, CDCl₃) δ 7.46 (d, 1H), 7.39 (m, 1H), 7.24 (m, 1H), 6.99 (dd, 1H), 6.81 (d, 1H), 6.66 (d, 1H), 6.20 (br. s, 1H, NH), 4.52 (s, 2H), 3.28 (s, 3H), 1.77 (m, 2H), 1.49 (m, 2H).

Example No. A1-170:
¹H-NMR (400 MHz, CDCl₃) δ 7.45 (m, 1H), 7.31 (m, 1H), 7.26 (m, 1H), 7.05 (dd, 1H), 6.84 (d, 1H), 6.68 (d, 1H), 6.27 (br. s, 1H, NH), 4.51 (s, 2H), 3.29 (s, 3H), 1.77 (m, 2H), 1.51 (m, 2H).

Example No. A1-171:
¹H-NMR (400 MHz, CDCl₃) δ 7.36 (m, 1H), 7.19 (m, 1H), 7.06 (m, 1H), 6.97 (dd, 1H), 6.85 (d, 1H), 6.67 (d, 1H), 6.21 (br. s, 1H, NH), 4.26 (s, 2H), 3.30 (s, 3H), 1.78 (m, 2H), 1.51 (m, 2H).

Example No. A1-176:
¹H-NMR (400 MHz, CDCl₃) δ 8.25 (m, 1H), 8.11 (m, 1H), 7.75 (m, 1H), 7.59 (m, 1H), 7.08 (dd, 1H), 6.89 (d, 1H), 6.76 (d, 1H), 6.16 (br. s, 1H, NH), 4.38 (s, 2H), 3.31 (s, 3H), 1.80 (m, 2H), 1.56 (m, 2H).

Example No. A1-177:
¹H-NMR (400 MHz, d₆-DMSO) δ 9.82 (br. s, 1H, NH), 8.02 (m, 1H), 7.71 (m, 1H), 7.63 (m, 1H), 7.50 (m, 1H), 7.07 (m, 1H), 7.04 (m, 1H), 6.79 (d, 1H), 4.86 (s, 2H), 3.21 (s, 3H), 1.57 (m, 2H), 1.54 (m, 2H).

Example No. A1-178:
¹H-NMR (400 MHz, d₆-DMSO) δ 9.63 (br. s, 1H, NH), 7.72 (d, 2H), 7.51 (d, 2H), 7.08 (dd, 1H), 7.02 (d, 1H), 6.79 (d, 1H), 4.54 (s, 2H), 3.20 (s, 3H), 1.56 (m, 2H), 1.53 (m, 2H).

Example No. A1-179:
¹H-NMR (400 MHz, CDCl₃) δ 7.66 (m, 1H), 7.59 (m, 1H), 7.54 (m, 1H), 7.49 (m, 1H), 7.01 (dd, 1H), 6.86 (d, 1H), 6.70 (d, 1H), 6.14 (br. s, 1H, NH), 4.34 (s, 2H), 3.30 (s, 3H), 1.78 (m, 2H), 1.52 (m, 2H).

Example No. A1-180:
¹H-NMR (400 MHz, CDCl₃) δ 7.71 (m, 2H), 7.56 (m, 1H), 7.48 (m, 1H), 6.96 (dd, 1H), 6.80 (d, 1H), 6.63 (d, 1H), 6.24 (br. s, 1H, NH), 4.57 (s, 2H), 3.28 (s, 3H), 1.77 (m, 2H), 1.50 (m, 2H).

Example No A1-182:
¹H-NMR (400 MHz, CDCl₃) δ 7.67 (m, 1H), 7.61 (m, 1H), 7.55 (m, 1H), 7.50 (m, 1H), 7.02 (dd, 1H), 6.88 (d, 1H), 6.73 (d, 1H), 6.22 (br. s, 1H, NH), 4.31 (s, 2H), 3.30 (s, 3H), 1.80 (m, 2H), 1.52 (m, 2H).

Example No. A1-190:
¹H-NMR (400 MHz, CDCl₃) δ 8.04 (d, 2H), 7.40 (d, 2H), 6.97 (dd, 1H), 6.83 (d, 1H), 6.66 (d, 1H), 6.09 (br. s, 1H, NH), 4.35 (s, 2H), 3.94 (s, 3H), 3.30 (s, 3H), 1.78 (m, 2H), 1.50 (m, 2H).

Example No. A1-191:
¹H-NMR (400 MHz, CDCl₃) δ 8.06 (m, 1H), 7.94 (m, 1H), 7.59 (m, 1H), 7.49 (m, 1H), 7.07 (dd, 1H), 6.87 (d, 1H), 6.69 (d, 1H), 6.12 (br. s, 1H, NH), 4.33 (s, 2H), 3.93 (s, 3H), 3.30 (s, 3H), 1.78 (m, 2H), 1.54 (m, 2H).

Example No. A1-192:
¹H-NMR (400 MHz, CDCl₃) δ 8.27 (d, 2H), 7.40 (d, 2H), 6.98 (dd, 1H), 6.85 (d, 1H), 6.66 (d, 1H), 6.24 (br. s, 1H, NH), 4.42 (q, 2H), 4.35 (s, 2H), 3.30 (s, 3H), 1.78 (m, 2H), 1.52 (m, 2H), 1.42 (t, 3H).

Example No. A1-226:
¹H-NMR (400 MHz, d₆-DMSO) δ 9.76 (br. s, 1H, NH), 7.51-7.46 (m, 2H), 7.40-7.35 (m, 2H), 7.10 (dd, 1H), 7.03 (d, 1H), 6.80 (d, 1H), 4.45 (s, 2H), 3.20 (s, 3H), 1.53 (m, 4H).

Example No. A1-291:
¹H-NMR (400 MHz, CDCl₃) δ 7.29 (d, 2H), 7.11 (d, 2H), 6.98 (dd, 1H), 6.83 (d, 1H), 6.65 (d, 1H), 6.30 (br. s, 1H, NH), 3.28 (s, 3H), 3.26 (m, 2H), 3.12 (m, 2H), 1.77 (m, 2H), 1.53 (m, 2H).

Example No. A1-292:
¹H-NMR (400 MHz, CDCl₃) δ 7.58 (d, 2H), 7.30 (d, 2H), 6.94 (dd, 1H), 6.83 (d, 1H), 6.71 (d, 1H), 6.10 (br. s, 1H, NH), 3.31 (m, 2H), 3.28 (s, 3H), 3.21 (m, 2H), 1.78 (m, 2H), 1.52 (m, 2H).

Example No. A1-301:
¹H-NMR (400 MHz, CDCl₃) δ 7.27 (dd, 1H), 6.90 (d, 1H), 6.88 (d, 1H), 6.31 (br. s, 1H, NH), 6.18 (s, 1H), 4.27 (s, 2H), 3.29 (s, 3H), 2.45 (s, 3H), 1.78 (m, 2H), 1.57 (m, 2H), Example No A1-332:
¹H-NMR (400 MHz, CDCl₃) δ 7.39 (d, 2H), 7.23 (d, 2H), 6.99 (dd, 1H), 6.85 (d, 1H), 6.74 (d, 1H), 6.08 (br. s, 1H, NH), 4.26 (s, 2H), 3.30 (s, 3H), 1.78 (m, 2H), 1.52 (m, 2H), 1.21 (s, 9H).

Example No. A1-461:
¹H-NMR (400 MHz, d₆-DMSO) δ 9.91 (br. s, 1H, NH), 7.43 (m, 1H), 7.38 (m, 1H), 7.27 (m, 1H), 7.13 (dd, 1H), 7.04 (d, 1H), 6.86 (d, 1H), 4.54 (s, 2H), 3.20 (s, 3H), 1.54 (m, 2H), 1.52 (m, 2H).

Example No. A2-45:
¹H-NMR (400 MHz, CDCl₃) δ 7.82 (d, 2H), 7.74 (d, 2H), 6.79 (m, 2H), 6.68 (d, 1H), 6.50 (br. s, 1H, NH), 3.81 (q, 2H), 1.77 (m, 2H), 1.47 (m, 2H), 1.28 (t, 3H).

Example No. A2-56:
¹H-NMR (400 MHz, CDCl₃) δ 8.01 (d, 1H), 7.91 (m, 1H), 7.85 (m, 1H), 7.61 (m, 1H), 6.82 (dd, 1H), 6.78 (d, 1H), 6.66 (d, 1H), 6.65 (br. s, 1H, NH), 3.82 (q, 2H), 1.77 (m, 2H), 1.47 (m, 2H), 1.28 (t, 3H).

Example No. A2-152:
¹H-NMR (400 MHz, CDCl₃) δ 7.21 (d, 2H), 7.18 (d, 2H), 7.02 (dd, 1H), 6.85 (d, 1H), 6.65 (d, 1H), 6.18 (br. s, 1H, NH), 4.25 (s, 2H), 3.85 (q, 2H), 2.36 (s, 3H), 1.76 (m, 2H), 1.50 (m, 2H), 1.30 (t, 3H).

Example No. A2-153:
¹H-NMR (400 MHz, CDCl₃) δ 7.26 (m, 1H), 7.19 (m, 1H), 7.11 (m, 2H), 6.99 (dd, 1H), 6.86 (d, 1H), 6.62 (d, 1H), 6.18 (br. s, 1H, NH), 4.26 (s, 2H), 3.85 (q, 2H), 2.34 (s, 2H), 1.78 (m, 2H), 1.49 (m, 2H), 1.30 (t, 3H).

Example No. A2-158:
¹H-NMR (400 MHz, CDCl₃) δ 7.31 (m, 2H), 7.08 (m, 2H), 6.98 (dd, 1H), 6.87 (d, 1H), 6.68 (d, 1H), 6.23 (br. s, 1H, NH), 4.27 (s, 2H), 3.85 (q, 2H), 1.78 (m, 2H), 1.51 (m, 2H), 1.29 (t, 3H).

Example No. A2-165:
¹H-NMR (400 MHz, CDCl₃) δ 7.35 (d, 2H), 7.27 (d, 2H), 6.98 (dd, 1H), 6.87 (d, 1H), 6.67 (d, 1H), 6.28 (br. s, 1H, NH), 4.26 (s, 2H), 3.85 (q, 2H), 1.78 (m, 2H), 1.51 (m, 2H), 1.30 (t, 3H).

Example No. A2-166:
¹H-NMR (400 MHz, CDCl₃) δ 7.36 (m, 1H), 7.34 (m, 1H), 7.32 (m, 1H), 7.25 (m, 1H), 7.04 (dd, 1H), 6.87 (d, 1H), 6.66 (d, 1H), 6.32 (br. s, 1H, NH), 4.26 (s, 2H), 3.85 (q, 2H), 1.78 (m, 2H), 1.51 (m, 2H), 1.31 (t, 3H).

Example No. A2-167:
¹H-NMR (400 MHz, CDCl₃) δ 7.45 (d, 1H), 7.36 (d, 1H), 7.21 (dd, 1H), 7.02 (dd, 1H), 6.88 (d, 1H), 6.67 (d, 1H), 6.18 (br. s, 1H, NH), 4.24 (s, 2H), 3.86 (q, 2H), 1.79 (m, 2H), 1.52 (m, 2H), 1.30 (t, 3H).

Example No. A2-178:
¹H-NMR (400 MHz, CDCl₃) δ 7.63 (d, 2H), 7.47 (d, 2H), 6.98 (dd, 1H), 6.87 (d, 1H), 6.73 (d, 1H), 6.33 (br. s, 1H, NH), 4.35 (s, 2H), 3.85 (q, 2H), 1.78 (m, 2H), 1.51 (m, 2H), 1.29 (t, 3H).

Example No. A2-181:
¹H-NMR (400 MHz, CDCl₃) δ 7.68 (d, 2H), 7.47 (d, 2H), 6.98 (dd, 1H), 6.89 (d, 1H), 6.75 (d, 1H), 6.18 (br. s, 1H, NH), 4.33 (s, 2H), 3.86 (q, 2H), 1.81 (m, 2H), 1.53 (m, 2H), 1.31 (t, 3H).

Example No. A2-182:
¹H-NMR (400 MHz, CDCl₃) δ 7.68 (m, 1H), 7.62 (m, 1H), 7.58 (m, 1H), 7.50 (m, 1H), 7.01 (dd, 1H), 6.90 (d, 1H), 6.73 (d, 1H), 6.21 (br. s, 1H, NH), 4.32 (s, 2H), 3.86 (q, 2H), 1.80 (m, 2H), 1.52 (m, 2H), 1.31 (t, 3H).

Example No. A2-291:
¹H-NMR (400 MHz, CDCl₃) δ 7.29 (d, 2H), 7.12 (d, 2H), 6.95 (dd, 1H), 6.84 (d, 1H), 6.63 (d, 1H), 6.03 (br. s, 1H, NH), 3.84 (q, 2H), 3.28 (m, 2H), 3.12 (m, 2H), 1.77 (m, 2H), 1.52 (m, 2H), 1.28 (t, 3H).

Example No. A2-292:
¹H-NMR (400 MHz, CDCl₃) δ 7.58 (d, 2H), 7.30 (d, 2H), 6.95 (dd, 1H), 6.85 (d, 1H), 6.71 (d, 1H), 6.17 (br. s, 1H, NH), 3.84 (q, 2H), 3.32 (m, 2H), 3.21 (m, 2H), 1.78 (m, 2H), 1.51 (m, 2H), 1.28 (t, 3H).

Example No. A3-45:
¹H-NMR (400 MHz, CDCl₃) δ 7.81 (d, 2H), 7.74 (d, 2H), 6.75 (m, 2H), 6.68 (d, 1H), 6.49 (br. s, 1H, NH), 3.70 (t, 2H), 1.77 (m, 2H), 1.70 (sext, 2H), 1.48 (m, 2H), 0.96 (t, 3H).

Example No. A3-56:
¹H-NMR (400 MHz, CDCl₃) δ 8.01 (m, 1H), 7.91 (m, 1H), 7.83 (m, 1H), 7.58 (m, 1H), 6.80 (dd, 1H), 6.75 (d, 1H), 6.65 (d, 1H), 6.57 (br. s, 1H, NH), 3.71 (t, 2H), 1.76 (m, 2H), 1.70 (sext, 2H), 1.48 (m, 2H), 0.96 (t, 3H).

Example No. A3-152:
¹H-NMR (400 MHz, CDCl₃) δ 7.20 (d, 2H), 7.17 (d, 2H), 7.01 (dd, 1H), 6.96 (br. s, 1H, NH), 6.84 (d, 1H), 6.65 (d, 1H), 4.25 (s, 2H), 3.75 (t, 2H), 2.36 (s, 3H), 1.77 (m, 2H), 1.73 (sext, 2H), 1.49 (m, 2H), 0.98 (t, 3H).

Example No. A3-153:
¹H-NMR (400 MHz, CDCl₃) δ 7.25 (m, 1H), 7.18 (m, 1H), 7.11 (m, 2H), 6.98 (dd, 1H), 6.85 (d, 1H), 6.62 (d, 1H), 6.23 (br. s, 1H, NH), 4.26 (s, 2H), 3.74 (t, 2H), 1.78 (m, 2H), 1.73 (sext, 2H), 1.49 (m, 2H), 0.99 (t, 3H).

Example No. A3-158:
¹H-NMR (400 MHz, CDCl₃) δ 7.32 (d, 2H), 7.08 (d, 2H), 6.96 (dd, 1H), 6.85 (d, 1H), 6.67 (d, 1H), 6.14 (br. s, 1H, NH), 4.27 (s, 2H), 3.74 (t, 2H), 1.78 (m, 2H), 1.74 (sext, 2H), 1.51 (m, 2H), 0.98 (t, 3H).

Example No. A3-165:
¹H-NMR (400 MHz, CDCl₃) δ 7.35 (d, 2H), 7.25 (d, 2H), 6.96 (dd, 1H), 6.85 (d, 1H), 6.66 (d, 1H), 6.20 (br. s, 1H, NH), 4.26 (s, 2H), 3.74 (t, 2H), 1.79 (m, 2H), 1.73 (sext, 2H), 1.51 (m, 2H), 0.99 (t, 3H).

Example No. A3-166:
¹H-NMR (400 MHz, CDCl₃) δ 7.34 (m, 1H), 7.31 (m, 1H), 7.29 (m, 1H), 7.24 (m, 1H), 7.01 (dd, 1H), 6.87 (d, 1H), 6.65 (d, 1H), 6.18 (br. s, 1H, NH), 4.26 (s, 2H), 3.75 (t, 2H), 1.78 (m, 2H), 1.75 (sext, 2H), 1.53 (m, 2H), 1.00 (t, 3H).

Example No. A3-176:
¹H-NMR (400 MHz, CDCl₃) δ 8.24 (m, 1H), 8.13 (m, 1H), 7.73 (d, 1H), 7.58 (m, 1H), 7.07 (dd, 1H), 6.87 (d, 1H), 6.76 (d, 1H), 6.33 (br. s, 1H, NH), 4.38 (s, 2H), 3.75 (t, 2H), 1.78 (m, 2H), 1.75 (sext, 2H), 1.55 (m, 2H), 1.01 (t, 3H).

Example No. A3-178:
¹H-NMR (400 MHz, CDCl₃) δ 7.64 (d, 2H), 7.47 (d, 2H), 6.96 (dd, 1H), 6.86 (d, 1H), 6.72 (d, 1H), 6.16 (br. s, 1H, NH), 4.35 (s, 2H), 3.74 (t, 2H), 1.78 (m, 2H), 1.75 (sext, 2H), 1.52 (m, 2H), 0.99 (t, 3H).

Example No. A3-181:
¹H-NMR (400 MHz, CDCl₃) δ 7.67 (d, 2H), 7.47 (d, 2H), 6.97 (dd, 1H), 6.87 (d, 1H), 6.75 (d, 1H), 6.29 (br. s, 1H, NH), 4.33 (s, 2H), 3.75 (t, 2H), 1.81 (m, 2H), 1.73 (sext, 2H), 1.53 (m, 2H), 0.99 (t, 3H).

Example No. A3-182:
¹H-NMR (400 MHz, CDCl₃) δ 7.68 (m, 1H), 7.61 (m, 2H), 7.50 (m, 1H), 7.01 (dd, 1H), 6.89 (d, 1H), 6.73 (d, 1H), 6.31 (br. s, 1H, NH), 4.31 (s, 2H), 3.75 (t, 2H), 1.79 (m, 2H), 1.74 (sext, 2H), 1.54 (m, 2H), 0.99 (t, 3H).

Example No. A3-291:
¹H-NMR (400 MHz, CDCl₃) δ 7.30 (d, 2H), 7.12 (d, 2H), 6.93 (dd, 1H), 6.83 (d, 1H), 6.63 (d, 1H), 6.10 (br. s, 1H, NH), 3.73 (t, 2H), 3.27 (m, 2H), 3.12 (m, 2H), 1.78 (m, 2H), 1.72 (sext, 2H), 1.51 (m, 2H), 0.98 (t, 3H).

Example No. A3-292:
¹H-NMR (400 MHz, CDCl₃) δ 7.58 (d, 2H), 7.31 (d, 2H), 6.94 (dd, 1H), 6.83 (d, 1H), 6.71 (d, 1H), 6.21 (br. s, 1H, NH), 3.73 (t, 2H), 3.30 (m, 2H), 3.21 (m, 2H), 1.78 (m, 2H), 1.71 (sext, 2H), 1.50 (m, 2H), 0.97 (t, 3H).

Example No. A4-45:
¹H-NMR (400 MHz, CDCl₃) δ 7.82 (d, 2H), 7.47 (d, 2H), 6.91 (d, 1H), 6.76 (dd, 1H), 6.66 (d, 1H), 6.56 (br. s, 1H, NH), 4.70 (sept, 1H), 1.76 (m, 2H), 1.47 (d, 6H), 1.45 (m, 2H).

Example No. A4-56:
¹H-NMR (400 MHz, CDCl₃) δ 8.02 (m, 1H), 7.92 (m, 1H), 7.83 (m, 1H), 7.60 (m, 1H), 6.91 (d, 1H), 6.78 (dd, 1H), 6.63 (d, 1H), 6.55 (br. s, 1H, NH), 4.70 (sept, 1H), 1.75 (m, 2H), 1.47 (d, 6H), 1.45 (m, 2H).

Example No. A4-152:
¹H-NMR (400 MHz, CDCl₃) δ 7.21 (d, 2H), 7.18 (d, 2H), 7.00 (d, 1H), 6.96 (dd, 1H), 6.59 (d, 1H), 6.15 (br. s, 1H, NH), 4.74 (sept, 1H), 4.26 (s, 2H), 2.37 (s, 3H), 1.74 (m, 2H), 1.50 (d, 6H), 1.47 (m, 2H).

Example No. A4-153:
¹H-NMR (400 MHz, CDCl₃) δ 7.26 (m, 1H), 7.19 (m, 1H), 7.12 (m, 2H), 7.01 (d, 1H), 6.95 (dd, 1H), 6.60 (d, 1H), 6.13 (br. s, 1H, NH), 4.75 (sept, 1H), 4.27 (s, 2H), 2.35 (s, 3H), 1.74 (m, 2H), 1.51 (d, 6H), 1.47 (m, 2H).

Example No. A4-158:
¹H-NMR (400 MHz, CDCl₃) δ 7.31 (d, 2H), 7.07 (d, 2H), 7.00 (d, 1H), 6.94 (dd, 1H), 6.66 (d, 1H), 6.23 (br. s, 1H, NH), 4.74 (sept, 1H), 4.27 (s, 2H), 1.76 (m, 2H), 1.51 (m, 8H).

Example No. A4-165:
¹H-NMR (400 MHz, CDCl₃) δ 7.35 (d, 2H), 7.28 (d, 2H), 7.02 (d, 1H), 6.94 (dd, 1H), 6.64 (d, 1H), 6.20 (br. s, 1H, NH), 4.73 (sept, 1H), 4.27 (s, 2H), 1.77 (m, 2H), 1.51 (d, 6H), 1.48 (m, 2H).

Example No. A4-166:
¹H-NMR (400 MHz, CDCl₃) δ 7.35 (m, 1H), 7.30 (m, 1H), 7.25 (m, 2H), 7.01 (m, 2H), 6.63 (d, 1H), 6.27 (br. s, 1H, NH), 4.74 (sept, 1H), 4.26 (s, 2H), 1.76 (m, 2H), 1.50 (m, 8H).

Example No. A4-167:
¹H-NMR (400 MHz, CDCl₃) δ 7.42 (d, 1H), 7.36 (d, 1H), 7.19 (dd, 1H), 7.00 (m, 2H), 6.66 (d, 1H), 6.31 (br. s, 1H, NH), 4.74 (sept, 1H), 4.24 (s, 2H), 1.77 (m, 2H), 1.51 (d, 6H), 1.49 (m, 2H).

Example No. A4-176:
¹H-NMR (400 MHz, CDCl₃) δ 8.25 (m, 1H), 8.13 (d, 1H), 7.75 (d, 1H), 7.58 (m, 1H), 7.04 (m, 2H), 6.74 (d, 1H), 6.33 (br. s, 1H, NH), 4.75 (sept, 1H), 4.38 (s, 2H), 1.78 (m, 2H), 1.54 (m, 2H), 1.52 (d, 6H).

Example No. A4-178:
¹H-NMR (400 MHz, CDCl₃) δ 7.63 (d, 2H), 7.46 (d, 2H), 7.02 (d, 1H), 6.95 (dd, 1H), 6.71 (d, 1H), 6.28 (br. s, 1H, NH), 4.74 (sept, 1H), 4.35 (s, 2H), 1.76 (m, 2H), 1.52 (m, 8H).

Example No. A4-181:
¹H-NMR (400 MHz, CDCl₃) δ 7.69 (d, 2H), 7.47 (d, 2H), 7.01 (m, 1H), 6.93 (dd, 1H), 6.74 (d, 1H), 6.16 (br. s, 1H, NH), 4.74 (sept, 1H), 4.34 (s, 2H), 1.78 (m, 2H), 1.51 (m, 8H).

Example No. A4-182:
¹H-NMR (400 MHz, CDCl₃) δ 7.68 (m, 1H), 7.60 (m, 2H), 7.49 (m, 1H), 7.03 (d, 1H), 6.97 (dd, 1H), 6.72 (d, 1H), 6.32 (br. s, 1H, NH), 4.73 (sept, 1H), 4.31 (s, 2H), 1.78 (m, 2H), 1.54 (m, 2H), 1.51 (d, 6H).

Example No. A4-291:
¹H-NMR (400 MHz, CDCl₃) δ 7.24 (d, 2H), 7.13 (d, 2H), 6.98 (d, 1H), 6.91 (dd, 1H), 6.61 (d, 1H), 6.07 (br. s, 1H, NH), 4.73 (sept, 1H), 3.27 (m, 2H), 3.12 (m, 2H), 1.77 (m, 2H), 1.50 (m, 8H).

Example No. A4-292:
¹H-NMR (400 MHz, CDCl₃) δ 7.58 (d, 2H), 7.31 (d, 2H), 7.00 (d, 1H), 6.92 (dd, 1H), 6.70 (d, 1H), 6.26 (br. s, 1H, NH), 4.73 (sept, 1H), 3.33 (m, 2H), 3.21 (m, 2H), 1.77 (m, 2H), 1.49 (m, 8H).

Example No. B1-165:
¹H-NMR (400 MHz, CDCl₃ δ, ppm) 7.38 (d, 2H), 7.20 (m, 3H), 7.02 (m, 1H), 6.74 (d, 1H), 6.11 (br. s, 1H, NH), 4.30 (s, 2H), 3.19 (s, 3H), 2.67 (m, 2H), 2.43-2.20 (m, 4H).

Example No. B1-178:
¹H-NMR (400 MHz, CDCl₃ δ, ppm) 7.65 (d, 2H), 7.50 (m, 2H), 7.34 (m, 1H), 7.01 (m, 1H), 6.74 (d, 1H), 6.14 (br. s, 1H, NH), 4.38 (s, 2H), 3.19 (s, 3H), 2.67 (m, 2H), 2.44-2.18 (m, 4H).

Example No. B1-181:
¹H-NMR (400 MHz, CDCl₃ δ, ppm) 7.68 (d, 2H), 7.47 (d, 2H), 7.29 (m, 1H), 7.01 (m, 1H), 6.75 (d, 1H), 6.14 (br. s, 1H, NH), 4.37 (s, 2H), 3.19 (s, 3H), 2.68 (m, 2H), 2.42-2.20 (m, 4H).

Example No. C1-45:
¹H-NMR (400 MHz, CDCl₃) δ 7.81 (d, 2H), 7.75 (d, 2H), 6.91 (d, 1H), 6.86 (dd, 1H), 6.69 (d, 1H), 6.39 (br. s, 1H, NH), 3.17 (s, 3H), 2.18-2.05 (m, 4H), 1.87 (m, 2H), 1.71 (m, 2H).

Example No. C1-152:
¹H-NMR (400 MHz, CDCl₃) δ 7.21 (d, 2H), 7.19 (d, 2H), 7.06 (dd, 1H), 6.95 (d, 1H), 6.77 (d, 1H), 6.04 (br. s, 1H, NH), 4.27 (s, 2H), 3.21 (s, 3H), 2.37 (s, 3H), 2.20-2.06 (m, 4H), 1.95 (m, 2H), 1.82 (m, 2H).

Example No. C1-165:
¹H-NMR (400 MHz, d₆-DMSO) δ 9.55 (br. s, 1H, NH), 7.41 (d, 2H), 7.29 (d, 2H), 7.09 (dd, 1H), 6.99 (d, 1H), 6.93 (d, 1H), 4.42 (s, 2H), 3.31 (s, 3H), 2.00-1.92 (m, 4H), 1.89 (m, 2H), 1.72 (m, 2H).

Example No. C1-166:
¹H-NMR (400 MHz, CDCl₃) δ 7.36 (m, 1H), 7.30 (m, 1H), 7.28 (m, 2H), 7.09 (dd, 1H), 6.98 (d, 1H), 6.79 (d, 1H), 6.23 (br. s, 1H, NH), 4.27 (s, 2H), 3.21 (s, 3H), 2.20-2.07 (m, 4H), 1.96 (m, 2H), 1.82 (m, 2H).

Example No. C1-181:
¹H-NMR (400 MHz, CDCl₃) δ 7.67 (d, 2H), 7.47 (d, 2H), 7.04 (m, 2H), 6.79 (d, 1H), 6.33 (br. s, 1H, NH), 4.35 (s, 2H), 3.21 (s, 3H), 2.21-2.08 (m, 4H), 1.97 (m, 2H), 1.81 (m, 2H).

Example No. C1-182:
¹H-NMR (400 MHz, CDCl₃) δ 7.68 (m, 1H), 7.60 (m, 2H), 7.52 (m, 1H), 7.06 (m, 1H), 7.02 (d, 1H), 6.80 (d, 1H), 6.12 (br. s, 1H, NH), 4.32 (s, 2H), 3.22 (s, 3H), 2.20-2.08 (m, 4H), 1.97 (m, 2H), 1.82 (m, 2H).

Example No. C1-291:
¹H-NMR (400 MHz, CDCl₃) δ 7.29 (d, 2H), 7.12 (d, 2H), 7.02 (dd, 1H), 6.99 (d, 1H), 6.75 (d, 1H), 6.16 (br. s, 1H, NH), 3.30 (m, 2H), 3.17 (s, 3H), 3.13 (m, 2H), 2.18-2.07 (m, 4H), 1.95 (m, 2H), 1.80 (m, 2H).

Example No. C2-45:
¹H-NMR (400 MHz, d₆-DMSO) δ 10.15 (br. s, 1H, NH), 8.05 (d, 2H), 7.82 (d, 2H), 6.92 (m, 2H), 6.83 (d, 1H), 3.63 (q, 2H), 1.98-1.87 (m, 4H), 1.77 (m, 2H), 1.57 (m, 2H), 1.09 (t, 3H).

Example No. C2-152:
¹H-NMR (400 MHz, CDCl₃) δ 7.22 (d, 2H), 7.19 (d, 2H), 7.07 (dd, 1H), 6.96 (d, 1H), 6.79 (d, 1H), 6.09 (br. s, 1H, NH), 4.27 (s, 2H), 3.78 (q, 2H), 2.37 (s, 3H), 2.20-2.08 (m, 4H), 1.95 (m, 2H), 1.81 (m, 2H), 1.27 (t, 3H).

Example No. C2-165:
¹H-NMR (400 MHz, CDCl₃) δ 7.35 (d, 2H), 7.28 (d, 2H), 7.04 (dd, 1H), 6.98 (d, 1H), 6.79 (d, 1H), 6.22 (br. s, 1H, NH), 4.28 (s, 2H), 3.76 (q, 2H), 2.20-2.07 (m, 4H), 1.94 (m, 2H), 1.80 (m, 2H), 1.28 (t, 3H).

Example No. C2-166:
¹H-NMR (400 MHz, CDCl₃) δ 7.36 (m, 1H), 7.32 (m, 1H), 7.28 (m, 2H), 7.08 (dd, 1H), 6.98 (d, 1H), 6.80 (d, 1H), 6.09 (br. s, 1H, NH), 4.28 (s, 2H), 3.77 (q, 2H), 2.20-2.08 (m, 4H), 1.96 (m, 2H), 1.81 (m, 2H), 1.28 (t, 3H).

Example No. C2-181:
¹H-NMR (400 MHz, CDCl₃) δ 7.68 (d, 2H), 7.48 (d, 2H), 7.04 (m, 2H), 6.80 (d, 1H), 6.29 (br. s, 1H, NH), 4.35 (s, 2H), 3.76 (q, 2H), 2.20-2.09 (m, 4H), 1.95 (m, 2H), 1.80 (m, 2H), 1.27 (t, 3H).

Example No. C2-182:
¹H-NMR (400 MHz, CDCl₃) δ 7.68 (m, 1H), 7.61 (m, 2H), 7.52 (m, 1H), 7.04 (m, 2H), 6.81 (d, 1H), 6.14 (br. s, 1H, NH), 4.33 (s, 2H), 3.77 (q, 2H), 2.21-2.08 (m, 4H), 1.97 (m, 2H), 1.81 (m, 2H), 1.27 (t, 3H).

Example No. C2-291:
¹H-NMR (400 MHz, CDCl₃) δ 7.29 (d, 2H), 7.13 (d, 2H), 7.00 (m, 2H), 6.75 (d, 1H), 6.17 (br. s, 1H, NH), 3.74 (q, 2H), 3.30 (m, 2H), 3.13 (m, 2H), 2.19-2.07 (m, 4H), 1.96 (m, 2H), 1.81 (m, 2H), 1.26 (t, 3H).

Example No. C3-45:
¹H-NMR (400 MHz, CDCl₃) δ 7.84 (d, 2H), 7.75 (d, 2H), 6.89 (d, 1H), 6.85 (dd, 1H) 6.70 (d, 1H), 6.53 (br. s, 1H, NH), 3.64 (t, 2H), 2.17-2.03 (m, 4H), 1.87 (m, 2H), 1.72 (m, 2H), 1.68 (sext, 2H), 0.93 (t, 3H).

Example No. C3-152:
¹H-NMR (400 MHz, CDCl₃) δ 7.22 (d, 2H), 7.18 (d, 2H), 7.05 (dd, 1H), 6.95 (d, 1H), 6.77 (d, 1H), 6.10 (br. s, 1H, NH), 4.27 (s, 2H), 3.68 (t, 2H), 2.38 (s, 3H), 2.19-2.06 (m, 4H), 1.94 (m, 2H), 1.82 (m, 2H), 1.71 (sext, 2H), 0.97 (t, 3H).

Example No. C3-165:
¹H-NMR (400 MHz, CDCl₃) δ 7.36 (d, 2H), 7.27 (d, 2H), 7.02 (dd, 1H), 6.97 (d, 1H), 6.77 (d, 1H), 6.14 (br. s, 1H, NH), 4.28 (s, 2H), 3.66 (t, 2H), 2.20-2.06 (m, 4H), 1.94 (m, 2H), 1.81 (m, 2H), 1.70 (sext, 2H), 0.97 (t, 3H).

Example No. C3-166:
¹H-NMR (400 MHz, CDCl₃) δ 7.37 (m, 1H), 7.33 (m, 1H), 7.29 (m, 2H), 7.07 (dd, 1H), 6.98 (d, 1H), 6.79 (d, 1H), 6.24 (br. s, 1H, NH), 4.28 (s, 2H), 3.68 (t, 2H), 2.20-2.07 (m, 4H), 1.96 (m, 2H), 1.83 (m, 2H), 1.72 (sext, 2H), 0.96 (t, 3H).

Example No. C3-181:
¹H-NMR (400 MHz, CDCl₃) δ 7.68 (d, 2H), 7.48 (d, 2H), 7.02 (m, 2H), 6.79 (d, 1H), 6.26 (br. s, 1H, NH), 4.35 (s, 2H), 3.67 (t, 2H), 2.21-2.08 (m, 4H), 1.95 (m, 2H), 1.81 (m, 2H), 1.71 (sext, 2H), 0.96 (t, 3H).

Example No. C3-182:
¹H-NMR (400 MHz, CDCl₃) δ 7.68 (m, 1H), 7.61 (m, 2H), 7.50 (m, 1H), 7.04 (m, 2H), 6.80 (d, 1H), 6.30 (br. s, 1H, NH), 4.33 (s, 2H), 3.69 (t, 2H), 2.20-2.09 (m, 4H), 1.96 (m, 2H), 1.82 (m, 2H), 1.72 (sext, 2H), 0.96 (t, 3H).

Example No. C3-291:
¹H-NMR (400 MHz, CDCl₃) δ 7.29 (d, 2H), 7.13 (d, 2H), 6.99 (m, 2H), 6.74 (d, 1H), 6.09 (br. s, 1H, NH), 3.65 (t, 2H), 3.29 (m, 2H), 3.14 (m, 2H), 2.19-2.05 (m, 4H), 1.95 (m, 2H), 1.80 (m, 2H), 1.70 (sext, 2H), 0.96 (t, 3H).

Example No. C4-45:
¹H-NMR (400 MHz, CDCl₃) δ 7.84 (d, 2H), 7.76 (d, 2H), 6.86 (m, 1H), 6.83 (m, 2H), 6.30 (br. s, 1H, NH), 4.60 (sept, 1H), 2.14-2.02 (m, 4H), 1.86 (m, 2H), 1.70 (m, 2H), 1.45 (d, 6H).

Example No. C4-152:
¹H-NMR (400 MHz, CDCl₃) δ 7.22 (d, 2H), 7.19 (d, 2H), 7.01 (m, 1H), 6.93 (m, 2H), 5.99 (br. s, 1H, NH), 4.64 (sept, 1H), 4.28 (s, 2H), 2.38 (s, 3H), 2.19-2.07 (m, 4H), 1.94 (m, 2H), 1.80 (m, 2H), 1.49 (d, 6H).

Example No. C4-165:
¹H-NMR (400 MHz, CDCl₃) δ 7.36 (d, 2H), 7.29 (d, 2H), 7.00 (m, 1H), 6.96 (d, 1H), 6.93 (d, 1H), 6.12 (br. s, 1H, NH), 4.65 (sept, 1H), 4.28 (s, 2H), 2.18-2.08 (m, 4H), 1.93 (m, 2H), 1.79 (m, 2H), 1.28 (d, 6H).

Example No. C4-166:
¹H-NMR (400 MHz, CDCl₃) δ 7.36 (m, 1H), 7.32 (m, 1H), 7.29 (m, 2H), 7.05 (dd, 1H), 6.97 (d, 1H), 6.95 (d, 1H), 6.09 (br. s, 1H, NH), 4.65 (sept, 1H), 4.28 (s, 2H), 2.19-2.05 (m, 4H), 1.94 (m, 2H), 1.81 (m, 2H), 1.48 (d, 6H).

Example No. C4-181:
¹H-NMR (400 MHz, CDCl₃) δ 7.68 (d, 2H), 7.49 (d, 2H), 7.01 (m, 2H), 6.93 (d, 1H), 6.14 (br. s, 1H, NH), 4.65 (sept, 1H), 4.35 (s, 2H), 2.19-2.08 (m, 4H), 1.96 (m, 2H), 1.80 (m, 2H), 1.48 (d, 6H).

Example No. C4-182:
¹H-NMR (400 MHz, CDCl₃) δ 7.68 (m, 1H), 7.62 (m, 2H), 7.52 (m, 1H), 7.01 (m, 2H), 6.94 (d, 1H), 6.11 (br. s, 1H, NH), 4.65 (sept, 1H), 4.33 (s, 2H), 2.19-2.08 (m, 4H), 1.96 (m, 2H), 1.81 (m, 2H).

Example No. C4-291:
¹H-NMR (400 MHz, CDCl₃) δ 7.29 (d, 2H), 7.14 (d, 2H), 6.94 (m, 2H), 6.90 (d, 1H), 5.97 (br. s, 1H, NH), 4.63 (sept, 1H), 3.30 (m, 2H), 3.14 (m, 2H), 2.18-2.05 (m, 4H), 1.94 (m, 2H), 1.78 (m, 2H).

Example No. D1-45:
¹H-NMR (400 MHz, CDCl₃) δ 7.79 (d, 2H), 7.74 (d, 2H), 7.12 (d, 1H), 6.92 (dd, 1H), 6.71 (d, 1H), 6.33 (br. s, 1H, NH), 3.17 (s, 3H), 2.06 (m, 2H), 1.81 (m, 2H), 1.72-1.64 (m, 4H), 1.47 (m, 2H).

Example No. D1-152:
¹H-NMR (400 MHz, CDCl₃) δ 7.23 (d, 2H), 7.20 (d, 2H), 7.10 (dd, 1H), 6.99 (d, 1H), 6.79 (d, 1H), 6.03 (br. s, 1H, NH), 4.28 (s, 2H), 3.20 (s, 3H), 2.37 (s, 3H), 1.97 (m, 2H), 1.85 (m, 2H), 1.75-1.66 (m, 4H), 1.58 (m, 2H).

Example No. D1-165:
¹H-NMR (400 MHz, CDCl₃) δ 7.36 (d, 2H), 7.28 (d, 2H), 7.22 (d, 1H), 7.08 (dd, 1H), 6.80 (d, 1H), 6.08 (br. s, 1H, NH), 4.29 (s, 2H), 3.20 (s, 3H), 1.98 (m, 2H), 1.84 (m, 2H), 1.74-1.66 (m, 4H), 1.57 (m, 2H).

Example No. D1-166:
¹H-NMR (400 MHz, CDCl₃) δ 7.36 (m, 1H), 7.31 (m, 1H), 7.29 (m, 2H), 7.23 (d, 1H), 7.11 (dd, 1H), 6.81 (d, 1H), 6.12 (br. s, 1H, NH), 4.28 (s, 2H), 3.20 (s, 3H), 1.98 (m, 2H), 1.85 (m, 2H), 1.73-1.66 (m, 4H), 1.57 (m, 2H).

Example No. D1-181:
¹H-NMR (400 MHz, CDCl₃) δ 7.67 (d, 2H), 7.47 (d, 2H), 7.30 (d, 1H), 7.09 (dd, 1H), 6.81 (d, 1H), 6.33 (br. s, 1H, NH), 4.36 (s, 2H), 3.21 (s, 3H), 2.21-1.08 (m, 2H), 1.99 (m, 2H), 1.86 (m, 2H), 1.75-1.65 (m, 4H), 1.56 (m, 2H).

Example No. D1-182:
¹H-NMR (400 MHz, CDCl₃) δ 7.67 (m, 1H), 7.60 (m, 2H), 7.50 (m, 1H), 7.31 (d, 1H), 7.11 (dd, 1H), 6.83 (d, 1H), 6.39 (br. s, 1H, NH), 4.34 (s, 2H), 3.21 (s, 3H), 1.98 (m, 2H), 1.84 (m, 2H), 1.75-1.63 (m, 4H), 1.57 (m, 2H).

Example No. D1-291:
¹H-NMR (400 MHz, CDCl₃) δ 7.30 (d, 2H), 7.24 (d, 1H), 7.13 (d, 2H), 7.02 (dd, 1H), 6.78 (d, 1H), 6.01 (br. s, 1H, NH), 3.31 (m, 2H), 3.18 (s, 3H), 3.14 (m, 2H), 1.97 (m, 2H), 1.82 (m, 2H), 1.75-1.65 (m, 4H), 1.56 (m, 2H).

Example No. E7-152:
¹H-NMR (400 MHz, CDCl₃) δ 7.21 (d, 2H), 7.19 (d, 2H), 7.07 (dd, 1H), 7.02 (d, 1H), 6.78 (d, 1H), 5.99 (br. s, 1H, NH), 5.88-5.81 (m, 3H), 5.24-5.20 (m, 2H), 4.36 (m, 2H), 4.26 (s, 2H), 3.02 (m, 2H), 2.61 (m, 2H), 2.37 (s, 3H).

Example No. G1-1:
¹H-NMR (400 MHz, CDCl₃) δ 7.16 (d, 1H), 7.14 (dd, 1H), 6.82 (d, 1H), 6.39 (br. s, 1H, NH), 3.22 (s, 3H), 2.99 (s, 3H), 1.38 (s, 6H).

Example No. G1-34:
¹H-NMR (400 MHz, CHCl₃) δ 7.71 (m, 2H), 7.11 (m, 2H), 6.91 (m, 2H), 6.71 (d, 1H), 6.39 (br. s, 1H, NH), 3.18 (s, 3H), 1.29 (s, 6H).

Example No. G1-37:
¹H-NMR (400 MHz, CHCl₃) δ 8.68 (d, 1H), 8.09 (m, 1H), 8.04 (d, 1H), 7.94 (m, 1H), 7.68-7.59 (m, 2H), 7.42 (m, 1H), 6.81 (m, 1H), 6.65 (br. s, 1H, NH), 6.59 (m, 1H), 6.57 (d, 1H), 3.10 (s, 3H), 1.12 (s, 6H).

Example No. G1-38:
¹H-NMR (400 MHz, CHCl₃) δ 7.58 (d, 2H), 7.54 (d, 2H), 6.90 (m, 2H), 6.72 (d, 1H), 6.40 (br. s, 1H, NH), 3.18 (s, 3H), 1.30 (s, 6H).

Example No. G1-42:
¹H-NMR (400 MHz, CHCl₃) δ 7.76 (d, 2H), 7.27 (d, 2H), 6.99 (dd, 1H), 6.88 (d, 1H), 6.82 (br. s, 1H, NH), 6.74 (d, 1H), 3.18 (s, 3H), 1.28 (s, 6H).

Example No. G1-56:
¹H-NMR (400 MHz, CHCl₃) δ 7.97 (d, 1H), 7.90 (m, 1H), 7.83 (m, 1H), 6.94 (dd, 1H), 6.89 (d, 1H), 6.74 (d, 1H), 6.52 (br. s, 1H, NH), 3.19 (s, 3H), 1.30 (s, 6H).

Example No. G1-66:
¹H-NMR (400 MHz, CHCl₃) δ 7.56 (m, 1H), 7.44 (m, 2H), 7.30 (m, 1H), 6.96 (dd, 1H), 6.90 (d, 1H), 6.72 (d, 1H), 6.53 (br. s, 1H, NH), 6.66-6.30 (t, 1H, OCHF₂), 3.18 (s, 3H), 1.28 (s, 6H).

Example No. G1-67:
¹H-NMR (400 MHz, CDCl₃) δ 7.65 (m, 1H), 7.53 (m, 1H), 7.49 (d, 1H), 7.40 (m, 1H), 6.95 (dd, 1H), 6.91 (d, 1H), 6.72 (d, 1H), 6.58 (br. s, 1H, NH), 3.18 (s, 3H), 1.28 (s, 6H).

Example No. G1-152:
¹H-NMR (400 MHz, CDCl₃) δ 7.22 (d, 2H), 7.19 (d, 2H), 7.08 (dd, 1H), 6.99 (d, 1H), 6.82 (d, 1H), 6.16 (br. s, 1H, NH), 4.28 (s, 2H), 3.21 (s, 3H), 2.33 (s, 3H), 1.37 (s, 6H).

Example No. G1-153:
¹H-NMR (400 MHz, CDCl₃) δ 7.25 (m, 2H), 7.15 (m, 1H), 7.10 (m, 1H), 7.08 (dd, 1H), 6.95 (d, 1H), 6.80 (d, 1H), 6.14 (br. s, 1H, NH), 4.28 (s, 2H), 3.22 (s, 3H), 2.35 (s, 3H), 1.36 (s, 6H).

Example No. G1-158:
¹H-NMR (400 MHz, CDCl₃) δ 7.30 (m, 2H), 7.08-7.02 (m, 3H), 6.98 (d, 1H), 6.80 (d, 1H), 6.33 (br. s, 1H, NH), 4.28 (s, 2H), 3.21 (s, 3H), 1.37 (s, 6H).

Example No G1-159:
¹H-NMR (400 MHz, CDCl₃) δ 7.35 (m, 1H), 7.11 (m, 3H), 7.04 (m, 1H), 6.98 (d, 1H), 6.81 (d, 1H), 6.33 (br. s, 1H, NH), 4.30 (s, 2H), 3.22 (s, 3H), 1.37 (s, 6H).

Example No. G1-161:
¹H-NMR (400 MHz, CHCl₃) δ 7.48 (m, 1H), 7.37 (m, 1H), 7.18 (m, 1H), 7.08 (m, 2H), 6.99 (d, 1H), 6.78 (d, 1H), 6.15 (br. s, 1H, NH), 4.41 (s, 2H), 3.21 (s, 3H), 1.36 (s, 6H).

Example No. G1-165:
¹H-NMR (400 MHz, CDCl₃) δ 7.34 (d, 2H), 7.26 (d, 2H), 7.06 (dd, 1H), 6.98 (d, 1H), 6.80 (d, 1H), 6.32 (br. s, 1H, NH), 4.28 (s, 2H), 3.22 (s, 3H), 1.37 (s, 6H).

Example No. G1-166:
¹H-NMR (400 MHz, CDCl₃) δ 7.38 (m, 1H), 7.33 (m, 1H), 7.30-7.23 (m, 2H), 7.10 (dd, 1H), 6.98 (d, 1H), 6.82 (d, 1H), 6.22 (br. s, 1H, NH), 4.28 (s, 2H), 3.22 (s, 3H), 1.37 (s, 6H).

Example No. G1-167:
¹H-NMR (400 MHz, CDCl₃) δ 7.44 (d, 1H), 7.37 (d, 1H), 7.19 (dd, 2H), 7.10 (dd, 1H), 7.01 (d, 1H), 6.81 (d, 1H), 6.42 (br. s, 1H, NH), 4.26 (s, 2H), 3.22 (s, 3H), 1.37 (s, 6H).

Example No. G1-169:
¹H-NMR (400 MHz, CDCl₃) δ 7.46 (d, 1H), 7.37 (d, 1H), 7.24 (dd, 2H), 7.07 (dd, 1H), 7.01 (d, 1H), 6.76 (d, 1H), 6.48 (br. s, 1H, NH), 4.54 (s, 2H), 3.20 (s, 3H), 1.35 (s, 6H).

Example No. G1-171:
¹H-NMR (400 MHz, CDCl₃) δ 7.38 (m, 1H), 7.21 (m, 2H), 7.12 (dd, 1H), 7.00 (d, 1H), 6.83 (d, 1H), 6.28 (br. s, 1H, NH), 4.24 (s, 2H), 3.22 (s, 3H), 1.38 (s, 6H).

Example No. G1-172:
¹H-NMR (400 MHz, CDCl₃) δ 7.51 (d, 2H), 7.20 (d, 2H), 7.04 (dd, 1H), 6.98 (d, 1H), 6.80 (d, 1H), 6.22 (br. s, 1H, NH), 4.26 (s, 2H), 3.22 (s, 3H), 1.37 (s, 6H).

Example No. G1-175:
¹H-NMR (400 MHz, CDCl₃) δ 8.24 (d, 2H), 7.53 (d, 2H), 7.06 (m, 2H), 6.83 (d, 1H), 6.18 (br. s, 1H, NH), 4.40 (s, 2H), 3.22 (s, 3H), 1.38 (s, 6H).

Example No. G1-178:
¹H-NMR (400 MHz, CDCl₃) δ 7.63 (m, 1H), 7.47 (m, 1H), 7.07 (dd, 1H), 7.04 (d, 1H), 6.80 (d, 1H), 6.31 (br. s, 1H, NH), 4.36 (s, 2H), 3.22 (s, 3H), 1.37 (s, 6H).

Example No. G1-179:
¹H-NMR (400 MHz, CDCl₃) δ 7.66 (d, 1H), 7.58 (m, 1H), 7.52 (m, 2H), 7.08 (dd, 1H), 7.03 (d, 1H), 6.81 (d, 1H), 6.38 (br. s, 1H, NH), 4.36 (s, 2H), 3.22 (s, 3H), 1.36 (s, 6H).

Example No. G1-180:
¹H-NMR (400 MHz, CDCl₃) δ 7.75 (d, 1H), 7.68 (d, 1H), 7.55 (m, 1H), 7.47 (m, 1H), 7.02 (dd, 1H), 6.99 (d, 1H), 6.75 (d, 1H), 6.31 (br. s, 1H, NH), 4.59 (s, 2H), 3.20 (s, 3H), 1.36 (s, 6H).

Example No. G1-181:
¹H-NMR (400 MHz, CDCl₃) δ 7.68 (d, 2H), 7.47 (d, 2H), 7.05 (m, 2H), 6.82 (d, 1H), 6.18 (br. s, 1H, NH), 4.35 (s, 2H), 3.22 (s, 3H), 1.38 (s, 6H).

Example No. G1-182:
¹H-NMR (400 MHz, CDCl₃) δ 7.69 (m, 1H), 7.60 (m, 2H), 7.52 (m, 1H), 7.08 (dd, 1H), 7.04 (d, 1H), 6.84 (d, 1H), 6.17 (br. s, 1H, NH), 4.33 (s, 2H), 3.23 (s, 3H), 1.38 (s, 6H).

Example No. G1-184:
¹H-NMR (400 MHz, CDCl₃) δ 7.37 (d, 2H), 7.21 (d, 2H), 7.06 (dd, 1H), 7.03 (d, 1H), 6.80 (d, 1H), 6.38 (br. s, 1H, NH), 4.31 (s, 2H), 3.22 (s, 3H), 1.37 (s, 6H).

Example No. G1-190:
¹H-NMR (400 MHz, CDCl₃) δ 8.03 (d, 2H), 7.41 (d, 2H), 7.08 (dd, 1H), 7.00 (d, 1H), 6.81 (d, 1H), 6.41 (br. s, 1H, NH), 4.36 (s, 2H), 3.92 (s, 3H), 3.22 (s, 3H), 1.36 (s, 6H).

Example No. G1-191:
¹H-NMR (400 MHz, CDCl₃) δ 8.05 (d, 1H), 7.98 (m, 1H), 7.57 (m, 1H), 7.46 (m, 1H), 7.11 (dd, 1H), 7.04 (d, 1H), 6.82 (d, 1H), 6.32 (br. s, 1H, NH), 4.35 (s, 2H), 3.92 (s, 3H), 3.22 (s, 3H), 1.37 (s, 6H).

Example No. G1-192:
¹H-NMR (400 MHz, CDCl₃) δ 8.03 (d, 2H), 7.41 (d, 2H), 7.08 (dd, 1H), 6.98 (d, 1H), 6.80 (d, 1H), 6.38 (br. s, 1H, NH), 4.39 (q, 2H), 4.36 (s, 2H), 3.21 (s, 3H), 1.40 (t, 3H), 1.36 (s, 6H).

Example No. G1-290:
¹H-NMR (400 MHz, CDCl₃) δ 7.15 (d, 4H), 7.13 (d, 4H), 6.71 (d, 1H), 6.63 (m, 2H), 4.52 (s, 4H), 3.14 (s, 3H), 2.33 (s, 6H), 1.28 (s, 6H), Example No. G1-291:
¹H-NMR (400 MHz, CDCl₃) δ 7.29 (d, 2H), 7.13 (d, 2H), 7.02 (dd, 1H), 6.94 (d, 1H), 6.78 (d, 1H), 6.06 (br. s, 1H, NH), 3.30 (m, 2H), 3.20 (s, 3H), 3.12 (m, 2H), 1.36 (s, 6H).

Example No. G1-292:
$^1$H-NMR (400 MHz, CDCl$_3$) δ 7.58 (d, 2H), 7.31 (d, 2H), 7.03 (m, 2H), 6.79 (d, 1H), 6.32 (br. s, 1H, NH), 3.33 (m, 2H), 3.23 (s, 3H), 3.13 (m, 2H), 1.36 (s, 6H).

Example No. G1-332:
$^1$H-NMR (400 MHz, CDCl$_3$) δ 7.40 (d, 2H), 7.26 (d, 2H), 7.08 (dd, 1H), 7.05 (d, 1H), 6.80 (d, 1H), 6.14 (br. s, 1H, NH), 4.27 (s, 2H), 3.22 (s, 3H), 1.38 (s, 6H), 1.32 (s, 9H).

Example No. G16-152:
$^1$H-NMR (400 MHz, d$_6$-DMSO) δ 9.46 (br. s, 1H, NH), 7.16 (m, 4H), 6.84 (m, 1H), 6.78 (m, 1H), 4.33 (s, 2H), 3.38 (s, 3H), 2.52 (s, 3H), 2.29 (s, 3H), 1.21 (s, 6H).

Example No. G16-165:
$^1$H-NMR (400 MHz, CDCl$_3$) δ 7.34 (d, 2H), 7.26 (d, 2H), 6.78 (m, 1H), 6.74 (m, 1H), 6.20 (br. s, 1H, NH), 4.28 (s, 2H), 3.49 (s, 3H), 2.61 (s, 3H), 1.34 (s, 6H).

Example No. G16-181:
$^1$H-NMR (400 MHz, CDCl$_3$) δ 7.68 (d, 2H), 7.46 (d, 2H), 6.84 (m, 1H), 6.77 (m, 1H), 6.21 (br. s, 1H, NH), 4.35 (s, 2H), 3.50 (s, 3H), 2.62 (s, 3H), 1.35 (s, 6H).

Example No. H1-54:
$^1$H-NMR (400 MHz, CDCl$_3$ δ, ppm) 7.81 (d, 2H), 7.76 (d, 2H), 7.08 (d, 1H), 6.94 (dd, 1H), 6.74 (d, 1H), 6.45 (br. s, 1H, NH), 4.25 (m, 2H), 3.85 (m, 2H), 3.18 (s, 3H), 1.78 (m, 4H).

Example No. H1-152:
$^1$H-NMR (400 MHz, CDCl$_3$ δ, ppm) 7.21 (d, 2H), 7.19 (d, 2H), 7.11 (dd, 1H), 7.08 (d, 1H), 6.81 (d, 1H), 6.09 (br. s, 1H, NH), 4.28 (s, 2H), 4.25 (m, 2H), 3.91 (m, 2H), 3.21 (s, 3H), 1.85 (m, 4H).

Example No. H1-165:
$^1$H-NMR (400 MHz, CDCl$_3$ δ, ppm) 7.37 (d, 2H), 7.29 (d, 2H), 7.14 (d, 1H), 7.07 (dd, 1H), 6.81 (d, 1H), 6.16 (br. s, 1H, NH), 4.29 (s, 2H), 4.27 (m, 2H), 3.90 (m, 2H), 3.21 (s, 3H), 1.84 (m, 4H).

Example No. H1-166:
$^1$H-NMR (400 MHz, CDCl$_3$ δ, ppm) 7.39-7.25 (m, 4H), 7.11 (d, 1H), 7.10 (dd, 1H), 6.82 (d, 1H), 6.18 (br. s, 1H, NH), 4.29 (s, 2H), 4.28 (m, 2H), 3.91 (m, 2H), 3.21 (s, 3H), 1.84 (m, 4H).

Example No. H1-182:
$^1$H-NMR (400 MHz, CDCl$_3$ δ, ppm) 7.69 (m, 1H), 7.64 (m, 1H), 7.57 (m, 1H), 7.52 (m, 1H), 7.20 (d, 1H), 7.11 (dd, 1H), 6.84 (d, 1H), 6.35 (br. s, 1H, NH), 4.35 (s, 2H), 4.27 (m, 2H), 3.90 (m, 2H), 3.22 (s, 3H), 1.85 (m, 4H).

Example No. H1-291:
$^1$H-NMR (400 MHz, CDCl$_3$ δ, ppm) 7.31 (d, 2H), 7.14 (d, 1H), 7.12 (d, 2H), 7.03 (dd, 1H), 6.79 (d, 1H), 6.16 (br. s, 1H, NH), 4.27 (m, 2H), 3.90 (m, 2H), 3.31 (m, 2H), 3.19 (s, 3H), 3.13 (m, 2H), 1.84 (m, 4H).

Example No. I1-152:
$^1$H-NMR (400 MHz, d$_6$-DMSO δ, ppm) 9.54 (s, 1H, NH), 7.18 (d, 2H), 7.13 (d, 2H), 7.10 (m, 2H), 6.94 (d, 1H), 4.31 (s, 2H), 3.55 (s, 2H), 3.10 (s, 3H), 2.29 (s, 3H).

Example No. I1-165:
$^1$H-NMR (400 MHz, d$_6$-DMSO δ, ppm) 9.60 (s, 1H, NH), 7.43 (d, 2H), 7.29 (d, 2H), 7.10 (m, 2H), 6.93 (d, 1H), 4.40 (s, 2H), 3.55 (s, 2H), 3.10 (s, 3H).

Example No. I1-181:
$^1$H-NMR (400 MHz, d$_6$-DMSO δ, ppm) 9.68 (s, 1H, NH), 7.84 (d, 2H), 7.48 (d, 2H), 7.10 (m, 2H), 6.94 (d, 1H), 4.53 (s, 2H), 3.55 (s, 2H), 3.11 (s, 3H).

The present invention furthermore provides for the use according to the invention of at least one substituted dihydrooxindolylsulfonamide of the general formula (I), and of any mixtures of these substituted dihydrooxindolylsulfonamides of the general formula (I) according to the invention with further agrochemically active compounds, for enhancement of the resistance of plants to abiotic stress factors, preferably drought stress, and for invigoration of plant growth and/or for increasing plant yield.

The present invention further provides a spray solution for treatment of plants, comprising an amount, effective for enhancement of the resistance of plants to abiotic stress factors, of at least one compound selected from the group consisting of substituted dihydrooxindolylsulfonamides of the general formula (I). The abiotic stress conditions which can be relativized may include, for example, heat, drought, cold and aridity stress (stress caused by aridity and/or lack of water), osmotic stress, waterlogging, elevated soil salinity, elevated exposure to minerals, ozone conditions, strong light conditions, limited availability of nitrogen nutrients, limited availability of phosphorus nutrients.

In one embodiment, it may be envisaged, for example, that the use according to the invention of the compounds envisaged, i.e. the appropriate substituted dihydrooxindolylsulfonamides of the general formula (I), are applied by spray application to appropriate plants or plant parts to be treated. The compounds of the general formula (I) or salts thereof are used as envisaged in accordance with the invention preferably with a dosage between 0.00005 and 3 kg/ha, more preferably between 0.0001 and 2 kg/ha, especially preferably between 0.0005 and 1 kg/ha, specifically preferably between 0.001 and 0.25 kg/ha.

The term "resistance to abiotic stress" is understood in the context of the present invention to mean various kinds of benefits for plants. Such advantageous properties are manifested, for example, in the following improved plant characteristics: improved root growth with regard to surface area and depth, increased stolon or tiller formation, stronger and more productive stolons and tillers, improvement in shoot growth, increased lodging resistance, increased shoot base diameter, increased leaf area, higher yields of nutrients and constituents, for example carbohydrates, fats, oils, proteins, vitamins, minerals, essential oils, dyes, fibers, better fiber quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soil and water, enhanced tolerance to ozone stress, improved compatibility with respect to herbicides and other plant treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

More particularly, the use according to the invention of one or more compounds of the general formula (I) exhibits the advantages described in spray application to plants and plant parts. In addition, the combined use of substituted dihydrooxindolylsulfonamides of the general formula (I) with genetically modified cultivars with a view to increased tolerance to abiotic stress is likewise possible.

The further various benefits for plants mentioned above can be combined in a known manner in component form, and generally applicable terms can be used to describe them. Such terms are, for example, the following names: phytotonic effect, resistance to stress factors, less plant stress, plant health, healthy plants, plant fitness, plant wellness, plant concept, vigor effect, stress shield, protective shield, crop health, crop health properties, crop health products, crop health management, crop health therapy, plant health, plant health properties, plant health products, plant health management, plant health therapy, greening effect or regreening effect, freshness, or other terms with which a person skilled in the art is entirely familiar.

In the context of the present invention, a good effect on resistance to abiotic stress is understood to mean, without limitation,
- at least an emergence improved by generally 3%, especially more than 5%, more preferably more than 10%,
- at least a yield enhanced by generally 3%, especially more than 5%, more preferably more than 10%,
- at least a root development improved by generally 3%, especially more than 5%, more preferably more than 10%,
- at least a shoot size rising by generally 3%, especially more than 5%, more preferably more than 10%,
- at least a leaf area increased by generally 3%, especially more than 5%, more preferably more than 10%,
- at least a photosynthesis performance improved by generally 3%, especially more than 5%, more preferably more than 10%, and/or
- at least a flower development improved by generally 3%, especially more than 5%, more preferably more than 10%, and the effects may occur individually or else in any combination of two or more effects.

The present invention further provides a spray solution for treatment of plants, comprising an amount, effective for enhancement of the resistance of plants to abiotic stress factors, of at least one compound from the group of the substituted dihydrooxindolylsulfonamides of the general formula (I). The spray solution may comprise other customary constituents, such as solvents, formulation auxiliaries, especially water. Further constituents may include active agrochemical ingredients which are described in more detail below.

The present invention further provides for the use according to the invention of corresponding spray solutions for increasing the resistance of plants to abiotic stress factors. The remarks which follow apply both to the use according to the invention of one or more compounds of the general formula (I) per se and to the corresponding spray solutions.

Preference is given to the use according to the invention of compounds of the general formula (I) on plants from the group of the useful plants, ornamentals, turfgrass types, commonly used trees which are used as ornamentals in the public and domestic sectors, and forestry trees. Forestry trees include trees for the production of timber, cellulose, paper and products made from parts of the trees. The term useful plants as used here refers to crop plants which are used as plants for obtaining foods, animal feeds, fuels or for industrial purposes.

The useful plants include, for example, the following types of plants: triticale, *durum* (hard wheat), turf, vines, cereals, for example wheat, barley, rye, oats, rice, corn and millet; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cocoa beans and peanuts; cucurbits, for example pumpkin/squash, cucumbers and melons; fiber plants, for example cotton, flax, hemp and jute; citrus fruits, for example oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco, nuts, coffee, eggplant, sugar cane, tea, pepper, grapevines, hops, bananas, latex plants and ornamentals, for example flowers, shrubs, deciduous trees and coniferous trees. This enumeration does not constitute a limitation.

The following plants are considered to be particularly suitable target crops for the application of the method of the invention: oats, rye, triticale, *durum*, cotton, eggplant, turf, pome fruit, stone fruit, soft fruit, corn, wheat, barley, cucumber, tobacco, vines, rice, cereals, pears, pepper, beans, soybeans, oilseed rape, tomato, bell pepper, melons, cabbage, potatoes and apples.

Examples of trees which can be improved by the method of the invention include: *Abies* sp., *Eucalyptus* sp., *Picea* sp., *Pinus* sp., *Aesculus* sp., *Platanus* sp., *Tilia* sp., Acer sp., *Tsuga* sp., *Fraxinus* sp., *Sorbus* sp., *Betula* sp., *Crataegus* sp., *Ulmus* sp., *Quercus* sp., *Fagus* sp., Salix sp., *Populus* sp.

Preferred trees which can be improved by the method of the invention include: from the tree species *Aesculus*: *A. hippocastanum*, *A. pariflora*, *A. carnes*; from the tree species *Platanus*: *P. aceriflora*, *P. occidentalis*, *P. racemosa*; from the tree species *Picea*: *P. abies*; from the tree species *Pinus*: *P. radiate*, *P. ponderosa*, *P. contorta*, *P. sylvestre*, *P. elliottii*, *P. montecola*, *P. albicaulis*, *P. resinosa*, *P. palustris*, *P. taeda*, *P. flexilis*, *P. jeffregi*, *P. baksiana*, *P. strobes*; from the tree species *Eucalyptus*: *E. grandis*, *E. globulus*, *E. camadentis*, *E. nitens*, *E. oblique*, *E. regnans*, *E. pilularus*.

Particularly preferred trees which can be improved by the method of the invention are: from the tree species *Pinus*: *P. radiate*, *P. ponderosa*, *P. contorta*, *P. sylvestre*, *P. strobes;* from the tree species *Eucalyptus*: *E. grandis*, *E. globulus* and *E. camadentis*.

Particularly preferred trees which can be improved by the method of the invention are: horse chestnut, Platanaceae, linden tree and maple tree.

The present invention can also be applied to any desired turfgrasses, including cool-season turfgrasses and warm-season turfgrasses. Examples of cool-season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annus* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* , and *Agrostis palustris* Huds.), and redtop (*Agrostis alba* L.);

fescues (*Festuca* spp.), such as red fescue (*Festuca rubra* spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and Italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm-season turfgrasses are Bermudagrass (*Cynodon* spp. L. C. Rich), zoysiagrass (*Zoysia* spp. Willd.), St. Augustine grass (*Stenotaphrum secundatum* Walt Kuntze), centipedegrass (*Eremochloa ophiuroides* Munro Hack.), carpetgrass (*Axonopus affinis* Chase), Bahia grass (*Paspalum notatum* Flugge), Kikuyugrass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.)). Cool-season turfgrasses are generally preferred for the use according to the invention. Particular preference is given to bluegrass, bentgrass and redtop, fescues and ryegrasses. Bentgrass is especially preferred.

Particular preference is given to using the compounds of the general formula (I) to treat plants of the respective commercially available or commonly used plant cultivars. Plant cultivars are understood to mean plants which have new properties ("traits") and which have been obtained by conventional breeding, by mutagenesis or with the aid of recombinant DNA techniques. Crop plants may accordingly be plants which can be obtained by conventional breeding and optimization methods or by biotechnological and genetic engineering methods or combinations of these methods, including the transgenic plants and including the plant cultivars which are protectable or non-protectable by plant breeders' rights.

The treatment method according to the invention can thus also be used for the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced into the nuclear, chloroplastic or hypochondrial genome gives the transformed plant new or improved agronomic or other properties by expressing a protein or polypeptide of interest or by downregulating or silencing (an)other gene(s) which is/are present in the plant (using for example antisense technology, cosuppression technology or RNAi technology [RNA interference]). A heterologous gene that is located in the genome is also called a transgene. A transgene that is defined by its specific presence in the plant genome is called a transformation or transgenic event.

Plants and plant varieties which are preferably treated with the compounds of the general formula (I) include all plants which have genetic material which imparts particularly advantageous, useful traits to these plants (whether obtained by breeding and/or biotechnological means or not).

Plants and plant varieties which can likewise be treated with the compounds of the general formula (I) are those plants which are resistant to one or more abiotic stress factors. Abiotic stress conditions may include, for example, heat, drought, cold and aridity stress, osmotic stress, waterlogging, increased soil salinity, increased exposure to minerals, ozone conditions, strong light conditions, limited availability of nitrogen nutrients, limited availability of phosphorus nutrients or shade avoidance.

Plants and plant cultivars which can likewise be treated with the compounds of the general formula (I) are those plants which are characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including but not limited to early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and oil composition, nutritional value, reduction in antinutritional compounds, improved processibility and better storage stability.

Plants that may also be treated with the compounds of the general formula (I) are hybrid plants that already express the characteristics of heterosis, or hybrid effect, which results in generally higher yield, higher vigor, better health and better resistance towards biotic and abiotic stress factors. Such plants are typically produced by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (for example in corn) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male crossbreeding parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species (WO 92/005251, WO 95/009910, WO 98/27806, WO 05/002324, WO 06/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 91/002069).

Plants or plant cultivars (obtained by plant biotechnology methods such as genetic engineering) which may also be treated with the compounds of the general formula (I) are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Thus, for example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a *petunia* EPSPS (Shah et al., Science (1986), 233, 478-481), a tomato EPSPS (Gasser et al., J. Biol. Chem. (1988), 263, 4280-4289) or an *Eleusine* EPSPS (WO 01/66704). It can also be a mutated EPSPS, as described, for example, in EP-A 0837944, WO 00/066746, WO 00/066747 or WO 02/026995.

Glyphosate-tolerant plants can also be obtained by expressing a gene that encodes a glyphosate oxidoreductase enzyme as described in U.S. Pat. Nos. 5,776,760 and 5,463,175. Glyphosate-tolerant plants can also be obtained by expressing a gene that encodes a glyphosate acetyl transferase enzyme as described, for example, in WO 02/036782, WO 03/092360, WO 05/012515 and WO 07/024782. Glyphosate-tolerant plants can also be obtained by selecting plants containing naturally occurring mutations of the abovementioned genes, as described, for example, in WO 01/024615 or WO 03/013226.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One example of an such effective detoxifying enzyme is an enzyme encoding a phosphinothricin acetyltransferase (such as the bar or pat protein from *Streptomyces* species). Plants expressing an exogenous phosphinothricin acetyltransferase are described, for example, in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally occurring resistant HPPD enzyme, or a gene encoding a mutated HPPD enzyme according to WO 96/038567, WO 99/024585 and WO 99/024586. Tolerance to HPPD inhibitors can also be obtained by transforming plants with genes encoding certain enzymes enabling the formation of homogentisate despite inhibition of the native HPPD enzyme by the HPPD inhibitor. Such plants and genes are described in WO 99/034008 and WO 2002/36787. Tolerance of plants to HPPD inhibitors can also be improved by transforming plants with a gene encoding a prephenate dehydrogenase enzyme in addition to a gene encoding an HPPD-tolerant enzyme, as described in WO 2004/024928.

Other herbicide-resistant plants are plants which have been rendered tolerant to acetolactate synthase (ALS) inhibitors. Known ALS inhibitors include, for example, sulfonylurea, imidazolinone, triazolopyrimidines, pyrimidinyloxy (thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also in U.S. Pat. Nos. 5,605,011, 5,378,824, 5,141,870 and 5,013,659. The production of sulfonylurea-tolerant plants and midazolinone-tolerant plants has been described in U.S. Pat. Nos. 5,605,011; 5,013,659; 5,141,870; 5,767,361; 5,731,180; 5,304,732; 4,761,373; 5,331,107; 5,928,937; and 5,378,824; and also in the international publication WO 96/033270. Further imidazolinone-tolerant plants have also been described, for example, in WO 2004/040012, WO 2004/106529, WO 2005/020673, WO 2005/093093, WO 2006/007373, WO 2006/015376, WO 2006/024351 and WO 2006/060634. Further sulfonylurea- and imidazolinone-tolerant plants have also been described, for example, in WO 2007/024782.

Further plants tolerant to ALS-inhibitors, in particular to imidazolinones, sulfonylureas and/or sulfamoylcarbonyltriazolinones can be obtained by induced mutagenesis, by selection in cell cultures in the presence of the herbicide or by mutation breeding, as described, for example, for soybeans in U.S. Pat. No. 5,084,082, for rice in WO 97/41218, for sugarbeet in U.S. Pat. No. 5,773,702 and WO 99/057965, for lettuce in U.S. Pat. No. 5,198,599 or for sunflower in WO 2001/065922.

Plants or plant cultivars (obtained by plant biotechnology methods such as genetic engineering) which may also be treated with the compounds of the general formula (I) are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding the following:

1) an insecticidal crystal protein from *Bacillus thuringiensis* or an insecticidal portion thereof, such as the insecticidal crystal proteins compiled by Crickmore et al., Microbiology and Molecular Biology Reviews (1998), 62, 807-813, updated by Crickmore et al. (2005) in the *Bacillus thuringiensis* toxin nomenclature (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR 604; or 5) an insecticidal secreted protein from *Bacillus thuringiensis* or *Bacillus cereus*, or an insecticidal portion thereof, such as the vegetative insecticidal proteins (VIPs) listed under the following link, for example proteins from the VIP3Aa protein class: http://www.lifesci.sussex.ac.uk/Home/Neil_Crickmore/Bt/vip.html, or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or
7) a hybrid insecticidal protein comprising parts from different secreted proteins from *Bacillus thuringiensis* or *Bacillus cereus*, such as a hybrid of the proteins in 1) or a hybrid of the proteins in 2) above; or
8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, the insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of the target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated with the compounds of the general formula (I) are tolerant to abiotic stress factors. Such plants can be obtained by genetic transformation, or by selection of plants containing a mutation imparting such stress resistance. Particularly useful stress-tolerant plants include:

a. plants which contain a transgene capable of reducing the expression and/or the activity of the poly(ADP-ribose) polymerase (PARP) gene in the plant cells or plants, as described in WO 2000/004173 or EP 04077984.5 or EP 06009836.5;
b. plants which contain a stress tolerance-enhancing transgene capable of reducing the expression and/or the activity of the PARG-encoding genes of the plants or plant cells, as described, for example, in WO 2004/090140;
c. plants which contain a stress tolerance-enhancing transgene encoding a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, for example, in EP 04077624.7 or WO 2006/133827 or PCT/EP07/002433.

Plants or plant varieties (obtained by plant biotechnology methods such as genetic engineering) which may also be treated with the compounds of the general formula (I) show altered quantity, quality and/or storage stability of the harvested product and/or altered properties of specific ingredients of the harvested product such as, for example:

1) Transgenic plants which synthesize a modified starch which, in its physicochemical characteristics, in particular the amylose content or the amylose/amylopectin ratio, the degree of branching, the average chain length, the side chain distribution, the viscosity behavior, the gelling strength, the starch granule size and/or the starch granule morphology, is changed in comparison with the synthesized starch in wild-type plant cells or plants, so that this modified starch is better suited to specific applications. These transgenic plants synthesizing a modified starch are described, for example, in EP 0571427, WO 95/004826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 95/26407, WO 96/34968, WO 98/20145, WO 99/12950, WO 99/66050, WO 99/53072, U.S. Pat. No. 6,734,341, WO 2000/11192, WO 98/22604, WO 98/32326, WO 2001/98509, WO 2001/98509, WO 2005/002359, U.S. Pat. Nos. 5,824,790, 6,013,861, WO 94/004693, WO 94/009144, WO 94/11520, WO 95/35026 and WO 97/20936.

2) Transgenic plants which synthesize non-starch carbohydrate polymers or which synthesize non-starch carbohydrate polymers with altered properties in comparison to wild-type plants without genetic modification. Examples are plants producing polyfructose, especially of the inulin and levan type, as described in EP 0663956, WO 96/001904, WO 96/021023, WO 98/039460 and WO 99/024593, plants producing alpha-1,4-glucans, as described in WO 95/031553, US 2002/031826, U.S. Pat. Nos. 6,284,479, 5,712,107, WO 97/047806, WO 97/047807, WO 97/047808 and WO 2000/14249, plants producing alpha-1,6-branched alpha-1,4-glucans, as described in WO 2000/73422, and plants producing alternan, as described in WO 2000/047727, EP 06077301.7, U.S. Pat. No. 5,908,975 and EP 0728213.

3) Transgenic plants which produce hyaluronan, as for example described in WO 06/032538, WO 2007/039314, WO 2007/039315, WO 2007/039316, JP 2006/304779 and WO 2005/012529.

Plants or plant cultivars (obtained by plant biotechnology methods such as genetic engineering) which may also be treated with the compounds of the general formula (I) are plants, such as cotton plants, with altered fiber characteristics. Such plants can be obtained by genetic transformation, or by selection of plants containing a mutation imparting such altered fiber characteristics and include:

a) plants, such as cotton plants, which contain an altered form of cellulose synthase genes, as described in WO 98/000549;
b) plants, such as cotton plants, which contain an altered form of rsw2 or rsw3 homologous nucleic acids, as described in WO 2004/053219;
c) plants, such as cotton plants, with an increased expression of sucrose phosphate synthase, as described in WO 2001/017333;
d) plants, such as cotton plants, with an increased expression of sucrose synthase as described in WO 02/45485;
e) plants, such as cotton plants, wherein the timing of the plasmodesmatal gating at the basis of the fiber cell is altered, for example through downregulation of fiber-selective β-1,3-glucanase as described in WO 2005/017157;

f) plants, such as cotton plants, which have fibers with altered reactivity, for example through expression of the N-acetylglucosamine transferase gene including nodC and chitin synthase genes, as described in WO 2006/136351.

Plants or plant cultivars (obtained by plant biotechnology methods such as genetic engineering) which may also be treated with the compounds of the general formula (I) are plants, such as oilseed rape or related *Brassica* plants, with altered oil profile characteristics. Such plants can be obtained by genetic transformation, or by selection of plants containing a mutation imparting such altered oil characteristics and include:

a) plants, such as oilseed rape plants, which produce oil having a high oleic acid content, as described, for example, in U.S. Pat. Nos. 5,969,169, 5,840,946 or 6,323,392 or 6,063,947;

b) plants, such as oilseed rape plants, which produce oil having a low linolenic acid content, as described in U.S. Pat. Nos. 6,270,828, 6,169,190 or 5,965,755;

c) plants, such as oilseed rape plants, which produce oil having a low level of saturated fatty acids, as described, for example, in U.S. Pat. No. 5,434,283.

Particularly useful transgenic plants which may be treated with the compounds of the general formula (I) are plants containing transformation events, or a combination of transformation events, and that are listed for example in the databases of various national or regional regulatory agencies.

Particularly useful transgenic plants which may be treated with the compounds of the general formula (I) are, for example, plants which comprise one or more genes which encode one or more toxins and are the transgenic plants available under the following trade names: YIELD GARDO® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants include are corn varieties, cotton varieties and soya bean varieties which are available under the following trade names: Roundup Ready® (tolerance to glyphosates, for example corn, cotton, soybeans), Liberty Link® (tolerance to phosphinothricin, for example oilseed rape), IMI® (tolerance to imidazolinone) and SCS® (tolerance to sulfonylurea), for example corn. Herbicide-resistant plants (plants bred in a conventional manner for herbicide tolerance) which may be mentioned include the varieties sold under the name Clearfield® (for example corn).

The compounds of the formula (I) to be used in accordance with the invention can be converted to customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers, and also microencapsulations in polymeric substances. In the context of the present invention, it is especially preferred when the compounds of the general formula (I) are used in the form of a spray formulation.

The present invention therefore additionally also relates to a spray formulation for enhancing the resistance of plants to abiotic stress. A spray formulation is described in detail hereinafter:

The formulations for spray application are produced in a known manner, for example by mixing the compounds of the general formula (I) for use in accordance with the invention with extenders, i.e. liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are produced either in suitable facilities or else before or during application.

The auxiliaries used may be those substances which are suitable for imparting, to the composition itself and/or to preparations derived therefrom (for example spray liquors), particular properties such as particular technical properties and/or else special biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

It is possible to use colorants such as inorganic pigments, for example iron oxide, titanium oxide and Prussian blue, and organic colorants such as alizarin colorants, azo colorants and metal phthalocyanine colorants, and trace nutrients such as salts of iron, manganese, boron, copper, cobalt, molybdenum and zinc.

Suitable wetting agents which may be present in the formulations which can be used in accordance with the invention are all substances which promote wetting and which are conventionally used for the formulation of agrochemical active substances. Preference is given to using alkyl naphthalenesulfonates, such as diisopropyl or diisobutyl naphthalenesulfonates.

Suitable dispersants and/or emulsifiers which may be present in the formulations which can be used in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristyrylphenol polyglycol ethers, and the phosphated or sulfated derivatives thereof. Suitable anionic dispersants are especiallylignosulfonates, polyacrylic acid salts and arylsulfonate-formaldehyde condensates.

Suitable antifoams which may be present in the formulations usable in accordance with the invention are all foam-inhibiting substances conventionally used for the formulation of active agrochemical ingredients. Silicone antifoams and magnesium stearate can be used with preference.

Preservatives which may be present in the formulations usable in accordance with the invention are all substances usable for such purposes in agrochemical compositions. Examples include dichlorophene and benzyl alcohol hemiformal.

Secondary thickeners which may be present in the formulations usable in accordance with the invention are all substances usable for such purposes in agrochemical compositions. Preferred examples include cellulose derivatives, acrylic acid derivatives, xanthan, modified clays and finely divided silica.

Stickers which may be present in the formulations usable in accordance with the invention include all customary binders usable in seed-dressing products. Preferred examples include polyvinylpyrrolidone, polyvinyl acetate, polyvinyl alcohol and tylose. Suitable gibberellins which may be present in the formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- und Schädlingsbekämpfungsmittel", vol. 2, Springer Verlag, 1970, pp. 401-412).

Further additives may be fragrances, mineral or vegetable, optionally modified oils, waxes and nutrients (including trace nutrients), such as salts of iron, manganese, boron, copper, cobalt, molybdenum and zinc. Additionally present may be stabilizers, such as cold stabilizers, antioxidants, light stabilizers or other agents which improve chemical and/or physical stability.

The formulations contain generally between 0.01 and 98% by weight, preferably between 0.5 and 90%, of the compound of the general formula (I).

The compounds of the general formula (I) according to the invention may be present in commercially available formulations, and also in the use forms, prepared from these formulations, in a mixture with other active compounds, such as insecticides, attractants, sterilizing agents, bactericides, acaricides, nematicides, fungicides, growth-regulating substances, herbicides, safeners, fertilizers or semiochemicals.

In addition, the described positive effect of the compounds of the formula (I) on the plants' own defenses can be supported by an additional treatment with active insecticidal, fungicidal or bactericidal compounds.

Preferred times for the application of compounds of the general formula (I) to be used according to the invention or salts thereof for enhancing resistance to abiotic stress are treatments of the soil, stems and/or leaves with the approved application rates.

In accordance with the invention, it has additionally been found that the application, to plants or in their environment, of one or more compounds of the general formula (I) in combination with at least one fertilizer as defined further below is possible.

Fertilizers which can be used in accordance with the invention together with the compounds of the general formula (I) elucidated in detail above are generally organic and inorganic nitrogen-containing compounds, for example ureas, urea/formaldehyde condensation products, amino acids, ammonium salts and ammonium nitrates, potassium salts (preferably chlorides, sulfates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonium sulfate nitrate (general formula $(NH_4)_2SO_4NH_4NO_3$), ammonium phosphate and ammonium sulfate. These fertilizers are generally known to the person skilled in the art; see also, for example, Ullmann's Encyclopedia of Industrial Chemistry, 5th edition, Vol. A 10, pages 323 to 431, Verlagsgesellschaft, Weinheim, 1987.

The fertilizers may additionally comprise salts of micronutrients (preferably calcium, sulfur, boron, manganese, magnesium, iron, boron, copper, zinc, molybdenum and cobalt) and of phytohormones (for example vitamin B1 and indole-(III)-acetic acid) or mixtures of these. Fertilizers used in accordance with the invention may also contain other salts such as monoammonium phosphate (MAP), diammonium phosphate (DAP), potassium sulfate, potassium chloride, magnesium sulfate. Suitable amounts for the secondary nutrients or trace elements are amounts of 0.5% to 5% by weight, based on the overall fertilizer. Further possible constituents are crop protection agents, insecticides or fungicides, growth regulators or mixtures thereof. Further details of these are given further down.

The fertilizers can be used, for example, in the form of powders, granules, prills or compactates. However, the fertilizers can also be used in liquid form, dissolved in an aqueous medium. In this case, dilute aqueous ammonia can also be used as a nitrogen fertilizer. Further possible ingredients for fertilizers are described, for example, in Ullmann's Encyclopedia of Industrial Chemistry, 5th edition, 1987, volume A 10, pages 363 to 401, DE-A 41 28 828, DE-A 19 05 834 and DE-A 196 31 764. The general composition of the fertilizers, which, in the context of the present invention, may take the form of straight and/or compound fertilizers, for example composed of nitrogen, potassium or phosphorus, may vary within a wide range. In general, a content of 1% to 30% by weight of nitrogen (preferably 5% to 20% by weight), of 1% to 20% by weight of potassium (preferably 3% to 15% by weight) and a content of 1% to 20% by weight of phosphorus (preferably 3% to 10% by weight) is advantageous. The microelement content is usually in the ppm range, preferably in the range from 1 to 1000 ppm.

In the context of the present invention, the fertilizer and one or more compounds of the general formula (I) may be administered simultaneously. However, it is also possible first to apply the fertilizer and then one or more compounds of the general formula (I), or first to apply one or more compounds of the general formula (I) and then the fertilizer. In the case of nonsynchronous application of one or more compounds of the general formula (I) and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours. In very particular embodiments of the present invention, one or more compounds of the formula (I) and the fertilizer are applied within a time frame of less than 1 hour, preferably less than 30 minutes, more preferably less than 15 minutes.

The invention is to be illustrated by the biological examples which follow, but without restricting it thereto.

BIOLOGICAL EXAMPLES

In Vivo:

Seeds of monocotyledonous and dicotyledonous crop plants were sown in sandy loam in plastic pots, covered with soil or sand and cultivated in a greenhouse under good growth conditions. The trial plants were treated at the early leaf stage (BBCH10-BBCH13). To assure uniform water supply before commencement of stress, the potted plants were supplied with water by dam irrigation prior to substance application.

The compounds according to the invention, formulated in the form of wettable powders (WP), were sprayed onto the green parts of the plants as an aqueous suspension at an equivalent water application rate of 600 l/ha with addition of 0.2% wetting agent (e.g. agrotin). Substance application was followed immediately by stress treatment of the plants.

Drought stress was induced by gradual drying out under the following conditions:
"Day": 14 hours with illumination at ~26-30° C.
"Night": 10 hours without illumination at ~18-20° C.

The duration of the respective stress phases was guided mainly by the condition of the stressed control plants. It was ended (by re-irrigating and transfer to a greenhouse with good growth conditions) as soon as irreversible damage was observed on the stressed control plants.

The end of the stress phase was followed by an about 4-7-day recovery phase, during which the plants were once again kept under good growth conditions in a greenhouse. The duration of the recovery phase was guided mainly by when the trial plants had attained a state which enables visual scoring of potential effects, and was therefore variable.

Once this juncture had been reached, the appearance of the plants treated with test substances was recorded in comparison to the stressed control plants by the following categories:
0 no positive effect
10 slight positive effect
20 clear positive effect
30 strong positive effect The values reported in Tables A1 and A2 below are results of at least two repeats.

Effects of selected compounds of the general formula (I) under drought stress:

TABLE A-1

| No. | Substance | Dosage | Unit | Effect (BRSNS) |
|---|---|---|---|---|
| 1 | A1-26 | 2.5 | g/ha | 20 |
| 2 | A2-45 | 25 | g/ha | 20 |
| 3 | A4-292 | 25 | g/ha | 20 |
| 4 | G1-159 | 250 | g/ha | 10-20 |

TABLE A-2

| No. | Substance | Dosage | Unit | Effect (TRZAS) |
|---|---|---|---|---|
| 1 | A1-1 | 250 | g/ha | 10-30 |
| 2 | A2-56 | 250 | g/ha | 10-20 |
| 3 | A3-153 | 25 | g/ha | 20 |
| 4 | G1-159 | 250 | g/ha | 20 |

In the above tables:
BRSNS=*Brassica napus*
TRZAS=*Triticum aestivum*

In Vitro:

Effects of the phytohormone abscisic acid (ABA) on the behavior of plants under abiotic stress and the mechanism of action of ABA are described in the literature (cf. Abrams et al., WO97/23441, Cutler, Park et al. Science, 2009, 324, 1068; Grill et al. Science, 2009, 324, 1064; Tanokura et al. Biophysics, 2011, 7, 123; Schroeder et al. Plant J. 2010, 61, 290). Therefore, it is possible with the aid of a suitable in vitro test system to derive a correlation between the action of ABA and the stress response of a plant under abiotic stress. In the event of water deficiency (drought stress), plants form the phytohormone abscisic acid (ABA). This binds, along with a co-regulator (Regulatory Component of ABA-Receptor=RCAR according to Grill et al. Science, 2009, 324, 1064 or PYR/PYL according to Cutler et al. Science, 2009, 324, 1068), to a phosphatase (e.g. ABI1, a type 2C protein phosphatase, also abbreviated to PP2C) and inhibits its activity. As a result, a "downstream" kinase (e.g. SnRK2) is no longer dephosphorylated. This kinase, which is thus active, via phosphorylation of transcription factors (e.g. AREB/ABF, vgl. Yoshida et al., Plant J. 2010, 61, 672), switches on a genetic protection programme to increase drought stress tolerance. The assay described hereinafter utilizes the inhibition of the phosphatase ABI1 via the co-regulator RCAR11/PYR1 aus *Arabidopsis thaliana*. For the determination of activity, the dephosphorylation of 4-methylumbelliferyl phosphate (MUP) was measured at 460 nm. The in vitro assay was conducted in Greiner 384-well PS microplates F-well, using two controls: a) dimethyl sulfoxide (DMSO) 0.5% (f.c.) and b) 5 µM (f.c.) abscisic acid (ABA). The assay described here was generally conducted with substance concentrations of the appropriate chemical test substances in a concentration range of 0.1 µM to 100 µM in a solution of DMSO and water. The substance solution thus obtained, if necessary, was stirred with esterase from porcine liver (EC 3.1.1.1) at room temperature for 3 h and centrifuged at 4000 rpm for 30 min. A total volume of 45 µl was introduced into each cavity of the microplate, having the following composition:

1) 5 µl of substance solution, i.e. a) DMSO 5% or b) abscisic acid solution or c) the corresponding example compound of the general formula (I) dissolved in 5% DMSO.
2) 20 µl of enzyme buffer mix, composed of a) 40% by vol. of enzyme buffer (10 ml contain equal proportions by volume of 500 mM Tris-HCl pH 8, 500 mM NaCl, 3.33 mM MnCl2, 40 mM dithiothreitol (DTT)), b) 4% by vol. of ABM dilution (protein stock solution was diluted so as to give, after addition, a final concentration in the assay of 0.15 µg ABI1/well), c) 4% by vol. of RCAR11 dilution (enzyme stock was diluted so as to give, on addition of the dilution to the enzyme buffer mix, a final concentration in the assay of 0.30 µg enzyme/well), d) 5% by vol. of Tween20 (1%), e) 47% by vol. H$_2$O bi-dist.
3) 20 µl of substrate mix, composed of a) 10% by vol. of 500 mM Tris-HCl pH8, b) 10% by vol. of 500 mM NaCl, c) 10% by vol. of 3.33 mM MnCl$_2$, d) 5% by vol. of 25 mM MUP, 5% by vol. of Tween20 (1%), 60% by vol. of H$_2$O bi-dist.

Enzyme buffer mix and substrate mix were made up 5 minutes prior to the addition and warmed to a temperature of 35° C. On completion of pipetting of all the solutions and on completion of mixing, the plate was incubated at 35° C. for 20 minutes. Finally, a relative fluorescence measurement was made at 35° C. with a BMG Labtech "POLARstar Optima" microplate reader using a 340/10 nm excitation filter and a 460 nm emission filter. The efficacy of the compounds of the general formula (I) is reported in the table which follows using abscisic acid as comparative substance according to the following classification: ++++ (≥90% inhibition), +++ (<90%, ≥70% inhibition), ++ (<70%, ≥50% inhibition), + (<50%, ≥30% inhibition).

Effects of selected compounds of the general formula (I) in the above-described in vitro assay at a concentration of 5 mM of the substance of the general formula (I) in question in a solution of DMSO and water:

TABLE A-1

| No. | Substance | ABI1 inhibition |
|---|---|---|
| 1 | A1-178 | ++ |
| 2 | A2-152 | +++ |
| 3 | A2-165 | +++ |
| 4 | A2-178 | +++ |
| 5 | A2-181 | ++ |
| 6 | A3-152 | ++++ |
| 7 | A3-158 | ++ |
| 8 | A3-165 | +++ |
| 9 | A3-178 | ++++ |
| 10 | A3-181 | +++ |
| 11 | A4-178 | ++ |
| 12 | B1-178 | +++ |
| 13 | C2-152 | +++ |
| 14 | C2-165 | ++ |
| 15 | C3-45 | ++ |
| 16 | C3-152 | ++ |
| 17 | C3-165 | +++ |
| 18 | E7-152 | ++ |
| 19 | G1-165 | ++ |
| 20 | G1-172 | +++ |
| 21 | G1-178 | ++ |
| 22 | G1-184 | ++ |
| 23 | I1-152 | +++ |
| 24 | I1-165 | ++ |
| 25 | abscisic acid | ++++ |

Similar results were also achievable with further compounds of the general formula (I), even on application to different plant species.

The invention claimed is:

1. A method for treating a plant to increase the plants resistance to an abiotic stress factor, comprising applying to the plant or an area where the plant grows, or to a seed of the plant, or to part of the plant, a nontoxic amount, effective for increasing the resistance of the plant to an abiotic stress factor of one or more compounds of formulae (Ia) to (Iz) or (Iab), or salt thereof

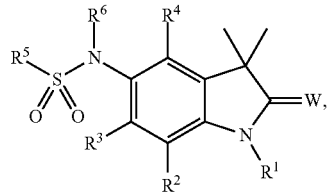
(Ia)

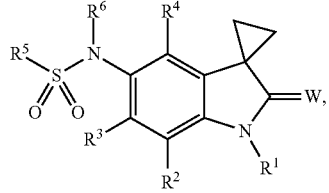
(Ib)

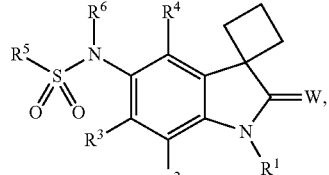
(Ic)

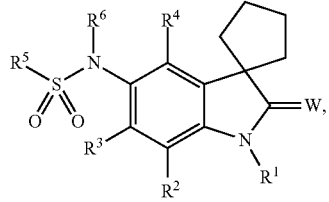
(Id)

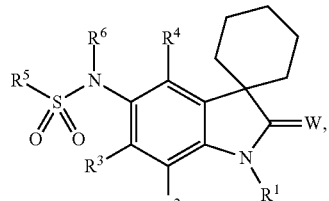
(Ie)

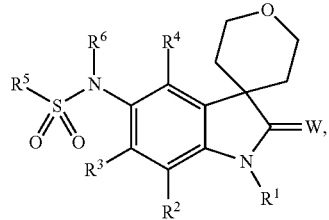
(If)

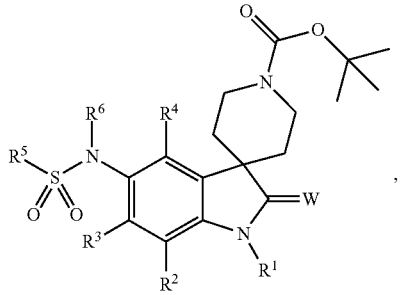
(Ig)

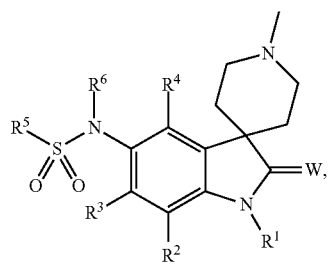 (Ih)
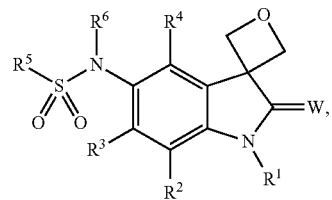 (Ii)
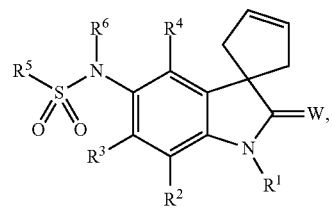 (Ij)
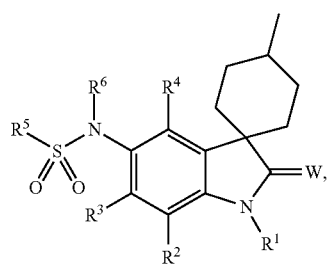 (Ik)
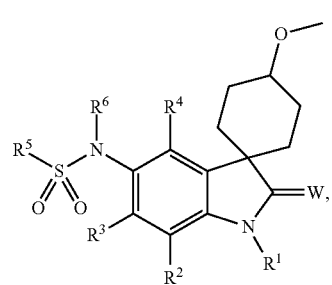 (Il)
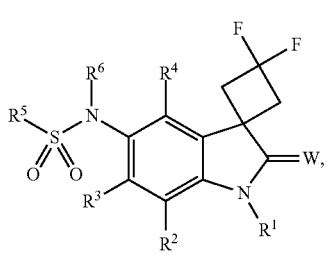 (Im)
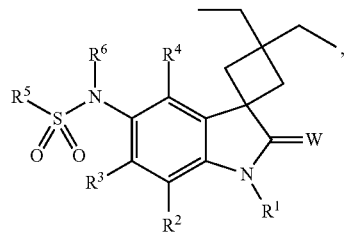 (In)
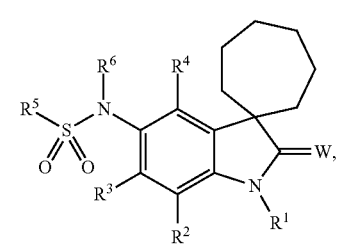 (Io)
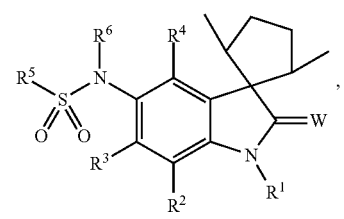 (Ip)
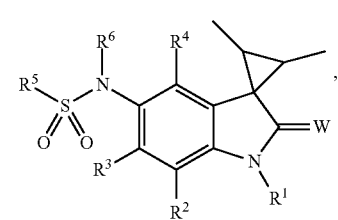 (Iq)
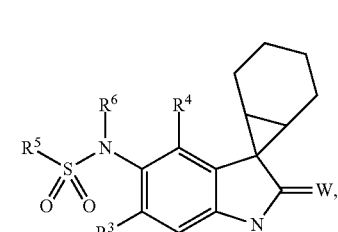 (Ir)
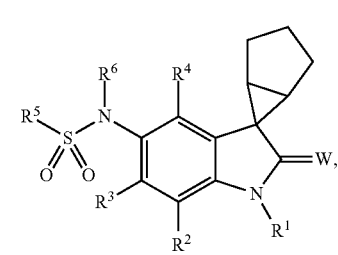 (Is)

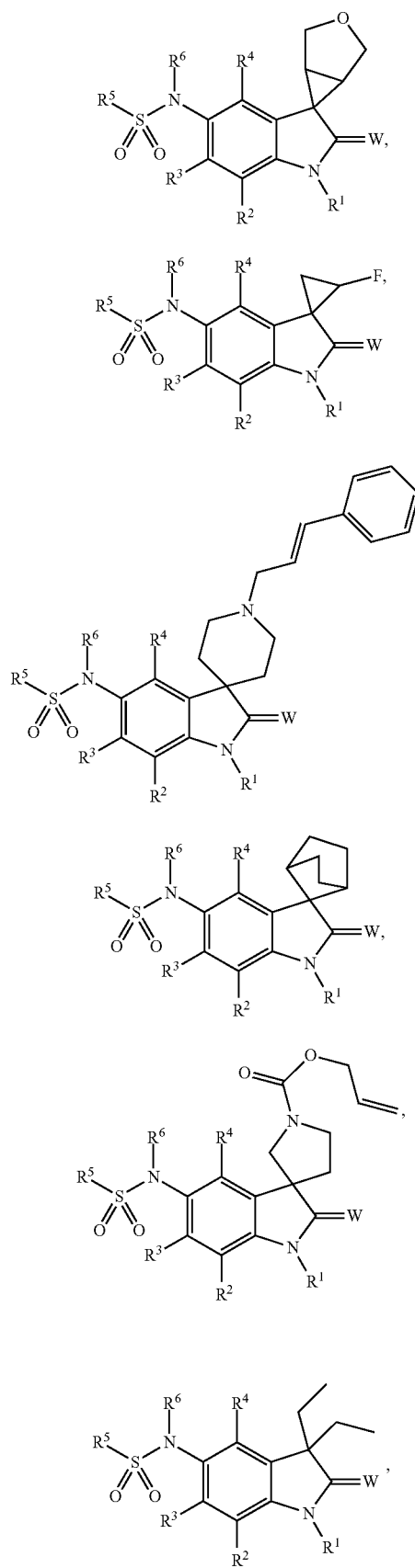

in which

R[1] represents hydrogen, $(C_1-C_6)$-alkyl, $(C_3-C_6)$-cycloalkyl, $(C_1-C_6)$-haloalkyl, $(C_3-C_6)$-halocycloalkyl, $(C_2-C_6)$-alkenyl, $(C_2-C_6)$-haloalkenyl, $(C_1-C_5)$-alkoxy-$(C_1-C_5)$-haloalkyl, $(C_2-C_5)$-alkynyl, aryl, aryl-$(C_1-C_5)$-alkyl, heteroaryl, heteroaryl-$(C_1-C_5)$-alkyl, $(C_3-C_6)$-cycloalkyl-$(C_1-C_5)$-alkyl, $(C_2-C_5)$-haloalkynyl, heterocyclyl, heterocyclyl-$(C_1-C_5)$-alkyl, $(C_1-C_5)$-alkoxy-$(C_1-C_5)$-alkyl, $(C_1-C_5)$-alkylcarbonyl-$(C_1-C_5)$-alkyl, hydroxycarbonyl-$(C_1-C_5)$-alkyl, $(C_1-C_5)$-alkoxycarbonyl-$(C_1-C_5)$-alkyl, $(C_2-C_5)$-alkenyloxycarbonyl-$(C_1-C_5)$-alkyl, $(C_2-C_5)$-alkynyloxycarbonyl-$(C_1-C_5)$-alkyl, aryl-$(C_1-C_5)$-alkoxycarbonyl-$(C_1-C_5)$-alkyl, $(C_3-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, heteroaryl-$(C_1-C_5)$-alkylaminocarbonyl-$(C_1-C_5)$-alkyl, $(C_1-C_5)$-alkoxy-$(C_1-C_5)$-alkoxy-$(C_1-C_5)$-alkyl, $(C_1-C_5)$-alkylcarbonyl, $(C_1-C_5)$-haloalkylcarbonyl, $(C_3-C_6)$-cycloalkylcarbonyl, $(C_1-C_5)$-alkoxycarbonyl, aryl-$(C_1-C_5)$-alkoxycarbonyl, arylcarbonyl, heteroarylcarbonyl, heterocyclylcarbonyl, aryl-$(C_1-C_6)$-alkylcarbonyl, $(C_1-C_6)$-alkylaminocarbonyl, $(C_3-C_6)$-cycloalkylaminocarbonyl, arylaminocarbonyl, aryl-$(C_1-C_6)$-alkylaminocarbonyl, heteroarylaminocarbonyl, heterocyclylaminocarbonyl, heteroaryl-$(C_1-C_6)$-alkylaminocarbonyl, heterocyclyl-$(C_1-C_6)$-alkylaminocarbonyl, $(C_1-C_6)$-alkylsulfonyl, $(C_3-C_6)$-cycloalkylsulfonyl, arylsulfonyl, aryl-$(C_1-C_6)$-alkylsulfonyl, heteroarylsulfonyl, heterocyclylsulfonyl, cyano-$(C_1-C_5)$-alkyl, bis-[$(C_1-C_5)$-alkyl]amino, $(C_3-C_6)$-cycloalkyl[$(C_1-C_5)$-alkyl]amino, R[2], R[3], R[4] independently of one another represent hydrogen, halogen, $(C_1-C_5)$-alkoxy, $(C_1-C_5)$-alkyl, $(C_1-C_5)$-haloalkyl, $(C_1-C_5)$-haloalkoxy, $(C_1-C_5)$-alkylthio, $(C_1-C_5)$-haloalkylthio, aryl, aryl-$(C_1-C_5)$-alkyl, heteroaryl, heteroaryl-$(C_1-C_5)$-alkyl, heterocyclyl, heterocyclyl-$(C_1-C_5)$-alkyl, $(C_3-C_6)$-cycloalkyl, nitro, amino, hydroxy, $(C_1-C_5)$-alkylamino, bis-[$(C_1-C_5)$-alkyl]amino, hydrothio, $(C_1-C_5)$-alkylcarbonylamino, $(C_3-C_6)$-cycloalkylcarbonylamino, arylcarbonylamino, heteroarylcarbonylamino, heterocyclylcarbonylamino, formyl, hydroxyiminomethyl, $(C_1-C_5)$-alkoxyiminomethyl, $(C_3-C_6)$-cycloalkoxyiminomethyl, aryloxyiminomethyl, $(C_3-C_6)$-cycloalkyl-$(C_1-C_5)$-alkoxyiminomethyl, thiocyanato, isothiocyanato, aryloxy, heteroaryloxy, $(C_3-C_6)$-cycloalkoxy, $(C_3-C_6)$-cycloalkyl-$(C_1-C_5)$-alkoxy, aryl-$(C_1-C_5)$-alkoxy, $(C_2-C_5)$-alkynyl, $(C_2-C_5)$-alkenyl, aryl-$(C_1-C_5)$-alkynyl, tris-[$(C_1-C_5)$-alkyl]silyl-$(C_2-C_5)$-alkynyl, bis-[$(C_1-C_5)$-alkyl](aryl)silyl-$(C_2-C_5)$-alkynyl, bis-aryl[$(C_1-C_5)$-alkyl]silyl-$(C_2-C_5)$-alkynyl, $(C_3-C_6)$-cycloalkyl-$(C_2-C_5)$-alkynyl, aryl-$(C_2-C_5)$-alkenyl, heteroaryl-$(C_2-C_5)$-alkenyl, $(C_3-C_6)$-cycloalkyl-$(C_2-C_5)$-alkenyl, $(C_2-C_5)$-haloalkynyl, $(C_2-C_5)$-haloalkenyl, $(C_4-C_5)$-cycloalkenyl, $(C_1-C_5)$-alkoxy-$(C_1-C_5)$-alkoxy-$(C_1-C_5)$-alkyl, $(C_1-C_5)$-alkylsulfonyl, arylsulfonyl, heteroarylsulfonyl, $(C_1-C_5)$-alkylsulfonylamino, arylsulfonylamino, aryl-$(C_1-C_5)$-alkylsulfonylamino, heteroarylsulfonylamino, heteroaryl-$(C_1-C_5)$-alkylsulfonylamino, bis-[$(C_1-C_5)$-alkyl]aminosulfonyl, $R^5$ represents amino, $(C_1-C_5)$-alkyl, $(C_3-C_6)$-cycloalkyl, $(C_3-C_6)$-cycloalkyl-$(C_1-C_5)$-alkyl, $(C_1-C_5)$-haloalkyl, $(C_3-C_6)$-halocycloalkyl, $(C_4-C_6)$-cycloalkenyl, aryl, heteroaryl, heterocyclyl, aryl-$(C_1-C_5)$-alkyl, heteroaryl-$(C_1-C_5)$-alkyl, heterocyclyl-$(C_1-C_5)$-alkyl, $(C_1-C_5)$-alkoxycarbonyl-$(C_1-C_5)$-alkyl, aryl-$(C_1-C_5)$-alkoxycarbonyl-$(C_1-C_5)$-alkyl, $(C_3-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, heteroaryl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, $(C_1-C_5)$-alkylamino, arylamino, $(C_3-C_6)$-cycloalkylamino, aryl-$(C_1-C_5)$-alkylamino, heteroaryl-$(C_1-C_5)$-alkylamino, heteroarylamino, heterocyclylamino, aryloxy-$(C_1-C_5)$-alkyl, $(C_1-C_5)$-alkoxy-$(C_1-C_5)$-alkyl, heteroaryloxy-$(C_1-C_5)$-alkyl, $(C_2-C_5)$-alkenyl, $(C_2-C_5)$-alkynyl, $(C_2-C_5)$-alkenylamino, $(C_2-C_5)$-alkynylamino, bis-[$(C_1-C_5)$-alkyl]amino, aryloxy, $(C_3-C_6)$-cycloalkyl-$(C_2-C_5)$-alkyl, bis-[$(C_1-C_5)$-alkyl]amino, aryl-$(C_2-C_5)$-alkenyl, heteroaryl-$(C_2-C_5)$-alkenyl, heterocyclyl-$(C_2-C_5)$-alkenyl, $R^6$ represents hydrogen, $(C_1-C_5)$-alkyl, $(C_3-C_6)$-cycloalkyl, cyano-$(C_1-C_5)$-alkyl, $(C_3-C_6)$-cycloalkyl-$(C_1-C_5)$-alkyl, $(C_1-C_5)$-alkylsulfonyl, arylsulfonyl, heteroarylsulfonyl, $(C_3-C_6)$-cycloalkylsulfonyl, heterocyclylsulfonyl, aryl-$(C_1-C_5)$-alkylsulfonyl, $(C_1-C_5)$-alkylcarbonyl, arylcarbonyl, heteroarylcarbonyl, $(C_3-C_6)$-cycloalkylcarbonyl, heterocyclylcarbonyl, $(C_1-C_5)$-alkoxycarbonyl, aryl-$(C_1-C_5)$-alkoxycarbonyl, $(C_1-C_5)$-haloalkylcarbonyl, $(C_2-C_5)$-alkenyl, $(C_2-C_5)$-alkynyl, $(C_1-C_5)$-haloalkyl, halo-$(C_2-C_5)$-alkynyl, halo-$(C_2-C_5)$-alkenyl, $(C_1-C_5)$-alkoxy-$(C_1-C_5)$-alkyl and W represents oxygen or sulfur.

2. The method as claimed in claim 1, wherein the abiotic stress conditions are one or more conditions selected from the group consisting of aridity, cold stress, heat stress, drought stress, osmotic stress, waterlogging, elevated soil salinity, elevated exposure to minerals, ozone conditions, strong light conditions, limited availability of nitrogen nutrients and limited availability of phosphorus nutrients.

3. The method as claimed in claim 1, wherein said applying comprises spraying the one or more compounds in combination with one or more active compounds selected from the group consisting of insecticides, attractants, acaricides, fungicides, nematicides, herbicides, growth regulators, safeners, and substances which affect plant maturity and bactericides.

4. The method as claimed in claim 1, wherein said applying comprises spraying plants and parts of plants with the one or more compounds in combination with fertilizers.

5. The method of claim 1, wherein the compound is applied to a genetically modified cultivars, the seed thereof, or to cultivated areas on which these cultivars grow.

6. The method of claim 1, comprising increasing stress tolerance in plants selected from the group of useful plants, ornamental plants, turfgrasses and trees, comprising applying the one or more compounds to an area where a corresponding effect is desired, comprising application to the plants, the seed thereof or to the area on which the plants grow.

7. The method as claimed in claim 6, wherein the resistance of the plants thus treated to abiotic stress is increased by at least 3% compared to untreated plants under otherwise identical physiological conditions.

8. The method as claimed in claim 1, wherein the one or more compounds are selected from one or more of formulae (Ib) to (If), (Ii) to (Iu) or (Iw), or a salt thereof.

9. The method as claimed in claim 8, wherein $R^1$ represents hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-allylcyclopropyl, 1-vinylcyclobutyl, 1-vinylcyclopropyl, 1-ethylcyclopropyl, 2-ethylcyclopropyl, 1-ethylcyclobutyl, 2-ethylcyclobutyl, 3-ethylcyclobutyl, 4-methylcyclohexyl, 4-methoxycyclohexyl, 4-ethoxycyclohexyl, 4-n-propyloxycyclohexyl, 4-hydroxycyclohexyl, 4-methoxycyclobutyl, 1-cyclopropylcyclobutyl, 1-prop-2-enylcyclobutyl, 2-ethyl-3-methylcyclobutyl, 1-propylcyclopropyl, 1-methyl-2-propylcyclopropyl, 2-propylcyclopropyl, 1-propylcyclobutyl, 2-propylcyclobutyl, 3-propylcyclobutyl, 1-isopropylcyclobutyl, 1-isopropylcyclopropyl, 2-isopropylcyclopropyl, 3-isopropylcyclobutyl, 2-dimethylaminocyclobutyl, 3-dimethylaminocyclobutyl, 1-butylcyclobutyl, 2-butylcyclobutyl, 1-butylcyclopropyl, 3-butylcyclobutyl, 2-butylcyclopropyl, 1-isobutylcyclobutyl, 3-tert-butylcyclobutyl, 3,3-diethylcyclobutyl, 2,2-diethylcyclopropyl, 2-methylidenecyclopropyl, 1-methoxymethylcyclopropyl, 1-isobutylcyclopropyl, 2,2-difluoroethyl, 2,2,2-trifluoroethyl, 3,3,3-trifluoropropyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl- 1-propenyl, 1-ethyl-2-propenyl, 1-hexenyl, 2-hexenyl, 3-hexenyl, 4-hexenyl, 5-hexenyl, 1-methyl-1-pentenyl, 2-methyl- 1-pentenyl, 3-methyl- 1-pentenyl, 4-methyl- 1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl- 1 -methyl-2-propynyl, $(C_3-C_6)$-halocycloalkyl, $(C_2-C_5)$-haloalkenyl, $(C_1-C_5)$-alkoxy-$(C_1-C_5)$-haloalkyl, benzyl, p-chlorobenzyl, p-methoxybenzyl, p-trifluoromethylbenzyl, p-methylbenzyl, p-fluorobenzyl, p-bromobenzyl, p-iodobenzyl, p-methylthiobenzyl, p-trifluoromethoxybenzyl, p-nitrobenzyl, p-trifluoromethylthiobenzyl, m-chlorobenzyl, m-methoxybenzyl, m-trifluoromethylbenzyl, m-methylbenzyl, m-fluorobenzyl, m-bromobenzyl, m-iodobenzyl, m-methylthiobenzyl, m-trifluoromethoxybenzyl, m-nitrobenzyl, m-trifluoromethylthiobenzyl, o-chlorobenzyl, o-methoxybenzyl, o-trifluoromethylbenzyl, o-methylbenzyl, o-fluorobenzyl, o-bromobenzyl, o-iodobenzyl, o-methylthiobenzyl, o-trifluoromethoxybenzyl, o-nitrobenzyl, o-trifluoromethylthiobenzyl, p-methoxycarbonylbenzyl, p-ethoxycarbonylbenzyl, m-methoxycarbonylbenzyl, m-ethoxycarbonylbenzyl, 2,4-dichlorobenzyl, 3,5-dichlorobenzyl, 2,4-difluorobenzyl, 3,5-difluorobenzyl, 3,4-dichlorobenzyl, 3,4-difluorobenzyl, 2,5-dichlorobenzyl, phenylethyl, p-chlorophenylethyl, p-methoxyphenylethyl, p-trifluoromethylphenylethyl, p-fluorophenylethyl, p-trifluoromethoxyphenylethyl, p-trifluoromethylthiophenylethyl, p-methylphenylethyl, p-nitrophenylethyl, p-methoxycarbonylphenylethyl, p-ethoxycarbonylphenylethyl, m-chlorophenylethyl, m-methoxyphenylethyl, m-trifluoromethylphenylethyl, m-fluorophenylethyl, m-trifluoromethoxyphenylethyl, m-trifluoromethylthiophenylethyl, m-methylphenylethyl, m-nitrophenylethyl, m-methoxycarbonylphenylethyl, m-ethoxycarbonylphenylethyl, o-chlorophenylethyl, o-methoxyphenylethyl, o-trifluoromethylphenylethyl, o-fluorophenylethyl, o-trifluoromethoxyphenylethyl, o-trifluoromethylthiophenylethyl, o-methylphenylethyl, o-nitrophenylethyl, o-methoxycarbonylphenylethyl, o-ethoxycarbonylphenylethyl, heteroaryl-$(C_1-C_5)$-alkyl, $(C_1-C_5)$-haloalkenyl, heterocyclyl, heterocyclyl-$(C_1-C_5)$-alkyl, $(C_1-C_5)$-alkoxy-$(C_1-C_5)$-alkyl, $(C_1-C_5)$-alkylcarbonyl-$(C_1-C_5)$-alkyl, hydroxycarbonyl-$(C_1-C_5)$-alkyl, $(C_1-C_5)$-alkoxycarbonyl-$(C_1-C_5)$-alkyl, $(C_2-C_5)$-alkenyloxycarbonyl-$(C_1-C_5)$-alkyl, $(C_2-C_5)$-alkynyloxycarbonyl-$(C_1-C_5)$-alkyl, aryl-$(C_1-C_5)$-alkoxycarbonyl-$(C_1-C_5)$-alkyl, $(C_3-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, heteroaryl-$(C_1-C_5)$-alkylaminocarbonyl-$(C_1-C_5)$-alkyl, $(C_1-C_5)$-alkylthio-$(C_1-C_5)$-alkyl, $(C_3-C_6)$-cycloalkylthio-$(C_1-C_5)$-alkyl, arylthio-$(C_1-C_5)$-alkyl, heterocyclylthio-$(C_1-C_5)$-alkyl, heteroarylthio-$(C_1-C_5)$-alkyl, aryl-$(C_1-C_5)$-alkylthio-$(C_1-C_5)$-alkyl, $(C_1-C_5)$-alkylsulfinyl-$(C_1-C_5)$-alkyl, $(C_1-C_5)$-alkylsulfonyl- $(C_1-C_5)$-alkyl, arylsulfinyl-$(C_1-C_5)$-alkyl, arylsulfonyl-$(C_1-C_5)$-alkyl, $(C_3-C_6)$-cycloalkylsulfinyl-$(C_1-C_5)$-alkyl, $(C_3-C_6)$-cycloalkylsulfonyl-$(C_1-C_5)$-alkyl, $(C_1-C_5)$-alkoxy-$(C_1-C_5)$-alkoxy-$(C_1-C_5)$-alkyl, $(C_1-C_5)$-alkylcarbonyl, $(C_3-C_6)$-cycloalkylcarbonyl, $(C_1-C_5)$-alkoxycarbonyl, aryl-$(C_1-C_5)$-alkoxycarbonyl, arylcarbonyl, heteroarylcarbonyl, heterocyclylcarbonyl, aryl-$(C_1-C_5)$-alkylcarbonyl, $(C_1-C_5)$-alkylaminocarbonyl, $(C_3-C_6)$-cycloalkylaminocarbonyl, arylaminocarbonyl, aryl-$(C_1-C_5)$-alkylaminocarbonyl, $(C_1-C_5)$-alkylsulfonyl, $(C_3-C_6)$-cycloalkylsulfonyl, arylsulfonyl, heteroarylsulfonyl, heterocyclylsulfonyl, bis-[$(C_1-C_5)$-alkyl]amino, $(C_3-C_6)$-cycloalkyl[$(C_1-C_5)$-alkyl]amino, $R^2$, $R^3$, $R^4$ independently of one another represent hydrogen, fluorine, chlorine, bromine, iodine, methoxy, ethoxy, n-propyloxy, isopropyloxy, methyl, ethyl, isopropyl, trifluoromethyl, difluoromethyl, pentafluoroethyl, trifluoromethoxy, difluoromethoxy, 2,2-difluoroethoxy, 3,3,3-trifluoroethoxy, methylthio, ethylthio, trifluoromethylthio, optionally substituted phenyl, heteroaryl, heterocyclyl, cyclopropyl, cyclobutyl, cyclopentyl, cyclohexyl, $R^5$ represents amino, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, spiro[2.2]pent-1- yl, spiro[2.3]hex-1-yl, spiro[2.3]hex-4-yl, 3-spiro[2.3]hex-5-yl, cyclopropylmethyl, cyclobutylmethyl, cyclopentylmethyl, cyclohexylmethyl, trifluoromethyl, difluoromethyl, 2,2-difluoroethyl, 2,2,2-trifluoroethyl, 3,3,3-trifluoropropyl, pentafluoroethyl, heptafluoro-n-propyl, heptafluoroisopropyl, nonafluoro-n-butyl, ($C_3$-$C_6$)-halocycloalkyl, ($C_4$-$C_6$)-cycloalkenyl, optionally substituted phenyl, heteroaryl, heterocyclyl, aryl-($C_1$-$C_5$)-alkyl, heteroaryl-($C_1$-$C_5$)-alkyl, heterocyclyl-($C_1$-$C_5$)-alkyl, ($C_1$-$C_5$)-alkoxycarbonyl-($C_1$-$C_5$)-alkyl, aryl-($C_1$-$C_5$)-alkoxycarbonyl-($C_1$-$C_5$)-alkyl, ($C_1$-$C_6$)-cycloalkoxycarbonyl-($C_1$-$C_5$)-alkyl, ($C_3$-$C_6$)-cycloalkyl-($C_1$-$C_5$)-alkoxycarbonyl-($C_1$-$C_5$)-alkyl, heteroaryl-($C_1$-$C_5$)-alkoxycarbonyl-($C_1$-$C_5$)-alkyl, aminocarbonyl-($C_1$-$C_5$)-alkyl, ($C_1$-$C_5$)-alkylaminocarbonyl-($C_1$-$C_5$)-alkyl, ($C_3$-$C_6$)-cycloalkylaminocarbonyl-($C_1$-$C_5$)-alkyl, aryl-($C_1$-$C_5$)-alkylaminocarbonyl-($C_1$-$C_5$)-alkyl, ($C_1$-$C_5$)-alkylamino, arylamino, ($C_3$-$C_6$)-cycloalkylamino, aryl-($C_1$-$C_5$)-alkylamino, heteroaryl-($C_1$-$C_5$)-alkylamino, heteroarylamino, heterocyclylamino, ($C_2$-$C_5$)-alkenylamino, ($C_2$-$C_5$)-alkynylamino, aryloxy-($C_1$-$C_5$)-alkyl, heteroaryloxy-($C_1$-$C_5$)-alkyl, ($C_1$-$C_5$)-alkoxy-($C_1$-$C_5$)-alkyl, phenylethenyl, p-chlorophenylethenyl, p-methylphenylethenyl, p-methoxyphenylethenyl, p-trifluoromethylphenylethenyl, p-fluorophenylethenyl, p-cyanophenylethenyl, p-trifluoromethoxyphenylethenyl, p-nitrophenylethenyl, p-bromophenylethenyl, p-iodophenylethenyl, m-chlorophenylethenyl, m-methylphenylethenyl, m-methoxyphenylethenyl, m-trifluoromethylphenylethenyl, m-fluorophenylethenyl, m-cyanophenylethenyl, m-trifluoromethoxyphenylethenyl, m-nitrophenylethenyl, m-bromophenylethenyl, m-iodophenylethenyl, p-methoxycarbonylphenylethenyl, m-methoxycarbonylphenylethenyl, o-methoxycarbonylphenylethenyl, p-ethoxycarbonylphenylethenyl, m-ethoxycarbonylphenylethenyl, o-ethoxycarbonylphenylethenyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, cyanoethyl, cyanomethyl, cyano-n-propyl, cyano-n-butyl, aryloxy, bis-[($C_1$-$C_5$)-alkyl]amino, aryl-($C_2$-$C_5$)-alkenyl, heteroaryl-($C_2$-$C_5$)-alkenyl, heterocyclyl-($C_2$-$C_5$)-alkenyl, $R^6$ represents hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, cyclopentylmethyl, cyclohexylmethyl, 2,2-difluoroethyl, 2,2,2-trifluoroethyl, 3,3,3-trifluoropropyl, cyanomethyl, cyanoethyl, cyano-n-propyl, cyclopropylcarbonyl, cyclobutylcarbonyl, cyclopentylcarbonyl, cyclohexylcarbonyl, methoxycarbonyl, ($C_1$-$C_5$)-alkylsulfonyl, arylsulfonyl, aryl-($C_1$-$C_5$)-alkylsulfonyl, heteroarylsulfonyl, ($C_3$-$C_6$)-cycloalkylsulfonyl, heterocyclylsulfonyl, ($C_1$-$C_5$)-alkylcarbonyl, arylcarbonyl, heteroarylcarbonyl, heterocyclylcarbonyl, ($C_1$-$C_5$)-alkoxycarbonyl, aryl-($C_1$-$C_5$)-alkoxycarbonyl, ($C_1$-$C_5$)-haloalkylcarbonyl, ($C_2$-$C_5$)-alkenyl, ($C_2$-$C_5$)-alkynyl, halo-($C_2$-$C_5$)-alkynyl, halo-($C_2$-$C_5$)-alkenyl, ($C_1$-$C_5$)-alkoxy-($C_1$-$C_5$)-alkyl and W represents oxygen or sulfur.

10. The method as claimed in claim 8, wherein
$R^1$ represents methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-allylcyclopropyl, 1-vinylcyclobutyl, 1-vinylcyclopropyl, 1-ethylcyclopropyl, 2-ethylcyclopropyl, 1-ethylcyclobutyl, 2-ethylcyclobutyl, 3-ethylcyclobutyl, 4-methylcyclohexyl, 4-methoxycyclohexyl, 4-ethoxycyclohexyl, 4-n-propyloxycyclohexyl, 4-hydroxycyclohexyl, 4-methoxycyclobutyl, 1-cyclopropylcyclobutyl, 1-prop-2-enylcyclobutyl, 2-ethyl-3-methylcyclobutyl,1-propylcyclopropyl, 1-methyl-2-propylcyclopropyl, 2-propylcyclopropyl, 1-propylcyclobutyl, 2-propylcyclobutyl, 3-propylcyclobutyl, 1-isopropylcyclobutyl, 1-isopropylcyclopropyl, 2-isopropylcyclopropyl, 3-isopropylcyclobutyl, 2-dimethylaminocyclobutyl, 3-dimethylaminocyclobutyl, 1-butylcyclobutyl, 2-butylcyclobutyl, 1-butylcyclopropyl, 3-butylcyclobutyl, 2-butylcyclopropyl, 1-isobutylcyclobutyl, 3-tert-butylcyclobutyl, 3,3-diethylcyclobutyl, 2,2-diethylcyclopropyl, 2-methylidenecyclopropyl, 1-methoxymethylcyclopropyl, 1-isobutylcyclopropyl, 2,2-difluoroethyl, 2,2,2-trifluoroethyl, 3,3,3-trifluoropropyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, $(C_3-C_6)$-halocycloalkyl, $(C_2-C_5)$-haloalkenyl, $(C_1-C_5)$-alkoxy-$(C_1-C_5)$-haloalkyl, benzyl, p-chlorobenzyl, p-methoxybenzyl, p-trifluoromethylbenzyl, p-methylbenzyl, p-fluorobenzyl, p-bromobenzyl, p-iodobenzyl, p-methylthiobenzyl, p-trifluoromethoxybenzyl, p-nitrobenzyl, p-trifluoromethylthiobenzyl, m-chlorobenzyl, m-methoxybenzyl, m-trifluoromethylbenzyl, m-methylbenzyl, m-fluorobenzyl, m-bromobenzyl, m-iodobenzyl, m-methylthiobenzyl, m-trifluoromethoxybenzyl, m-nitrobenzyl, m-trifluoromethylthiobenzyl, o-chlorobenzyl, o-methoxybenzyl, o-trifluoromethylbenzyl, o-methylbenzyl, o-fluorobenzyl, o-bromobenzyl, o-iodobenzyl, o-methylthiobenzyl, o-trifluoromethoxybenzyl, o-nitrobenzyl, o-trifluoromethylthiobenzyl, p-methoxycarbonylbenzyl, p-ethoxycarbonylbenzyl, m-methoxycarbonylbenzyl, m-ethoxycarbonylbenzyl, 2,4-dichlorobenzyl, 3,5-dichlorobenzyl, 2,4-difluorobenzyl, 3,5-difluorobenzyl, 3,4-dichlorobenzyl, 3,4-difluorobenzyl, 2,5-dichlorobenzyl, phenylethyl, p-chlorophenylethyl, p-methoxyphenylethyl, p-trifluoromethylphenylethyl, p-fluorophenylethyl, p-trifluoromethoxyphenylethyl, p-trifluoromethylthiophenylethyl, p-methylphenylethyl, p-nitrophenylethyl, p-methoxycarbonylphenylethyl, p-ethoxycarbonylphenylethyl, m-chlorophenylethyl, m-methoxyphenylethyl, m-trifluoromethylphenylethyl, m-fluorophenylethyl, m-trifluoromethoxyphenylethyl, m-trifluoromethylthiophenylethyl, m-methylphenylethyl, m-nitrophenylethyl, m-methoxycarbonylphenylethyl, m-ethoxycarbonylphenylethyl, o-chlorophenylethyl, o-methoxyphenylethyl, o-trifluoromethylphenylethyl, o-fluorophenylethyl, o-trifluoromethoxyphenylethyl, o-trifluoromethylthiophenylethyl, o-methylphenylethyl, o-nitrophenylethyl, o-methoxycarbonylphenylethyl, o-ethoxycarbonylphenylethyl, heteroaryl-$(C_1-C_5)$-alkyl, $(C_1-C_5)$-haloalkenyl, heterocyclyl, heterocyclyl-$(C_1-C_5)$-alkyl, $(C_1-C_5)$-alkoxy-$(C_1-C_5)$-alkyl, $(C_1-C_5)$-alkylcarbonyl-$(C_1-C_5)$-alkyl, hydroxycarbonyl-$(C_1-C_5)$-alkyl, $(C_1-C_5)$-alkoxycarbonyl-$(C_1-C_5)$-alkyl, $(C_2-C_5)$-alkenyloxycarbonyl-$(C_1-C_5)$-alkyl, $(C_2-C_5)$-alkynyloxycarbonyl-$(C_1-C_5)$-alkyl, aryl-$(C_1-C_5)$-alkoxycarbonyl-$(C_1-C_5)$-alkyl, $(C_3-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, heteroaryl-$(C_1-C_5)$-alkylaminocarbonyl-$(C_1-C_5)$-alkyl, $(C_1-C_5)$-alkylthio-$(C_1-C_5)$-alkyl, $(C_3-C_6)$-cycloalkylthio-$(C_1-C_5)$-alkyl, arylthio-$(C_1-C_5)$-alkyl, heterocyclylthio-$(C_1-C_5)$-alkyl, heteroarylthio-$(C_1-C_5)$-alkyl, aryl-$(C_1-C_5)$-alkylthio-$(C_1-C_5)$-alkyl, $(C_1-C_5)$-alkylsulfinyl-$(C_1-C_5)$-alkyl, $(C_1-C_5)$-alkylsulfonyl-$(C_1-C_5)$-alkyl, arylsulfinyl-$(C_1-C_5)$-alkyl, arylsulfonyl-$(C_1-C_5)$-alkyl, $(C_3-C_6)$-cycloalkylsulfinyl-$(C_1-C_5)$-alkyl, $(C_3-C_6)$-cycloalkylsulfonyl-$(C_1-C_5)$-alkyl, $(C_1-C_5)$-alkoxy-$(C_1-C_5)$-alkoxy-$(C_1-C_5)$-alkyl, $(C_1-C_5)$-alkylcarbonyl, $(C_3-C_6)$-cycloalkylcarbonyl, $(C_1-C_5)$-alkoxycarbonyl, aryl-$(C_1-C_5)$-alkoxycarbonyl, arylcarbonyl, heteroarylcarbonyl, heterocyclylcarbonyl, aryl-$(C_1-C_5)$-alkylcarbonyl, $(C_1-C_5)$-alkylaminocarbonyl, $(C_3-C_6)$-cycloalkylaminocarbonyl, arylaminocarbonyl, aryl-$(C_1-C_5)$-alkylaminocarbonyl, $(C_1-C_5)$-alkylsulfonyl, $(C_3-C_6)$-cycloalkylsulfonyl, arylsulfonyl, heteroarylsulfonyl, heterocyclylsulfonyl, bis-[$(C_1-C_5)$-alkyl]amino, $(C_3-C_6)$-cycloalkyl[$(C_1-C_5)$-alkyl]amino, $R^2$, $R^3$, $R^4$ independently of one another represent hydrogen, fluorine, chlorine, bromine, iodine, methoxy, ethoxy, n-propyloxy, isopropyloxy, methyl, ethyl, isopropyl, trifluoromethyl, difluoromethyl, pentafluoroethyl, trifluoromethoxy, difluoromethoxy, 2,2-difluoroethoxy, 3,3,3-trifluoroethoxy, methylthio, ethylthio, trifluoromethylthio, optionally substituted phenyl, heteroaryl, heterocyclyl, cyclopropyl, cyclobutyl, cyclopentyl, cyclohexyl, $R^5$ represents optionally substituted phenyl, heteroaryl, heterocyclyl, aryl-$(C_1-C_5)$-alkyl, heteroaryl-$(C_1-C_5)$-alkyl, heterocyclyl-$(C_1-C_5)$-alkyl, $(C_1-C_5)$-alkoxycarbonyl-$(C_1-C_5)$-alkyl, aryl-$(C_1-C_5)$-alkoxycarbonyl-$(C_1-C_5)$-alkyl, $(C_1-C_6)$-cycloalkoxycarbonyl-$(C_1-C_5)$-alkyl, $(C_3-C_6)$-cycloalkyl-$(C_1-C_5)$-alkoxycarbonyl-$(C_1-C_5)$-alkyl, heteroaryl-$(C_1-C_5)$-alkoxycarbonyl-$(C_1-C_5)$-alkyl, aminocarbonyl-$(C_1-C_5)$-alkyl, $(C_1-C_5)$-alkylaminocarbonyl-$(C_1-C_5)$-alkyl, $(C_3-C_6)$-cycloalkylaminocarbonyl-$(C_1-C_5)$-alkyl, aryl-$(C_1-C_5)$-alkylaminocarbonyl-$(C_1-C_5)$-alkyl, aryloxy-$(C_1-C_5)$-alkyl, heteroaryloxy-$(C_1-C_5)$-alkyl, phenylethenyl, p-chlorophenylethenyl, p-methylphenylethenyl, p-methoxyphenylethenyl, p-trifluoromethylphenylethenyl, p-fluorophenylethenyl, p-cyanophenylethenyl, p-trifluoromethoxyphenylethenyl, p-nitrophenylethenyl, p-bromophenylethenyl, p-iodophenylethenyl, m-chlorophenylethenyl, m-methylphenylethenyl, m-methoxyphenylethenyl, m-trifluoromethylphenylethenyl, m-fluorophenylethenyl, m-cyanophenylethenyl, m-trifluoromethoxyphenylethenyl, m-nitrophenylethenyl, m-bromophenylethenyl, m-iodophenylethenyl, p-methoxycarbonylphenylethenyl, m-methoxycarbonylphenylethenyl, o-methoxycarbonylphenylethenyl, p-ethoxycarbonylphenylethenyl, m-ethoxycarbonylphenylethenyl, o-ethoxycarbonylphenylethenyl, heteroaryl-$(C_2-C_5)$-alkenyl, heterocyclyl-$(C_2-C_5)$-alkenyl, $R^6$ represents hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, cyclopentylmethyl, cyclohexylmethyl, 2,2-difluoroethyl, 2,2,2-trifluoroethyl, 3,3,3-trifluoropropyl, cyanomethyl, cyanoethyl, cyano-n-propyl, cyclopropylcarbonyl, cyclobutylcarbonyl, cyclopentylcarbonyl, cyclohexylcarbonyl, methoxycarbonyl, $(C_1-C_5)$-alkylsulfonyl, arylsulfonyl, aryl-$(C_1-C_5)$-alkylsulfonyl, heteroarylsulfonyl, $(C_3-C_6)$-cycloalkylsulfonyl, heterocyclylsulfonyl, $(C_1-C_5)$-alkylcarbonyl, arylcarbonyl, heteroarylcarbonyl, heterocyclylcarbonyl, $(C_1-C_5)$-alkoxycarbonyl, aryl-$(C_1-C_5)$-alkoxycarbonyl, $(C_1-C_5)$-haloalkylcarbonyl, $(C_2-C_5)$-alkenyl, $(C_2-C_5)$-alkynyl, halo-$(C_2-C_5)$-alkynyl, halo-$(C_2-C_5)$-alkenyl, $(C_1-C_5)$-alkoxy-$(C_1-C_5)$-alkyl and W represents oxygen or sulfur.

11. The method as claimed in claim 8, wherein said applying comprises spraying.

12. The method according to claim 1, wherein the compound is of formula (Ib),

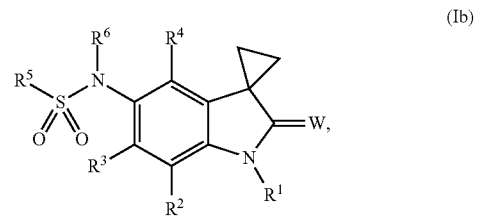

(Ib)

wherein
$R^1$ represents cyclopropylmethyl;
$R^2$ represents hydrogen;
$R^3$ represents hydrogen;
$R^4$ represents hydrogen;
$R^5$ represents

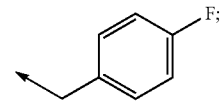

$R^6$ represents hydrogen; and
W represents oxygen.

13. The method of claim 1, wherein said method increases plant yield.

14. The method according to claim 1, wherein the at least one compound is of formula (Ib).

15. The method according to claim 1, wherein the at least one compound is of formula (Ic).

16. The method according to claim 1, wherein the at least one compound is of formula (Id).

17. The method according to claim 1, wherein the at least one compound is of formula (Ie).

18. The method according to claim 1, wherein the at least one compound is of formula (If).

19. The method according to claim 1, wherein the at least one compound is of formula (Ii).

20. The method according to claim 1, wherein the at least one compound is of formula (Ib)-(Ie), (Ij)-(Is), (Iu), or (Iw).

* * * * *